US010570152B2

(12) United States Patent
Sengupta et al.

(10) Patent No.: US 10,570,152 B2
(45) Date of Patent: Feb. 25, 2020

(54) ANTIBACTERIAL THERAPEUTICS AND PROPHYLACTICS

(71) Applicant: VYOME BIOSCIENCES PVT. LTD., New Dehli (IN)

(72) Inventors: Shiladitya Sengupta, New Dehli (IN); Shamik Ghosh, New Dehli (IN); Sumana Ghosh, New Dehli (IN); Mau Sinha, Uttar Pradesh (IN); Suresh Sadhasivam, Tamil Nadu (IN); Anamika Bhattacharyya, New Dehli (IN); Siva Ganesh Mavuduru, Andhra Pradesh (IN); Nupar Tandon, New Dehli (IN); Deepak Kumar, Haryana (IN)

(73) Assignee: Vyome Therapeutics Limited, New Delhi (IN)

( * ) Notice: Subject to any disclaimer, the term of this patent is extended or adjusted under 35 U.S.C. 154(b) by 0 days.

(21) Appl. No.: 15/744,922

(22) PCT Filed: Jul. 28, 2016

(86) PCT No.: PCT/IB2016/054506
§ 371 (c)(1),
(2) Date: Jan. 15, 2018

(87) PCT Pub. No.: WO2017/017631
PCT Pub. Date: Feb. 2, 2017

(65) Prior Publication Data
US 2018/0265523 A1 Sep. 20, 2018

(30) Foreign Application Priority Data
Jul. 28, 2015 (IN) .......................... 2298/DEL/2015

(51) Int. Cl.
| C07D 513/04 | (2006.01) |
| C07D 405/14 | (2006.01) |
| C07D 413/12 | (2006.01) |
| C07D 417/12 | (2006.01) |
| C07D 263/24 | (2006.01) |
| C07D 263/48 | (2006.01) |
| A61P 31/04 | (2006.01) |
| A01N 43/46 | (2006.01) |
| A01N 43/76 | (2006.01) |
| A01N 43/78 | (2006.01) |
| A01N 43/90 | (2006.01) |
| A61K 9/00 | (2006.01) |
| A61K 9/06 | (2006.01) |
| A61K 47/10 | (2017.01) |
| A61K 47/12 | (2006.01) |
| A61K 47/34 | (2017.01) |
| A61K 47/36 | (2006.01) |
| A61K 47/38 | (2006.01) |

(52) U.S. Cl.
CPC .......... *C07D 513/04* (2013.01); *A01N 43/46* (2013.01); *A01N 43/76* (2013.01); *A01N 43/78* (2013.01); *A01N 43/90* (2013.01); *A61K 9/0014* (2013.01); *A61K 9/0019* (2013.01); *A61K 9/0053* (2013.01); *A61K 9/06* (2013.01); *A61K 47/10* (2013.01); *A61K 47/12* (2013.01); *A61K 47/34* (2013.01); *A61K 47/36* (2013.01); *A61K 47/38* (2013.01); *A61P 31/04* (2018.01); *C07D 263/24* (2013.01); *C07D 263/48* (2013.01); *C07D 405/14* (2013.01); *C07D 413/12* (2013.01); *C07D 417/12* (2013.01)

(58) Field of Classification Search
CPC ........ A01N 42/46; A01N 42/76; A01N 42/78; A01N 42/90; A61K 47/10; A61K 47/12; A61K 47/34; A61K 47/36; A61K 47/38; A61K 9/0014; A61K 9/0019; A61K 9/0053; A61K 9/06; A61P 31/04; C07C 323/59; C07C 323/60; C07D 215/56; C07D 239/96; C07D 263/24; C07D 263/38; C07D 263/48; C07D 311/22; C07D 401/12; C07D 403/12; C07D 405/12; C07D 405/14; C07D 413/12; C07D 413/14; C07D 417/12; C07D 471/00; C07D 487/04; C07D 513/04
See application file for complete search history.

(56) References Cited

PUBLICATIONS

Saeed Emami, et al, 7-Piperazinylquinolones with methylene-bridged nitrofuran scaffold as new antibacterial agents, Med. Chem. Res., 22:5940-5947 (2013). (Year: 2013).*

* cited by examiner

*Primary Examiner* — Erich A Leeser
(74) *Attorney, Agent, or Firm* — Foley & Lardner LLP

(57) ABSTRACT

The present disclosure relates generally to novel molecules, compositions, and formulations for treatment of bacterial infections in general and more specifically to bacterial infections with antibiotic resistant pathogens.

20 Claims, 2 Drawing Sheets

ANTIBACTERIAL THERAPEUTICS AND PROPHYLACTICS

RELATED APPLICATIONS

This application is a U.S. National Phase Application under 35 U.S.C. § 371 of International Application No. PCT/IB2016/054506, filed on Jul. 28, 2016, which in turn claims benefit under one or more of 35 U.S.C. § 119(a)-119 (d) of Indian Patent Application No. 2298/DEL/2015, filed on Jul. 28, 2015, the contents of which are incorporated by reference in their entireties into the present disclosure.

FIELD OF THE INVENTION

The present disclosure relates generally to novel molecules, compositions, and formulations for treatment of bacterial infections in general and more specifically to bacterial infections with antibiotic resistant pathogens.

BACKGROUND OF THE INVENTION

A serious challenge in today's global health scenario is the wide spread of drug resistant bacterial strains capable of evading even the most recently developed generation of antibiotics (Fait & Tor 2014, Perspect Medicin Chem 6: 25; Michael et al 2014, Front Public Health 2: 145.). Bacteria adopt various strategies to acquire drug resistant phenotypes (Dever & Dermody 1991, Arch Intern Med 151: 886). The bacterial genetic elements provide a number of resistance modalities to the pathogen (Davies & Davies 2010, Microbiol Mol Biol Rev 74: 417). Some genes encode enzymes that are responsible for modifying or degrading the antibiotic while some result in mutation of the antibiotic target enzyme or metabolic process that hinders the interaction of the antibiotic with the target protein. Other genetic elements may decrease the permeability or the uptake of the antibiotic. At times the microbe can activate efflux mechanisms to extrude the antibiotic to the exterior after its uptake. Residing in biofilms, bacteria can efficiently retard the access of antibiotics using the protective matrix as a hindrance (Høiby et al 2010, Int J Antimicrob Agents 35: 322). This leads to establishment of antibiotic gradients conducive for the seeding of resistance. Therefore, development of new strategies is essential to address the threat from multidrug resistant superbugs implicated in various infectious diseases. An astute way forward would be to design molecules that would not only work against existing drug resistant microbes but also reduce the chances of the targeted bacteria to evolve into resistant strains. Such efficacious molecules endowed with features that not only help them act against prevalent resistance but also aid in preventing the development of resistance can be a major advancement in the treatment of microbial diseases caused by both susceptible and/or resistant bacteria.

The present disclosure addresses, in part, these needs of the art.

SUMMARY OF THE INVENTION

An understanding of the mechanistic and structural aspects of bacterial resistance from the plethora of available crystallographic information on biological target macromolecules and ligand-target complex structures in addition to the genomics data of susceptible and resistant target proteins enables us to design smart molecules to combat emergence of bacterial resistance and also work against existing resistant pathogens. Here, the inventors describe a rational structure-based drug discovery approach based on a particular strategy "Dual Action Rational Therapeutics" where in logical yet creative new properties can be incorporated into drug molecules to either bypass and/or suppress antibiotic resistance by multiple mechanisms. Using this strategy, on one hand the inventors adopted fragment-based in silico drug design approach to generate novel lead molecules against completely new or already known active or allosteric site of selected target proteins and on the other, they carried out novel and nonobvious chemical modifications of existing antibiotics to obtain structurally and functionally novel molecules.

The present disclosure provides compounds having antibacterial activity. The complete synthetic process of the compounds representative of the FORMULAE I-VII and their respective intermediates are also described herein. It is noted that the intermediates described herein are the useful intermediates for the synthesis of other classes of compounds as well.

In one aspect, the invention provides a compound of Formula I:

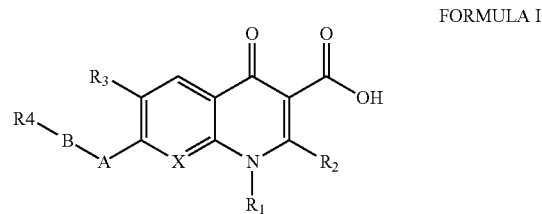

FORMULA I

In compounds of Formula I, $R_1$ is a $C_1$-$C_3$ alkyl or a cyclopropyl. Exemplary alkyl groups for $R_1$ include, but are not limited to, methyl, ethyl, propyl and isopropyl. In some embodiments, $R_1$ is a linker connecting the nitrogen ($R_1$ is attached to) to the $R_2$ or X. A linker can be any linker described herein. Exemplary linkers include $C_1$-$C_4$ alkyl and thioalkyl linkers. In some embodiments, $R_1$ is —CH(CH$_3$)—, —CH(CH$_3$)CH$_2$O— or —CH(CH$_3$)CH$_2$CH$_2$—.

In compounds of Formula I, $R_2$ can be hydrogen, thioalkyl or alkyl group. As noted-above, $R_2$ can be linked to the nitrogen to which $R_1$ is attached. In some embodiments, $R_2$ is S and $R_1$ is —CH(CH$_3$)—.

In compounds of Formula I, X can be C, N, or CR$_8$, where $R_8$ is a H, $C_1$-$C_6$alkyl, $C_1$-$C_6$alkoxy or halo. In some embodiments, $R_8$ is methyl, methoxy, fluoro, or chloro. As noted-above, $R_2$ can be linked to the nitrogen to which $R_1$ is attached. Thus, in some embodiments, X is C and $R_1$ is —CH(CH$_3$)CH$_2$O—, where O or $R_1$ is linked to X. In some other embodiments, X is C and $R_1$ is —CH(CH$_3$) CH$_2$CH$_2$—. When $R_1$ is —CH(CH$_3$)CH$_2$CH$_2$—, X can be connected to either end. For example, $R_1$ and X together are —CH(CH$_3$)CH$_2$O—X or —CH(CH$_3$)CH$_2$CH$_2$—X.

$R_3$ in compounds of Formula I can be H or halo. In some embodiments, $R_3$ is H, F or Cl.

In some compounds of Formula I, A can be absent or a linker. In some embodiments, A can be absent, a bond or selected from the group consisting of piperazinyl; 3-methylpiperazine; 3-methylamino piperidine; pyrrolidinyl [3,4-b]piperidine; or piperind-4-ol.

In some embodiments, A is

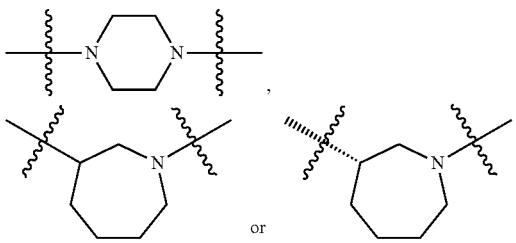

or

In some embodiments, A is a bond.

In some embodiments, A is 1-H-benzoimidazol-2-yl; (1-H-benzoimidazol-2-yl)-amino; 2-Amino-1-H-benzoimidazolyl; 5,6-mono and di-substituted 1-H-benzoimidazol-2-yl. Exemplary substitutions for 5,6-mono and di-substituted 1-H-benzoimidazol-2-yl include, but are not limited to, alkyl (e.g., $C_1$-$C_{11}$ alkyl), halo (e.g., F, Cl, Br), nitro, carboxyl, amino, thiol, mono or di or polyguanidino group (—NH[C(M)NHC(M)]$_n$-D where M is NH, O, S or CH; n is 1-10; D is $NH_2$, COOH or $CONH_2$), amino acid analogues, spermine, norspermidine, spermidine analogues, guanidino amino acid, spermine linked through an amide linkage, norspermidine linked through an amide linkage, spermidine analogues linked through an amide linkage, or any combinations thereof.

In some embodiments, A is 6-Carboxyl-2-pyridyl ring, 5-Bromo-2-pyridyl ring or 5 or 6 mono or di-substituted 2-pyridyl ring where 3, 4, 5 or 6 can be independently substituted with hydrogen atom, alkyl group —$CH_3$ or $CH_3$—$(CH_2)_n$—, n=1-10, any halogen atom (F, Cl, Br) or nitro group, amino group, carboxyl group, methyl amino, thiol group or —$R_7(CH_2)_n$NHCO— or —$R_7(CH_2)_n$CONH—, or —$R_7(CH_2)_n$—OCO— or —$R_7(CH_2)_n$—COO—, where $R_7$=NH or S and n=0-10 or mono or di or polyguanidino group —NH[C(M)NHC(M)]$_n$-D where M=NH or oxygen atom or sulfur atom, CH, D=$NH_2$, COOH, $CONH_2$, n=1-10 or coupled with amino acid analogues or spermine or norspermidine or spermidine analogues or guanidino amino acid, spermine or norspermidine or spermidine analogues through amide linkage.

In some embodiments, A can be directly functionalized with (CO—$R_L$—CY')$_n$—Z' or (CS—$R_4$—CY')$_n$—Z', where n is 1-10; $R_L$ is NH; Y' is NH, O, S or CH; and Z' is $NH_2$, COOH, $CONH_2$, OH, SH or alkyl group.

In compounds of Formula I, B can be absent or a linker. A linker for B can be of any chain length, e.g., straight or branched alkyl chain, —$(CH_2)$, n=1-10 or functionalized alkyl chain, e.g., —$CH_2CH(R_8)(CH_2)$—, $R_8$=hydroxyl, chloro, fluoro, etc., —$(CH_2)_n$CO— or —$O(CH_2)_n$— or —$C(O)(CH_2)_n$—, n=0-10 or alkyl chain with ester or amide linkages e.g. —$(CH_2)_n$OCO— or —$(CH_2)_n$COO—, —$(CH_2)_n$CONH—, —$(CH_2)_n$NHCO— or —C(O)—$(CH_2)_n$NHCO— or —CO$(CH_2)_n$CONH— or —$CH_2COO(CH_2)_n$, n=0-10. Some exemplary linkers for B include, but are not limited to, a bond, —$CH_2CH(OH)CH_2$—, $C_1$-$C_6$ alkylene (e.g., methylene, ethylene, propylene, butylene), —C(O)$CH_2$—, —C(O)$CH_2$NH—, —NHC(O)$CH_2$—, —C(O)—, —C(O)NH$(CH_2)_m$C(O)— (m is 1, 2, 3, 4 or 5), —CH=N—, —NH—, —OCH$_2$CH$_2$—, (OH)NHC(O)CH$_2$, [(HO)NHC(O)]CH[{CH$_3$(OH)}CH] and [(HO)NHC(O)]CH[CH$_2$(OH)CH] or —CH$_2$CH$_2$NHCH$_2$CH$_2$—.

In some embodiments B is —CH$_2$(CO)NH(CO)NH—Ar (Ar represents aryl or phenyl substituted or not substituted)

In some embodiments B is —CO-cysteine, —CO—(S-dodecane cysteine), —CO—S—(N-acetyl cysteine), —CO—S—(N-acetyl dodecane cysteine)

In compounds of Formula I, $R_4$ is a 5-membered aryl or heteroaryl, optionally substituted with 1, 2 or 3 substituents; or $R_4$ is a 6-membered aryl or heteroaryl, optionally substituted with 1, 2 or 3 substituents; or $R_4$ is a fused ring 9-10-membered aryl or heteroaryl, optionally substituted with 1 1, 2 or 3 substituents. In some embodiments, $R_4$ is a fused ring 9-10-membered cyclyl or heterocyclyl, optionally substituted with 1, 2 or 3 substituents In some embodiments, $R_4$ is a 5-membered heteroaryl represented by

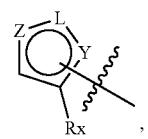

where Rx is nitro, amino, thiol, —$CONH_2$, mono or di or polyguanidino group —NH[C(M)NHC(M)]$_n$D (where M is NH, O, S or CH, D is $NH_2$, COOH or $CONH_2$, and n is 1-10); Z, L and Y are selected independently from C, $CR_{11}$, N, O and S, where $R_{11}$ is H or $C_1$-$C_6$ alkyl, provided that at least one of Z, L and Y is not C or $CR_{11}$. In some embodiments, Rx is —$NO_2$ —$NH_2$ or —NHC(=NH)$NH_2$. Exemplary 5-membered heteroaryls include, but are not limited to substituted thiazoles, furans and oxazoles.

Without limitations, L, Z, Y can be the same, all different or two are same and the other is different. For example, L and Z can be same and Y different, or L and Y same and Z different, or Z and Y same and L different. In some embodiments, L is —$C(CH_3)$. In some embodiments, L is —$C(CH_3)$ and Y and Z are N. In some embodiments, L is —$C(NH_2)$ or —C[NHC(=NH)$NH_2$], Y is N and Z is S or Y is N and Z is O or Y is N and Z is N.

In some embodiments, L is a C linked to rest of Formula I and Y is S and Z is N. In some embodiment, L is a C linked to rest of Formula I and Y is O and Z is CH.

It is noted that the 5-membered heteroaryl represented by

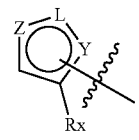

can be attached to rest of Formula I at Z, L or Y. Accordingly, in some embodiments, L is C attached to rest of Formula I. In some embodiments, Y is N attached to rest of the molecule. In some embodiments, Rx can be the rest of Formula I.

In some embodiments, $R_4$ is a fused ring 9-membered heteroaryl of structure

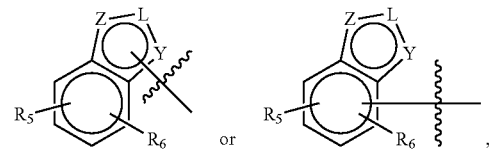

, where $R_5$ and $R_6$ are independently H, nitro, amino, thiol, halo, —$CONH_2$, mono or di or polyguanidino group —NH[C(M)NHC(M)]$_n$D (where M is NH, O, S or CH, D is $NH_2$, COOH or $CONH_2$, and n is 1-10); Z, L and Y are selected independently from C, $CR_{11}$, N, O and S, where $R_{11}$ is H, $C_1$-$C_6$alkyl or amino, provided that at least one of Z, L and Y is not C or $CR_{11}$.

$R_5$ and $R_6$ can be same or different. In some embodiments, $R_5$ and $R_6$ are different. In other embodiments, they are same. In some embodiments, at least one of $R_5$ and $R_6$ is not H. In some embodiments, one of $R_5$ and $R_6$ is H. In some embodiments, at least one of $R_5$ and $R_6$ is —$NH_2$, —$NO_2$, Cl or C(=NH)$CH_2CH_2N(CH_3)_2$. In some embodiments, $R_5$ is H and $R_6$ is —$NH_2$, —$NO_2$, Cl or C(=NH)$CH_2CH_2N(CH_3)_2$. In some other embodiments, $R_6$ is H and $R_5$ is —$NH_2$, —$NO_2$, —Cl or —C(=NH)$CH_2CH_2N(CH_3)_2$. In some embodiments, $R_5$ and $R_6$ are Cl.

Without limitations, L, Z, Y can be the same, all different or two are same and the other is different. For example, L and Z can be same and Y different, or L and Y same and Z different, or Z and Y same and L different. In some embodiments, L is —$CNH_2$. In some embodiments, Y and Z are N. In some embodiments, L is C, and one of Y and Z is C and the other is N. In some embodiments, L is —$CNH_2$ and Y and Z are N. In some embodiment, L is a C linked to rest of Formula I. In some embodiments, Y is a N or C linked to rest of Formula I.

In some embodiments, $R_4$ is

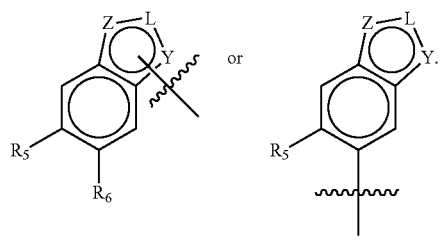

It is noted that the 9-membered heteroaryl can be attached to rest of Formula I at Z, L or Y. Accordingly, in some embodiments, L is C attached to rest of Formula I. In some embodiments, Y is N or C attached to rest of the molecule.

Exemplary 9-membered heteroaryl groups include, but are not limited to, 1-H-benzoimidazol-2-yl; (1-H-benzoimidazol-2-yl)-amino; 2-Amino-1-H-benzoimidazolyl; 5,6-mono and di-substituted 1-H-benzoimidazol-2-yl. Exemplary substitutions for 5,6-mono and di-substituted 1-H-benzoimidazol-2-yl include, but are not limited to, alkyl (e.g., $C_1$-$C_{11}$alkyl), halo (e.g., F, Cl, Br), nitro, carboxyl, amino, thiol, mono or di or polyguanidino group (—NH[C(M)NHC(M)]$_n$-D where M is NH, O, S or CH; n is 1-10; D is $NH_2$, COOH or $CONH_2$), amino acid analogues, spermine, norspermidine, spermidine analogues, guanidino amino acid, spermine linked through an amide linkage, norspermidine linked through an amide linkage, spermidine analogues linked through an amide linkage, or any combinations thereof.

In some embodiments, $R_4$ is a 6-membered heteroaryl, optionally substituted with 1 or 2 substituents. The 6-membered heteroaryl can be a pyridinyl, optionally substituted with 1 or 2 substituents. In some embodiments, $R_4$ is pyridin-2-yl, 4-nitro-pyridin-2-yl, 5-bromo-pyridin-2-yl, 5-guanidino-pyridin-2-yl, 5-guanidinomethyl-pyridin-2-yl,

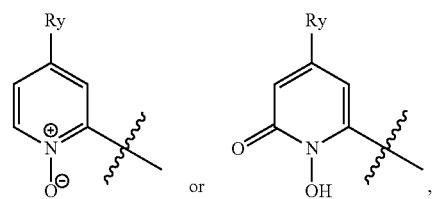

where Ry is H, methylamino, methyl or nitro. In some embodiments, $R_4$ is pyridin-2-yl substituted at the 5-position with —C(O)NH($CH_2$)$_2$NH($CH_2$)$_3$NHC(=NH)$NH_2$.

In some embodiments, $R_4$ is a 6-membered heteroaryl of structure

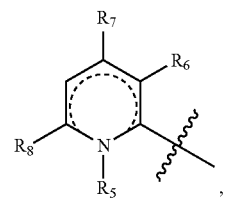

where $R_5$ can be absent, hydrogen, —O— or hydroxyl; $R_6$, $R_7$ and $R_8$ are independently hydrogen, oxygen atom, sulfur atom, hydroxyl, —$CONH_2$, amino, methyl amino, nitro, any halogen atom (F, Cl, Br), alkyl group —($CH_2$)$_n$$CH_3$ (n=1-10), or mono or di or polyguanidino group —NH[C(M)NHC(M)]$_n$-D, where M is NH or oxygen atom or sulfur atom or CH, D is $NH_2$, COOH or $CONH_2$, and n is 1-10.

In some embodiments, $R_4$ is a fused ten membered heterocyclic, optionally substituted with 1 or 2 substituents. Exemplary substituents for the fused ten membered heterocyclic include, but are not limited to halogen, hydroxyl, thiol, —$CONH_2$, amino, methyl amino and nitro.

In some embodiments, $R_4$ is

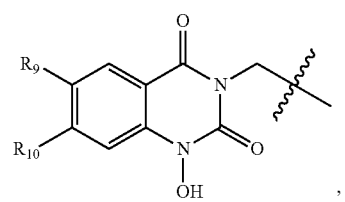

where $R_9$ and $R_{10}$ are independently selected from the group consisting of hydrogen, halogen, hydroxyl, thiol, —$CONH_2$, amino, methyl amino and nitro.

In some embodiments, $R_4$ is

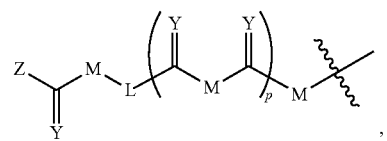

where p is 0-10 (preferably p is 1-10); M is CH, NH, or S; Y is NH, CH, O or S; L is linker or Z; and Z is $NH_2$, OH, SH, alkyl, —COOH, or $CONH_2$. In some embodiments, M is CH, NH, or S. Y is NH, CH, O or S, L is Z where Z is $NH_2$, OH, SH, alkyl, —COOH, or $CONH_2$. In some embodiments, M is CH, NH, or S. Y is NH, CH, O or S, L is linker with amino, phenyl amino, substituted phenyl amino, straight or branched alkyl chain, —(CH$_2$)$_n$—, n=1-10, (CH$_2$)$_n$ —NH— (CH$_2$)$_n$, n=1-10 or —CO(CH$_2$)$_n$—R$_5$, where R$_5$=OH, NH$_2$, N-alkyl amine, alkyl, thiol or any halogen atoms and n=0-10 or CO—C(NHCOCH$_3$)—CH$_2$SH, and Z is NH$_2$, OH, SH, alkyl, —COOH, or CONH$_2$.

The invention also provides salts of compounds of Formula I. Exemplary salts of Formula I include, but are not limited to, salts of arginine, lysine, halo acids, fumarate, lactic acid, maleic acid, tartaric acid, fumaric acid, glutamic acid and L-aspartic acid In some embodiments, the compound is of Formula II:

FORMULA II

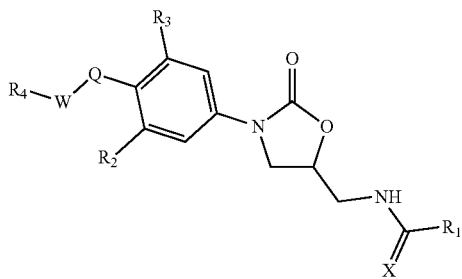

In compounds of Formula II, X can be O, S, or N. In some embodiments, X is O or S.

In compounds of Formula II, R$_1$ can be H, C$_1$-C$_6$alkyl, —COCHY$_2$ or —COCH$_2$Y (where Y is H or halo), haloalkyl (e.g., CX$_3$, CHX$_2$ or CH$_2$X, where X=F, Cl, Br); CH$_2$CN, amino, OCH$_3$, COOCH$_3$, SO$_2$CH$_3$, COCH$_2$OH, mono or di or polyguanidino group —[NHC(R$_7$)]$_n$-M where R$_7$ is NH, O, S or CH, M is NH$_2$, COOH, CONH$_2$, and n is 1-10. In some embodiments, R$_1$ is CH$_3$ or NH$_2$.

In compounds of Formula II, R$_2$ and R$_3$ are independently H or halo. Without limitations, R$_2$ and R$_3$ can be same or different. In some embodiments, at least one of R$_2$ and R$_3$ is halo. In some embodiments, one of R$_2$ and R$_3$ is halo. In some embodiments, one of R$_2$ and R$_3$ is F and the other is H.

In some compounds of Formula II, Q can be absent or a linker. In some embodiments, Q can be absent, a bond or selected from the group consisting of piperazinyl; 3-methylpiperazine; 3-methylamino piperidine; pyrrolidinyl [3,4-b]piperidine; or piperind-4-ol.

In some embodiments, Q is

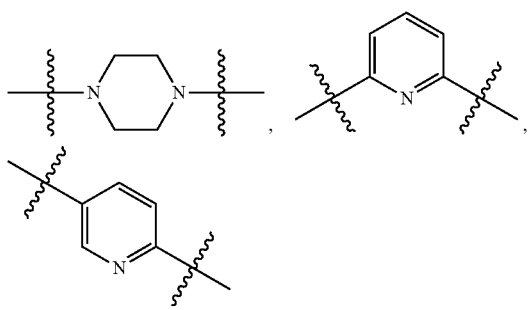

or a bond. It is noted that when Q is a 2-pyridyl analogue, the 3-, 4-, 5- or 6-position of the 2-pyridyl analogue can be independently substituted with —R$_8$—(CH$_2$)$_n$—NHCO— or —R$_8$—(CH$_2$)$_n$—CONH—, —R$_8$—(CH$_2$)$_n$—OCO— or —R$_8$H—(CH$_2$)$_n$—COO—, where R$_8$=NH or S and n=0-10.

In compounds of Formula II, W is absent or a linker. A linker for W can be of any chain length, e.g., straight or branched alkyl chain, —(CH$_2$), n=1-10 or functionalized alkyl chain, e.g. —CH$_2$CH(R$_8$)(CH$_2$)—, R$_8$=hydroxyl, chloro, fluoro, etc., —(CH$_2$)$_n$CO— or —O(CH$_2$)$_n$— or —S(CH$_2$)$_n$—, —N(CH$_2$)$_n$—C(O)(CH$_2$)$_n$—, n=0-10 or alkyl chain with ester or amide linkages e.g. —(CH$_2$)$_n$OCO— or —(CH$_2$)$_n$COO—, —(CH$_2$)$_n$CONH—, —(CH$_2$)$_n$NHCO— or —C(O)—(CH$_2$)$_n$NHCO— or —CO(CH$_2$)$_n$CONH— or —CH$_2$COO(CH$_2$)$_n$, n=0-10 or amino or mono or di or polyguanidino group —NH[C(R$_7$)NHC(R$_7$)]$_n$-D where R$_7$=NH or oxygen atom or sulfur atom, CH, D=NH$_2$, COOH, CONH$_2$, n=1-10 or coupled any amino acid analogues or spermine or norspermidine or spermidine analogues or guanidino amino acid, spermine or norspermidine or spermidine analogues through amide linkage Some exemplary linkers for W include, but are not limited to, a bond, —CH$_2$CH(OH)CH$_2$—, C$_1$-C$_6$ alkylene (e.g., methylene, ethylene, propylene, butylene), —C(O)CH$_2$—, —C(O)CH$_2$NH—, —NHC(O)CH$_2$—, —C(O)—, —C(O)NH(CH2)$_m$C(O)— (m is 1, 2, 3, 4 or 5), —CH=N—, —NH—, —OCH$_2$CH$_2$—, or (OH)NHC(O)CH$_2$, [(HO)NHC(O)]CH[{CH$_3$(OH)}CH] and [(HO)NHC(O)]CH[CH$_2$(OH)CH], —CH$_2$CH$_2$NHCH$_2$CH$_2$—.

In some embodiments W is —CH$_2$(CO)NH(CO)NH—Ar, where Ar is an optionally substituted aryl. In some embodiments, Ar is an optionally substituted phenyl.

In some embodiments, W is 2-amino-3-mercapto propanoyl, 2-acetamido-3-mercapto propanoyl, 2-amino-3-(dodecylthio)propanoyl and 2-acetamido-3-(dodecylthio)propanoyl.

In compounds of Formula II, R$_4$ is a 5-membered aryl or heteroaryl, optionally substituted with 1 or 2 substituents; or R$_4$ is a 6-membered aryl or heteroaryl, optionally substituted with 1, 2 or 3 substituents; or R$_4$ is a fused ring 9-10-membered aryl or heteroaryl, optionally substituted with 1, 2 or 3 substituents; or R$_4$ is a fused ring 9-10-membered cyclyl or heterocyclyl, optionally substituted with 1, 2 or 3 substituents; or R$_4$ is a carbohydrate.

In some embodiments, R$_4$ is a 5-membered heteroaryl represented by

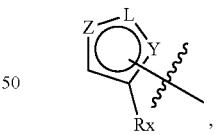

where Rx is nitro, amino, thiol, —CONH$_2$, mono or di or polyguanidino group —NH[C(M)NHC(M)]$_n$D (where M is NH, O, S or CH, D is NH$_2$, COOH or CONH$_2$, and n is 1-10); Z, L and Y are selected independently from C, CR$_{11}$, N, O and S, where R$_{11}$ is H or C$_1$-C$_6$alkyl, provided that at least one of Z, L and Y is not C or CR$_{11}$. In some embodiments, Rx is —NO$_2$—NH$_2$ or —NHC(=NH)NH$_2$. Exemplary 5-membered heteroaryls include, but are not limited to substituted thiazoles, furans and oxazoles.

Without limitations, L, Z, Y can be the same, all different or two are same and the other is different. For example, L and Z can be same and Y different, or L and Y same and Z different, or Z and Y same and L different. In some embodiments, L is —C(CH$_3$). In some embodiments, L is —C(CH$_3$)

and Y and Z are N. In some embodiments, L is —C(NH$_2$) or C[NHC(=NH)NH$_2$], Y is N and Z is S or Y is N and Z is O or Y is N and Z is N.

In some embodiment, L is a C linked to rest of Formula II and Y is S and Z is N. In some embodiment, L is a C linked to rest of Formula II and Y is O and Z is CH.

It is noted that the 5-membered heteroaryl represented by

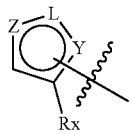

can be attached to rest of Formula II at Z, L or Y. Accordingly, in some embodiments, L is C attached to rest of Formula II. In some embodiments, Y is N attached to rest of the molecule. In some embodiments, R$_x$ can be the rest of Formula II.

In some embodiments, R$_4$ is a fused ring 9-membered heteroaryl of structure

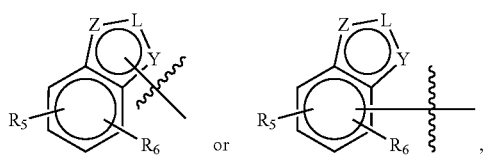

where R$_5$ and R$_6$ are independently H, nitro, amino, thiol, halo, —CONH$_2$, mono or di or polyguanidino group —NH[C(M)NHC(M)]$_n$D (where M is NH, O, S or CH, D is NH$_2$, COOH or CONH$_2$, and n is 1-10); Z, L and Y are selected independently from C, CR$_{11}$, N, O and S, where R$_{11}$ is H, C$_1$-C$_6$alkyl or amino, provided that at least one of Z, L and Y is not C or CR$_{11}$.

R$_5$ and R$_6$ can be same or different. In some embodiments, R$_5$ and R$_6$ are different. In other embodiments, they are same. In some embodiments, at least one of R$_5$ and R$_6$ is not H. In some embodiments, one of R$_5$ and R$_6$ is H. In some embodiments, at least one of R$_5$ and R$_6$ is —NH$_2$, —NO$_2$, Cl or C(=NH)CH$_2$CH$_2$N(CH$_3$)$_2$. In some embodiments, R$_5$ is H and R$_6$ is —NH$_2$, —NO$_2$, Cl or C(=NH)CH$_2$CH$_2$N (CH$_3$)$_2$. In some other embodiments, R$_6$ is H and R$_5$ is —NH$_2$, —NO$_2$, —Cl or —C(=NH)CH$_2$CH$_2$N(CH$_3$)$_2$. In some embodiments, R$_5$ and R$_6$ are Cl.

Without limitations, L, Z, Y can be the same, all different or two are same and the other is different. For example, L and Z can be same and Y different, or L and Y same and Z different, or Z and Y same and L different. In some embodiments, L is —CNH$_2$. In some embodiments, Y and Z are N. In some embodiments, L is C, and one of Y and Z is C and the other is N. In some embodiments, L is —CNH$_2$ and Y and Z are N. In some embodiment, L is a C linked to rest of Formula II. In some embodiments, Y is a N or C linked to rest of Formula II.

In some embodiments, R$_4$ is

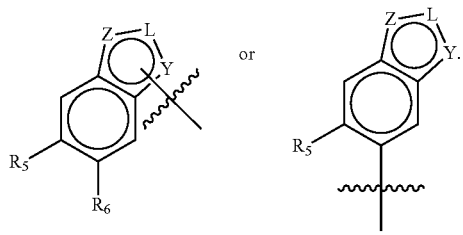

It is noted that the 9-membered heteroaryl can be attached to rest of Formula II at Z, L or Y. Accordingly, in some embodiments, L is C attached to rest of Formula II. In some embodiments, Y is N or C attached to rest of the molecule.

Exemplary 9-membered heteroaryls include, but are not limited to, 1-H-benzoimidazol-2-yl; (1-H-benzoimidazol-2-yl)-amino; 2-Amino-1-H-benzoimidazolyl; 5,6-mono and di-substituted 1-H-benzoimidazol-2-yl. Exemplary substitutions for 5,6-mono and di-substituted 1-H-benzoimidazol-2-yl include but are not limited to alkyl (e.g., C$_1$-C$_{11}$alkyl), halo (e.g., F, Cl, Br), nitro, carboxyl, amino, thiol, mono or di or polyguanidino group (—NH[C(M)NHC(M)]$_n$-D where M is NH, O, S or CH; n is 1-10; D is NH$_2$, COOH or CONH$_2$), amino acid analogues, spermine, norspermidine, spermidine analogues, guanidino amino acid, spermine linked through an amide linkage, norspermidine linked through an amide linkage, spermidine analogues linked through an amide linkage, or any combinations thereof.

In some embodiments, R$_4$ is a 6-membered heteroaryl, optionally substituted with 1 or 2 substituents. The 6-membered heteroaryl can be a pyridinyl, optionally substituted with 1 or 2 substituents. In some embodiments, R$_4$ is pyridin-2-yl, 4-nitro-pyridin-2-yl, 5-bromo-pyridin-2-yl, 5-guanidino-pyridin-2-yl, 5-guanidinomethyl-pyridin-2-yl,

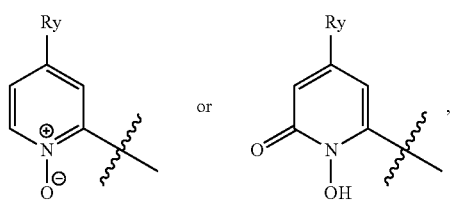

where Ry is H, methylamino, methyl or nitro. In some embodiments, R$_4$ is pyridin-2-yl substituted at the 5-position with —C(O)NH(CH$_2$)$_2$NH(CH$_2$)$_3$NHC(=NH)NH$_2$. In some embodiments, R$_4$ is

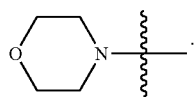

In some embodiments, R$_4$ is a 6-membered heteroaryl, optionally substituted with 1, 2 or 3 substituents. Exemplary substituents include, but are not limited to —O—, hydroxyl, oxygen atom, sulfur atom, hydroxyl, —CONH$_2$, amino, methyl amino, nitro, halogen, alkyl group —(CH$_2$)$_n$CH$_3$ (n=1-10), or mono or di or polyguanidino group.

In some embodiments, $R_4$ is a 6-membered heteroaryl of structure

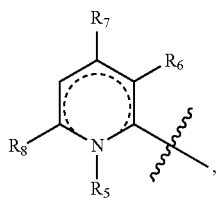

where $R_5$ is absent, hydrogen, —O⁻ or hydroxyl; $R_6$, $R_7$ and $R_8$ are independently hydrogen, oxygen atom, sulfur atom, hydroxyl, —CONH$_2$, amino, methyl amino, nitro, any halogen atom (F, Cl, Br), alkyl group —(CH$_2$)$_n$CH$_3$ (n=1-10), or mono or di or polyguanidino group —NH[C(M)NHC(M)]$_n$-D, where M is NH or oxygen atom or sulfur atom or CH, D is NH$_2$, COOH or CONH$_2$, and n is 1-10.

In some embodiments, $R_4$ is

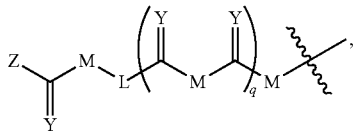

where q is 0-10 (preferably q is 1-10); M is CH, NH, or S; is NH, CH, O or S; L is a linker or Z; and Z is NH$_2$, OH, SH, alkyl, —COOH, or CONH$_2$. In some embodiments, M is CH, NH, or S; Y is NH, CH, O or S; L is Z; and Z is NH$_2$, OH, SH, alkyl, —COOH, or CONH$_2$. In some other embodiments, M is CH, NH, or S. Y is NH, CH, O or S, L is linker with amino, phenyl amino, substituted phenyl amino, straight or branched alkyl chain, —(CH$_2$)$_n$—, n=1-10, (CH$_2$)$_n$—NH—(CH$_2$)$_n$, n=1-10 or —CO(CH$_2$)$_n$—R$_5$, where $R_5$=OH, NH$_2$, N-alkyl amine, alkyl, thiol or any halogen atoms and n=0-10 or CO—C(NHCOCH$_3$)—CH$_2$SH, and Z is NH$_2$, OH, SH, alkyl, —COOH, or CONH$_2$.

The invention also provides salts of the compounds of Formula II. E

The invention also provides salts of the compounds of Formula II. Exemplary salts of compounds of Formula II include, but are not limited to salts of arginine, lysine, halo acids, lactate lactic acid, maleic acid, tartaric acid, fumaric acid, glutamic acid and L-aspartic acid.

In some embodiments, the compounds is of Formula III:

FORMULA III

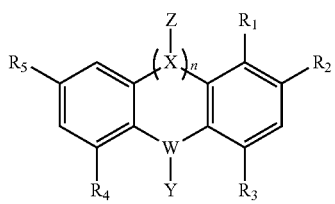

n = 1 and 2 wherein:
(a) n is 1;
X and Y are oxygen atom;
W is carbon atom;
Z is absent;

$R_1$ is hydrogen atom, hydroxyl, methoxy, amino, —NH—(CH$_2$)$_p$—R, where p is 0, 1, 2, 3, 4 or 5; R is hydrogen atom, amine, guanidine, piperazine, morpholine, NHCOCH$_3$, NHSO$_2$CH$_3$, NHSO$_2$—C$_6$H$_5$ or -L$_1$-B—R$_7$, $L_1$ is —(CH$_2$)$_q$—, —(CH$_2$)$_q$—CH=CH—(CH$_2$)$_q$, —(CH$_2$)$_q$—O—(CH$_2$)$_q$—, —(CH$_2$)$_q$—NH—(CH$_2$)$_q$—, where q is 0, 1, 2 or 3;

A and B are independently a cyclyl, heterocyclyl, aryl or heteroaryl, where the cyclyl, heterocyclyl, aryl or heteroaryl can be optionally substituted with 1, 2 or 3 substituents;

$R_7$ is hydrogen atom, hydroxyl, halo, nitro, carboxylic acid, methyl ester of carboxylic acid, OMe, nitrile, C(NH)—NH$_2$, amino, —NHCOCH$_3$, NHSO$_2$CH$_3$, NHSO$_2$-benzene, where the benzene can be optionally and independently substituted at ortho, meta or para position;

$R_2$ is -L$_1$-A-R$_7$;

$R_3$ is H;

$R_4$ and $R_5$ independently are hydrogen, halogen, hydroxyl, or —O—(CH$_2$)$_t$—R$_8$, where $R_8$ is C$_1$-C$_6$alkyl, amino, di(C$_1$-C$_6$alkyl)amino, aminocyclopropane, aminocyclopentane, piperazino, or morpholine, and t is 0-10; or (b) n is 1;

X and W are carbon atom, or X is carbon atom and W is nitrogen atom;

Y is —NH(CH$_2$)$_q$—R$_6$ or (CH$_2$)$_q$—R$_6$, where q=0 to 10;

$R_6$ is —COOH, amine, guanidine, piperazine, morpholine;

Z is hydrogen, methyl, NHR, COCH$_3$, SO$_2$CH$_3$, or —NH—(CH$_2$)$_l$—COOH, where l is 0-10;

$R_1$ and $R_3$ independently hydrogen atom, hydroxyl, methoxy, amino, or -L$_1$-A-R$_6$ R is CH$_3$, —(CH$_2$)$_p$—CH$_3$, where p=0 to 10;

$L_1$ is —(CH$_2$)$_n$—, —(CH$_2$)$_t$—CH=CH—(CH$_2$)$_t$—, —(CH$_2$)$_t$—O—(CH$_2$)$_t$—, —(CH$_2$)$_t$—NH—(CH$_2$)$_t$—, where t is 0, 1, 2, or 3;

A is cyclyl, heterocyclyl, aryl or heteroaryl, where the cyclyl, heterocyclyl, aryl or heteroaryl can be optionally substituted with 1, 2 or 3 substituents;

$R_6$ is hydrogen atom, hydroxyl, halo, nitro, carboxylic acid, methyl ester of carboxylic acid, OMe, nitrile, C(NH)—NH$_2$, amino, —NHCOCH$_3$, NHSO$_2$CH$_3$, NHSO$_2$-benzene, where the benzene can be optionally and independently substituted at ortho, meta or para position;

$R_2$ is hydrogen atom;

$R_4$ and $R_5$ are independently hydrogen, halogen, hydroxyl, or —O(CH$_2$)$_x$—R$_8$, where $R_8$ is C$_1$-C$_6$alkyl, amino, di(N(CH$_3$)$_2$, N(C$_2$H$_5$)$_2$, N(i-Pr)$_2$, aminocyclopropane, aminocyclopentane, piperazino or morpholine, and x is 0-10.

(c) n is 2;

X and W are carbon atom;

Y is —NH(CH$_2$)$_q$—R$_6$ or (CH$_2$)$_q$—R$_6$, where q=0 to 10;

$R_6$ is —COOH, amine, guanidine, piperazine, morpholine;

Z is hydrogen, methyl, NHR, COCH$_3$, SO$_2$CH$_3$, or —NH—(CH$_2$)$_l$—COOH, where l is 0-10;

$R_1$ and $R_3$ independently hydrogen atom, hydroxyl, methoxy, amino, or -L$_1$-A-R$_6$ R is $CH_3$, —$(CH_2)_p$—$CH_3$, where p=0 to 10;
$L_1$ is —$(CH_2)_n$—, —$(CH_2)_t$—CH=CH—$(CH_2)_t$—, —$(CH_2)_t$—O—$(CH_2)_t$—, —$(CH_2)_t$—NH—$(CH_2)_t$—, where t is 0, 1, 2, or 3;
A is cyclyl, heterocyclyl, aryl or heteroaryl, where the cyclyl, heterocyclyl, aryl or heteroaryl can be optionally substituted with 1, 2 or 3 substituents;
$R_6$ is hydrogen atom, hydroxyl, halo, nitro, carboxylic acid, methyl ester of carboxylic acid, OMe, nitrile, C(NH)—$NH_2$, amino, —$NHCOCH_3$, $NHSO_2CH_3$, $NHSO_2$-benzene, where the benzene can be optionally and independently substituted at ortho, meta or para position;
$R_2$ is hydrogen atom;
$R_4$ and $R_5$ are independently hydrogen, halogen, hydroxyl, or —$O(CH_2)_x$—$R_8$, where
$R_8$ is $C_1$-$C_6$alkyl, amino, di($N(CH_3)_2$, $N(C_2H_5)_2$, $N(i\text{-}Pr)_2$, aminocyclopropane, aminocyclopentane, piperazino or morpholine, and x is 0-10, and
Compounds of Formula III can also be defined as follows.

In compounds of Formula III, when n is 1, X and Y are oxygen atom, and W is carbon atom, then $R_1$ represents hydrogen atom, hydroxyl, methoxy, amino, substituted amine like NH—$(CH_2)_n$—R where, n ranges from 0 to 5, R can be amine, guanidine, piperazine, morpholine, $NHCOCH_3$, $NHSO_2CH_3$, $NHSO_2$—$C_6H_5$ or -$L_1$-B—$R_7$ where $L_1$ can be —$(CH_2)_n$—, —$(CH_2)_n$—CH=CH—$(CH_2)_n$—, —$(CH_2)_n$—O—$(CH_2)_n$—, —$(CH_2)_n$—NH—$(CH_2)_n$—, where n ranges from 0 to 3, B is a cyclic moiety which can be represented by phenyl, benzimidazolyl, cycloalkyl or heterocyclic ring like thiazole, furan, thiphene, imidazole group or 5 membered ring fused with benzene scaffold like benzimidazole, benzofuran, indole, benzothiazole etc. $R_7$ is a substituent placed at ortho or meta or para position of benzene scaffold or 5 membered heterocyclic scaffold or $6^{th}$ position of benzimidazole or benzothiazole or benzofuran or indole derivative. $R_7$ can be hydrogen atom or hydroxyl, halogenated atom (F, Cl, Br), nitro, carboxylic acid, methyl ester of carboxylic acid, OMe, nitrile, C(NH)—$NH_2$, amino, —$NHCOCH_3$, $NHSO_2CH_3$, $NHSO_2$—$C_6H_5$, —independently substituted at ortho or meta or para position. $R_2$ represents -$L_1$-A-$R_7$ as above. $R_3$ represents hydrogen atom. $R_4$ and $R_5$ can be hydrogen, halogen (F, Cl, Br), hydroxyl, or O alkylated compound like O—$(CH_2)_n$—$R_8$ ($R_8$=$CH_3$, amino, $N(CH_3)_2$, $N(C_2H_5)_2$, $N(iPr)_2$, aminocyclopropane, aminocyclopentane, piperazino, morpholine).

In compounds of Formula III, where n is 1, X and W are carbon atom; or n is 1, X is carbon atom and W is nitrogen atom; or n is 2 and X is carbon, then Y can be —$NH(CH_2)_n$—$R_6$ or $(CH_2)_n$—$R_6$, where n=0 to 10, $R_6$ can be —COOH, amine, guanidine, piperazine, morpholine. Z can be hydrogen, methyl, substituted amine like NHR where R=$CH_3$, —$(CH_2)_n$—$CH_3$, where n=0 to 10, $COCH_3$, $SO_2CH_3$, —NH—$(CH_2)_n$—COOH. $R_1$ and $R_3$ represents hydrogen atom, hydroxyl, methoxy, amino, or -$L_1$-A-$R_6$ where $L_1$ can be —$(CH_2)_n$—, —$(CH_2)_n$—CH=CH—$(CH_2)_n$—, —$(CH_2)_n$—O—$(CH_2)_n$—, —$(CH_2)_n$—NH—$(CH_2)_n$—, where n ranges from 0 to 3, A is a cyclic moiety which can be represented by phenyl, benzimidazolyl, cycloalkyl or heterocyclic ring like thiazole, furan, thiphene, imidazole group or 5 membered ring fused with benzene scaffold like benzimidazole, benzofuran, indole, benzothiazole etc. $R_6$ is a substituent placed at ortho or meta or para position of benzene scaffold or 5 membered heterocyclic scaffold or $6^{th}$ position of benzimidazole or benzothiazole or benzofuran or indole derivative. $R_6$ can be hydrogen atom or hydroxyl, halogenated atom (F, Cl, Br), nitro, carboxylic acid, methyl ester of carboxylic acid, OMe, nitrile, C(NH)—$NH_2$, amino, —$NHCOCH_3$, $NHSO_2CH_3$, $NHSO_2$—$C_6H_5$, $C_6H_5$ optionally and independently substituted at ortho or meta or para position. $R_2$ is hydrogen atom. $R_4$ and $R_5$ can be hydrogen, halogen (F, Cl, Br), hydroxyl, or O alkylated compound like $O(CH_2)_n$—$R_8$ ($R_8$=$CH_3$, amino, $N(CH_3)_2$, —$N(C_2H_5)_2$, $N(i\text{-}Pr)_2$, aminocyclopropane, aminocyclopentane, piperazino, morpholine.

When n is 1, X and Y are oxygen and W is carbon, compounds of Formula III are xanthene-9-one derivatives. When n is 1, X and W are carbon, then compounds of Formula III are s 9,10-dihydroanthracene derivatives. When n is 1, X is carbon and W is nitrogen, then compounds of Formula III are 9,10-dihydroacridine derivatives. When n is 2 and X is carbon, then compounds of Formula III are 10,11-Dihydro-5H-dibenzo(a,d)cycloheptene derivatives.

In some embodiments, the compounds is of Formula IV:

FORMULA IV

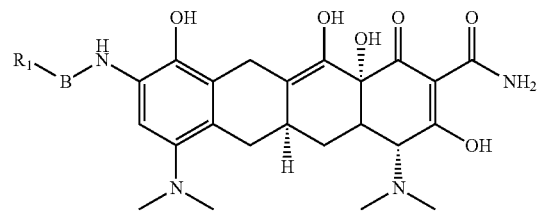

In compounds of Formula IV, B is absent or a linker. A linker for B can be of any chain length e.g. straight or branched alkyl chain, —$(CH_2)_n$, n=1-10 or functionalized alkyl chain, e.g., —$CH_2CH(R_8)(CH_2)$—, $R_8$=hydroxyl, chloro, fluoro, etc., —$(CH_2)_nCO$— or —$O(CH_2)_n$— or —$C(O)(CH_2)_n$, n=0-10 or alkyl chain with ester or amide linkages e.g. —$(CH_2)_nOCO$— or —$(CH_2)_nCOO$—, —$(CH_2)_nCONH$—, —$(CH_2)_nNHCO$— or —C(O)—$(CH_2)_n$NHCO— or —$CO(CH_2)_nCONH$— or —$CH_2COO(CH_2)_n$, n=0-10. Some exemplary linkers for B include, but are not limited to, a bond, —$CH_2CH(OH)CH_2$—, $C_1$-$C_6$ alkylene (e.g., methylene, ethylene, propylene, butylene), —C(O)$CH_2$—, —$C(O)CH_2NH$—, —$NHC(O)CH_2$—, —C(O)—, —C(O)NH($CH2$)$_m$C(O)— (m is 1, 2, 3, 4 or 5), —CH=N—, —NH—, —$OCH_2CH_2$—, or —$CH_2CH_2NHCH_2CH_2$—.

In compounds of Formula IV, $R_1$ is a 5-membered aryl or heteroaryl, optionally substituted with 1 or 2 substituents; or $R_1$ is a 6-membered aryl or heteroaryl, optionally substituted with 1, 2 or 3 substituents; or $R_1$ is a fused ring 9-10-membered aryl or heteroaryl, optionally substituted with 1, 2 or 3 substituents.

In some embodiments, $R_1$ is a 5-membered heteroaryl represented by

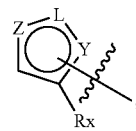, where Rx is nitro, amino, thiol, —$CONH_2$, mono or di or polyguanidino group —NH[C(M)NHC(M)]$_n$D (where M is NH, O, S or CH, D is $NH_2$, COOH or $CONH_2$, and n is 1-10); Z, L and Y are selected independently from C, $CR_{11}$, N, O and S, where $R_{11}$ is H or $C_1$-$C_6$alkyl, provided that at least one of Z, L and Y is not C or $CR_{11}$. In some embodiments, Rx is $-NO_2-NH_2$ or $-NHC(=NH)NH_2$. Exemplary 5-membered heteroaryls include, but are not limited to substituted thiazoles, furans and oxazoles.

Without limitations, L, Z, Y can be the same, all different or two are same and the other is different. For example, L and Z can be same and Y different, or L and Y same and Z different, or Z and Y same and L different. In some embodiments, L is $-C(CH_3)$. In some embodiments, L is $-C(CH_3)$ and Y and Z are N. In some embodiments, L is $NH_2$ or $NHC(=NH)NH_2$, Y is N and Z is S.

In some embodiment, L is a C linked to rest of Formula IV and Y is S and Z is N. In some embodiment, L is a C linked to rest of Formula IV and Y is O and Z is CH.

It is noted that the 5-membered heteroaryl represented by

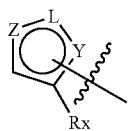

can be attached to rest of Formula IV at Z, L or Y. Accordingly, in some embodiments, L is C attached to rest of Formula IV. In some embodiments, Y is N attached to rest of the molecule. In some embodiments, Rx can be the rest of Formula IV.

In some embodiments, $R_1$ is a fused ring 9-membered heteroaryl of structure

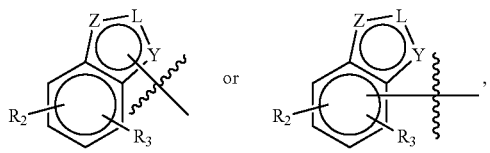

where $R_3$ and $R_3$ are independently H, nitro, amino, thiol, halo, $-CONH_2$, mono or di or polyguanidino group $-NH[C(M)NHC(M)]_nD$ (where M is NH, O, S or CH, D is $NH_2$, COOH or $CONH_2$, and n is 1-10); Z, L and Y are selected independently from C, $CR_{11}$, N, O and S, where $R_{11}$ is H, $C_1$-$C_6$alkyl or amino, provided that at least one of Z, L and Y is not C or $CR_{11}$.

$R_5$ and $R_6$ can be same or different. In some embodiments, $R_2$ and $R_2$ are different. In other embodiments, they are same. In some embodiments, at least one of $R_2$ and $R_3$ is not H. In some embodiments, one of $R_2$ and $R_3$ is H. In some embodiments, at least one of $R_2$ and $R_3$ is $-NH_2$, $-NO_2$, Cl or $C(=NH)CH_2CH_2N(CH_3)_2$. In some embodiments, $R_2$ is H and $R_3$ is $-NH_2$, $-NO_2$, Cl or $C(=NH)CH_2CH_2N(CH_3)_2$. In some other embodiments, $R_3$ is H and $R_2$ is $-NH_2$, $-NO_2$, $-Cl$ or $-C(=NH)CH_2CH_2N(CH_3)_2$. In some embodiments, $R_2$ and $R_3$ are Cl.

Without limitations, L, Z, Y can be the same, all different or two are same and the other is different. For example, L and Z can be same and Y different, or L and Y same and Z different, or Z and Y same and L different. In some embodiments, L is $-CNH_2$. In some embodiments, Y and Z are N. In some embodiments, L is C, and one of Y and Z is C and the other is N. In some embodiments, L is $-CNH_2$ and Y and Z are N. In some embodiment, L is a C linked to rest of Formula IV. In some embodiments, Y is a N or C linked to rest of Formula IV.

In some embodiments, $R_4$ is

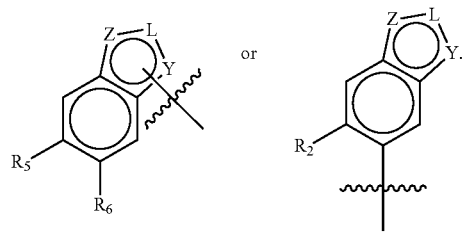

It is noted that the 9-membered heteroaryl can be attached to rest of Formula IV at Z, L or Y. Accordingly, in some embodiments, L is C attached to rest of Formula IV. In some embodiments, Y is N or C attached to rest of the molecule.

Exemplary 9-membered heteroaryls include, but are not limited to, 1-H-benzoimidazol-2-yl; (1-H-benzoimidazol-2-yl)-amino; 2-Amino-1-H-benzoimidazolyl; 5,6-mono and di-substituted 1-H-benzoimidazol-2-yl. Exemplary substitutions for 5,6-mono and di-substituted 1-H-benzoimidazol-2-yl include but are not limited to alkyl (e.g., $C_1$-$C_{11}$alkyl), halo (e.g., F, Cl, Br), nitro, carboxyl, amino, thiol, mono or di or polyguanidino group ($-NH[C(M)NHC(M)]_n$-D where M is NH, O, S or CH; n is 1-10; D is $NH_2$, COOH or $CONH_2$), amino acid analogues, spermine, norspermidine, spermidine analogues, guanidino amino acid, spermine linked through an amide linkage, norspermidine linked through an amide linkage, spermidine analogues linked through an amide linkage, or any combinations thereof.

In some embodiments, $R_1$ is a 6-membered heteroaryl, optionally substituted with 1 or 2 substituents. The 6-membered heteroaryl can be a pyridinyl, optionally substituted with 1 or 2 substituents. In some embodiments, $R_1$ is pyridin-2-yl, 4-nitro-pyridin-2-yl, 5-bromo-pyridin-2-yl, 5-guanidino-pyridin-2-yl, 5-guanidinomethyl-pyridin-2-yl,

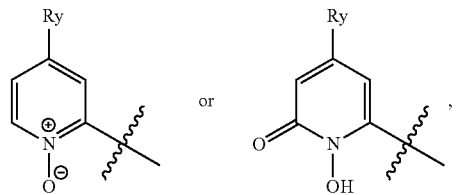

where Ry is H, methylamino, methyl or nitro. In some embodiments, $R_4$ isopyridin-2-yl substituted at the 5-position with $-C(O)NH(CH_2)_2NH(CH_2)_3NHC(=NH)NH_2$.

In some embodiments, the compound is of Formula V:

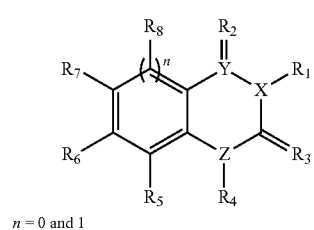

FORMULA V $n = 0$ and 1

In compounds of Formula V, X and Z are independently C or N. Without limitations, X and Z can be same or different. In some embodiments, X is N and Z is C. In some other embodiments, X is C and Z is N. In some embodiments, both X and Z are N.

In compounds of Formula V, Y can be C, N or O. In some embodiments, Y is C.

In compounds of Formula V $R_1$ can be H or -$L_1$-A, where $L_1$ is absent or a linker; A is a cyclyl, heterocyclyl, aryl or heteroaryl, where cyclyl, heterocyclyl, aryl and heteroaryl can be optionally substituted with 1, 2 or 3 substituent. In some embodiments, $R_1$ is H.

As noted-above, $L_1$ can be absent, a bond or a linker. A linker for $L_1$ can of any chain length e.g. straight or branched alkyl chain, —$(CH_2)_n$—, n=1-10 or functionalized alkyl chain, e.g. —$CH_2CH(R_8)(CH_2)$—, $R_8$=hydroxyl, chloro, fluoro, etc., —$(CH_2)_nCO$— or —$O(CH_2)_n$— or —$C(O)(CH_2)_n$—, n=0-10 or alkyl chain with ester or amide linkages e.g. —$(CH_2)_nOCO$— or —$(CH_2)_nCOO$—, —$(CH_2)_nCONH$—, —$(CH_2)_nNHCO$— or —$C(O)$—$(CH_2)_nNHCO$— or —$CO(CH_2)_nCONH$— or —$CH_2COO(CH_2)_n$, n=0-10. Some exemplary linkers for L1 include, but are not limited to, a bond, —$CH_2CH(OH)CH_2$—, $C_1$-$C_6$ alkylene (e.g., methylene, ethylene, propylene, butylene), —$C(O)CH_2$—, —$C(O)CH_2NH$—, —$NHC(O)CH_2$—, —$C(O)$—, —$C(O)NH(CH2)_mC(O)$— (m is 1, 2, 3, 4 or 5), —CH=N—, —NH—, —$OCH_2CH_2$—, or —$CH_2CH_2NHCH_2CH_2$—. In some embodiments, $L_1$ is absent, a bond, —$(CH_2)_n$— or —$(CH_2)_n$—CH=CH—$(CH_2)_n$—, where n is 0, 1, 2 or 3.

In some embodiments, A can be an aryl or heteroaryl. In some embodiments, A is a 6-membered aryl or heteroaryl, optionally substituted with 1 or 2 substituents; or A is a fused ring 9-membered aryl or heteroaryl, optionally substituted with 1 or 2 substituents. Exemplary substituents for A include, but are not limited to, halogen, trifluoromethyl, alkyl, alkoxy, hydroxyl, aryloxy, acyloxy, amino, di-alkylamino, —$CO_2H$, nitro, nitrile, —$NHSO_2CH_3$, —$NHSO_2Ph$, —$NHCOCH_3$, —NHCOPh and any combinations thereof.

In some embodiments, A is 4-cyanophenyl, 2-methylsulfonylaminophenyl, or 5-cyano-1H-benzoimidazol-2-yl.

In compounds of Formula V, $R_4$ can be hydrogen, oxygen, sulphur, hydroxyl, methoxy or -$L_2$-B, where $L_2$ is absent, a bond or a linker; B is a cyclyl, heterocyclyl, aryl or heteroaryl, where cyclyl, heterocyclyl, aryl and heteroaryl can be optionally substituted with 1, 2 or 3 substituent. In some embodiments, $R_4$ is H.

As noted-above, $L_2$ can be absent, a bond or a linker. A linker for $L_2$ can of any chain length e.g. straight or branched alkyl chain, —$(CH_2)_n$—, n=1-10 or functionalized alkyl chain, e.g. —$CH_2CH(R_8)(CH_2)$—, $R_8$=hydroxyl, chloro, fluoro, etc., —$(CH_2)_nCO$— or —$O(CH_2)_n$— or —$C(O)(CH_2)_n$—, n=0-10 or alkyl chain with ester or amide linkages e.g. —$(CH_2)_nOCO$— or —$(CH_2)_nCOO$—, —$(CH_2)_nCONH$—, —$(CH_2)_nNHCO$— or —$C(O)$—$(CH_2)_nNHCO$— or —$CO(CH_2)_nCONH$— or —$CH_2COO(CH_2)_n$, n=0-10. Some exemplary linkers for $L_2$ include, but are not limited to, a bond, —$CH_2CH(OH)CH_2$—, $C_1$-$C_6$ alkylene (e.g., methylene, ethylene, propylene, butylene), —$C(O)CH_2$—, —$C(O)CH_2NH$—, —$NHC(O)CH_2$—, —$C(O)$—, —$C(O)NH(CH2)_mC(O)$— (m is 1, 2, 3, 4 or 5), —CH=N—, —NH—, —$OCH_2CH_2$—, or —$CH_2CH_2NHCH_2CH_2$—. In some embodiments, $L_2$ is absent, a bond, —$(CH_2)_n$— or —$(CH_2)_n$—CH=CH—$(CH_2)_n$—, where n is 0, 1, 2 or 3.

In some embodiments, B can be an aryl or heteroaryl. In some embodiments, B is a 6-membered aryl or heteroaryl, optionally substituted with 1 or 2 substituents; or B is a fused ring 9-membered aryl or heteroaryl, optionally substituted with 1 or 2 substituents. Exemplary substituents for B include, but are not limited to, halogen, trifluoromethyl, alkyl, alkoxy, hydroxyl, aryloxy, acyloxy, amino, di-alkylamino, —$CO_2H$, nitro, nitrile, —$NHSO_2CH_3$, —$NHSO_2Ph$, —$NHCOCH_3$, —NHCOPh and any combinations thereof.

In some embodiments, B is 4-cyanophenyl, 2-methylsulfonylaminophenyl, or 5-cyano-1H-benzoimidazol-2-yl.

In compounds of Formula V, $R_2$ can be O or S.

In compounds of Formula V, $R_3$ can be O or S.

In compounds of Formula V, $R_5$, $R_6$, $R_7$ and $R_8$ are independently hydrogen, hydroxyl, fluoro, chloro, bromo, cycloalkyl, heterocyclyl, aryl, heteroaryl, hydroxyl, amino substituted hexose moieties, or guanidine. In some embodiments, $R_5$, $R_6$ and $R_8$ are selected from the group consisting of hydrogen, hydroxyl, fluoro, chloro, bromo, cycloalkyl, hydroxyl, amino substituted hexose moieties, and any combinations thereof.

In some embodiments, $R_7$ is selected from the group consisting of hydrogen, hydroxyl, halogen (F, Cl, Br), cyclopropyl, cyclobutyl, cyclopentyl, morpholine, piperazinyl, piperidyl, pyrazolidine, pyrazolidinyl, pyrazolinyl, pyrrolidine, pyrroline, quinuclidine, and guanidine.

In compounds of Formula V, n is 0 or 1. When n is 0, then the $R_5$/$R_6$/$R_7$/$R_8$ ring represents a 5 membered heterocyclic ring, such as an imidazole, thiazole, furan, thiophene or pyrrole ring, with or without $R_6$-substitution. When present $R_6$ can be selected from nitro, amino, nitrile, carboxylic, hydroxyl, any halogenated atom, guanidine groups like —$NHC(NH)NH_2$ or $NHC(O)NH_2$ or $NHC(S)NH_2$.

When n is 1, then the $R_5$/$R_6$/$R_7$/$R_8$ ring represents a six membered substituted benzene scaffold where $R_5$ is hydrogen atom, methyl or methoxy; $R_7$ and $R_8$ are independently hydrogen atom or halo (such as fluorine atom); and $R_6$ is a hydrogen atom, halo (such as fluorine atom), aminocyclopentane, piperazine, N-substituted piperazine group like —$(CH_2)n$-, —$(CH_2)n$-X, —$CONH_2$, —COOH, —CONHR, (R can be different alkyl group) —$CH_2OH$, —$CH_2NH_2$, —$COCH_2NH_2$.

In some embodiments, the compound is of Formula VI:

FORMULA VI

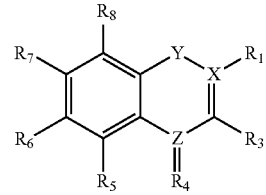

In compounds of Formula VI, X and Z are independently C or N. Without limitations, X and Z can be same or different. In some embodiments, X is N and Z is C. In some other embodiments, X is C and Z is N. In some embodiments, both X and Z are C.

In compounds of Formula VI, Y can be $CH_2$, NH or O. In some embodiments, Y is O.

In compounds of Formula VI, $R_1$ can be H, OH or -$L_1$-A, where $L_1$ is absent or a linker; A is a cyclyl, heterocyclyl, aryl or heteroaryl, where cyclyl, heterocyclyl, aryl and heteroaryl can be optionally substituted with 1, 2 or 3 substituent. In some embodiments, $R_1$ is OH As noted-above, $L_1$ can be absent, a bond or a linker. A linker for $L_1$ can of any chain length e.g. straight or branched alkyl chain, —$(CH_2)_n$—, n=1-10 or functionalized alkyl chain, e.g. —$CH_2CH(R_8)(CH_2)$—, $R_8$=hydroxyl, chloro, fluoro, etc., —(CH$_2$)$_n$CO— or —O(CH$_2$)$_n$— or —C(O)(CH$_2$)$_n$—, n=0-10 or alkyl chain with ester or amide linkages e.g. —(CH$_2$)$_n$OCO— or —(CH$_2$)$_n$COO—, —(CH$_2$)$_n$CONH—, —(CH$_2$)$_n$NHCO— or —C(O)—(CH$_2$)$_n$NHCO— or —CO(CH$_2$)$_n$CONH— or —CH$_2$COO(CH$_2$)$_n$, n=0-10. Some exemplary linkers for L1 include, but are not limited to, a bond, —CH$_2$CH(OH)CH$_2$—, C$_1$-C$_6$ alkylene (e.g., methylene, ethylene, propylene, butylene), —C(O)CH$_2$—, —C(O)CH$_2$NH—, —NHC(O)CH$_2$—, —C(O)—, —C(O)NH(CH2)$_m$C(O)— (m is 1, 2, 3, 4 or 5), —CH=N—, —NH—, —OCH$_2$CH$_2$—, or —CH$_2$CH$_2$NHCH$_2$CH$_2$—. In some embodiments, L$_1$ is absent, a bond, —(CH$_2$)$_n$— or —(CH$_2$)$_n$—CH=CH—(CH$_2$)$_n$—, where n is 0, 1, 2 or 3. In some embodiments, L$_1$ is —CH=CH—.

In some embodiments, A can be an aryl or heteroaryl. In some embodiments, A is a 6-membered aryl or heteroaryl, optionally substituted with 1 or 2 substituents; or A is a fused ring 9-membered aryl or heteroaryl, optionally substituted with 1 or 2 substituents. Exemplary substituents for A include, but are not limited to, halogen, trifluoromethyl, alkyl, alkoxy, hydroxyl, aryloxy, acyloxy, amino, di-alkylamino, —CO$_2$H, nitro, nitrile, —NHSO$_2$CH$_3$, NHSO$_2$Ph, —NHCOCH$_3$, —NHCOPh and any combinations thereof.

In some embodiments, A is 4-cyanophenyl, 2-methylsulfonylaminophenyl, or 5-cyano-1H-benzoimidazol-2-yl. In some embodiments, A is 4-cyanophenyl.

In compounds of Formula IV, R$_3$ can be hydrogen, OH, oxygen, sulphur, hydroxyl, methoxy or -L$_2$-B, where L$_2$ is absent, a bond or a linker; B is a cyclyl, heterocyclyl, aryl or heteroaryl, where cyclyl, heterocyclyl, aryl and heteroaryl can be optionally substituted with 1, 2 or 3 substituent.

As noted-above, L$_2$ can be absent, a bond or a linker. A linker for L$_2$ can of any chain length e.g. straight or branched alkyl chain, —(CH$_2$)$_n$, n=1-10 or functionalized alkyl chain, e.g. —CH$_2$CH(R$_8$)(CH$_2$)—, R$_8$=hydroxyl, chloro, fluoro, etc., —(CH$_2$)$_n$CO— or —O(CH$_2$)$_n$— or —C(O)(CH$_2$)$_n$—, n=0-10 or alkyl chain with ester or amide linkages e.g. —(CH$_2$)$_n$OCO— or —(CH$_2$)$_n$COO—, —(CH$_2$)$_n$CONH—, —(CH$_2$)$_n$NHCO— or —C(O)—(CH$_2$)$_n$NHCO— or —CO(CH$_2$)$_n$CONH— or —CH$_2$COO(CH$_2$)$_n$, n=0-10. Some exemplary linkers for L$_2$ include, but are not limited to, a bond, —CH$_2$CH(OH)CH$_2$—, C$_1$-C$_6$ alkylene (e.g., methylene, ethylene, propylene, butylene), —C(O)CH$_2$—, —C(O)CH$_2$NH—, —NHC(O)CH$_2$—, —C(O)—, —C(O)NH(CH2)$_m$C(O)— (m is 1, 2, 3, 4 or 5), —CH=N—, —NH—, —OCH$_2$CH$_2$—, or —CH$_2$CH$_2$NHCH$_2$CH$_2$—. In some embodiments, L$_2$ is absent, a bond, —(CH$_2$)$_n$— or —(CH$_2$)$_n$—CH=CH—(CH$_2$)$_n$—, where n is 0, 1, 2 or 3.

In some embodiments, B can be an aryl or heteroaryl. In some embodiments, B is a 6-membered aryl or heteroaryl, optionally substituted with 1 or 2 substituents; or B is a fused ring 9-membered aryl or heteroaryl, optionally substituted with 1 or 2 substituents. Exemplary substituents for B include, but are not limited to, halogen, trifluoromethyl, alkyl, alkoxy, hydroxyl, aryloxy, acyloxy, amino, di-alkylamino, —CO$_2$H, nitro, nitrile, —NHSO$_2$CH$_3$, —NHSO$_2$Ph, —NHCOCH$_3$, —NHCOPh and any combinations thereof.

In some embodiments, B is 4-cyanophenyl, 2-methylsulfonylaminophenyl, or 5-cyano-1H-benzoimidazol-2-yl. In some embodiments, B is 4-cyanophenyl.

In compounds of Formula VI, R$_4$ can be O or S. In some embodiments, R$_4$ is O.

In compounds of Formula VI, R$_5$, R$_6$, R$_7$ and R$_8$ are independently hydrogen, hydroxyl, fluoro, chloro, bromo, cycloalkyl, heterocyclyl, aryl, heteroaryl, hydroxyl, amino substituted hexose moieties, or guanidine. In some embodiments, at least two of R$_5$, R$_6$, R$_7$ and R$_8$ are not hydrogen. In some embodiments, R$_5$, R$_6$, and R$_8$ selected from the group consisting of hydrogen, hydroxyl, fluoro, chloro, bromo, cycloalkyl, hydroxyl, amino substituted hexose moieties, and any combinations thereof.

In some embodiments, R$_7$ is selected from the group consisting of hydrogen, hydroxyl, halogen (F, Cl, Br), cyclopropyl, cyclobutyl, cyclopentyl, morpholine, piperazinyl, piperidyl, pyrazolidine, pyrazolidinyl, pyrazolinyl, pyrrolidine, pyrroline, quinuclidine, and guanidine.

In some embodiments, R$_5$ and R$_7$ are hydroxyl.

In some embodiments, the compound is of Formula VII

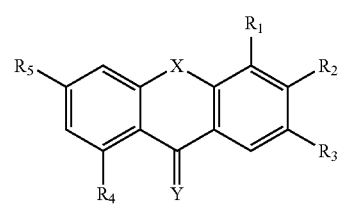

FORMULA VII

In compounds of Formula VII, X can be CHR$_{12}$, C=R$_{13}$, NH, S or O, where R$_{12}$ is H, amino, hydroxyl, or thiol, and R$_{13}$ is O, S or NH. In some embodiments, X is O.

In compounds of Formula VII, Y can be O or S. In some embodiments, Y is O.

In compounds of Formula VII, R$_1$ can be H, alkylamino, —OH or -L$_1$-A, where L$_1$ is absent or a linker; A is a cyclyl, heterocyclyl, aryl or heteroaryl, where cyclyl, heterocyclyl, aryl and heteroaryl can be optionally substituted with 1, 2 or 3 substituent. In some embodiments, R$_1$ is H or —NH(CH$_2$)$_2$NH$_2$.

As noted-above, L$_1$ can be absent, a bond or a linker. A linker for L$_1$ can of any chain length e.g. straight or branched alkyl chain, —(CH$_2$)$_n$, n=1-10 or functionalized alkyl chain, e.g. —CH$_2$CH(R$_8$)(CH$_2$)—, R$_8$=hydroxyl, chloro, fluoro, etc., —(CH$_2$)$_n$CO— or —O(CH$_2$)— or —C(O)(CH$_2$)—, n=0-10 or alkyl chain with ester or amide linkages e.g. —(CH$_2$)OCO— or —(CH$_2$)COO—, —(CH$_2$)$_n$CONH—, —(CH$_2$)$_n$NHCO— or —C(O)—(CH$_2$)$_n$NHCO— or —CO(CH$_2$)$_n$CONH— or —CH$_2$COO(CH$_2$)$_n$, n=0-10. Some exemplary linkers for L1 include, but are not limited to, a bond, —CH$_2$CH(OH)CH$_2$—, C$_1$-C$_6$ alkylene (e.g., methylene, ethylene, propylene, butylene), —C(O)CH$_2$—, —C(O)CH$_2$NH—, —NHC(O)CH$_2$—, —C(O)—, —C(O)NH(CH2)$_m$C(O)— (m is 1, 2, 3, 4 or 5), —CH=N—, —NH—, —OCH$_2$CH$_2$—, or —CH$_2$CH$_2$NHCH$_2$CH$_2$—. In some embodiments, L$_1$ is absent, a bond, —(CH$_2$)$_n$—, —(CH$_2$)$_n$—CH=CH—(CH$_2$)$_n$—, —(CH$_2$)$_n$—O—(CH$_2$)$_n$—, —(CH$_2$)$_n$—NH—(CH$_2$)$_n$—, where n is 0, 1, 2 or 3. In some embodiments, L$_1$ is —CH$_2$NHCH$_2$CH$_2$— or —CH=CH—.

In some embodiments, A can be an aryl or heteroaryl. In some embodiments, A is a 6-membered aryl or heteroaryl, optionally substituted with 1 or 2 substituents; or A is a fused ring 9-membered aryl or heteroaryl, optionally substituted with 1 or 2 substituents. Exemplary substituents for A include, but are not limited to, halogen, trifluoromethyl, alkyl, alkoxy, acyloxy, amino, di-alkylamino, —CO$_2$H, nitro, nitrile, —NHSO$_2$CH$_3$, and any combinations thereof.

In some embodiments, A is phenyl or benzoimidazoyl, where the phenyl and the benzoimidazoyl are optionally substituted with 1 or 2 substituents selected from the group consisting of halo, trifluoromethyl, alkyl, alkoxy, acyloxy, amino, di-alkylamino, —CO$_2$H, nitro, nitrile, —NHSO$_2$CH$_3$ group. In some embodiments, A is 4-cyanophenyl, 2-methylsulfonylaminophenyl, or 5-cyano-1H-benzoimidazol-2-yl. In some embodiments, A is 4-cyanophenyl or

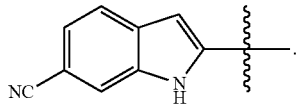 [SMILES: *c1cc2ccc(C#N)cc2[nH]1]

In compounds of Formula VII, R$_2$ and R$_3$ are independently hydrogen, hydroxyl of or -L$_2$-B, where L$_2$ is absent, a bond or a linker; B is a cyclyl, heterocyclyl, aryl or heteroaryl, where cyclyl, heterocyclyl, aryl and heteroaryl can be optionally substituted with 1, 2 or 3 substituent. In some embodiments, R$_2$ is H. In some embodiments, R$_3$ is H. In some embodiments, R$_2$ and R$_3$ are H.

As noted-above, L$_2$ can be absent, a bond or a linker. A linker for L$_2$ can of any chain length e.g. straight or branched alkyl chain, —(CH$_2$)$_n$, n=1-10 or functionalized alkyl chain, e.g. —CH$_2$CH(R$_8$)(CH$_2$)—, R$_8$=hydroxyl, chloro, fluoro, etc., —(CH$_2$)$_n$CO— or —O(CH$_2$)$_n$— or —C(O)(CH$_2$)$_n$—, n=0-10 or alkyl chain with ester or amide linkages e.g. —(CH$_2$)$_n$OCO— or —(CH$_2$)$_n$COO—, —(CH$_2$)$_n$CONH—, —(CH$_2$)$_n$NHCO— or —C(O)—(CH$_2$)$_n$NHCO— or —CO(CH$_2$)$_n$CONH— or —CH$_2$COO(CH$_2$)$_n$, n=0-10. Some exemplary linkers for L$_2$ include, but are not limited to, a bond, —CH$_2$CH(OH)CH$_2$—, C$_1$-C$_6$ alkylene (e.g., methylene, ethylene, propylene, butylene), —C(O)CH$_2$—, —C(O)CH$_2$NH—, —NHC(O)CH$_2$—, —C(O)—, —C(O)NH(CH$_2$)$_m$C(O)— (m is 1, 2, 3, 4 or 5), —CH=N—, —NH—, —OCH$_2$CH$_2$—, or —CH$_2$CH$_2$NHCH$_2$CH$_2$—. In some embodiments, L$_2$ is absent, a bond, —(CH$_2$)$_n$— or —(CH$_2$)$_n$—CH=CH—(CH$_2$)$_n$—, where n is 0, 1, 2 or 3.

In some embodiments, B can be an aryl or heteroaryl. In some embodiments, B is a 6-membered aryl or heteroaryl, optionally substituted with 1 or 2 substituents; or B is a fused ring 9-membered aryl or heteroaryl, optionally substituted with 1 or 2 substituents. Exemplary substituents for B include, but are not limited to, halogen, trifluoromethyl, alkyl, alkoxy, acyloxy, amino, di-alkylamino, —CO$_2$H, nitro, nitrile, —NHSO$_2$CH$_3$, and any combinations thereof.

In some embodiments, B is 4-cyanophenyl, 2-methylsulfonylaminophenyl, or 5-cyano-1H-benzoimidazol-2-yl.

In compounds of Formula VII, R$_4$ and R$_5$ are independently selected from the group consisting of hydrogen, halogen (F, Cl, Br), hydroxyl, or —(CH$_2$)$_n$—O—(CH$_2$)$_n$-D-R$_8$, —(CH$_2$)$_n$—NH—(CH$_2$)$_n$-D-R$_8$, where n is 0, 1, 2 or 3, R$_8$ is H, hydroxyl, halo, trifluoromethyl, alkyl, alkoxy, acyloxy, amino, dialkylamino, —CO$_2$H, nitro, nitrile or —NHSO$_2$CH$_3$, D is cyclyl, heterocyclyl, aryl or heteroaryl, where the cyclyl, heterocyclyl, aryl or heteroaryl can be optionally substituted with 1 or 2 substituents. Exemplary substituents for D include, but are not limited to halogen, trifluoromethyl, alkyl, alkoxy, acyloxy, amino, di-alkylamino, —CO$_2$H, nitro, nitrile, —NHSO$_2$CH$_3$, and any combinations thereof.

In some embodiments, D is a phenyl or benzoimidazoyl, where the phenyl and the benzoimidazoyl can be optionally substituted with 1 or 2 substituents.

The invention also provides salts of compounds of Formulas I-VII. In some embodiments, a pharmaceutically acceptable salt of a compound of Formulas I-VII is also provided. As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional non-toxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Without wishing to be bound by a theory, the compounds of the invention can be used to treat infections, such as susceptible and resistant infections. Accordingly, the invention also provides a method for treating infection, such as a bacterial infection. Generally, the method comprises administering a therapeutically effective amount of a compound described herein to a subject in need thereof. The compounds of the invention are particularly effective for treatment of bacterial infections caused mainly by MRSA and other opportunistic pathogens like *Staphylococcus epidermidis* and quinolone resistant *S. aureus* and *S. epidermidis* or various Gram positive and Gram negative pathogens.

For administration to a subject, the compound(s) described herein can be formulated into pharmaceutical compositions. Thus, the invention also provides pharmaceutical compositions comprising compound(s) disclosed herein with pharmaceutically acceptable excipients or carriers.

Also provided herein are formulations comprising a compound of the invention. Without limitations, the compounds described herein can be formulated in form of beads, injectable hydrogel, hydrogel, polymeric films, foams, in-situ gel, hydrocolloids. These can be used for the treatment of inflammatory bone infections so called osteomyelitis, implant associated infections, surgical site infection, diabetic foot infections, diabetic ulcer, mild to moderate wound infections etc.

In some embodiments, the compounds described herein can be formulated into slow or controlled release formulations. This can provide improved delivery of the compound at the site of infection to achieve sustained release of optimal concentration over a prolonged period of time. This type of local treatment can minimize nephrotoxicity, ototoxicity and gastrointestinal side effects generally caused by long exposure (4 to 6 weeks) of high drug concentration in serum for some of the known antibiotics prescribed for oral and parenteral treatment of osteomyelitis. The present invention further provides an effective formulation with new antibiotics that could inhibit or prevent biofilm formation with substantial antibacterial and anti-inflammatory effects.

In some embodiments, the compound can be formulated with biodegradable or non-biodegradable polymer to obtain beads with particular dimension, e.g., nano- or micro-particles. Such formulations can release the compound through the matrix in a controlled manner for an extended period of time for the treatment and prevention of infection, for example, for treatment and prevention of osteomyelitis mainly caused by MRSA and other opportunistic pathogens and even by VRSA.

DETAILED DESCRIPTION OF THE INVENTION

Figure 1:
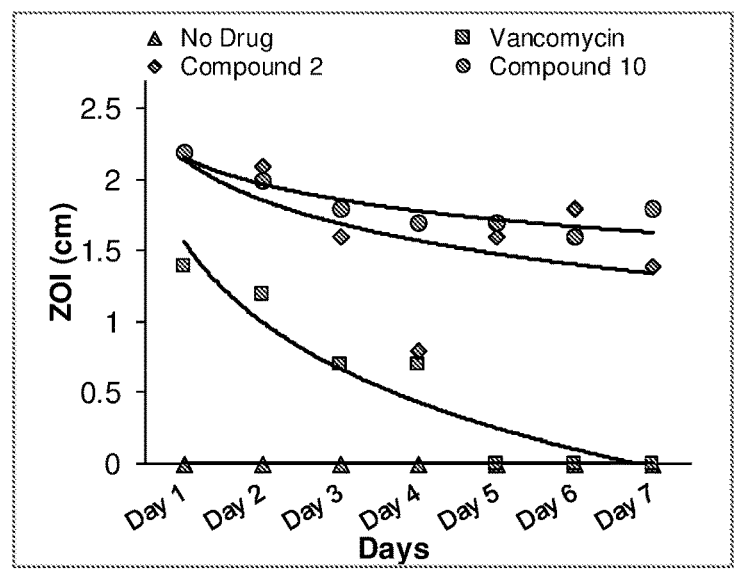
FIG. 1 is a line graph showing zone of inhibition over time for some exemplary compounds of the invention.

Multiple strategies were considered to achieve the aforementioned properties in the new antibiotics synthesized. Molecules were designed to possess one or more mechanism (s) of action, targeting the processes of replication (DNA synthesis), translation (protein expression), and cell homeostasis (cell wall/membrane integrity), alone or in combination thereof. One strategy was to engineer molecules that bind to target(s) with higher affinity through novel interactions. Multiplicity of interactions decreases the chances of resistance development as the microbe will have to accrue multiple mutations at the target site in order to prevent binding of the molecule. Additionally, new interactions may allow binding even to mutated targets in existing resistant strains. Second, to have molecules with distinct motifs that enable binding to multiple target sites even spatially and/or temporally unrelated. In these cases, mutations at one target may not render the bug resistant to the dual acting molecule if the other target is efficiently inhibited. Such dual acting molecules may also be effective in infection scenarios with mixed population of resistant strains wherein some cells may be mutated at one target and others at the second target. Though dual acting molecules have been described in literature earlier (WO2002059116, US20060105941, U.S. Pat. Nos. 9,149,536, 5,641,6139, Pokrovskaya & Baasov 2010, Expert Opin Drug Discov 5: 883), but the key remains in balancing their activities in terms of specificity and sensitivity towards each target. Structures may be sensibly outlined with specific moieties to act on a bacterial target while simultaneously inhibiting antibiotic degrading enzymes secreted by bacteria. The latter will be based on the prior knowledge of the active site residues of the antibiotic degrading enzymes and their mode of action. Thirdly, molecules with biofilm inhibition properties in addition to antibiotic effects may help in preventing the formation of a biofilm matrix ensuring exposure of the targeted bug to appropriate inhibitory concentrations of the molecule and thus stave-off resistance. A fourth strategy was to include biofilm disrupting property in some dual action molecules to allow penetration of the molecule through existing biofilms and reach the site of action on/within the microbe. Another strategy was to design molecules against carefully chosen targets in order to warrant broad spectrum activity of the antibiotic against both Gram negative and Gram positive bacteria. On the contrary, certain molecules were selectively developed to target specific pathogens and not others (narrow spectrum). In the seventh approach, molecules were designed to possess features beyond antibiotic action to address other aspects of certain infections like inflammation, wound healing etc. In such cases the molecules were structured to encompass properties that are meant to be exerted on the infected host tissue. Some molecules covered more than one of the above mentioned strategies.

Inventors have used rational structure based drug design as an approach to design and synthesize new compounds. In this approach, the inventors include several target classes and different structure based derivatization in order to depict the broad applicability of the strategies disclosed herein. Here, the inventors disclose broadly and specifically the structure-function relationship of quinolones/fluoroquinoloes and oxazolidones class of antibiotics. In silico fragment based and docking analysis involve different known protein scaffolds like penicillin binding protein-2a (PBP2a), β-lactamases and metallo β-lactamases like NDM-1 to develop new structural and chemical entities or de novo molecules. These molecules can interact at one target site or can bind to multiple target sites of a pathogen simultaneously without compromising activity at either site.

There are many reports that describe different kinds of structural modifications on quinolones and oxazolidinone class of molecules (Locke et al, Antimicrob. Agents Chemother. 2010, 54, 5337; Alovero et al, Antimicrob. Agents Chemother. 2000, 44, 320, EP1656370, U.S. Pat. No. 9,149,536) The chemical design strategy presented herein was developed to meet certain objectives. For example, one of the strategies involves structural and chemical modifications of known antibiotics to either incorporate additional interactions to strengthen the ligand-protein complexes or to remove certain interactions with residues that are prone to mutate and known to cause resistance or to have a completely altered mode of binding at active site or even bind towards a completely new active site. Such attributes might equip these molecules to act against resistant pathogens and/or reduce the probability of resistance development in the targeted microbes against these new molecules. In other instance, molecules were structurally modified in such a way that they might act either at one or two or multiple target sites simultaneously without affecting each other's binding affinity, or interaction at one target site might promote binding of the same drug or different drug at a spatially and temporally different active site. The approach also involves structural modifications that would potentially lead to generation of molecules with anti-inflammatory properties or biofilm inhibitory or disruptive properties along with their bactericidal properties. This strategy also seeks to find out new target site(s) and develop novel antibiotics by fragment-based approach followed by docking analysis to obtain one or more lead molecules. The approach further encompasses possibility of developing new antibiotics or potentiators that might help to enhance antibacterial action of known antibiotics, or rejuvenate the action of certain antibiotics that fail to act against particular pathogens, or have synergistic action with known antibiotics.

Last but not the least, the strategy can lead to development of new bactericidal antibiotic(s) that can be specific for local/topical treatment, i.e., with improved hydrophobicity and log P values, easy formulatibility aspects with improved skin/bone penetration properties and overall satisfying Lipinski's rule of 5 to meet the criteria of excellent topical antibiotic(s).
As discussed in the Summary of the Invention section, the invention provides compounds of Formulas I-VII. Some exemplary compounds of the invention are as follows:
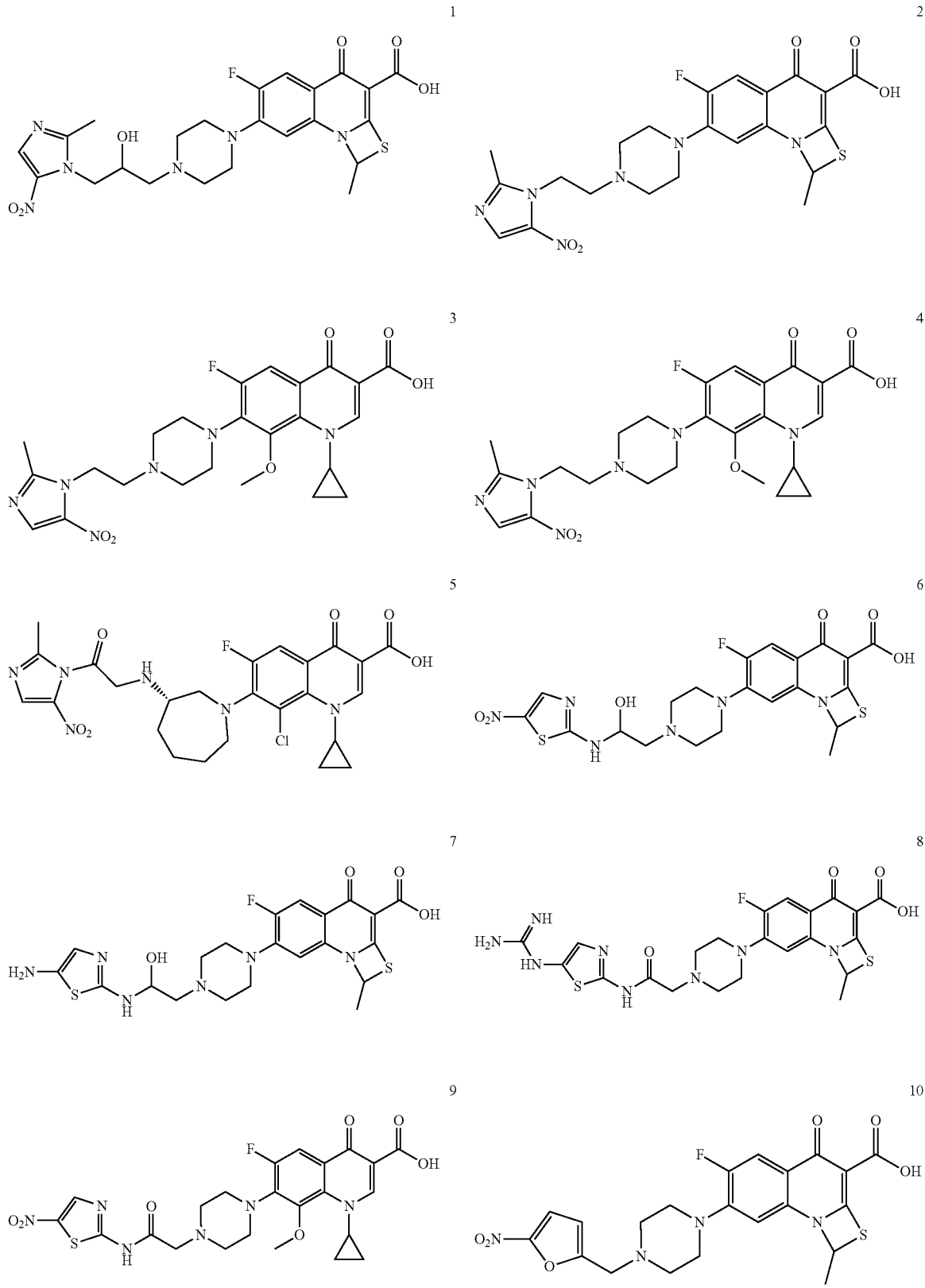

-continued
11
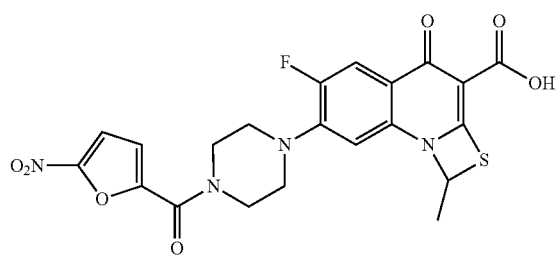
12
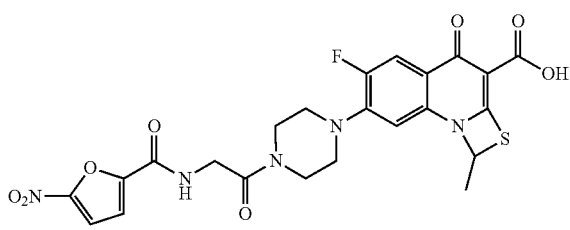
13
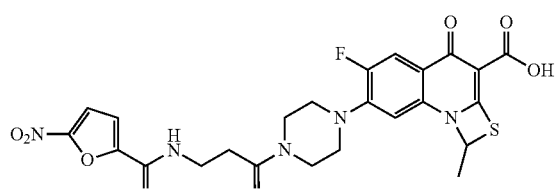
14
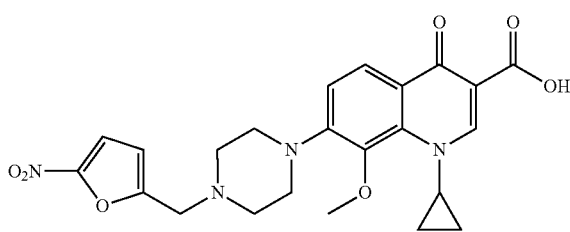
15
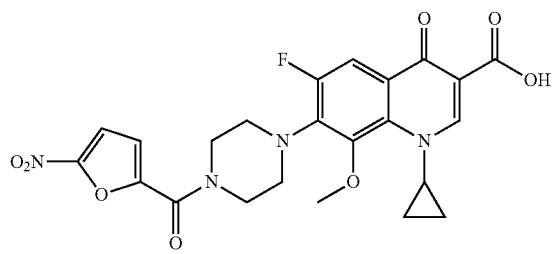
16
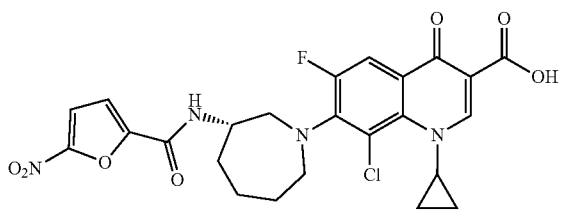
17
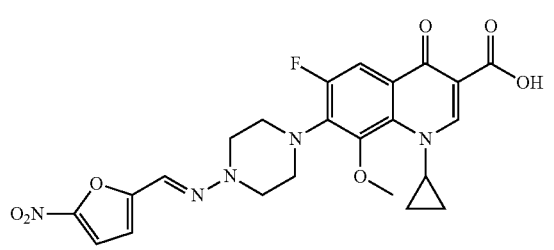
18
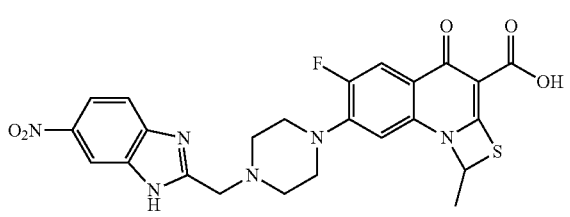
19
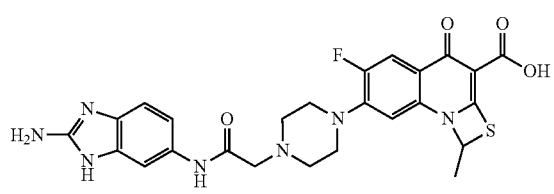
20
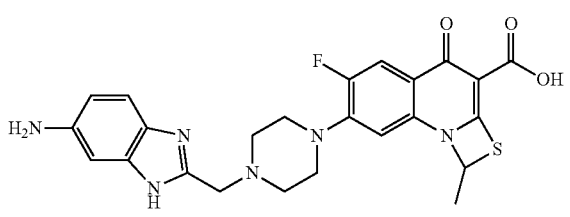
21
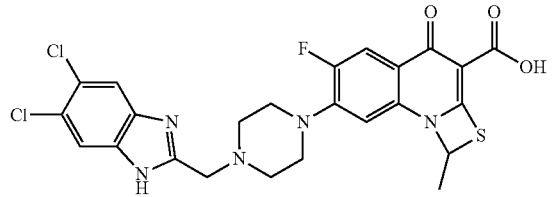
22
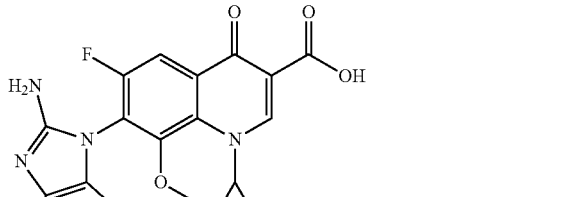

-continued
23
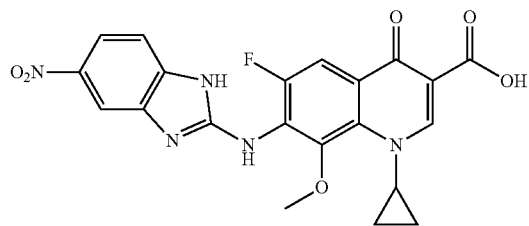
24
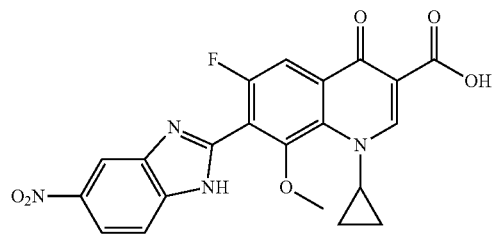
25
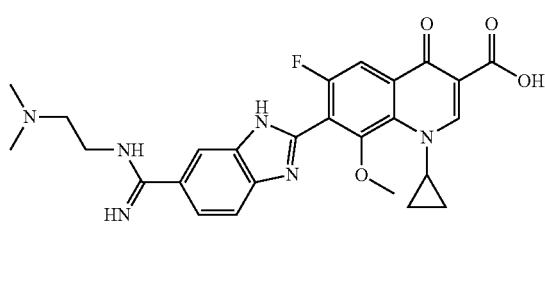
26
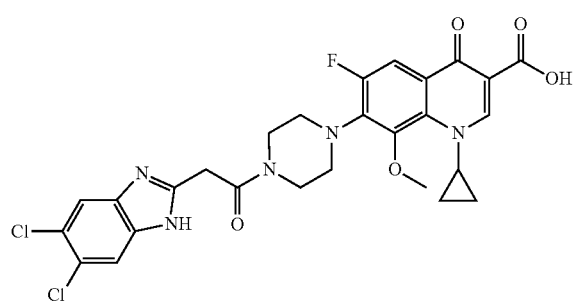
27
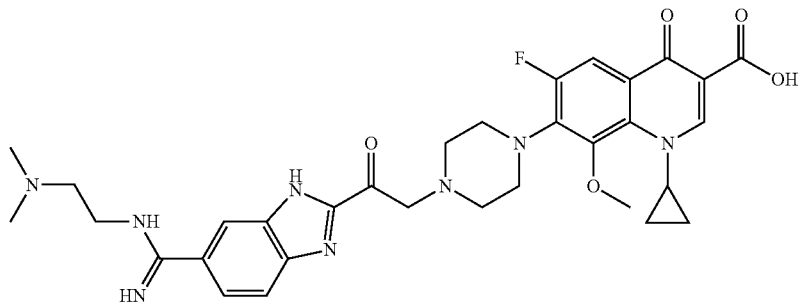
28
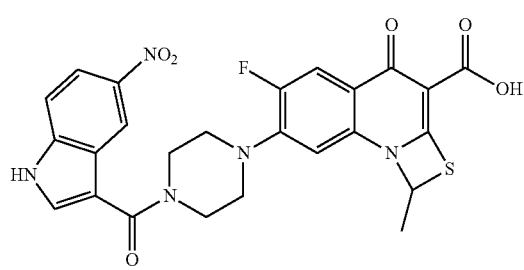
29
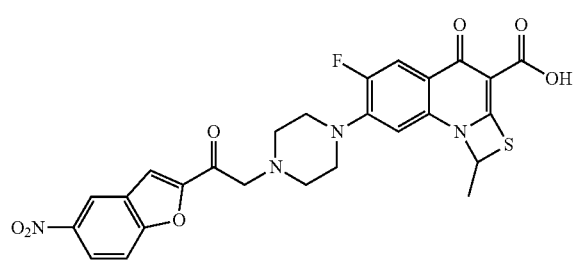
30
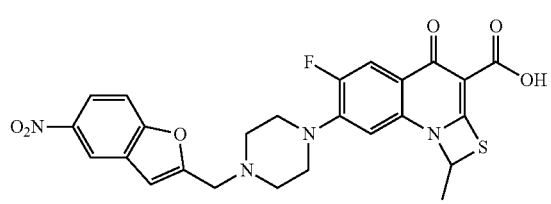
31
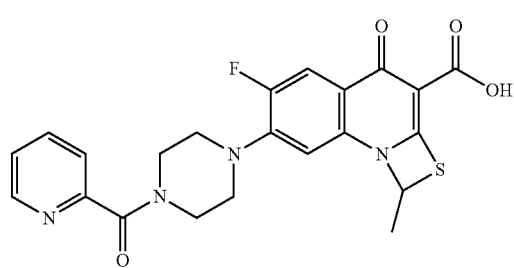

-continued
32
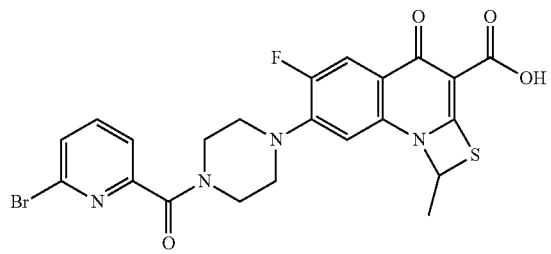
33
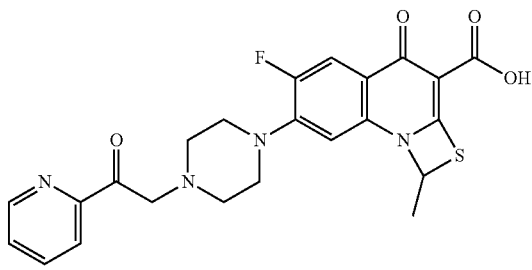
34
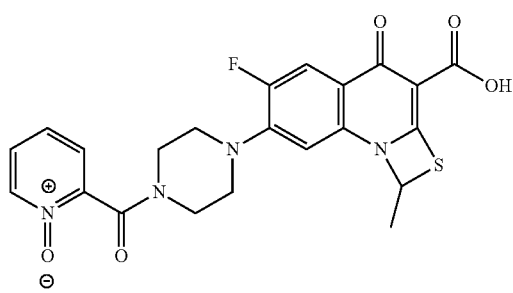
35
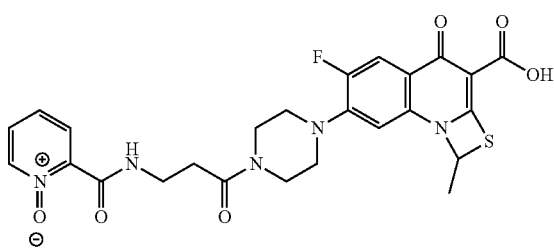
36
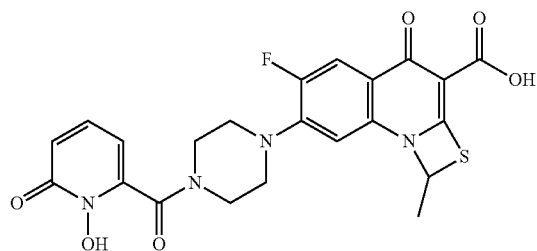
37
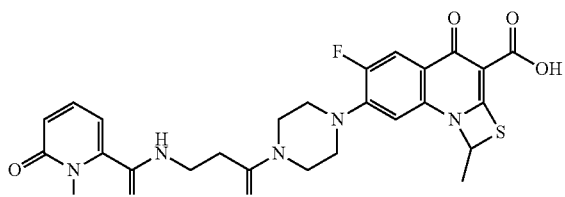
38
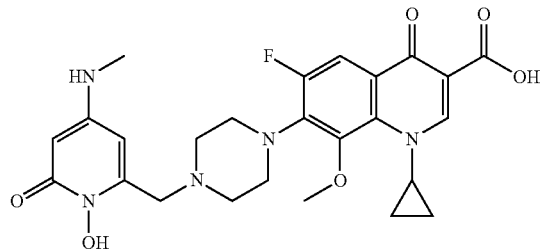
39
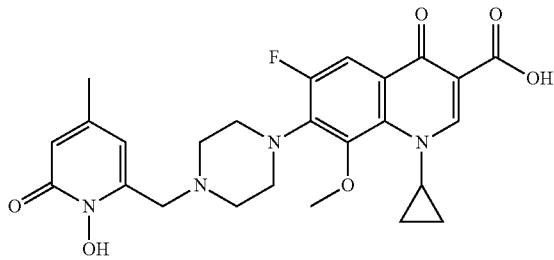
40
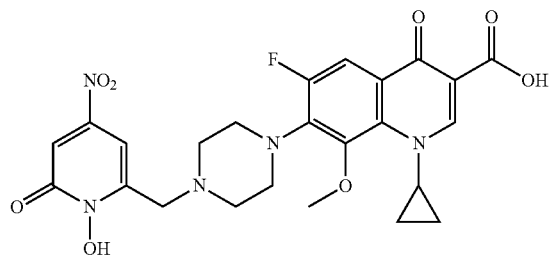
41
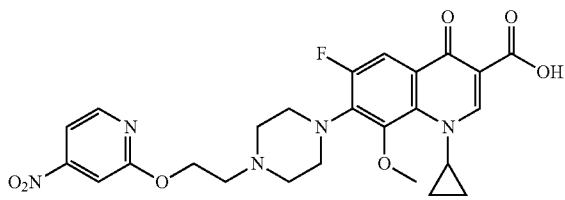

-continued
42
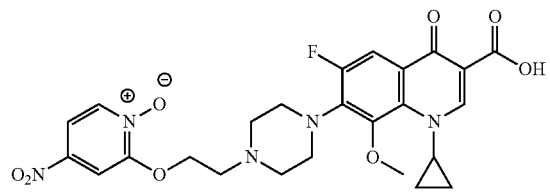
43
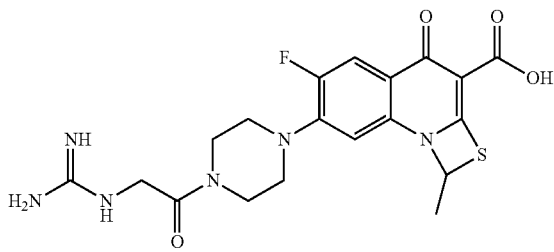
44
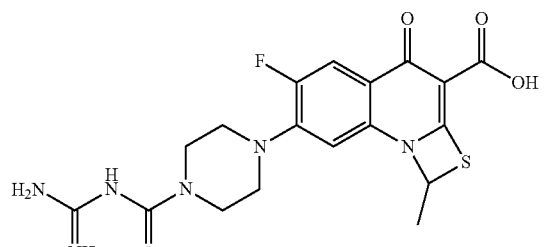
45
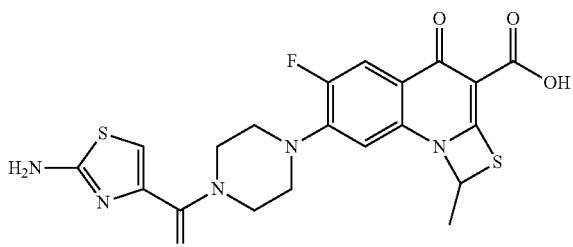
46
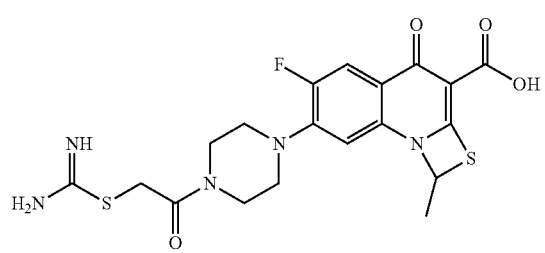
47
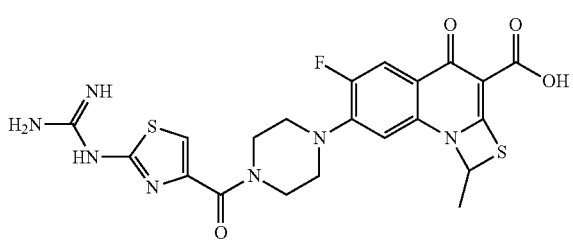
48
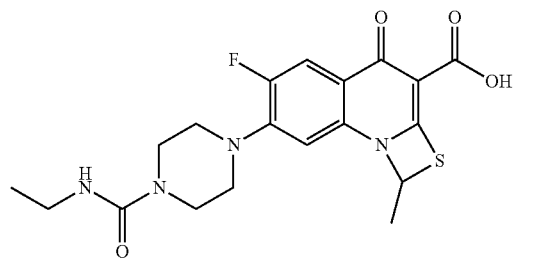
49
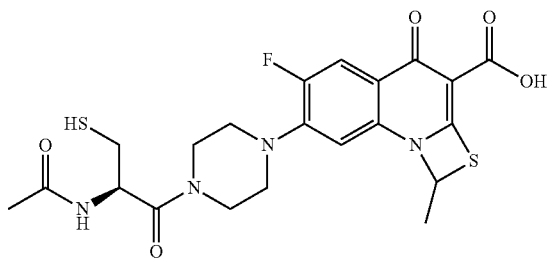
50
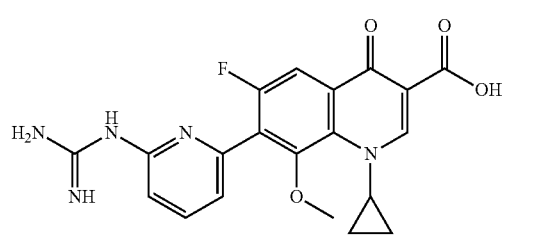
51
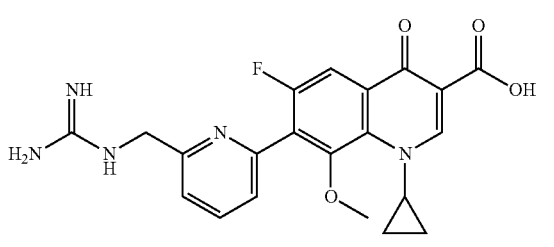
52
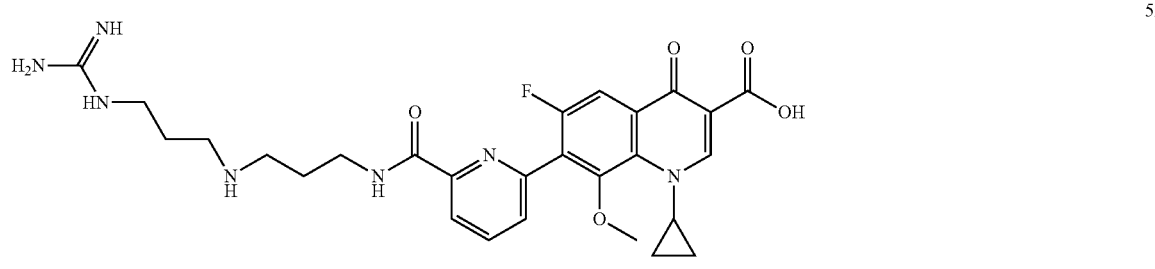

-continued
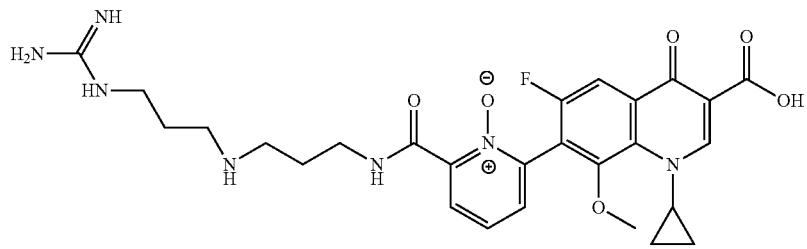
53
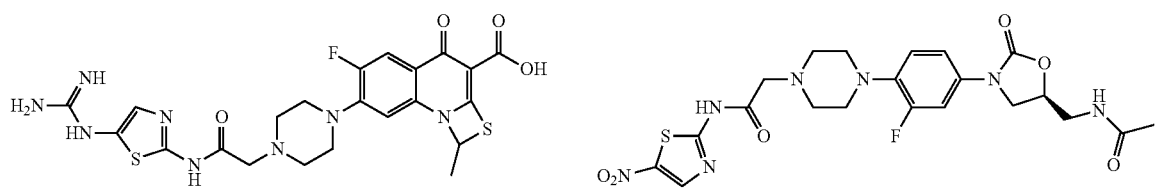
54
55
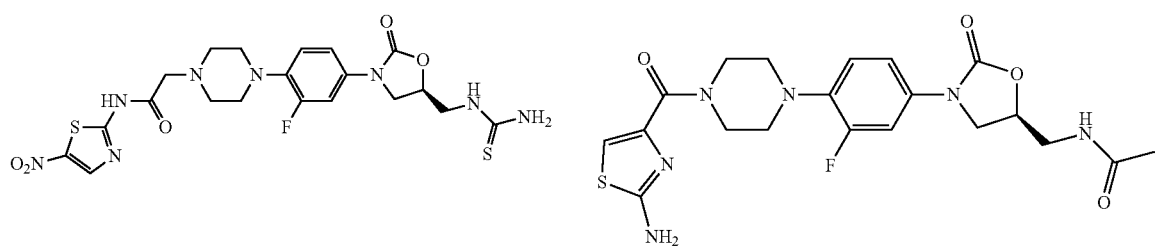
56
57
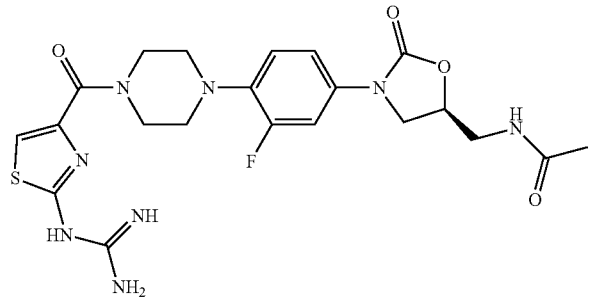
58
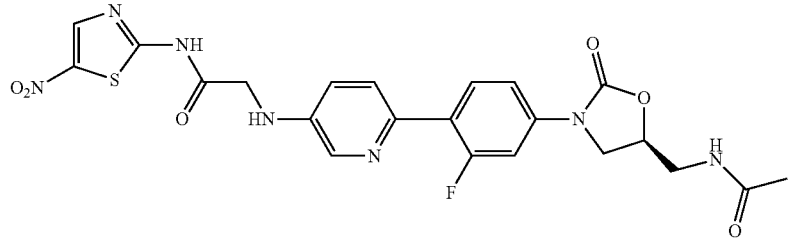
59
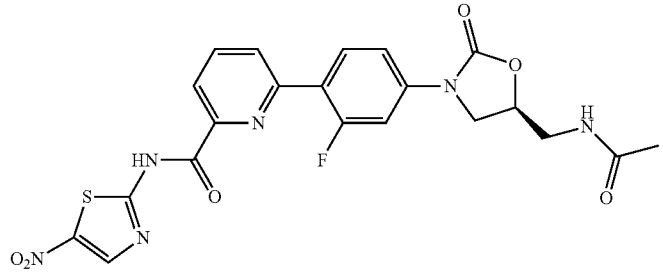
60

-continued
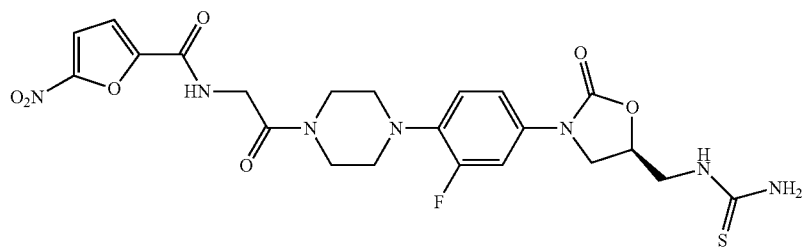
61
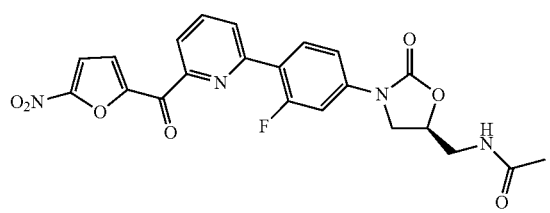
62
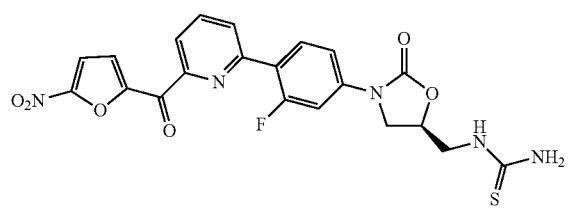
63
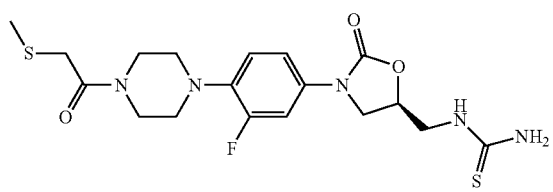
64
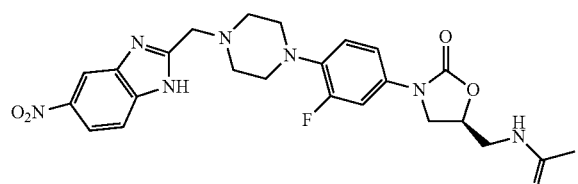
65
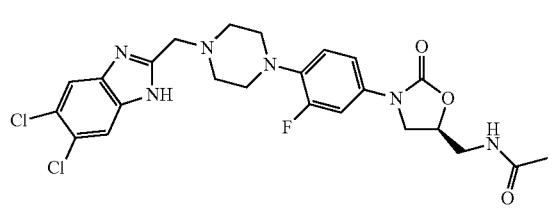
66
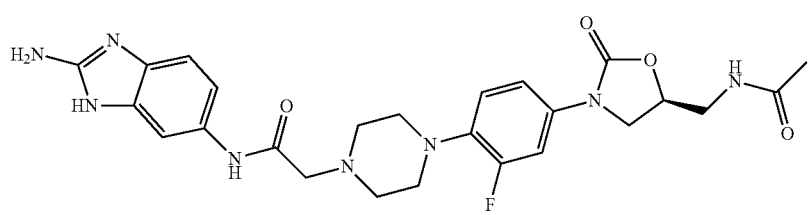
67
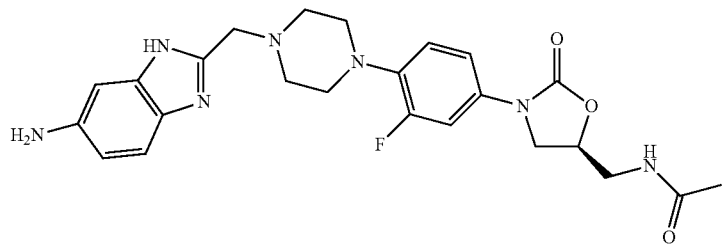
68
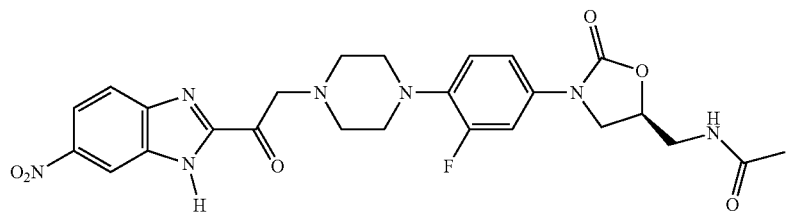
69
70

-continued
71 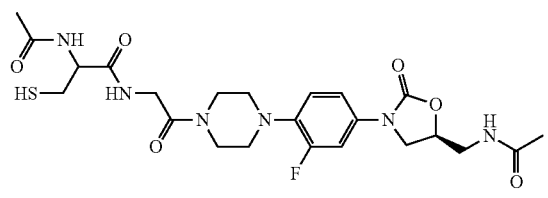
72 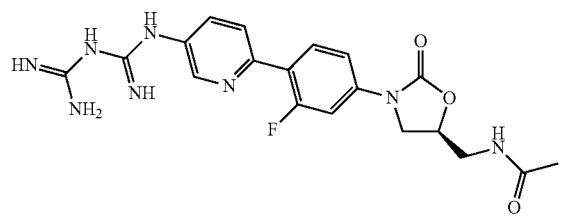
73 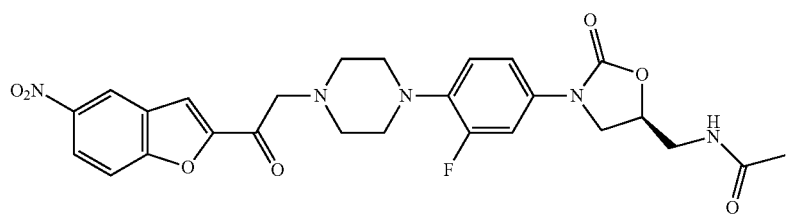
74 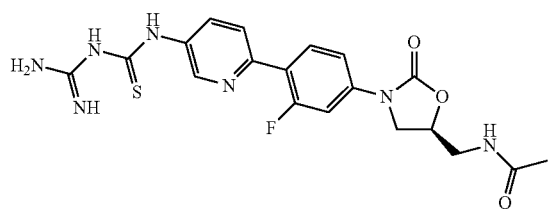
75 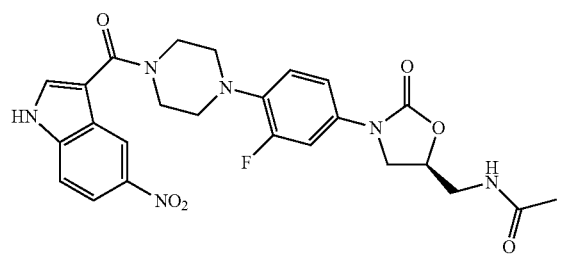
76 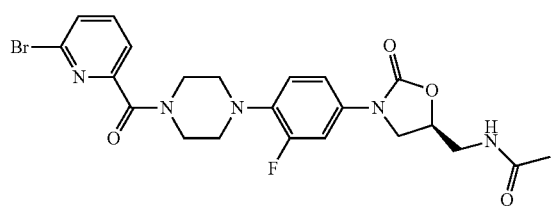
77 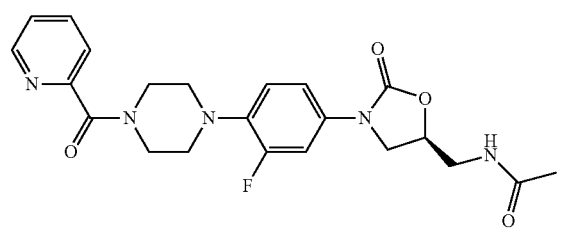
78 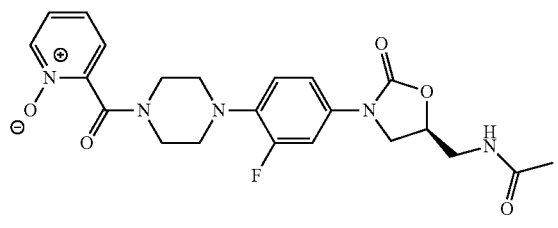
79 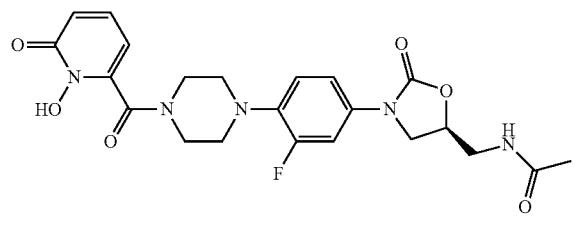
80 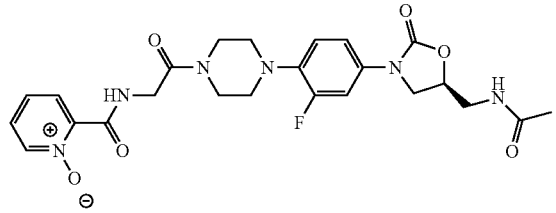
81 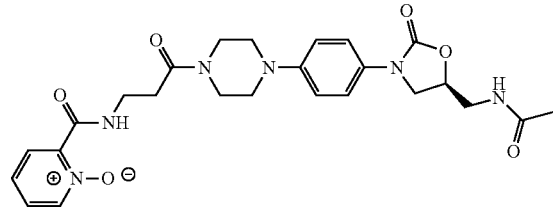

-continued
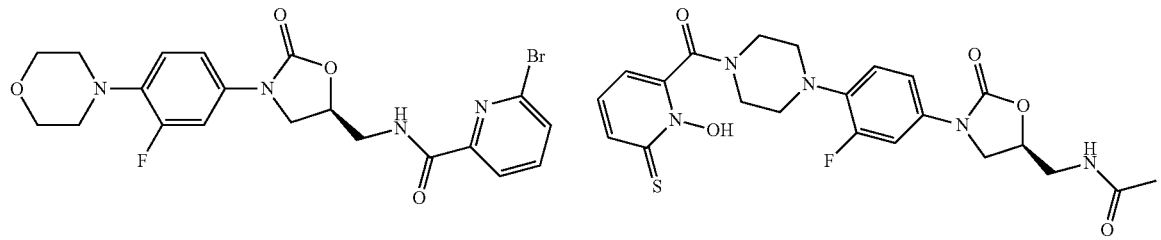
82
83
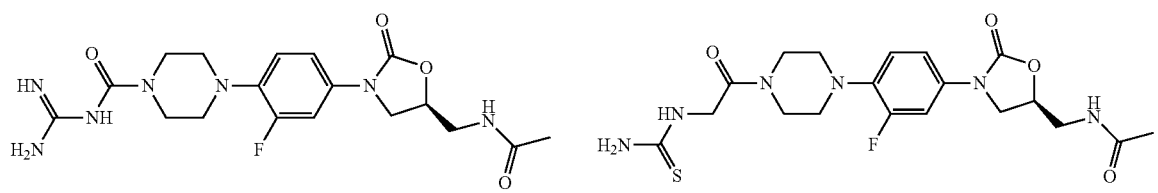
84
85
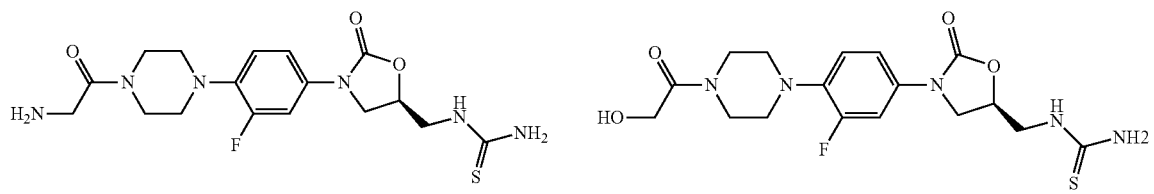
86
87
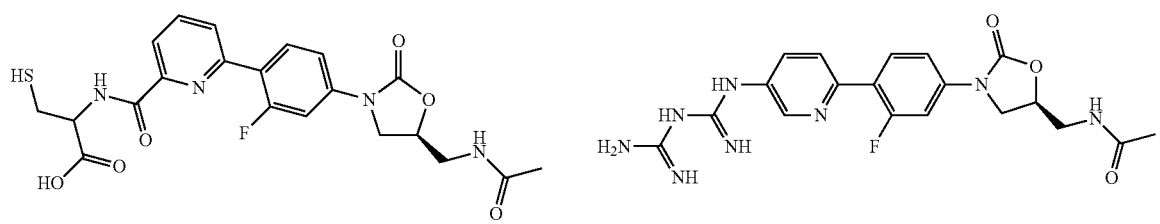
88
89
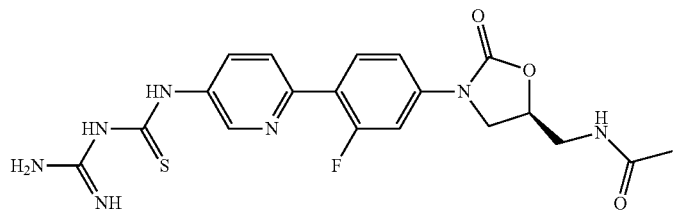
90
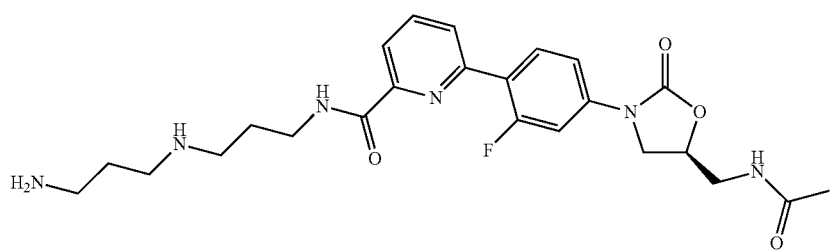
91

-continued
92
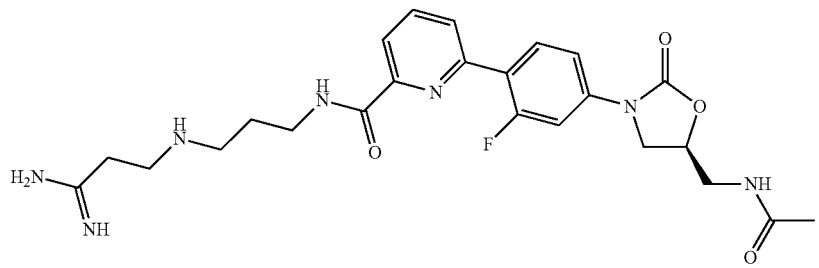
93
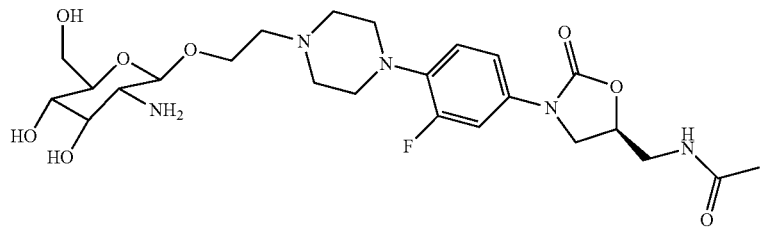
94
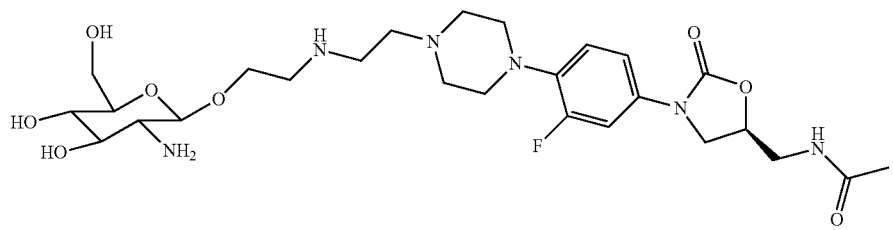
95
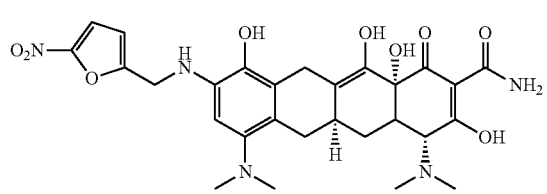
96
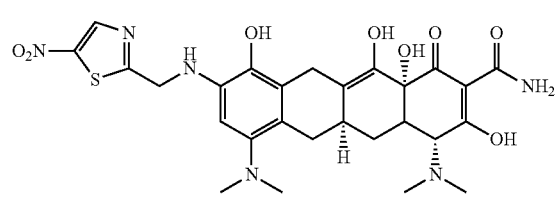
97
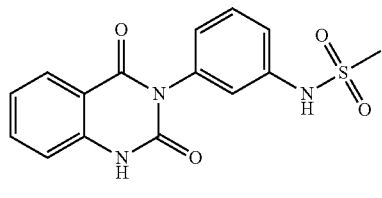
98
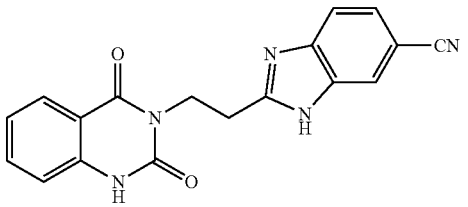
99
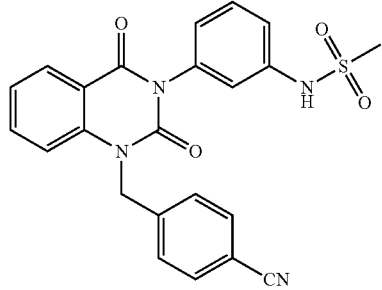
100
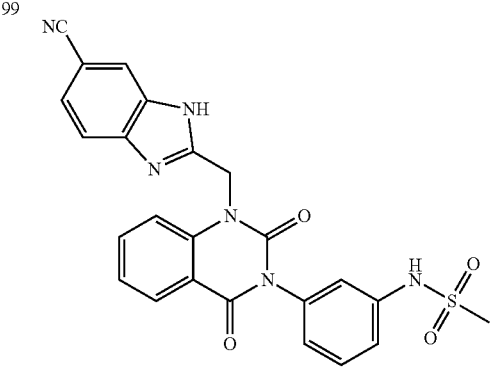

-continued
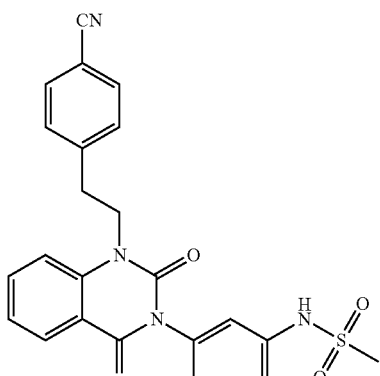
101
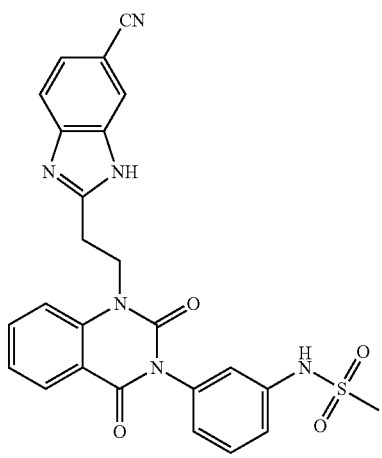
102
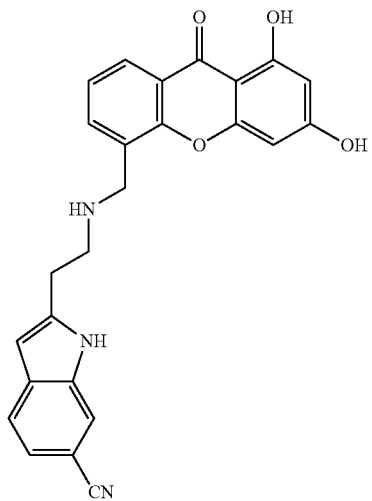
103
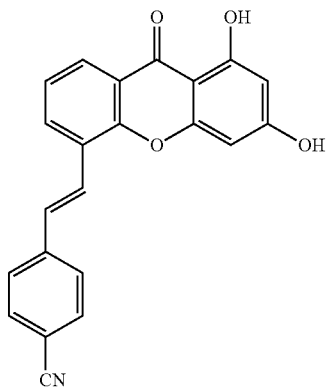
104
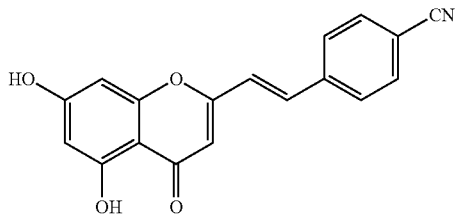
105
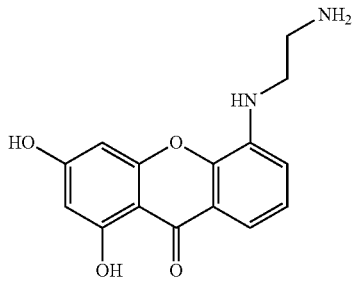
106
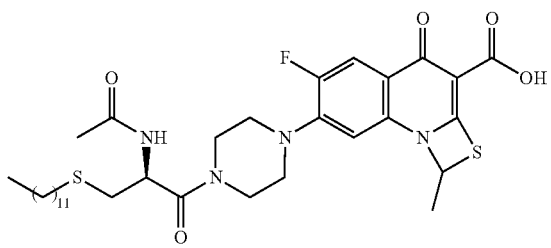
107
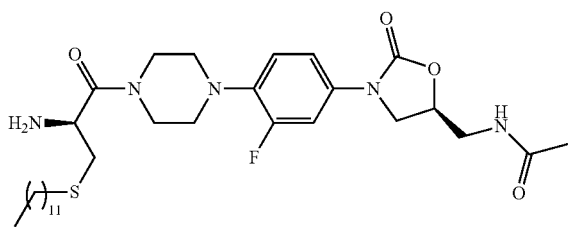
108

109
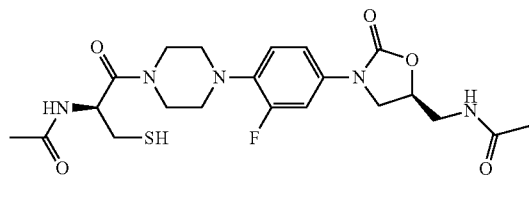
110
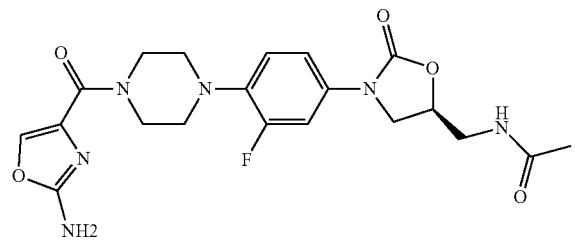
111
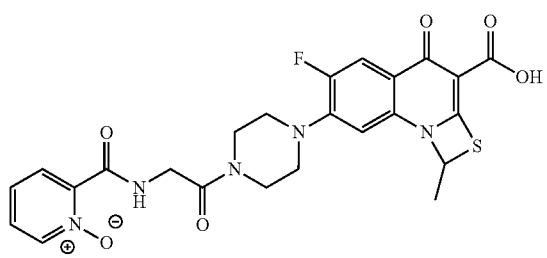
112
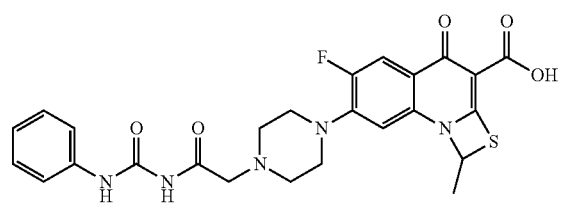
113
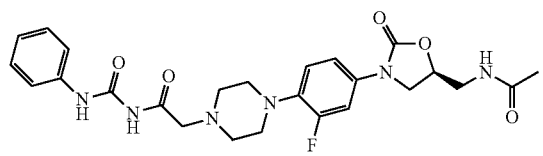
114
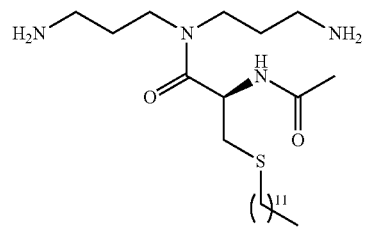
115
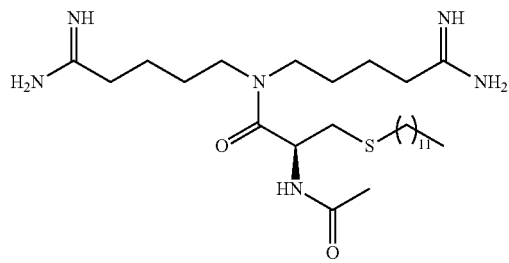
116
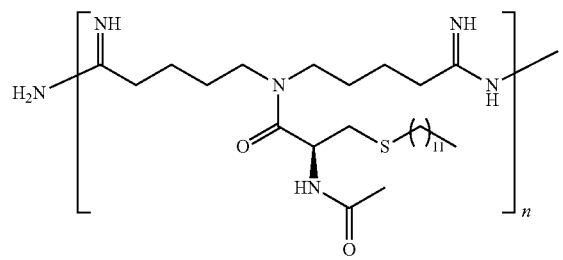
117
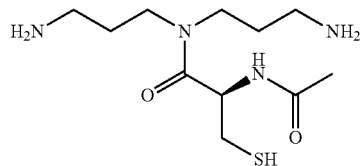
118
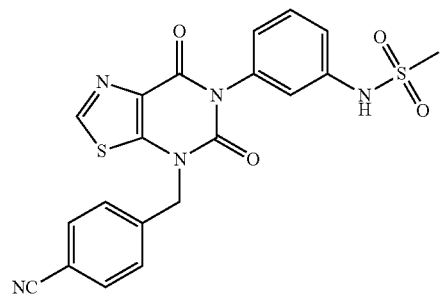

119 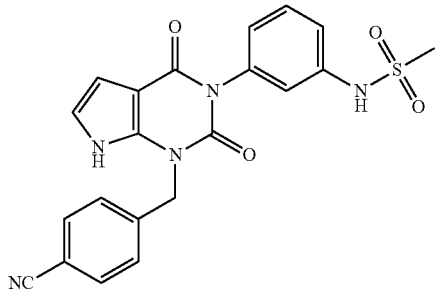
120 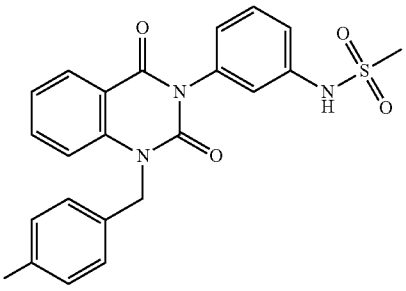
121 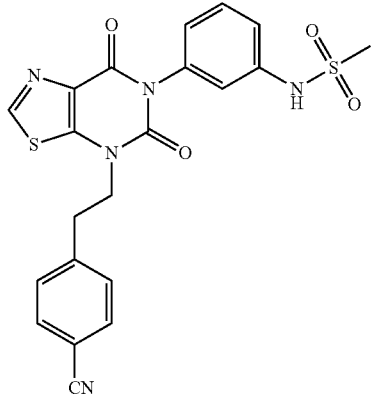
122 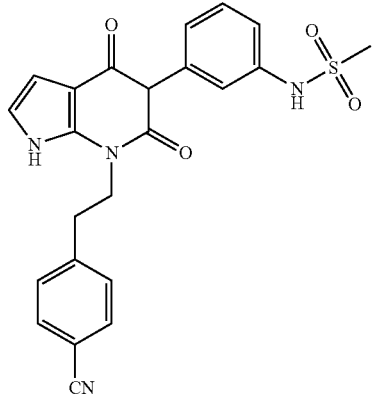
123 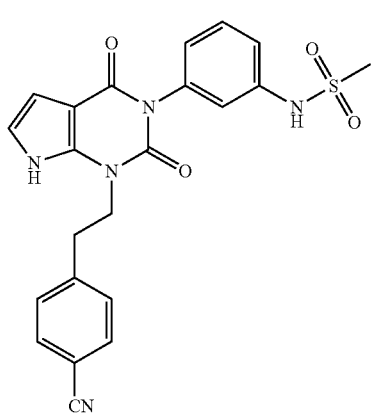
124 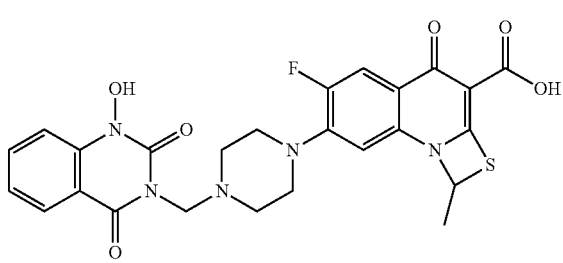
125 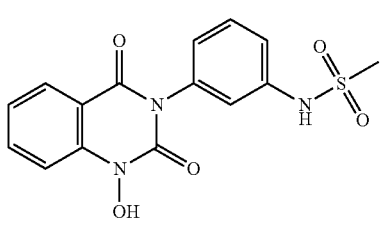
126 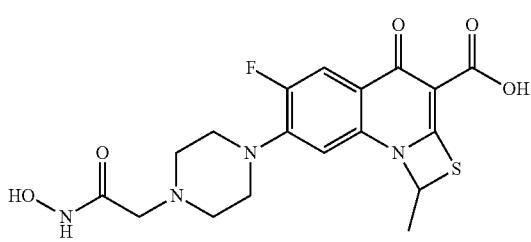
127 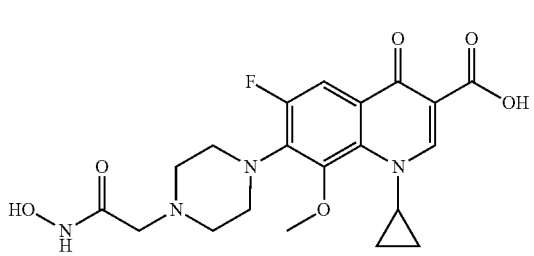
128 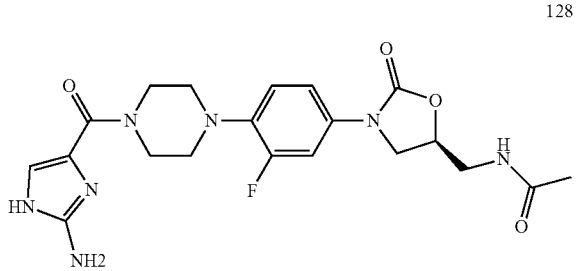

-continued
129
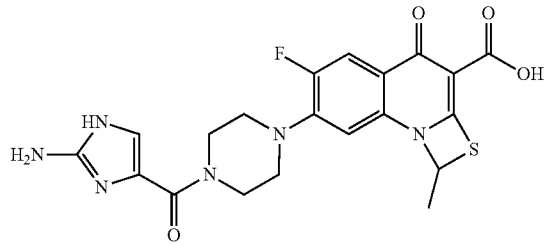
130
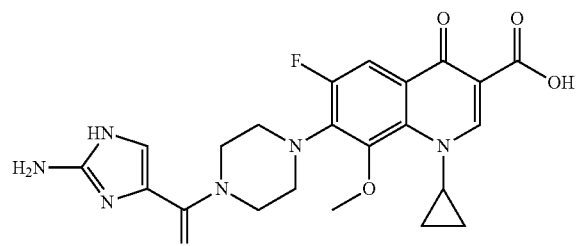
131
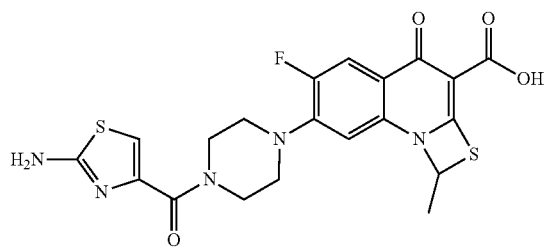
132
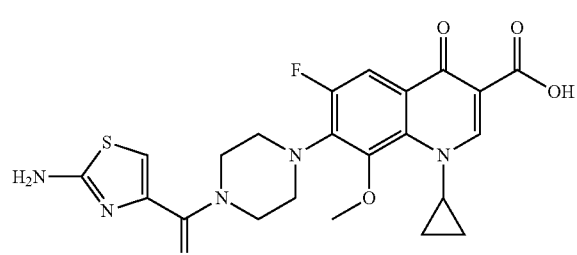
133
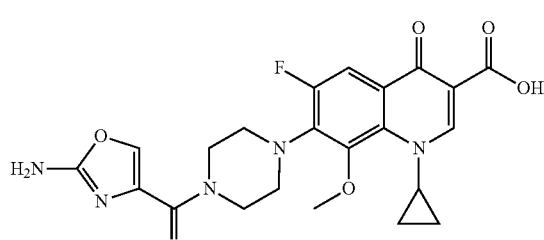
134
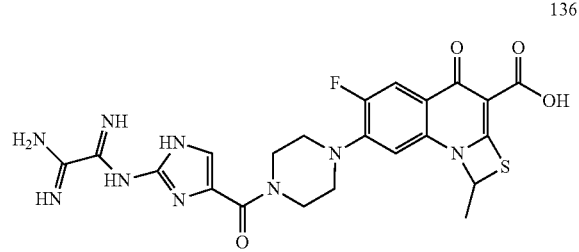
135
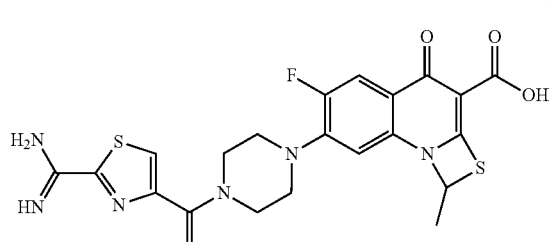
136
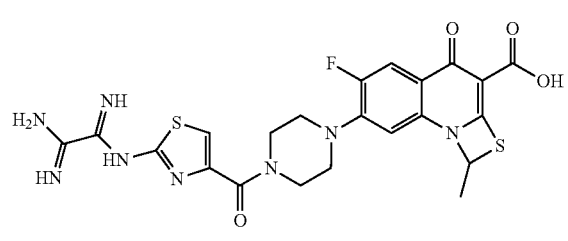
137
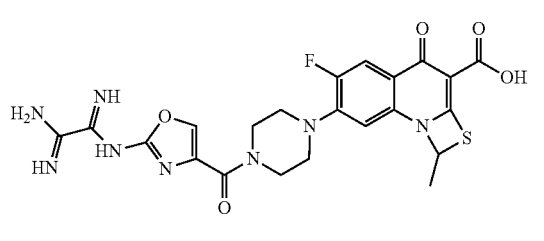
138
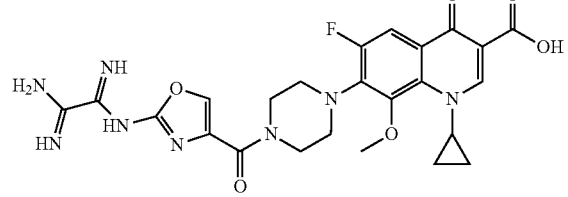
139
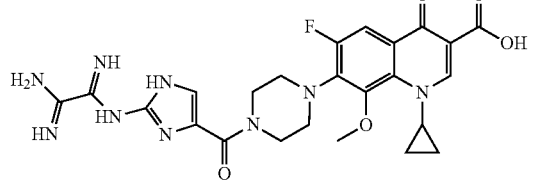
140

141 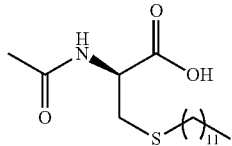

142 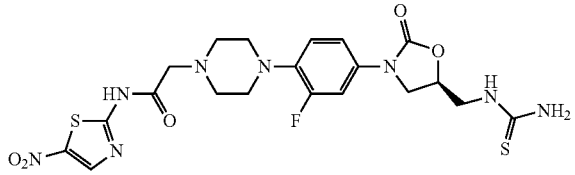

The compounds of the invention can be prepared based on the synthesis of the exemplary compounds shown in Examples 1-34.

The compounds described herein can be used for treating an infection, for example a bacterial infection. Generally, the method comprises administering a therapeutically effective amount of a compound described herein to a subject in need thereof.

The compounds described herein can be used to target susceptible, intermediate and resistant bacteria, such as, but not limited to, *Enterococcus faecium, Staphylococcus aureus, Klebsiella pneumoniae, Acinetobacter baumannii, Pseudomonas aeruginosa* and *Enterobacter* spp., acronymically dubbed "ESKAPE pathogens". These microbes are capable of "escaping" the biocidal action of antibiotics and mutually represent new paradigms in pathogenesis, transmission and resistance in the context of many serious infections in hospitals (Boucher et al 2009, Clin Infect Dis 48: 1). These molecules can be used as therapeutics in different diseases like urinary tract infections, skin and soft tissue infections, endocarditis, intra-abdominal infections, septic arthritis, osteomyelitis, ophthalmic infections, bacteremia, lower respiratory tract infection, impetigo, sepsis, boils, cellulitis, folliculitis, carbuncles, scaled skin syndrome, abscesses, diarrhea, neonatal meningitis, pneumonia, endocarditis, toxic shock syndrome, gastroenteritis, wound infection and septicemia caused by ESKAPE pathogens.

The compounds described herein can also target healthcare-associated infections involving ESKAPE pathogens that remain a major challenge in terms of morbidity and mortality (Boucher et al 2009, Clin Infect Dis 48: 1). Implant-associated infections include primarily infections associated with joint prosthesis (hip, knee, shoulder, ankle, etc.) or in case of surgeries with internal devices (plates, screws, nails implant for fractures); surgical wound infections (due to superficial or deep skin incisions); or catheter related infections (Sanderson 1991, J Hosp Infect 18: Suppl A367; Aamot et al. 2012, Eur J Clin Microbiol Infect Dis 31: 1999; Zapotoczna et al 2015, J Infect Dis 212: 1883). Though majority of implant coupled infections involve *Staphylococcus aureus* [both susceptible and methicillin resistant (MRSA)] (Montanaro et al 2011, Int J Artif Organs 34: 781), opportunistic pathogens like coagulase-negative *Staphylococci, Staphylococcus epidermidis*, and *Propionibacterium acnes* are the major etiological factors in prosthetic joint, catheter, and large wound infections (Montanaro et al 2011, Future Microbiol 6:1329; Aubin et al 2014, Med Mal Infect 44: 241). Thus potent molecules have been screened against ESKAPE pathogens and opportunistic pathogens. Medical device related infections are difficult to eradicate because the above-mentioned form biofilms which play a critical role in the spread of antibiotic resistance by efficient horizontal transfer of resistance and virulence genes within the high dense bacterial population (Deva et al 2013, Plast Reconstr Surg 132: 1319). Hence, potent molecules that can inhibit biofilms or disrupt their formation apart from imparting antibiotic activity can be preferentially selected for these indications.

Recently, the spread of some Gram negative rods like *Escherichia coli, Klebsiella* spp., *Acinetobacter* spp., *Pseudomonas* spp. etc. expressing New Delhi Metallo-β-lactamase (NDM-1) protein has become a potentially major global health threat (Rolain et al 2010, Clin Microbiol Infect 16: 1699). NDM-1-producing bacteria have been recovered from various patients having urinary tract infections, pneumonia, septicemia, or wound or device-associated infections (Wei et al 2015, Chin Med J (Engl) 128: 1969). These strains are resistant to most of the commonly prevalent antibiotics including carbapenems, leaving few or no therapeutic options (Jean et al. 2015, Future Microbiol 10: 407). Since its discovery in 2008, NDM-1-producing strains have disseminated globally and spread the plasmids carrying the $bla_{NDM-1}$ gene encoding this acquired carbapenemase (Poirel et al 2010, Antimicrob. Agents Chemother. 54: 4914). Thus an immediate response to the emergence of NDM-producing bacteria is an urgent priority worldwide. As NDM-1 is able to hydrolyze the carbapenems by catalyzing the cleavage of the substrate amide bond, it is necessary to understand the active structure of the enzyme and design specific inhibitors that can prevent its action. Since structure of NDM-1 from some species has been deciphered already (Zhang & Hao 2011, FASEB J 25: 2574), bioinformatics tools are used to provide clues about the basic scaffold that can bind strongly at the active site of the enzyme. Such fragments may be further modified by tethering specific moieties to effectively design candidate molecules that can inhibit its hydrolytic action and at the same time act on other bacterial targets. These inhibitors can work against other variants of metallo-β-lactamases which share a common structural-fold at the active sites with that of NDM-1.

Without wishing to be bound by a theory, the compounds disclosed herein can be used for the treatment of multi-drug resistant bacterial diseases caused by AGNB (Anaerobic Gram Negative Bacilli) pathogens. These AGNB are common residents of mucous membranes throughout the human body but often invade as opportunistic pathogens through a break in the mucosa (Medical Microbiology 4th ed. Galveston (Tex.): 1996. Baron S, Editor). Although there are several AGNB genera, the clinically relevant ones include *Bacillus, Prevotella* and *Fusobacterium* spp. They commonly cause oral, dental, pleuro-pulmonary, intra-abdominal, uro-genital, skin, soft tissue and bone infections. Infections involving such Gram-negative anaerobic bacilli often are characterized by abscess formation and tissue destruction. Inadequate therapy and resistance development cause serious global health concerns. The *Bacillus* strains frequently show broadspectrum resistance towards cephalosporins, clindamycin, tetracycline, ticarcillin clavulanate etc, many mediated through plasmids. Hence the need to develop new molecules against AGNB pathogens with strong inhibitory property and reduced tendency to lead to resistance. The new molecules with dual action can be effective against skin and soft tissue infections like cutaneous ulcers, cellulitis, secondary diaper rash, gastrostomy or tracheostomy site wounds, infected subcutaneous sebaceous or incusion cysts, eczema, scabies or kerion infections, paronychia, hidradenitis suppurativa, pyoderma, cutaneous and subcutaneous abscesses, decubitus ulcers, infected diabetic (vascular or trophic) ulcers, breast abscesses, bite wounds, anaerobic cellulitis and gas gangrene, bacterial synergistic gangrene, infected piloidal cyst or sinus, Meleney ulcer, and burn wound infection, necrotizing fasciitis, necrotizing synergistic cellulitis, crepitus cellulitis, necrotizing cellulitis and myositis. These molecules can also be effective against various other AGNB infections but not limited to: (a) CNS infections including brain abscess, subdural empyema, epidural abscess and meningitis. (b) Dental infections including periodontal disease, gingivitis, pulpitis, acute necrotizing ulcerative gingivitis, localized juvenile periodontitis, adult periodontitis, endodontitis, periapical and dental abscesses and post-extraction infections. (c) Head and neck infections as chronic otitis media; sinusitis; mastoiditis; tonsillar, peritonsillar and retropharyngeal abscesses; cervical lymphadenitis; all deep neck space infections (sinusitis, tonsillitis); thyroiditis; odontogenic infections; and postsurgical and nonsurgical head and neck wounds and abscesses. (d) Pleuro-pulmonary infections including community acquired aspiration pneumonia and in about one third of patients with nosocomial aspiration pneumonia, empyema, lung abscess, and pneumonia associated with tracheostomy. (e) Intra-abdominal infections like secondary peritonitis and abdominal abscesses. (f) Female genital tract infection including bacterial vaginosis; soft tissue perineal, vulvar and Bartholin gland abscesses; endometritis; pyometra; salpingitis; tubo-ovarian abscesses; adnexal abscess; pelvic inflammatory disease which may include pelvic cellulitis and abscess; amnionitis; septic pelvic thrombophlebitis; vaginal cuff cellulitis; intrauterine device-associated infection; septic abortion; and post-surgical obstetric and gynecologic infections. (g) Bacteremia.

The emergence of multidrug resistant tuberculosis (MDR-TB) and extensively drug resistant TB (XDR-TB) is a serious health concern worldwide (Shearer 1994, J Am Dent Assoc 125: 42). The current first line of anti-TB therapy includes treatment with isoniazide, rifampicin, ethambutol, streptomycin and pyrazinamide. However, resistance against these drugs is widespread. Newer therapy line suggests treatment with quinolones like levofloxacin and moxifloxacin (Kang et al 2016, Ann Am Thorac Soc 13: 364). There is an unmet need to develop drugs for MDR-TB with novel mechanisms of action to achieve cure within shorter duration and hence retard the chances of resistance development. The new molecules of the present invention described herein can be used for treating MDR-TB.

Apart from pulmonary TB, compounds of the invention can also be used for treating skeletal tuberculosis. Skeletal tuberculosis leads to severe bone destruction. Early diagnosis is crucial to prevent serious bone and joint destruction. Interestingly, histopathology of biopsy material from the bone infected area sometimes showed tuberculous tissues (Vohra et al 1997, J Bone Joint Surg Br 79: 562; Kritsaneepaiboon 2016, TB Corner 2: 1). Tuberculous osteomyelitis or skeletal tuberculosis sometimes fails to be diagonosed by orthopaedic surgeon that requires complete course of anti-tuberculosis drugs. In this regard, compounds invention can be have scaffolds that can be active against *Mycobacterium tuberculosis* as well as multi drug resistant *Mycobacterium* species.

Antibiotic resistance that affects *H. pylori* eradication treatment is a challenging situation worldwide. *H. pylori* is a common bacteria infecting approximately 50% of the world's population, majorly causing upper gastrointestinal diseases, including peptic ulcer disease (gastric and duodenal), chronic gastritis (Kao et al 2016, Biomed J 39: 14). Prolonged infection sometimes leads to gastric cancer and gastric mucosal-associated lymphoid tissue lymphoma. Multiple regimen therapy is commonly used for treatment. Some of the dual action compounds of the present invention are perfectly suited to be effective in case of failure of the existing dual/triple regimen action of the prevalent drugs. The chemical properties of these synthesized molecules will further aid in optimum functioning, given the known pH of the environment of the bacteria residing in the human body.

Without limitation, the infection to be treated can be a Gram-positive or a Gram-negative pathogen infection. Further, inventors have discovered inter alia that the compounds of the invention are particularly effective against quinolone resistant pathogens. Thus, in some embodiments, the infection that needs treatment is that caused by a quinolone resistant pathogen.

In some embodiments, the infection is caused by a methicillin-resistant or vancomycin-resistant pathogen.

In some embodiments, infection to be treated is an infection caused by *Bartonella henselae, Borrelia burgdorferi, Campylobacter jejuni, Campylobacterfetus, Chlamydia trachomatis, Chlamydia pneumnoniae, Chylamnydia psittaci, Simnkania negevensis, Escherichia coli* (e.g., O157:H7 and K88), *Ehrlichia chafeensis, Clostridium botulinumn, Clostridiumn perfringens, Clostridium tetani, Enterococcus faecalis, Haemnophilius influenzae, Haemnophilius ducreyi, Coccidioides immitis, Bordetella pertussis, Coxiella burnetii, Ureaplasma urealyticumn, Mycoplasma genitaliumn, Trichomnatis vaginalis, Helicobacter pylori, Helicobacter hepaticus, Legionella pneumnophila, Mycobacteriumn tuberculosis, Mycobacterium bovis, Mycobacterium africanumn, Mycobacteriumn leprae, Mycobacterium asiaticumn, Mycobacterium avium, Mycobacterium celatumn, Mycobacteriumn celonae, Mycobacteriumn fortuitumn, Mycobacterium genavense, Mycobacterium haemnophilumn, Mycobacterium intracellulare, Mycobacterium kansasii, Mycobacterium mnalmnoense, Mycobacteriumn mnarinumn, Mycobacterium scrofulaceumn, Mycobacterium simniae, Mycobacteriumn szulgai, Mycobacterium ulcerans, Mycobacteriumn xenopi, Corynebacterium diptheriae, Rhodococcus equi, Rickettsia aeschlimnannii, Rickettsia africae, Rickettsia conorii, Arcanobacterium haemnolyticumn, Bacillus anthracis, Bacillus cereus, Lysteria mnonocytogenes, Yersinia pestis, Yersinia enterocolitica, Shigella dysenteriae, Neisseria mneningitides, Neisseria gonorrhoeae, Streptococcus bovis, Streptococcus hemnolyticus, Streptococcus mnutans, Streptococcus pyogenes, Streptococcus pneumnoniae, Staphylococcus aureus, Staphylococcus epidermnidis, Staphylococcus pneumnoniae, Staphylococcus saprophyticus, Vibrio cholerae, Vibrio parahaemnolyticus, Salmonella typhi, Salmonella paratyphi, Salmonella enteritidis, Treponemna pallidumn, Candida, Cryptcooccus, Cryptosporidiumn, Giardia lamnblia, Microsporidia, Plasmnodiumn vivax, Pneumnocystis carinii, Toxoplasmna gondii, Trichophyton mnentagrophytes, Enterocytozoon bieneusi, Cyclospora cayetanensis,*

*Encephalitozoon hellemn, Encephalitozoon cuniculi*, among other bacteria, archaea, protozoa, fungi, or any combinations thereof.

In some embodiments, infection is a *S. aureus, S. epidermidis, E. faecalis* or *E. aerogenes* infection.

In some embodiments, infection is a methicillin-resistant *S. aureus* (MRSA) infection. In some embodiments, infection is a quinolone-resistant *S. aureus* (QRSA) infection.

In some embodiments, infection is a vancomycin-resistant *S. aureus* (VRSA) infection.

For administering to a subject, the compounds disclosed herein can be formulated into pharmaceutically acceptable compositions. The pharmaceutical composition can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, gel, hydrogel, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. The compounds may be applied using a local delivery matrix, for example, loaded in a bone cement and applied at the site of bone infection or used in the form of coating or hydrogel coating for implant devices. Additionally, the compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, contents of all of which are incorporated herein by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The amount of a compound described herein that can be combined with a carrier material to produce a single dosage form will generally be that amount of the compound that produces a therapeutic effect. Generally, out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that the compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 g/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that compound or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

Without limitations the compounds described herein can be formulated for administration by any appropriate route known in the art including, but not limited to, topical (including buccal and sublingual) and oral or parenteral routes, including intravenous, intramuscular, subcutaneous, transdermal, airway (aerosol), pulmonary, nasal, and rectal administration. Exemplary modes of administration include, but are not limited to, topical, injection, infusion, instillation, inhalation, or ingestion. "Injection" includes, without limitation, intravenous, intramuscular, intra-arterial, intrathecal, intraventricular, intracapsular, intraorbital, intracardiac, intradermal, intraperitoneal, intralymphnodal, transtracheal, subcutaneous, subcuticular, intra-articular, sub capsular, subarachnoid, intraspinal, intracerebral, spinal, and intracisternal injection and infusion.

In some embodiments, the pharmaceutical composition comprising a compound of the invention can be a formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient (s) with liquid carriers, finely divided solid carriers, or both, and then shaping the product into the desired presentation if necessary.

Typical oral dosage forms of the compositions are prepared by combining the compound of Formulas I-VII in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the compounds described herein. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the compounds described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations described herein can encompass, in some embodiments, anhydrous pharmaceutical compositions and dosage forms comprising the compounds described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

In some embodiments, the pharmaceutical composition comprising a compound of the invention can be a parenteral dosage form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose dumping.

An injectable composition comprises an acceptable vehicle. This vehicle can be, in particular, a sterile, isotonic saline solution (monosodium or disodium phosphate, sodium, potassium, calcium or magnesium chloride, and the like, or mixtures of such salts), or dry, in particular lyophilized, compositions, which on addition, as appropriate, of sterile water or physiological saline, enable the preparation of injectable solutions. Generally, the composition is sterile and fluid to the extent that it may be easily filled in syringe. In some embodiments, the injectable composition can be a solution or suspension in a pharmaceutically acceptable solvent or diluent.

In some embodiments, the injectable composition contains a carrier which can be a solvent or a dispersion medium containing, for example, water, ethanol, polyol (such as glycerol, propylene glycol, liquid polyethylene glycol, and the like), suitable mixtures thereof, or a vegetable oil. Proper fluidity can be maintained, for example, by the use of a coating such as lecithin, by the maintenance of required particle size, or by the use of surfactants. Prevention of the action of microorganisms can be achieved as necessary by the use of antibacterial or antifungal agents. In many cases it may be preferable to include in the composition isotonic agents, such as sugars, polyalcohols (such as mannitol or sorbitol), sodium chloride. Prolonged absorption of the injectable composition may be brought about by including in the composition an agent that delays absorption, for example, aluminum monostearate or gelatin.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, a composition as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm & Haas, Spring House, Pa. USA).

In some embodiments, a compound described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred in chronic infections, as each pulse dose can be reduced and the total amount of the compound administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising a compound described herein can be prepared. Suitable examples of sustained-release preparations include semipermeable matrices of solid hydrophobic polymers containing the compound, in which matrices are in the form of shaped articles, e.g., particles, films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In some embodiments, the formulation can be in the form for topical administration, i.e., a topical formulation. The topical formulations disclosed herein can comprise several types of cosmetically-acceptable topical vehicles including, but not limited to, solutions, colloidal suspensions, dispersions, emulsions (microemulsions, nanoemulsions, multiple and non-aqueous emulsions), hydrogels, and vesicles (liposomes, niosomes, novasomes). Components and formulation methods of suitable cosmetically-acceptable topical vehicles are well known in the art and are described, for example, in U.S. Pat. No. 6,797,697 and U.S. Pat. App. Pub. No. 2005/0142094 and No. 2005/0008604, Int. Pat. App. Pub. No. 2006/029818 and No. 2000/062743, content of all of which is incorporated herein by reference. Those skilled in the art will appreciate the various methods for producing these various product forms.

In some embodiments, the topical formulation can be in the form of a cream, oil, lotion, serum, gel, hydrogel, sunscreen, nail varnish, ointment, foam, spray, aerosol, powder, stick, solution, suspension, dispersion, paste, peel, and impregnated fabric (e.g., a "wipe" or tissue). Generally, the composition comprises an effective amount of the active agent. As used here, the term "effective amount" is that amount of the formulation containing the active agent necessary to achieve the desired improvement. In some embodiments, the formulation is a topical formulation.

In some embodiments, the topical formulation can be in a form selected from the group consisting of lotions, creams, gels, emulgel, oils, serums, powders, sprays, ointments, solutions, suspensions, dispersions, pastes, foams, peels, films, masks, patches, sticks, rollers, cleansing liquid washes, cleansing solid bars, pastes, foams, powders, shaving creams, impregnated fabric (e.g., a "wipe" or tissue), and the like.

For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure.

Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 22$^{nd}$ Ed., Mack Publishing, Easton, Pa. (2012) and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer a compound described herein include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms of the compounds described herein are well known to those skilled in the pharmaceutical arts, and depend on the particular tissue or organ to which a given pharmaceutical composition or dosage form will be applied.

A compound described can be administered directly to the airways in the form of an aerosol or by nebulization. Accordingly, for use as aerosols, in some embodiments, the compound described herein can be packaged in a pressurized aerosol container together with suitable propellants, for example, hydrocarbon propellants like propane, butane, or isobutane with conventional adjuvants. In other embodiments, the compound can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the compounds described herein. Exemplary gases include, but are not limited to, nitrogen, argon or helium.

In other embodiments, the compound can be administered directly to the airways in the form of a dry powder. For use as a dry powder, the compound can be administered by use of an inhaler. Exemplary inhalers include metered dose inhalers and dry powdered inhalers.

Suitable powder compositions include, by way of illustration, powdered preparations of a compound described herein thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

In some embodiments, compounds described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

The increased prevalence of vancomycin-resistant *S. aureus* and poor bone penetration and distribution profile of vancomycin limits its usage in implant-associated infections. This has led to an intensive search and development of new effective antimicrobial agents with low emergence of resistance against *Staphylococcus* species. A compound described can be loaded into PMMA bone cement that when applied at the implant surface can maintain optimal local drug concentration through controlled drug release over long durations (3-4 weeks) that can provide relief to the patient from implant associated infection, recurrence, pain and finally result in lower health care costs. The antibiotics (a compound described herein) loaded drug cement can be used during bone surgeries at the particular site to have both prophylactic and therapeutic action. Both biodegradable and non-biodegradable polymers are known for locally delivering the drug at implant site. But the major problems with these systems are the initial burst release of the drug, the duration of the release and the nature of drug penetrating into bone surface to eradicate bacterial infection. For example, the delivery of gentamicin from non-biodegradable PMMA beads was limited to only 7.5% of the loaded amount since most of the drug was not able to diffuse through the pores of the polymer. Additionally, non-biodegradable polymer matrices require a follow up surgical procedure for removal after 4-6 weeks after initial implantation. In general, antibiotic elutes slowly from non-biodegradable spacer in comparison to the biodegradable ones. Biodegradable carriers such as calcium sulphate, calcium phosphate, hydroxyapatite, etc. additionally help in bone regeneration and regrowth process.

The invention also includes bone cement formulations comprising a compound of the invention and a biodegradable or non-biodegradable polymer matrix. In some embodiments, the non-biodegradable matrix comprises PMMA (polymethylmethacrylate, commercially available as smart set HV® (DePuy International Limited), simplex-P® (Stryker)) and the monomeric liquid component methyl methacrylate. In case of bio-degradable matrix, the preferable carrier is calcium phosphate or calcium nitrate or hydroxyapatite or calcium sulfate hemihydrates or calcium sulfate dihydrate (commercially available as Stimulan Rapid Cure® (Biocomposites) and the bead is made by homogenous mixing of active with calcium sulfate matrix in the presence of mixing solution. The biodegradable matrix is, in general, tissue compatible and may act as binder, facilitating healing and preventing loss of the grafting material.

Additionally, to increase the porosity of the matrix to enhance drug diffusion through the matrix, different kinds of additives such as polyvinyl pyrrolidone (PVP K90), polyvinyl alcohol (PVA) can be incorporated into the cement mixture. To obtain additional antibacterial, anti-inflammatory and bio-film inhibitory properties into the drug impregnated PMMA or $CaSO_4$ bead, anti-inflammatory agents like hyaluronic acid or sodium hyaluronate or any other antimicrobial agents or different natural and synthetic bio-film inhibitors (like trans cinnamaldehyde, DMDM hydantoin, polyhexamethylenebiguanide (PHMB), N-acetyl cysteine, N-acetyl cysteine derivatives like compound 141) are added into the cement-drug mixture to obtain an effective antibiotic impregnated bead for treatment of osteomyelitis and other inflammatory bone infections caused by opportunistic pathogens and MRSA.

The compounds described herein were found to be compatible with the cement composition and maintained sustained drug release at concentrations higher than their respective MIC values against particular pathogens. In vitro drug release studies and sequential ZIB assays indicated that PMMA cement formulations comprising Compound 2 or Compound 10, maintained controlled drug release profile above MIC threshold over a week. Example 16 shows that drug release profile from PMMA depends on the nature of fluoroquinolone, for example in vitro release of PMMA impregnated Compound 2 was found to be better than PMMA impregnated Compound 10 over 7 days.

The present invention describes one more approach to deliver the active(s) at the site of infection in the form of hydrogel or in presence of biodegradable polymeric carrier that can form in situ gel at the site of application. Such thermosensitive/pH sensitive/ion-sensitive in situ bio-degradable gel or hydrogel for the treatment of osteomyelitis or inflammatory bone infection or implant associated infection provides several advantages over cement beads, including minimal surgical procedures, ease of preparation, biodegradable nature of polymer, high drug encapsulation ability with both hydrophobic and hydrophilic drug substance, linear sustained release profile over extended time with additional antibacterial and safety characteristics and with less systemic toxicity profile.

The in situ gel composition can comprise a compound described herein and additional components. The composition consists of either pH sensitive polymers such as carbopol 934P or thermo-sensitive polymers such as chitosan, PLA, PLGA, mPEG, poloxamers or ion-sensitive polymers such as sodium alginate. The composition further consists of cross linking agents such as 3-glycerophosphate which keeps chitosan gel in solution form at neutral pH, but changed to gel form upon heating to body temperature, 37° C. The in situ gel composition also consists of humectants like glycerin, propylene glycol to increase the release rate of active through the gel matrix. The composition also consists of preservatives such as methyl paraben or propyl paraben or sodium benzoate or combinations thereof. The in situ gel composition provides as a sol-gel drug delivery system for the treatment of osteomyelitis and other implant associated infections.

In some embodiments, the implant may be a transcutaneously implanted device (that is, a device that passes through an access site in the patient's skin (such as transcutaneous catheters). In other embodiments, the implant may be a cardiovascular device, such as cardiac valve, alloplastic vessel wall support, or total artificial heart implant. Other exemplary cardiovascular implants include ventricular assist devices, vascular allografts, stents, electrical signal carrying devices such as a pacemaker, neurological leads, defibrillator leads, and the like. In further embodiments, the implant may be an orthopedic or dental implant, such as implants that replace bone or provide fixation to bone, replace articulating surfaces of a joint, provide abutment for a prosthetic, or combinations thereof. In other embodiments, the implant may be for ear, nose, throat (ENT) applications. Some examples of ENT implants include ear tubes, ventilation tubes, endotracheal tubes, cochlear implants, bone anchored hearing devices. In some embodiments, the surface of an implant may be coated with a compound or composition of the present invention. In some embodiments, a compounds or composition of the present invention may be administered locally at the implant site.

Wound healing hydrogel composition consists of active compound(s), polymers as carrier or gelling agent like ascorbyl palmitate, alginates, polyacrylic acid based polymers, cellulose derivative such as hydroxyethyl cellulose, hydroxypropyl cellulose, hydroxypropylmethyl cellulose, solubilizers such as diethyleneglycolmonoethyl ether, capric/caprylic glycerides, di-isopropyladipate, propylene glycol monolaurateetc, surfactants such as tween 80, poloxamer 407, span 40 etc., various cross linking agents like calcium chloride, calcium sulfate, polyvinyl alcohol, glutaraldehyde etc., preservatives like methyl paraben, propyl paraben, sodium benzoate, phenoxyethanol and antioxidants as per requirement to obtain stable hydrogel formulation. Different additional agents like known bio-film inhibitor or new bio-film inhibitor (compound 141) anti-inflammatory agents or wound healing agents like collagens, growth factors added alone or in combination to obtain hydrogel formulation with good therapeutic efficacy.

Ascorbyl palmitate liposomal hydrogel consists of active compound(s), lipids such as phosphatidylcholine, lecithin, diacetyl phosphate etc and cholesterol. Ascorbyl palmitate specifically increases the packing of phospholipid molecules and reduces the bilayer permeation by any non-electrolyte and electrolyte solutes, thus prevent the vesicles from aggregation. This would help the lipid bilayer more rigid, thereby improves the stability of the formulation. Additional gelling agents such as polyacrylic acid based polymers, cellulose derivative such as hydroxyethyl cellulose, hydroxypropyl cellulose, hydroxypropylmethyl cellulose provides uniformity and proper viscosity to the formulation.

The compounds described herein are also effective for treatment of acute and chronic wounds caused by both Gram positive and Gram negative pathogens. Burn associated wound infections and surgical site wound infections are major wound related infections worldwide. In most of the cases, antiseptic wound dressings, antiseptic hydrogel with silver nanoparticles, silver sulfadiazine (SSD), povidone iodine or chlorhexidine are clinically widely employed. All these antiseptics have demonstrated broad spectrum of activity against both Gram-positive and Gram-negative bacterial species. The non-specific action of these antiseptics have severe side effects for example application of $Ag^+$ has resulted in permanent skin discoloration (argyria), povidone iodine has shown to be toxic to fibroblasts in vitro thus the use of povidone iodine is seriously restricted in wound related infection. Microbial biofilm is one of the serious threats associated with chronic wound infection and requires almost 1000 times higher antibiotic concentration to eradicate the bacteria associated in biofilm formation at wound site. Biofilms are found to be remarkably resistant to both host defenses and systemic antibiotics. Further, the antiseptics both PVP-I and chlorhexidine have been shown to be ineffective at treating biofilm of Pseudomonas aeruginosa and Enterococcus faecalis, both common pathogens found to cause wound infections. Therefore, there is an unmet need to develop new antibiotics that would have broadspectrum activity, would be able to prevent biofilm formation or have the propensity to penetrate through the slime layers of biofilm and destroy the formed biofilm at the infection site. The antibiotics would also provide good hydrophobicity and skin penetration profile. The present invention describes topical formulations of some of the novel antibiotics as described in FORMULAE I-VII in the form of topical hydrogel or polymeric film or wound dressing for prophylactic and treatment of bacterial infection at wound sites with minimum systemic cytotoxicity. The formulation ensures sustained release of the drug over extended time. Other than inhibiting and preventing biofilm, one more important challenge is to promote wound healing.

Thus, the invention also provides topical formulations of the compounds described herein in the form of hydrogel or wound dressing. These formulations can be used to prevent or inhibit biofilm, to kill bacterial pathogen along with good wound healing property. Generally, wound healing hydrogel composition consists of active compound at particular percentage ranges from 0.05-10%, more preferably 0.5-5%, different carrier(s) for encapsulating hydrophobic or hydrophilic substances like sodium alginate, ascorbyl palmitate, gelling agents like polyacrylic acid based polymers, cellulose derivative such as hydroxyethyl cellulose, hydroxypropyl cellulose, hydroxypropylmethyl cellulose, poloxamers, solubilizers such as transcutol-P, capric/caprylic glycerides, diisopropyl adipate, propylene glycol monolaurate etc., humectants like glycerol, propylene glycol, polyethylene glycol etc., cross linking agents such as calcium chloride, calcium sulfate, polyvinyl alcohol, glutaraldehyde etc required for different vehicles and preservatives such as methyl paraben, propyl paraben, sodium benzoate, phenoxyethanol. The formulation can comprise additional components to promote healing at wound surface, such as collagen, proteins, growth factors, etc.

The formulations comprising a compound described herein to be used for in vivo administration are preferably sterile. This is readily accomplished by filtration through, for example, sterile filtration membranes, and other methods known to one of skill in the art.

Without wishing to be bound by a theory, it is noted that Compound 2 is effective against opportunistic pathogens like MRSA and S. epidermidis and can be used in osteomyelitis and has anti-inflammatory activity that can be used in other inflammatory diseases like Rosacea, atopic dermatitis etc. It has low emergence of resistant against S. aureus and S. epidermidis. It shows 2-4×MIC enhancement upto $28^{th}$ generation. Compound 6 is active against QRSA and Gram positive specific pathogens. Compound 10 and 11 are broad spectrum antibiotic work against all kinds of susceptible Gram negative pathogens. Compound 10, 11, 16 are very much potent against QRSA. Compound 11 is active against resistant P. aeruginosa and A. baumanni unlike compound 10 where both compound 10 and 11 have similar structural scaffold. Compound 16 is specifically active against certain Gram negative pathogen like susceptible P. aeruginosa and A. baumanni but failed to act against susceptible E. coli and Enterobacter aurogens. Compound 33 is a broad spectrum antibiotic and work against all susceptible and resistant Gram positive and Gram negative pathogens. This antibiotic can be used for multimodal infections caused by both pathogens. Compound 55 is especially active against all kind of susceptible and resistant Gram positive pathogen and specially against E. faecium and QRSA. Compound 55 is 8 times more active against MRSA than linezolid analogue. Compound 141 is a potent bio-film inhibitor and can be used in combination with any other effective antibiotic to enhance the antibacterial activity against biofilm associated infections. Compound 142 is another effective molecule against Gram positive pathogen (susceptible and resistant) and specially against QRSA and better than linezolid analogue.

SOME SELECTED DEFINITIONS

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials can be used in the practice or testing of the invention, the methods, devices, and materials in this regard are described herein.

As used herein, the term "herein" means the whole of the disclosure and as such is not meant to be limited to a particular section or subsection of the disclosure.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages can mean±5%, ±4%, ±3%, ±2.5%, ±2%, ±1.5%, ±1%, or ±0.5% of the value being referred to.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the phrase "therapeutically-effective amount" or "effective amount" means that amount of a compound described which is effective for producing some desired therapeutic effect in at least a sub-population of cells in a subject at a reasonable benefit/risk ratio applicable to any medical treatment. For example, an amount of a compound administered to a subject that is sufficient to produce a statistically significant, measurable change in at least one symptom of an infection. Determination of a therapeutically effective amount is well within the capability of those skilled in the art. Generally, a therapeutically effective amount can vary with the subject's history, age, condition, sex, as well as the severity and type of the medical condition in the subject, and administration of other agents for treating infection.

As used herein, the term "treatment" refers to administering a composition of the invention to effect an alteration or improvement of the disease or condition, such as an infection. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "subject" or "patient" refers to any organism to which a composition disclosed herein can be administered, e.g., for experimental, diagnostic, and/or therapeutic purposes. Typical subjects include animals (e.g., mammals such as mice, rats, rabbits, non-human primates, and humans) and/or plants. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to with domesticated animals and/or pets.

In some embodiments, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. In some embodiments, the subject can be of European ancestry. In some embodiments, the subject can be of African American ancestry. In some embodiments, the subject can be of Asian ancestry.

As used herein, the term "administer" refers to the placement of a compound or composition described herein into a subject by a method or route which results in at least partial localization of the compound or composition at a desired site such that desired effect is produced. Routes of administration suitable for the methods of the invention include both local and systemic administration. Generally, local administration results in more of the compound or composition being delivered to a specific location as compared to the entire body of the subject, whereas, systemic administration results in delivery to essentially the entire body of the subject In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "wound" refers to physical disruption of the continuity or integrity of tissue structure caused by a physical (e.g., mechanical) force, a biological (e.g., thermic or actinic force), or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. In particular, the term encompasses ulcerations (i.e., ulcers), preferably ulcers of the skin. The term "wound" also includes surgical wounds.

The wound can be acute or chronic. As used herein, the term "chronic wound" refers to a wound that does not fully heal even after a prolonged period of time (e.g., 2 to 3 months or longer). Chronic wounds, including pressure sores, venous leg ulcers and diabetic foot ulcers, can simply be described as wounds that fail to heal. Whilst the exact molecular pathogenesis of chronic wounds is not fully understood, it is acknowledged to be multi-factorial. As the normal responses of resident and migratory cells during acute injury become impaired, these wounds are characterized by a prolonged inflammatory response, defective wound extracellular matrix (ECM) remodelling and a failure of re-epithelialisation.

The wound can be an internal wound, e.g. where the external structural integrity of the skin is maintained, such as in bruising or internal ulceration, or external wounds, particularly cutaneous wounds, and consequently the tissue can be any internal or external bodily tissue. In some embodiment the tissue is skin (such as human skin), i.e. the wound is a cutaneous wound, such as a dermal or epidermal wound.

Wounds can be classified in one of two general categories, partial thickness wounds or full thickness wounds. A partial thickness wound is limited to the epidermis and superficial dermis with no damage to the dermal blood vessels. A full thickness wound involves disruption of the dermis and extends to deeper tissue layers, involving disruption of the dermal blood vessels. The healing of the partial thickness wound occurs by simple regeneration of epithelial tissue. Wound healing in full thickness wounds is more complex.

In some embodiments, the wound is selected from the group consisting of cuts and lacerations, surgical incisions or wounds, punctures, grazes, scratches, compression wounds, abrasions, friction wounds (e.g. nappy rash, friction blisters), decubitus ulcers (e.g. pressure or bed sores); thermal effect wounds (burns from cold and heat sources, either directly or through conduction, convection, or radiation, and electrical sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g. psoriasis and eczema, stomach or intestinal ulcers, oral wounds, including a ulcers of the mouth, damaged cartilage or bone, amputation wounds, corneal lesions, and any combinations thereof.

In some embodiments, the wound can be selected from the group consisting of cuts and lacerations, surgical incisions, punctures, grazes, scratches, compression wounds, abrasions, friction wounds, chronic wounds, ulcers, thermal effect wounds, chemical wounds, wounds resulting from pathogenic infections, skin graft/transplant donor and recipient sites, immune response conditions, oral wounds, stomach or intestinal wounds, damaged cartilage or bone, amputation sites, corneal lesions and lung punctures.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., $(C_6$-$C_{10})$aryl$(C_0$-$C_3)$alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkyls that have a chain of between 1 and 6 carbons and at least one triple bond, e.g., ethynyl, 1-propynyl, 2-propynyl, 1-butynyl, isopentenyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkaline, and alkynylene" radicals. Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo [1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto, and can be represented by one of —O-alkyl, —O— alkenyl, and —O-alkynyl. Representative alkoxyl groups include methoxy, ethoxy, propyloxy, tert-butoxy, n-propyloxy, iso-propyloxy, n-butyloxy, iso-butyloxy, and the like. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example, —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$— pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$— pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino" —NH-(alkyl)-(cycloalkyl), such as —NHCH$_2$— cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH3) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used herein, the term "linker" means an organic moiety that connects two parts of a compound. Linkers typically comprise a direct bond or an atom such as oxygen or sulfur, a unit such as NR$^1$, C(O), C(O)NH, C(O)O, NHC(O)O, OC(O)O, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $NR^1$, C(O), C(O)NH, C(O)O, NHC(O)O, OC(O)O, $SO_2NH$, cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of 5 or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.5, 6.0, 5.5, 5.0, or lower), or by agents such as enzymes that can act as a general acid.

A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as HCl, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-methylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, triethanolamine and the like).

EXAMPLES

The disclosure is further illustrated by the following examples which should not be construed as limiting. The examples are illustrative only, and are not intended to limit, in any manner, any of the aspects described herein. The following examples do not in any way limit the invention.

Example 1: Synthesis of Compound 2

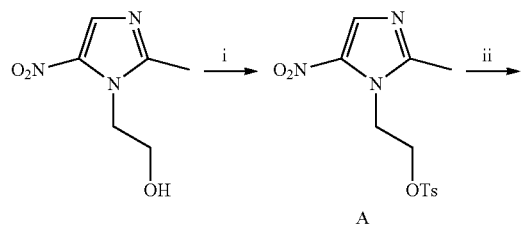

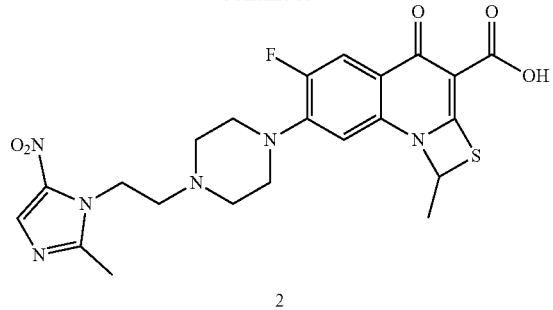

Reagents and conditions:
i) p-Toluenesulfonyl chloride, 4-Dimethylaminopyridine, Et₃N, DCM, 5 h, R.T.;
ii) 6-Fluoro-1-methyl-4-oxo-7-(piperazin-1-yl)-1H,4H-[1,3]thiazeto[3,2-a]quinoline-3-carboxylic acid, Tetrabutylammonium bromide, Et₃N, DMF, 20 h, 90° C.

2-(2-Methyl-5-nitro-1H-imidazol-1-yl)ethyl 4-methylbenzenesulfonate (A)

2-(2-Methyl-5-nitro-1H-imidazol-1-yl)ethan-1-ol (15 g, 88 mmol), 4-dimethylaminopyridine (1.8 g, 15 mmol) and triethylamine (56 ml, 400 mmol) were dissolved in DCM (280 ml) and a solution of p-toluenesulfonyl chloride (23 g, 121 mmol) in DCM was added slowly at 0° C. Then the reaction mixture was stirred at room temperature for 5 hours. After completion, the reaction mixture was successively washed with 5% HCl, saturated sodium bicarbonate solution, brine and finally dried over sodium sulphate. On evaporation of solvent A was obtained as off white solid (27 g, 94%). $^1$H NMR (CDCl$_3$): δ 7.81 (s, 1H, ArH), 7.60 (d, 2H, $J_{AB}$=8.4 Hz, ArH), 7.30 (d, 2H, $J_{AB}$=8.4 Hz, ArH), 4.54 (t, 2H, $J_{AB}$=4.8 Hz, CH$_2$N), 4.37 (t, 2H, $J_{AB}$=4.8 Hz, CH$_2$N), 2.52 (s, 3H, CH$_3$), 2.45 (s, 3H, CH$_3$).

6-Fluoro-1-methyl-7-(4-(2-(2-methyl-5-nitro-1H-imidazol-1-yl)ethyl)piperazin-1-yl)-4-oxo-1H,4H-[1,3]thiazeto[3,2-a]quinoline-3-carboxylic acid (2)

6-Fluoro-1-methyl-4-oxo-7-(piperazin-1-yl)-1H,4H-[1,3]thiazeto[3,2-a]quinoline-3-carboxylic acid (3 g, 8.60 mmol) was suspended in DMF (50 ml) under argon atmosphere and heated at 90° C. After obtaining a clear solution, triethylamine (2.4 ml, 17.10 mmol), compound A (2.12 g, 6.50 mmol) and tetrabutylammonium bromide (107 mg, 0.33 mmol) were added. Then the reaction mixture was heated for another 20 h at 90° C. After completion of the reaction, it was allowed to cool to room temperature and ethyl acetate was added into the reaction mixture. The obtained precipitate was filtered and filtrate was evaporated to dryness. The crude mass was re-dissolved in DCM and methanol and excess amount diethyl ether was added into this solution to obtain a brown mass which was purified by flash column chromatography over silica gel and pure compound 2 was eluted with 3% methanol-DCM mixture as a beige solid (250 mg) with 8% isolated yield. $^1$H NMR (CDCl$_3$): δ 14.23 (brs, 1H, COOH), 7.92 (s, 1H, ArH), 7.89 (d, 1H, $J_{AB}$=12.0 Hz, ArH), 6.38 (d, 1H, $J_{AB}$=8 Hz, ArH), 6.09 (q, 1H, $J_{AB}$=4 Hz, SCHN), 4.51-4.41 (m, 2H, NCH$_2$), 3.26-3.20 (m, 4H, CH$_2$N), 2.74 (t, 2H, $J_{AB}$=4 Hz, NCH$_2$), 2.69-2.67 (m, 4H, CH$_2$N), 2.20 (d, 3H, $J_{AB}$=4 Hz, CH$_3$). ESI-MS (m/z): 503.20 (M+H).

Example 2: Synthesis of Compound 6

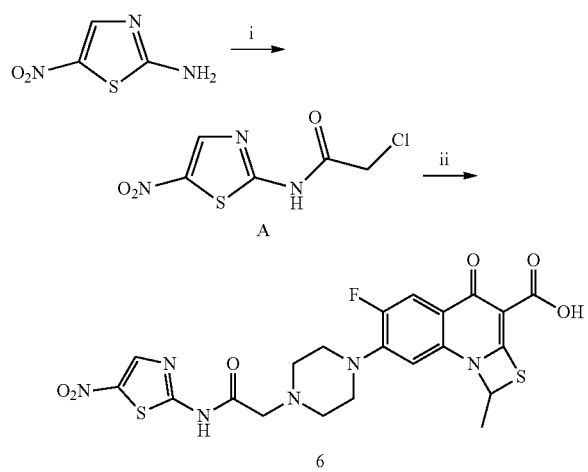

Reagents and condition:
i) Chloroacetyl chloride, Et₃N, CH₃CN, 4 h, R.T.;
ii) 6-Fluoro-1-methyl-4-oxo-7-(piperazin-1-yl)-1H,4H-[1,3]thiazeto[3,2-a]quinoline-3-carboxylic acid, Et₃N, DMF, overnight, R.T.

2-Chloro-N-(5-nitrothiazol-2-yl)-acetamide (A)

To a stirred solution of 5-nitrothiazol-2-amine (2 g, 13.80 mmol) and triethylamine (2.85 ml, 20.60 mmol) in acetonitrile, chloroacetyl chloride (1.44 ml, 17.80 mmol) was added slowly at 0° C. and the reaction mixture was stirred at room temperature for four hours. Then solvent was evaporated at reduced pressure and extracted with ethyl acetate. The organic layer was washed with 1 N HCl, brine and finally dried over sodium sulphate to obtain the compound A which was directly used for next reaction without further purification (2.6 g, 85%). $^1$H NMR (CDCl$_3$): δ 8.29 (s, 1H, ArH), 4.28 (s, 1H, CH$_2$).

6-Fluoro-1-methyl-7-(4-(2-((5-nitrothiazol-2-yl)amino)-2-oxoethyl)piperazin-1-yl)-4-oxo-1H,4H-[1,3]-thiazeto[3,2-a]quinoline-3-carboxylic acid (6)

To a stirred solution of 6-fluoro-1-methyl-4-oxo-7-(piperazin-1-yl)-1H,4H-[1,3]thiazeto[3,2-a]quinoline-3-carboxylic acid (1.70 g, 4.87 mmol) and triethylamine (1.33 ml, 9.62 mmol) in DMF (20 ml), a solution of compound A (1.63 g, 7.33 mmol) in DMF was added and the reaction mixture was stirred at room temperature for overnight. Excess ethyl acetate was added into the reaction mixture and washed with 1N HCl. After evaporation of the organic layer the crude mass was purified by flash column chromatography over silica gel. The compound 6 eluted in 6% methanol-DCM mixture and obtain as yellow solid (514 mg, 20%). $^1$H NMR (DMSO-d$_6$): δ 14.63 (brs, 1H, COOH), 8.61 (s, 1H, ArH), 7.87 (d, 1H, $J_{AB}$=13.6 Hz, ArH), 6.94 (d, 1H, $J_{AB}$=7.2 Hz, ArH), 6.38 (q, 1H, $J_{AB}$=6 Hz, SCHN), 3.57 (s, 2H, COCH$_2$), 2.81-2.66 (m, 4H, NCH$_2$), 2.12 (d, 3H, $J_{AB}$=6 Hz, CH$_3$). ESI-MS (m/z): 535.07 (M+H).

Example 3: Synthesis of Compound 10

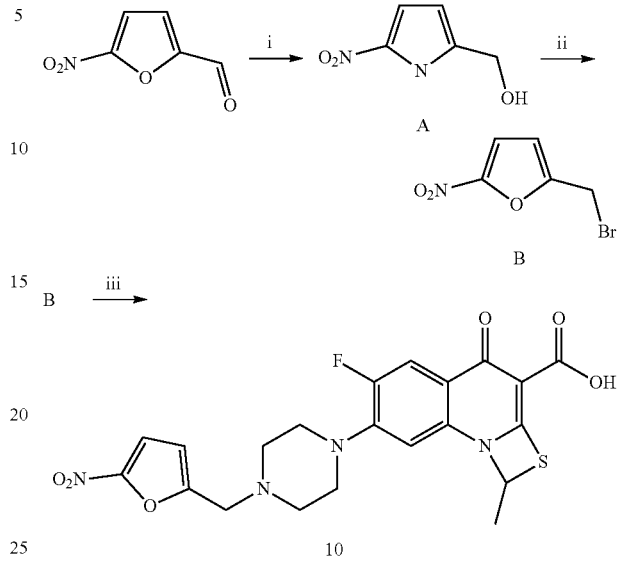

Reagents and conditions:
i) Sodium borohydride, methanol, 1 h, R.T.;
ii) Phosphorus tribromide, DCM, 1 h, R.T.;
iii) 6-Fluoro-1-methyl-4-oxo-7-(piperazin-1-yl)-1H,4H-[1,3]thiazeto[3,2-a]quinoline-3-carboxylic acid, Et₃N, DMF, overnight, R.T.

(5-Nitrofuran-2-yl)methanol (A)

To a solution 5-nitrofuran-2-carbaldehyde (794 mg, 5.63 mmol) in dry methanol (10 ml), sodium borohydride (320 mg, 8.44 mmol) was added in portions at 0° C. Then the reaction mixture was stirred at room temperature for another 1 h. After completion, the reaction mixture was acidified with 3 N HCl and extracted with ethyl acetate. Organic layer was washed with brine, dried over sodium sulphate and finally solvent evaporated under vacuum to obtain the compound A. This was directly used for the next step without further purification (670 mg, 83%).

2-(Bromomethyl)-5-nitrofuran (B)

To a stirred solution of A (928 mg, 6.50 mmol) in DCM (20 ml), phosphorus tribromide (0.80 ml, 8.40 mmol) was added slowly at 0° C. and reaction mixture was stirred at room temperature for one hour. On completion, the reaction mixture was poured into crushed ice, neutralized with sodium bicarbonate solution and extracted with DCM, which on evaporation obtain the compound B (800 mg) in 60% isolated yield. $^1$H NMR (CDCl$_3$): δ 7.29 (d, 1H, $J_{AB}$=3.5 Hz, ArH), 6.65 (d, 1H, $J_{AB}$=3.5 Hz, ArH), 4.49 (s, 2H, CH$_2$).

6-Fluoro-1-methyl-7-(4-((5-nitrofuran-2-yl)methyl)piperazin-1-yl)-4-oxo-1H,4H-[1,3]thiazeto[3,2-a]-quinoline-3-carboxylic acid (10)

To a stirred solution 6-fluoro-1-methyl-4-oxo-7-(piperazin-1-yl)-1H,4H-[1,3]thiazeto[3,2-a]quinoline-3-carboxylic acid (650 mg, 1.86 mmol) and triethylamine (0.39 ml, 2.80 mmol) in DMF (10 ml) a solution of B (480 mg, 2.30 mmol) in DMF was added and reaction mixture was stirred at room temperature for overnight. Excess ethyl acetate was added into the reaction mixture and washed with 1N HCl. The organic layer was evaporated to obtain the crude mass which was purified by silica column chromatography with 3% methanol-DCM eluent to obtain the final compound 10 as a pale yellow solid (450 mg, 50%). $^1$H NMR (DMSO-d$_6$): δ 14.37 (s, 1H, COOH), 7.52 (d, 1H, J$_{AB}$=14 Hz ArH), 7.42 (d, 1H, J$_{AB}$=3.5 Hz, ArH), 6.65 (d, 1H, J$_{AB}$=7.5 Hz, ArH), 6.54 (d, 1H, J$_{AB}$=3.5 Hz, ArH), 6.10 (q, 1H, J$_{AB}$=6 Hz, SCHN), 3.49 (s, 2H, NCH$_2$), 3.07-3.03 (m, 4H, CH$_2$N), 2.39-2.38 (m, 4H, CH$_2$N), 1.83 (d, 3H, J$_{AB}$=5.5 Hz, CH$_3$). ESI-MS (m/z): 475.09 (M+H).

Example 4: Synthesis of Compound 11

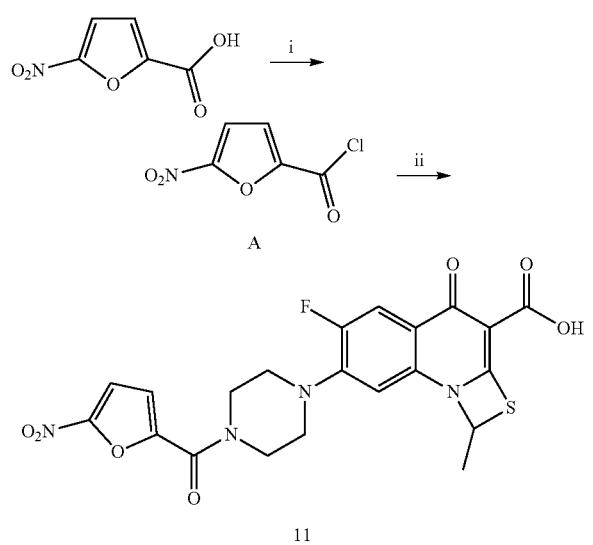

11

Reagents and condition: i) Oxalyl chloride, DCM, 3 h, R.T.; ii) 6-Fluoro-1-methyl-4-oxo-7-(piperazin-1-yl)-1H,4H-[1,3]thiazeto[3,2-a]quinoline-3-carboxylic acid, Et$_3$N, DMF, 18 h, R.T.

5-Nitrofuran-2-carbonyl Chloride (A)

To an ice cold solution of 5-nitrofuran-2-carboxylic acid (450 mg, 2.90 mmol) in DCM (10 ml) oxalyl chloride (2.50 L, 29 mmol) was added followed by addition of catalytic amount of DMF at 0° C. and the reaction mixture was allowed to stir for 3 h at room temperature. On completion, the solvent was evaporated under reduced pressure to obtain the acid chloride A with a quantitative yield (498 mg).

6-Fluoro-1-methyl-7-(4-(5-nitrofuran-2-carbonyl) piperazin-1-yl)-4-oxo-1H,4H-[1,3]thiazeto[3,2-a]-quinoline-3-carboxylic acid (11)

To a stirred solution of 6-fluoro-1-methyl-4-oxo-7-(piperazin-1-yl)-1H,4H-[1,3]thiazeto[3,2-a]quinoline-3-carboxylic acid (1.2 g, 3.44 mmol) in DMF, triethylamine (0.80 ml, 5.7 mmol) was added, followed by addition of A (500 mg, 2.80 mmol) in DMF at 0° C. Then reaction mixture was stirred at room temperature for 18 h. After completion of the reaction excess ethyl acetate was added into the reaction mixture and the solid was filtered out. Upon evaporation of the solvent, the resultant crude was purified by silica column chromatography with 3% methanol-DCM eluent to finally obtain the compound 11 as an off white solid (235 mg, 14%). $^1$H NMR (DMSO-d$_6$): δ 14.63 (brs, 1H, COOH), 7.85 (d, 1H, J$_{AB}$=13.5 Hz, ArH), 7.82 (d, 1H, J$_{AB}$=4 Hz, ArH), 7.36 (d, 1H, J$_{AB}$=4 Hz, ArH), 6.99 (d, 1H, J$_{AB}$=7.5 Hz, ArH), 6.38 (q, 1H, J$_{AB}$=6 Hz, SCHN), 3.98-3.78 (m, 2H, NCH$_2$), 3.46-3.38 (m, 4H, CH$_2$N), 2.13 (d, 3H, J$_{AB}$=6.5 Hz, CH$_3$). ESI-MS (m/z): 489.18 (M+H).

Example 5: Synthesis of Compound 16

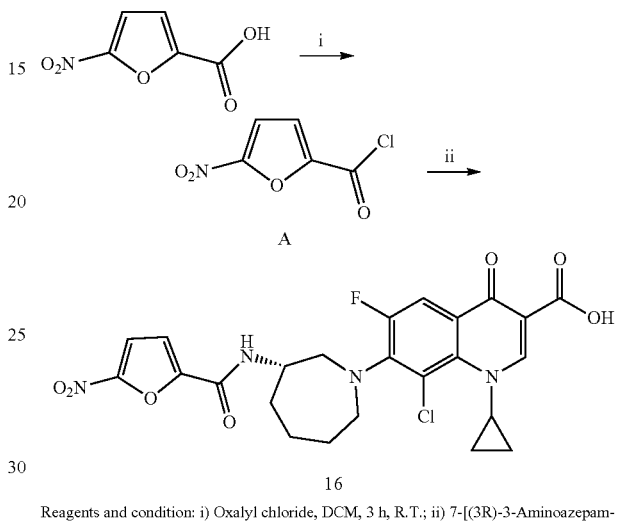

16

Reagents and condition: i) Oxalyl chloride, DCM, 3 h, R.T.; ii) 7-[(3R)-3-Aminoazepam-1-yl]-8-chloro-1-cyclopropyl-6-fluoro-4-oxo-1,4-dihydroquinoline-3-carboxylic acid hydrochloride salt, Et$_3$N, DMF, R.T., 18 h.

5-Nitrofuran-2-carbonyl Chloride (A)

To an ice cold solution of 5-nitrofuran-2-carboxylic acid (450 mg, 2.9 mmol) in DCM (10 ml), oxalyl chloride (2.50 ml, 29 mmol) was added followed by addition of catalytic amount of DMF at 0° C. The reaction mixture was allowed to stir for another three h at room temperature and finally solvent was evaporated under reduced pressure to obtain the compound A with a quantitative yield (498 mg).

7-[(3R)-3-(5-Nitrofuran-2-carboxamido)azepan-1-yl)-1]-8-chloro-1-cyclopropyl-6-fluoro-4-oxo-1,4-dihydroquinoline-3-carboxylic acid (16)

To a suspension of 7-[(3R)-3-aminoazepam-1-yl]-8-chloro-1-cyclopropyl-6-fluoro-4-oxo-1,4-dihydroquinoline-3-carboxylic acid hydrochloride salt (900 mg, 3.28 mmol) and triethylamine (0.88 ml, 6.27 mmol) in DMF, compound A (364 mg, 3.28 mmol) was added at 0° C. and reaction mixture was stirred at room temperature for 16 h. On completion, the solvent was evaporated and extracted with ethyl acetate. The crude solid obtained after evaporation was purified by flash column chromatography over silica gel using 2% DCM-MeOH eluent to obtain 16 as an off white solid (185 mg, 17%). $^1$H NMR (CDCl$_3$): δ 14.23 (brs, 1H, COOH), 8.96 (s, 1H, CH), 8.14 (d, 1H, J$_{AB}$=8 Hz, ArH), 7.72 (brs, 1H, NH), 7.34 (d, 1H, J$_{AB}$=3.5 Hz, ArH), 7.21 (d, 1H, J$_{AB}$=3.5 Hz, ArH), 4.52-4.46 (m, 1H, CpHN), 4.45-4.36 (m, 1H, NCH), 3.86 (d, 2H, J$_{AB}$=15 Hz, NCH$_2$), 3.36-3.18 (m, 4H, CH$_2$N), 2.14-2.06 (m, 2H, CH$_2$), 1.93-1.75 (m, 4H, CH$_2$), 1.46-1.38 (m, 1H, CpCH$_2$), 1.33-1.28 (m, 1H, CpC'H$_2$), 1.24-1.16 (m, 1H, CpCH$_2$), 0.99-0.91 (m, 1H, CpC'H$_2$); ESI-MS (m/z): 555.05 (M+H).

Example 6: Synthesis of Compound 18

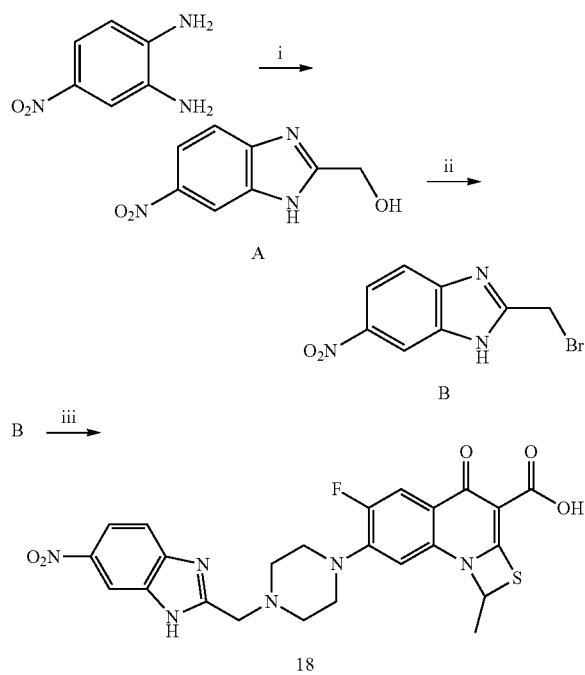

Reagents and condition: i) Glycolic acid, 6N HCl, overnight, reflux; ii) Thionyl bromide, DMF, Benzene, 18 h, reflux; iii) 6-Fluoro-1-methyl-4-oxo-7-(piperazin-1-yl)-1H,4H-[1,3]thiazeto[3,2-a]quinoline-3-carboxylic acid, Et$_3$N, DMF, RT, 18 h.

(6-Nitro-1H-benzoimidazol-2-yl)-methanol (A)

A solution of 1,2-diamino-4-nitrobenzene (5.00 g, 32.60 mol) and glycolic acid (3.72 g, 49 mol) in 6 N hydrogen chloride (50 ml) was refluxed overnight. The reaction mixture was cooled and neutralized with 10% sodium hydroxide solution. The precipitate was filtered and dried to obtain A as a pale brown solid (5 g, 80%). $^1$H NMR (DMSO-d$_6$): δ 13.04 (bs, 1H, NH), 8.37 (s 1H, ArH), 8.07 (d, 1H, dd, J$_{AB}$=10 Hz, ArH), 7.65 (d, 1H, J=5 Hz, ArH), 5.94 (bs, 1H, NH), 4.76 (s, 2H, CH$_2$).

2-(Bromomethyl)-6-nitro-1H-benzo[d]imidazole (B)

To a stirred solution of A (300 mg, 1.55 mmol) in benzene, thionyl bromide (0.16 ml, 2 mmol) and catalytic amount of DMF (0.20 ml) were added at 0° C. and reaction mixture was refluxed for 18 h. After completion the solvent was evaporated and crude was dissolved in DCM. The organic layer was washed with water, dried over sodium sulphate and evaporated under reduced pressure to obtain crude mass which was further purified by silica column chromatography and compound B was obtained in 2% methanol-DCM eluents an off white solid (330 mg, 84%). $^1$H NMR (DMSO-d$_6$): δ 8.48 (d, 1H, J$_{AB}$=2.0 Hz, ArH), 8.14 (dd, 1H, J$_{AB}$=8.75 Hz, J$_m$=2.5 Hz, ArH), 7.74 (d, 1H, J$_{AB}$=9 Hz, ArH), 4.86 (s, 2H, CH$_2$).

6-Fluoro-1-methyl-7-(4-((6-nitro-1H-benzo[d]imidazol-2-yl)methyl)piperazin-1-yl)-4-oxo-1H,4H-[1,3]thiazeto[3,2-a]quinoline-3-carboxylic acid (18)

To a stirred solution of 6-fluoro-1-methyl-4-oxo-7-(piperazin-1-yl)-1H,4H-[1,3]thiazeto[3,2-a]quinoline-3-carboxylic acid (690 mg, 1.98 mmol) in DMF (10 ml), triethylamine (0.55 ml, 3.95 mmol) and compound B (500 mg, 1.97 mmol) were added and the reaction mixture was stirred at room temperature for 18 h. After completion of the reaction excess ethyl acetate was added into the reaction mixture and solids were filtered out. The crude obtained after concentrating the filtrate, was purified by flash column chromatography over silica gel using 8% methanol-DCM eluent to obtain 18 (135 mg, 13%) $^1$H NMR (DMSO-d$_6$): δ 14.65 (brs, 1H, COOH), 13.09 (brs, 1H, NH), 8.47-8.35 (m, 1H, ArH), 8.12-8.08 (m, 1H, ArH), 7.79 (d, 1H, J$_{AB}$=13.5 Hz, ArH), 7.65 (d, 1H, J$_{AB}$=8.5 Hz, ArH), 6.92 (d, 1H, J$_{AB}$=7.0 Hz, ArH), 6.37 (q, 1H, J$_{AB}$=5.5 Hz, SCHN), 3.91 (s, 2H, CH$_2$), 2.76-2.62 (m, 4H, CH$_2$N), 2.01 (d, 3H, J$_{AB}$=6.0 Hz, CH$_3$). ESI-MS (m/z): 525.07 (M+H).

Example 7: Synthesis of Compound 19

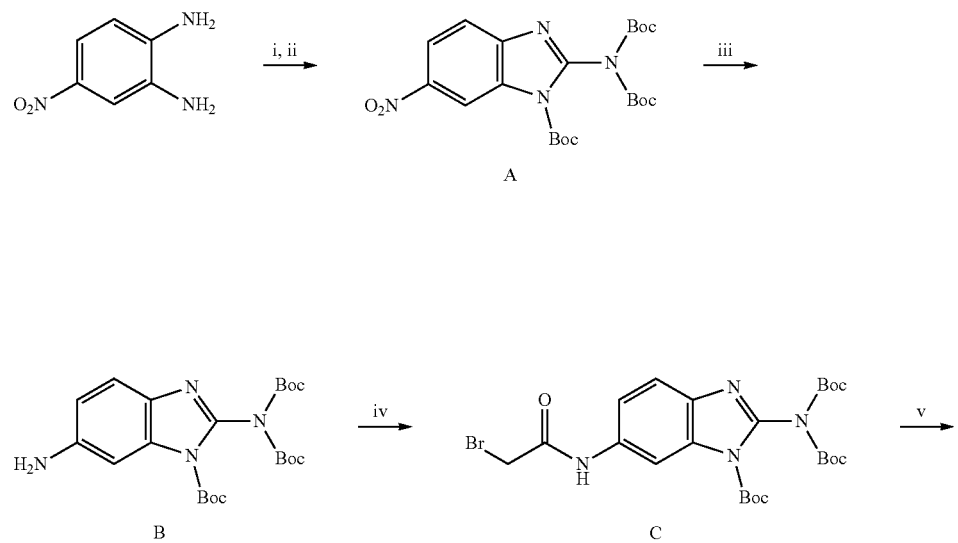

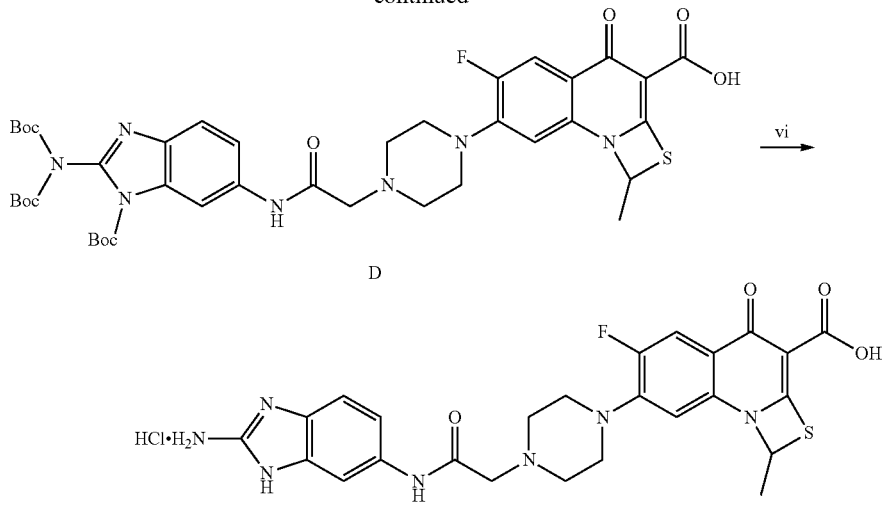

19

Reagents and condition: i) Cyanogen bromide, methanol; ii) Di-tert-butyl-dicarbonate, 4-dimethyl-aminopyridine, THF; iii) Zinc, ammonium chloride, ethanol-H₂O; iv) Bromoacetyl bromide, Et₃N, DCM, v) 6-Fluoro-1-methyl-4-oxo-7-(piperazin-1-yl)-1H,4H-[1,3]thiazeto[3,2-a]quinoline-3-carboxylic acid, Et₃N, DMF, RT, 18 h. vi) 6N HCl, THF, overnight, R.T.

Tris-N-boc 2-amino-4-nitrobenzimidazole (A)

4-Nitro-1,2-phenylenediamine (2.76 g, 17.66 mmol) was suspended in methanol (200 ml) and 5 M cyanogen bromide (4 ml) in acetonitrile was added dropwise over a period of 20 min followed by addition of 50 ml water. The resulting reaction mixture was stirred at room temperature for overnight. At end additional 30 ml water was added into the reaction mixture and was concentrated to about 80 ml. The final mixture was made basic with a saturated NaHCO₃ solution. The yellow precipitate formed was filtered, washed with cold water and dried to obtain 2-amino-4-nitrobenzimidazole as a yellow solid (2.94 g, 93%). $^1$H NMR (DMSO-d₆): δ 11.90 (brs, 1H, NH), 7.87 (d, 1H, $J_{AB}$=2.5 Hz, ArH), 7.81 (1H, dd, $J_{AB}$=11 Hz, $J_m$=2.5 Hz, ArH), 7.12 (1H, d, $J_{AB}$=9 Hz, ArH), 6.87 (s, 2H, NH₂). Di-tert-butyl-dicarbonate (12 ml, 50 mmol) was added into a suspension of 2-amino-4-nitrobenzimidazole (3.6 g, 20 mmol) in THF (200 ml). The mixture was stirred at room temperature for 5 h. Then another portion of di-tert-butyl dicarbonate (12 ml, 50 mmol) and 4-dimethylaminopyridine (250 mg, 2.05 mmol) was added into the reaction mixture. The final mixture was stirred at room temperature for overnight. Finally, the solvent was evaporated and the residue was purified by chromatography over silica gel (eluent: DCM) to obtain the A as an off-white solid which was a mixture of two isomers (6.0 g, 63%). $^1$H NMR (CDCl₃): isomer I: δ 8.96 (d, 1H, $J_{AB}$=2.5 Hz, ArH), 8.29 (dd, 1H, $J_{AB}$=11 Hz, $J_m$=2.5 Hz, ArH), 7.85 (d, 1H, $J_{AB}$=9.0 Hz, ArH), 1.70 (s, 9H, CH₃), 1.42 (s, 18H, CH₃); Isomer II: δ 8.64 (d, 1H, $J_{AB}$=2.0 Hz, ArH), 8.33 (dd, 1H, $J_{AB}$=9.2 Hz, $J_m$=2.0 Hz, ArH), 8.15 (d, 1H, $J_{AB}$=9.0 Hz, ArH), 1.68 (s, 9H, CH₃), 1.42 (s, 18H, CH₃).

Tris-N-boc-2,4-diaminobenzimidazole (B)

To a suspension of A (300 mg, 0.62 mmol) in ethanol-water (3:1, 5 ml), zinc powder (500 mg, 7.5 mmol) and ammonium chloride (400 mg, 7.5 mmol) were added at 0° C. and reaction mixture was stirred at room temperature for two hours. On completion of the reaction, ammonium hydroxide solution was added and inorganic materials were filtered out and filtrate was extracted with DCM and dried over sodium sulphate. On evaporation of the solvent compound B was obtained as white solid (200 mg, 71%)$^1$H NMR (CDCl₃): isomer I: δ 7.74 (d, 1H, $J_{AB}$=8.5 Hz, ArH), 7.00 (d, 1H, $J_{AB}$=2 Hz, ArH), 6.73 (dd, 1H, $J_{AB}$=10 Hz, $J_m$=2.0 Hz, ArH), 1.64 (s, 9H, CH₃), 1.39 (s, 18H, CH₃); Isomer II: δ 7.48 (d, 1H, $J_{AB}$=8.5 Hz, ArH), 7.33 (d, 1H, $J_{AB}$=2 Hz, ArH), 6.71 (dd, 1H, $J_{AB}$=10 Hz, $J_m$=2.0 Hz, ArH), 1.64 (s, 9H, CH₃), 1.39 (s, 18H, CH₃).

Tris-N-boc-N-(2-amino-1H-benzo[d]imidazol-6-yl)-2-bromoacetamide (C)

To a stirred solution of B (1 g, 2.23 mmol) and triethylamine (0.5 ml, 3.60 mmol) in DCM, bromoacetyl bromide (0.25 ml, 3.0 mmol) was added at 0° C. and reaction mixture was stirred at room temperature for four hours. After completion, the reaction mixture was washed with water and organic layer was dried over sodium sulphate to obtain compound C which was used for next step without further purification (1 g, 85%).

Tris-N-boc-7-(4-(2-((2-amino-1H-benzo[d]imidazol-6-yl)amino)-2-oxoethyl)piperazin-1-yl)-6-fluoro-1-methyl-4-oxo-1H,4H-[1,3]thiazeto[3,2-a]quinoline-3-carboxylic acid (D)

To a stirred solution of 6-fluoro-1-methyl-4-oxo-7-(piperazin-1-yl)-1H,4H-[1,3]thiazeto[3,2-a]quinoline-3-carboxylic acid (280 mg, 0.80 mmol) and triethylamine (0.3 ml, 2.16 mmol) in DMF (5 ml), compound C (570 mg, 1 mmol) was added and final solution was stirred at room temperature for overnight. After completion, the solvent was evaporated, extracted with ethyl acetate and washed with water. The organic extract was evaporated to obtain the crude mass which was further purified by flash column chromatography over silica gel using 2% methanol-DCM as eluent to obtain the compound D as an off white solid (220 mg, 48%). $^1$H NMR (DMSO-d$_6$): $^1$H NMR (CDCl$_3$): isomer I: δ 14.66 (s, 1H, COOH), 10.07 (s, 1H, NH), 8.66 (d, 1H, J$_{AB}$=1.5 Hz, ArH), 7.96 (s, 1H, ArH), 7.82 (d, 1H, J$_{AB}$=14.0 Hz, ArH), 7.70-7.66 (m, 1H, ArH), 6.95 (d, 1H, J$_{AB}$=7.0 Hz, ArH), 6.40 (q, 1H, J$_{AB}$=6 Hz, SCHN), 3.44-3.37 (m, 4H, CH$_2$N), 3.29 (s, 2H, CH$_2$), 2.80-2.75 (m, 4H, CH$_2$N), 2.13 (d, 3H, J$_{AB}$=6.0 Hz, CH$_3$), 1.64 (s, 9H, CH$_3$), 1.36 (s, 18H, CH$_3$); Isomer II: δ 14.66 (s, 1H, COOH), 10.01 (s, 1H, NH), 8.15 (d, 1H, J$_{AB}$=1.5 Hz, ArH), 7.90 (d, 1H, J$_{AB}$=9 Hz, ArH), 7.82 (d, 1H, J$_{AB}$=14.0 Hz, ArH), 7.70-7.66 (m, 1H, ArH), 7.51 (dd, 1H, J$_{AB}$=8.5 Hz, J$_m$=1.5 Hz, ArH), 6.95 (d, 1H, J$_{AB}$=7.0 Hz, ArH), 6.40 (q, 1H, J$_{AB}$=6 Hz, SCHN), 3.44-3.37 (m, 4H, CH$_2$N), 3.29 (s, 2H, CH$_2$), 2.80-2.75 (m, 4H, CH$_2$N), 2.13 (d, 3H, J$_{AB}$=6.0 Hz, CH$_3$), 1.64 (s, 9H, CH$_3$), 1.36 (s, 18H, CH$_3$).

7-(4-(2-((2-Amino-1H-benzo[d]imidazol-6-yl)-amino)-2-oxoethyl)piperazin-1-yl)-6-fluoro-1-methyl-4-oxo-1H,4H-[1,3]thiazeto[3,2-a]quinoline-3-carboxylic acid (19)

Compound D (100 mg, 0.12 mmol) was suspended in THF (5 ml) and 6 N HCl (5 ml) was added into the reaction mixture at 0° C. Reaction mixture was stirred at room temperature for overnight and precipitated solid was centrifuged and washed several times with water. After drying 19 was obtained as an off white solid (50 mg, 78%). $^1$H NMR (DMSO-d$_6$): δ (S, 2H, NH$_2$), 7.88 (S, 2H, ArH), 7.85 (d, 2H, J$_{AB}$=13.6 Hz, ArH), 7.42-7.40 (m, 1H, ArH), 7.36-7.33 (m, 1H, ArH), 7.09 (d, 1H, J$_{AB}$=7.2 Hz, ArH), 6.41 (q, 1H, J$_{AB}$=6 Hz, SCHN), 4.34 (s, 2H, CH$_2$) 3.98-3.74 (m, 4H, CH$_2$N), 2.14 (d, 3H, J$_{AB}$=6.0 Hz, CH$_3$). ESI-MS (m/z): 530.12 (M+H).

Example 8: Synthesis of Compound 20

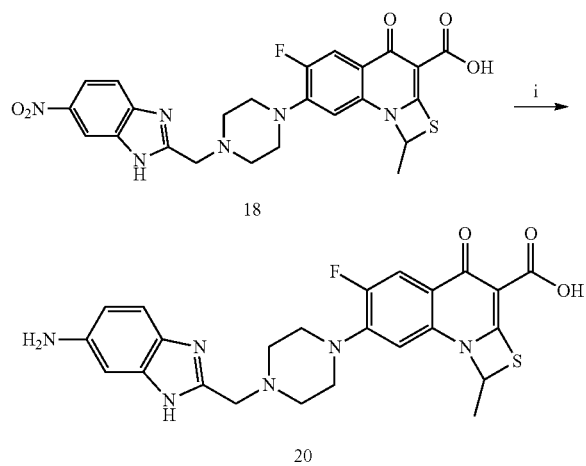

7-(4-((6-Amino-1H-benzo[d]imidazol-2-yl)methyl) piperazin-1-yl)-6-fluoro-1-methyl-4-oxo-1H,4H-[1,3]thiazeto[3,2-a]quinoline-3-carboxylic acid (20)

A mixture of compound 18 (230 mg, 0.44 mmol), activated palladium (10%, 100 mg) were suspended in methanol-DCM (3:1, 20 mL) mixture and stirred at room temperature for overnight under hydrogen atmosphere (2 atm pressure). The mixture was filtered through celite bed, and the solvent was removed under reduced pressure to obtain almost pure 20 as brown solid (80 mg, 40%). $^1$H NMR (DMSO-d$_6$): δ 14.68 (brs, 1H, COOH), 11.79 (brs, 1H, NH), 7.81 (d, 1H, J$_{AB}$=13.5 Hz, ArH), 7.23-7.12 (m, 1H, ArH), 6.93 (d, 1H, J$_{AB}$=7.0 Hz, ArH), 6.66-6.54 (m, 1H, ArH), 6.53-43 (m, 1H, ArH), 6.42-6.36 (m, 1H, SCHN), 4.88 (brs, 2H, NH$_2$), 3.70 (s, 2H, CH$_2$), 2.69-2.61 (m, 4H, CH$_2$N), 2.11 (d, 3H, J$_{AB}$=6.0 Hz, CH$_3$). ESI-MS (m/z): 495.17 (M+H).

Example 9: Synthesis of Compound 21

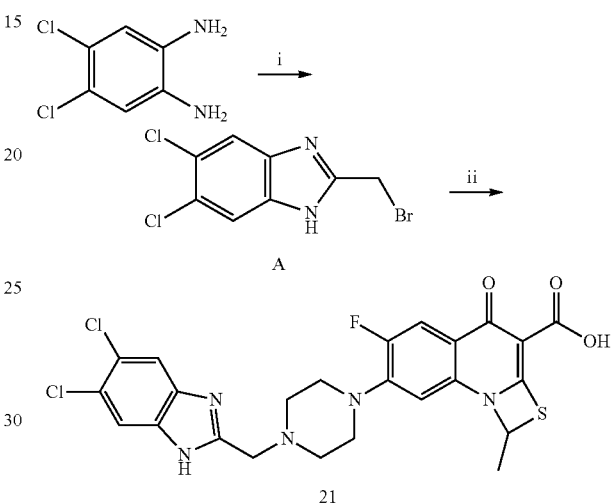

Reagents and condition: i) Bromoacetic acid, 6N HCl, overnight, reflux; ii) 6-Fluoro-1-methyl-4-oxo-7-(piperazin-1-yl)-1H,4H-[1,3]thiazeto[3,2-a]-quinoline-3-carboxylic acid, Et$_3$N, DMF, 18 h, R.T.

2-(Bromomethyl)-5,6-dichloro-1H-benzo[d]imidazole (A)

To a stirred solution of 4,5-dichlorobenzene-1,2-diamine (1 g, 5.65 mmol) in 6 N HCl, bromoacetic acid (2.51 g, 18.08 mmol) was added and reaction mixture was refluxed for overnight. After completion, the reaction mixture was cooled and neutralized with 10% sodium hydroxide solution. The resulting precipitate was filtered and dried to obtain compound A as a beige solid (1.57 g, 64%). $^1$H NMR (DMSO-d$_6$): δ 7.61 (s 1H, ArH), 4.69 (s, 2H, CH$_2$).

7-(4-((5,6-Dichloro-1H-benzo[d]imidazol-2-yl) methyl)piperazin-1-yl)-6-fluoro-1-methyl-4-oxo-1H, 4H-[1,3]thiazeto[3,2-a]quinoline-3-carboxylic acid (21)

To a stirred solution of 6-fluoro-1-methyl-4-oxo-7-(piperazin-1-yl)-1H,4H-[1,3]thiazeto[3,2-a]quinoline-3-carboxylic acid (500 mg, 1.43 mmol) in DMF (10 ml), triethylamine (0.4 ml, 2.86 mmol) and compound A (400 mg, 1.43 mmol) were added and the reaction mixture was stirred at room temperature for 18 h. After completion, excess ethyl acetate was added into the reaction mixture and the obtain solid was filtered and discarded. The filtrate was evaporated to dryness and the crude was purified by flash column chromatography over silica gel using 6% methanol-DCM to obtain final compound 21 as a pale yellow solid (78 mg, 10%). $^1$H NMR (CDCl$_3$+CD$_3$OD): δ 7.78 (d, 1H, J$_{AB}$=13.5

Hz, ArH), 7.62-7.34 (m, 2H, ArH), 6.42 (d, 1H, $J_{AB}$=6.5 Hz, ArH), 6.06 (q, 1H, $J_{AB}$=6 Hz, SCHN), 3.78 (s, 2H, CH$_2$), 3.33-3.28 (m, 4H, CH$_2$N), 2.68-2.62 (m, 4H, CH$_2$N), 2.08 (d, 3H, $J_{AB}$=6.5 Hz, CH$_3$). ESI-MS (m/z): 547.87 (M+H).

Example 10: Synthesis of Compound 31

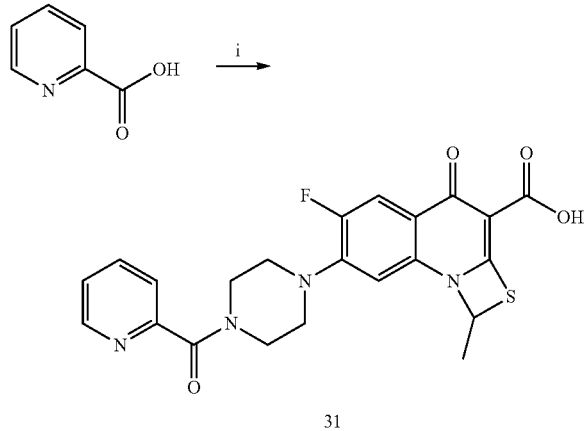

31

Reagents and condition: i) 6-Fluoro-1-methyl-4-oxo-7-(piperazin-1-yl)-1H,4H-[1,3]thiazeto[3,2-a]quinoline-3-carboxylic acid, Hydroxybenzotriazole, 1-Ethyl-3-(3-dimethylaminopropyl)-carbodiimide hydrochloride, N,N-Diisopropylethylamine, DMF, 18 h, R.T.

6-Fluoro-1-methyl-4-oxo-7-(4-picolinoylpiperazin-1-yl)-1H,4H-[1,3]thiazeto[3,2-a]quinoline-3-carboxylic acid (31)

To a stirred solution of 1-ethyl-3-(3-dimethylaminopropyl)carbodiimide hydrochloride (EDC.HCl, 575 mg, 3.0 mmol) in DMF at 0° C., 2-picolinic acid (246 mg, 2.0 mmol) was added followed by addition of hydroxybenzotriazole (HOBt, 405 mg, 3.0 mmol) and the final reaction mixture was stirred at 0° C. After 30 min 6-fluoro-1-methyl-4-oxo-7-(piperazin-1-yl)-1H,4H-[1,3]thiazeto[3,2-a]-quinoline-3-carboxylic acid (700 mg, 2.01 mmol) and N,N-diisopropylethylamine (0.53 ml, 3 mmol) were added and reaction mixture was allowed to stir at room temperature for overnight. After completion, the reaction mixture was evaporated, remaining mass was triturated 2-3 times and dried to obtain compound 31 as an off white solid (250 mg, 28%). $^1$H NMR (DMSO-d$_6$): δ 14.61 (brs, 1H, COOH), 8.62 (d, 1H, $J_{AB}$=4.5 Hz, ArH), 7.96 (t, 1H, $J_{AB}$=7.5 Hz, ArH), 7.82 (d, 1H, $J_{AB}$=13.5 Hz, ArH), 7.64 (d, 1H, $J_{AB}$=7.5 Hz, ArH), 7.52 (dd, 1H, $J_{AB}$=7.0 Hz, J, =5.0 Hz, ArH), 6.98 (d, 1H, $J_{AB}$=7.0 Hz, ArH), 6.36 (q, 1H, $J_{AB}$=6.0 Hz, SCHN), 3.89-3.81 (m, 2H, CH$_2$N), 3.66-3.52 (m, 2H, C'H$_2$N), 2.11 (d, 3H, $J_{AB}$=6.5 Hz, CH$_3$). ESI-MS (m/z): 454.92 (M+H).

Example 11: Synthesis of Compound 32

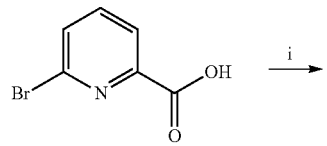

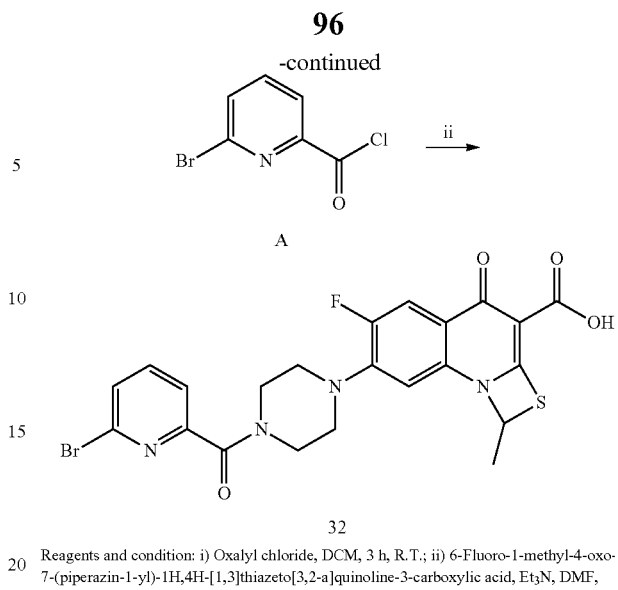

32

Reagents and condition: i) Oxalyl chloride, DCM, 3 h, R.T.; ii) 6-Fluoro-1-methyl-4-oxo-7-(piperazin-1-yl)-1H,4H-[1,3]thiazeto[3,2-a]quinoline-3-carboxylic acid, Et$_3$N, DMF, 18 h, R.T.

6-Bromopicolinoyl Chloride (A)

To a suspension of 6-bromo-pyridin-2-carboxylic acid (500 mg, 2.5 mmol) in DCM (50 ml) oxalyl chloride (0.25 ml, 7.50 mmol) was added dropwise followed by catalytic amount of DMF at 0° C. and allowed to stir the reaction mixture at room temperature for three hours. After completion, the reaction mixture was concentrated under vacuum to obtain the compound A as a yellow solid with a quantitative yield (545 mg).

7-(4-(6-Bromopicolinoyl)piperazin-1-yl)-6-fluoro-1-methyl-4-oxo-1H,4H-[1,3]thiazeto[3,2-a]-quinoline-3-carboxylic acid (32)

To a stirred solution of 6-fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid (700 mg, 2.01 mmol), triethylamine (0.7 ml, 5.0 mmol) in DMF (10 ml), compound A (523 mg, 2.37 mmol) was added at 0° C. After addition, the reaction mixture was stirred at room temperature for overnight. After completion, the reaction mixture was concentrated under vacuum and crude was purified by silica column chromatography using 4% methanol-DCM as eluent to obtain the final compound 32 as a yellow solid (150 mg, 15%). $^1$H NMR (DMSO-d$_6$): δ 14.61 (s, 1H, COOH), 7.93 (t, $J_{AB}$=8 Hz, 1H, ArH), 7.84 (d, 1H, $J_{AB}$=13.5 Hz, ArH), 7.80 (d, 1H, $J_{AB}$=8.0 Hz, ArH), 7.70 (d, 1H, $J_{AB}$=7.5 Hz, ArH), 6.99 (d, 1H, $J_{AB}$=7.0 Hz, ArH), 6.38 (q, 1H, $J_{AB}$=6.0 Hz, SCHN), 3.72-3.58 (m, 2H, CH$_2$N), 3.48-3.40 (m, 2H, C'H$_2$N), 2.13 (d, 3H, $J_{AB}$=6.5 Hz, CH$_3$). ESI-MS (m/z): 532.81 (M+H).

Example 12: Synthesis of Compound 33

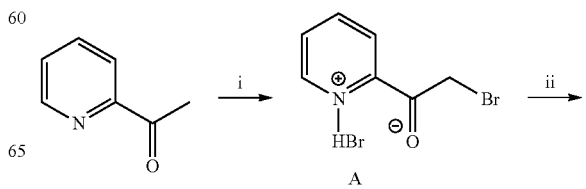

97

-continued

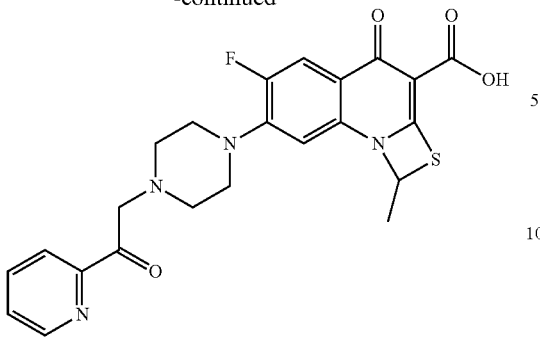

33

Reagents and condition: i) Bromine, CCl₄, reflux; ii) K₂CO₃,; 6-Fluoro-1-methyl-4-oxo-7-(piperazin-1-yl)-1H,4H-[1,3]thiazeto[3,2-a]quinoline-3-carboxylic acid, Et₃N, DMF, 18 h, R.T.

(2-Bromoacetyl)pyridin-1-ium bromide (A)

To a stirred solution of 1-(pyridin-2-yl)ethan-1-one (2.0 g, 16.6 mmol) in CCl₄ (60 ml), bromine (2.7 g, 16.60 mmol) was added dropwise. After complete addition the final reaction mixture was refluxed for 1 h. The precipitate was collected by filtration and washed 2-3 times with diethylether and dried to obtain compound A as a beige solid (2.94 g, 93%).

6-Fluoro-1-methyl-4-oxo-7-(4-(2-oxo-2-(pyridin-2-yl)ethyl)piperazin-1-yl)-2a,3-dihydro-1H,4H-[1,3]thiazeto[3,2-a]quinoline-3-carboxylic acid (33)

To a suspended solution of 6-fluoro-1-methyl-7-(4-((5-nitro-1H-benzo[d]imidazol-2-yl)methyl)piperazin-1-yl)-4-oxo-1H,4H-[1,3]thiazeto[3,2-a]-quinoline-3-carboxylic acid (1.05 g, 3 mmol) and potassium carbonate (1.25 g, 9 mmol) in DMF, compound A (850 mg, 3 mmol) was added and the reaction mixture was stirred at room temperature for overnight. On completion, the final reaction mixture was poured into water and pH of the medium was adjusted to neutral by adding 1N HCl. Obtained precipitate was filtered, washed with water, ethyl acetate and dried to obtain 33 as an off white solid (700 mg, 50%). ¹H NMR (DMSO-d₆): δ 14.56 (brs, 1H, COOH), 8.67 (d, 1H, $J_{AB}$=4.0 Hz, ArH), 8.14 (s, 1H, ArH), 7.98-7.42 (m, 1H, ArH), 7.79 (d, 1H, $J_{AB}$=14.0 Hz, ArH), 7.62-7.58 (m, 1H, ArH), 6.88 (d, 1H, $J_{AB}$=6.0 Hz, ArH), 6.38 (q, 1H, $J_{AB}$=6.0 Hz, SCHN), 4.2 (s, 2H, CH₂), 3.43-3.35 (m, 4H, CH₂N), 2.87-2.77 (m, 4H, CH₂N), 2.14 (d, 3H, $J_{AB}$=6.0 Hz, CH₃). ESI-MS (m/z): 469.08 (M+H).

Example 13: Synthesis of Compound 34

98

-continued

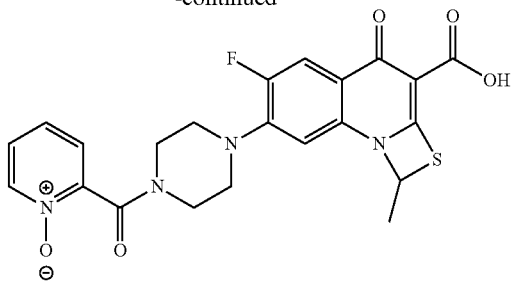

34

Reagents and condition: i) Hydrogen peroxide (30%, w/w) TFA, reflux; ii) 6-Fluoro-1-methyl-4-oxo-7-(piperazin-1-yl)-1H,4H-[1,3]thiazeto[3,2-a]quinoline-3-carboxylic acid, Hydroxybenzotriazole, 1-Ethyl-3-(3-dimethylaminopropyl)-carbodiimide hydrochloride, N,N-Diisopropylethylamine, DMF, 18 h, R.T.

2-Carboxypyridine 1-oxide (A)

2-Picolinic acid (1.23 g, 10 mmol) was suspended in trifluoroacetic acid (25 ml) and hydrogen peroxide (30% w/w, 16 ml) was added into it. The final reaction mixture was refluxed for 16 h. At end, all the volatiles were evaporated under reduced pressure and crude mass was washed 2-3 times with cold water. Upon drying under vacuum compound A was obtained as a white solid (1 g, 72%).

2-(4-(3-Carboxy-6-fluoro-1-methyl-4-oxo-1H,4H-[1,3]thiazeto[3,2-a]quinolin-7-yl)piperazine-1-carbonyl)pyridine-1-oxide (34)

To a stirred solution of 1-ethyl-3-(3-dimethylaminopropyl)-carbodiimide hydrochloride (EDC.HCl, 575 mg, 3 mmol) in DMF at 0° C., compound A (278 mg, 2.0 mmol) was added, followed by hydroxybenzotriazole (HOBt, 405 mg, 3 mmol). The reaction mixture was stirred at 0° C. for 30 min and 6-fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid (700 mg, 2.01 mmol) and N,N-diisopropylethylamine (DIPEA 0.35 ml, 3 mmol) were added and the resultant solution was allowed to stir at room temperature for overnight. After completion of the reaction DMF was evaporated and crude mass was digested with methanol, obtained precipitate was filtered and dried to obtain crude, which was further purified by silica column chromatography using 20% methanol-DCM eluent to obtain the final compound 34 as an off white solid (113 mg, 12%). ¹H NMR (CD₃OD-CDCl₃): δ 8.18 (d, 1H, $J_{AB}$=4 Hz, ArH), 7.86-7.83 (m, 1H, ArH), 7.47-7.43 (m, 2H, ArH), 7.35 (s, 1H, ArH), 6.58-6.55 (m, 1H, ArH), 6.18-6.011 (m, 1H, SCHN), 3.79-3.51 (m, 4H, CH₂N), 3.39-3.36 (m, 4H, CH₂N), 2.13 (d, 3H, $J_{AB}$=4.0 Hz, CH₃). ESI-MS (m/z): 470.94 (M+H).

Example 14: Synthesis of Compound 43

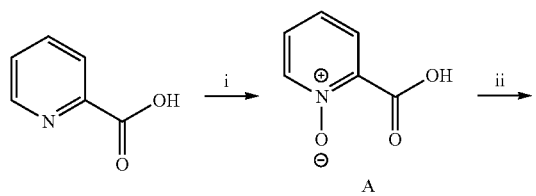

A

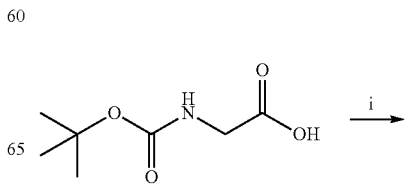

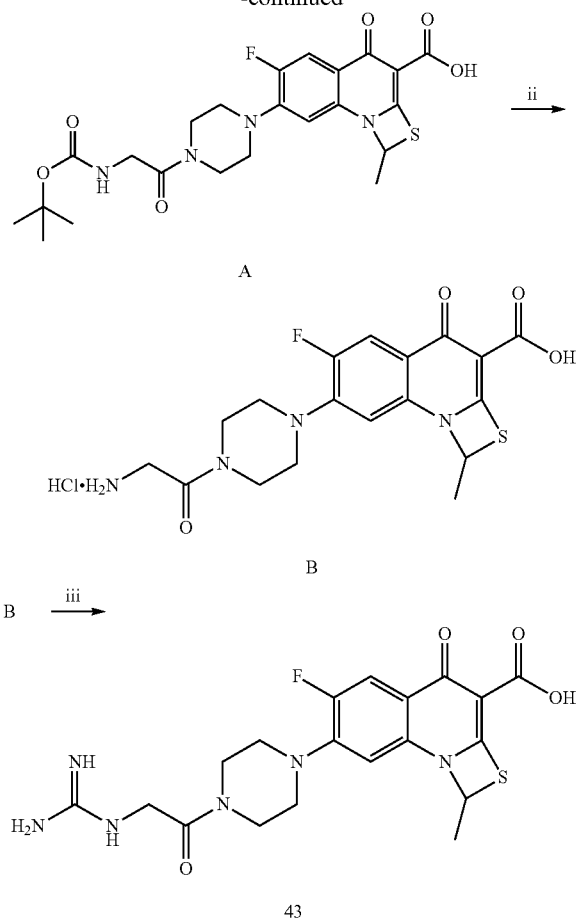

7-(4-((tert-Butoxycarbonyl)glycyl)piperazin-1-yl)-6-fluoro-1-methyl-4-oxo-1H,4H-[1,3]thiazeto[3,2-a]quinoline-3-carboxylic acid (A)

To a stirred solution of DCC (0.9 g, 4.3 mmol) in DMF (20 ml), BOC-glycine (0.5 g, 2.85 mmol) and hydroxybenzotriazole (HOBt, 0.5 g, 4.3 mmol) were added at 0° C. and the mixture was allowed to stir for 4 h, followed by addition of 6-fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid (0.9 g, 2.85 mmol) and triethylamine (0.4 g, 0.6 ml, 4.3 mmol) at 0° C. The reaction mixture was allowed to stir for overnight at room temperature. After completion, the final solution was then concentrated under reduced pressure to obtain the crude product which was purified by flash column chromatography over silica gel using 3% methanol-DCM as eluent to afford compound A as pale yellow solid (0.75 g, yield: 65%). $^1$H NMR (DMSO-$d_6$): δ 14.62 (brs, 1H, COOH), 7.84 (d, 1H, $J_{AB}$=14.0 Hz, ArH), 6.95 (d, 1H, $J_{AB}$=7.0 Hz, ArH), 6.81 (t, 1H, $J_{AB}$=6.0 Hz, NH), 6.39 (q, 1H, $J_{AB}$=6.5 Hz, SCHN), 3.85 (d, 2H, $J_{AB}$=6.0 Hz, CH$_2$), 3.64-3.56 (m, 4H, CH$_2$N), 2.12 (d, 3H, $J_{AB}$=6.0 Hz, CH$_3$). ESI-MS (m/z): 495.16 (M+H).

6-Fluoro-7-(4-glycylpiperazin-1-yl)-1-methyl-4-oxo-1H,4H-[1,3]thiazeto[3,2-a]quinoline-3-carboxylic acid (B)

A suspension of compound A (950 mg, 1.88 mmol) in 6N HCl (20 mL) was stirred for overnight, after which solvent was evaporated and crude mass was dissolved in methanol-dichloromethane followed by addition of diethyl ether, to obtain the precipitated solid. This process was repeated 2-3 times and finally the solid was washed with cold dichloromethane to obtain almost pure compound B as yellow solid (500 mg, 66%).

7-(4-(Carbamimidoylglycyl)piperazin-1-yl)-6-fluoro-1-methyl-4-oxo-1H,4H-[1,3]thiazeto[3,2-a]quinoline-3-carboxylic acid (43)

To a solution of compound B (70 mg, 0.17 mmol) in ethanol (5 mL), S-methylisothiourea hemisulfate (30 mg, 0.2 mmol) was added and the reaction mixture was refluxed for overnight. After completion of the reaction, the obtained precipitate was centrifuged and washed several times with cold ethanol and dried to obtain pure compound 43 as yellow solid (46 mg, 60%).

Example 15: Synthesis of Compound 44

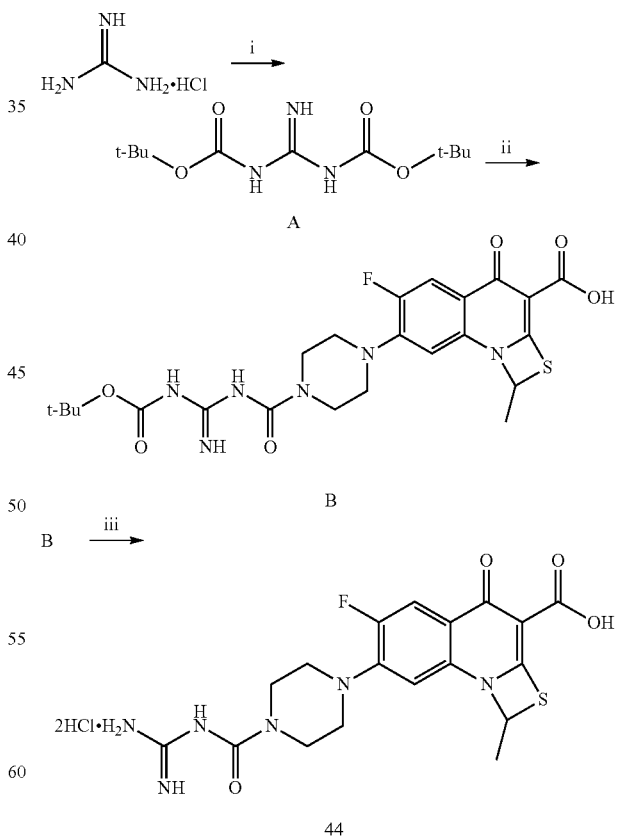

Reagents and condition: i) Di-tert-butyl dicarbonate, NaOH, H$_2$O, 16 h, R.T.; ii) 6-Fluoro-1-methyl-4-oxo-7-(piperazin-1-yl)-1H,4H-[1,3]thiazeto[3,2-a]quinoline-3-carboxylic acid, DMF, 18 h, 80° C.; iii) 6N HCl, THF, overnight, R.T.

Di-(tert-butoxycarbonyl)-guanidine (A)

Guanidine hydrochloride (1.23 g, 12.80 mmol) and sodium hydroxide (2.10 g, 52.5 mmol) were dissolved in water (15 ml), 1,4-dioxane (25 ml) mixture. The mixture was cool at 0° C. and Di-tert-butyl dicarbonate (6.3 g, 28.90 mmol) was added slowly into the solution. The mixture was allowed to stir at room temperature for 16 h. The reaction mixture was concentrated under vacuum to one-third of its initial volume and extracted with ethyl acetate. The organic phase was then washed with 10% citric acid, water and brine, dried over anhydrous sodium sulfate and concentrated under reduced pressure to obtain compound A which was used for the next step without further purification.

7-(4-((N-(tert-butoxycarbonyl)carbamimidoyl)carbamoyl)piperazin-1-yl)-6-fluoro-1-methyl-4-oxo-1H,4H-[1,3]thiazeto[3,2-a]quinoline-3-carboxylic acid (B)

To a stirred solution of 6-fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid (350 mg, 1 mmol) in DMF (5 ml), compound A (260 mg, 1 mmol) was added and reaction mixture was heated at 80° C. for overnight. After completion of the reaction, solvent was evaporated and crude was purified by silica column chromatography with 4% methanol-DCM as eluent to obtain the compound B (320 mg, 60%).

7-(4-(Carbamimidoylcarbamoyl)piperazin-1-yl)-6-fluoro-1-methyl-4-oxo-1H,4H-[1,3]thiazeto[3,2-a]quinoline-3-carboxylic acid (44)

Compound B (200 mg, 0.37 mmol) was dissolved in THF (10 mL) and 6 N HCl (10 ml) was added into the reaction mixture at 0° C. The final solution was stirred at room temperature for overnight. After completion, solvent was evaporated under reduced pressure and obtained mass was washed 2-3 times with cold water and dried to obtained compound 44 as an off white solid (100 mg, 62%). $^1$H NMR (DMSO-d$_6$): δ 14.62 (brs, 1H, COOH), 11.06 (brs, 1H, NH), 8.62 (brs, 2H, NH$_2$), 8.26 (brs, 2H, NH$_2$), 7.83 (d, 1H, $J_{AB}$=13.5 Hz, ArH), 6.99 (d, $J_{AB}$=5.5 Hz, ArH), 6.48-6.32 (m, 1H, SCHN), 3.98-3.56 (m, 4H, CH$_2$N), 2.12 (d, 3H, $J_{AB}$=5.5 Hz, CH$_3$). ESI-MS (m/z): 434.93 (M+H).

Example 16: Synthesis of Compound 48

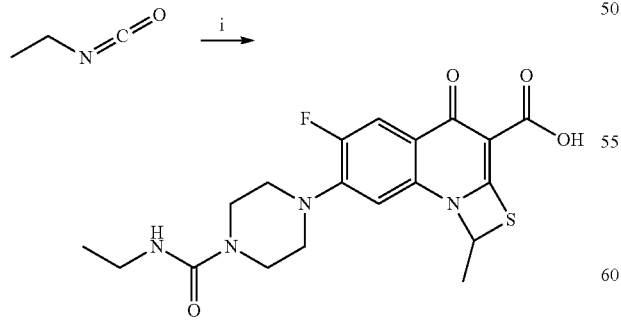

48

Reagents and condition: i) Ethyl isocyanate, 6-Fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid, THF, overnight, reflux.

7-(4-(Ethylcarbamoyl)piperazin-1-yl)-6-fluoro-1-methyl-4-oxo-1H,4H-[1,3]thiazeto[3,2-a]quinoline-3-carboxylic acid (48)

To a stirred solution of 6-fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid (0.3 g, 0.86 mmol) in anhydrous THF (8 ml), ethyl isocyanate (0.05 mL, 0.57 mmol in 2 ml THF) was added dropwise and allowed to reflux for overnight at 80° C. After completion, the reaction mixture was concentrated under reduced pressure to obtain the crude product, washed with cold water (4-5 times), filtered to afford pure 48 as yellow solid (270 mg, yield: 75%). $^1$H NMR (DMSO-d$_6$): δ 7.83 (d, 1H, $J_{AB}$=13.0 Hz, ArH), 6.65 (s, 1H, ArH), 5.74 (s, 2H, SCHN, NH), 3.52-3.42 (m, 4H, CH$_2$N), 3.133-3.08 (m, 2H, CH$_2$N), 2.12 (d, 3H, $J_{AB}$=6.0 Hz, CH$_3$), 1.04 (t, 3H, $J_{AB}$=7.0 Hz, CH$_3$). ESI-MS (m/z): 421.16 (M+H).

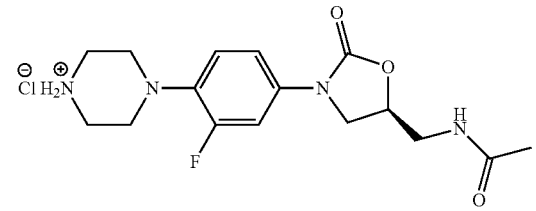

Linezolid Analogue (LA)
(S)-N-((3-(3-fluoro-4-(piperazin-1-yl)phenyl)-2-oxooxazolidin-5-yl)methyl)acetamidehydrochloride (LA)

The linezolid analogue (LA) has been synthesized according to the procedure mentioned in the literature "Syntheses and biological evaluation of new cephalosporin-oxazolidinone conjugates", Shanshan Yan, Marvin J. Miller, Timothy A. Wencewicza and Ute Millmannb, *Med. Chem. Commun.*, 2010, 1, 145-148.

$^1$H NMR (CD$_3$OD): δ 7.57 (dd, 1H, $J_{AB}$=11.6 Hz, J, =2 Hz, ArH), 7.23 (dd, 1H, $J_{AB}$=7 Hz, $J_m$=2 Hz, ArH), 7.14 (t, 1H, $J_{AB}$=7.2 Hz, ArH), 4.83-4.78 (m, 1H, CHOCO), 4.14 (t, 1H, $J_{AB}$=7.2 Hz, CH$_2$NHCO), 3.84-3.81 (m, 1H, CH$_2$NHCO), 3.58 (d, 2H, $J_{AB}$=4 Hz, CH$_2$NCO), 3.42-3.40 (m, 4H, CH$_2$N—Ar), 3.34-3.33 (m, 4H, CH$_2$NH), 1.98 (s, 3H, CH$_3$). ESI-MS (m/z): 337 (M+H). Specific rotation, $[\alpha]_\lambda^T$=-11.11° at 28.7° C. and 589 nm at 9 mg/ml chloroform solution (0.9%).

Example 17: Synthesis of Compound 55

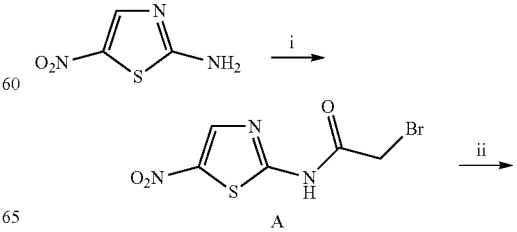

-continued

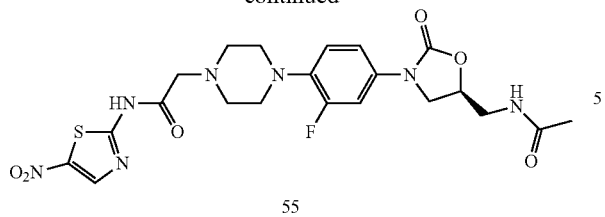

55

Reagents and condition: i) Bromoacetyl bromide, Et₃N, CH₃CN, 4 h, R.T.; ii) (S)-N-((3-(3-fluoro-4-(piperazin-1-yl)phenyl)-2-oxooxazolidin-5-yl)methyl)acetamide hydrochloride (LA, Linezolid Analogue), Et₃N, DMF, overnight, R.T.

2-Bromo-N-(5-nitrothiazol-2-yl)acetamide (A)

To a stirred solution of 5-nitrothiazol-2-amine (2 g, 13.80 mmol) and triethylamine (2.85 ml, 20.60 mmol) in acetonitrile, bromoacetyl bromide (1.55 ml, 17.80 mmol) was added slowly at 0° C. After completion of the addition, the reaction mixture was stirred at room temperature for four hours. Then solvent was evaporated at reduced pressure and extracted with ethyl acetate. The organic layer was washed with 1 N HCl followed by brine and dried over sodium sulphate and evaporated to dryness to obtain A which was used for next reaction without further purification (2.6 g, 85%).

(S)-2-(4-(4-(5-(Acetamidomethyl)-2-oxooxazolidin-3-yl)-2-fluorophenyl)piperazin-1-yl)-N-(5-nitrothiazol-2-yl)acetamide (55)

To a stirred solution of LA (0.15 g, 0.4 mmol) and triethylamine (0.4 ml, 2.85 mmol) in DMF (10 ml), a solution of compound A (0.28 g, 1.08 mmol) in DMF was added and reaction mixture was stirred at room temperature for overnight. After successful completion, the reaction mixture was extracted with excess ethyl acetate and washed with 1N HCl. The organic layer was concentrated and crude mass was purified by flash column chromatography over silica gel with 4% methanol-DCM eluent to obtain 55 as pale yellow solid (45 mg, 25.8%). $^1$H NMR (DMSO-d₆): δ 8.92 (brs, 1H, NH), 8.60 (s, 1H, ArH), 8.19 (t, 1H, $J_{AB}$=4.8, NH), 7.48 (dd, 1H, $J_{AB}$=11.8 Hz, J, =1.6 Hz, ArH), 7.18 (dd, 1H, $J_{AB}$=8 Hz, $J_m$=3.6 Hz, ArH), 7.10 (t, 1H, $J_{AB}$=7.6 Hz, ArH), 4.72-4.68 (m, 1H, CHOCO), 4.08 (t, 1H, $J_{AB}$=7.2 Hz, CH₂NHCO), 3.72-3.69 (m, 1H, CH₂NHCO), 3.58 (s, 2H, COCH₂N), 3.40 (t, 2H, $J_{AB}$=4 Hz, CH₂NCO), 3.08-3.05 (m, 4H, CH₂N—Ar), 2.88-2.81 (m, 4H, CH₂NH), 1.83 (s, 3H, CH₃). ESI-MS (m/z): 522.07 (M+H). Specific rotation, $[\alpha]_\lambda^T$=-2.22° at 30.6° C. and 589 nm at 9 mg/mL 1:1 chloroform:methanolmixture, (0.9%).

Example 18: Synthesis of Compound 57

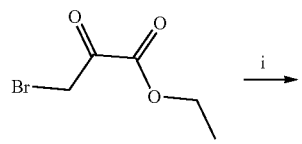

-continued

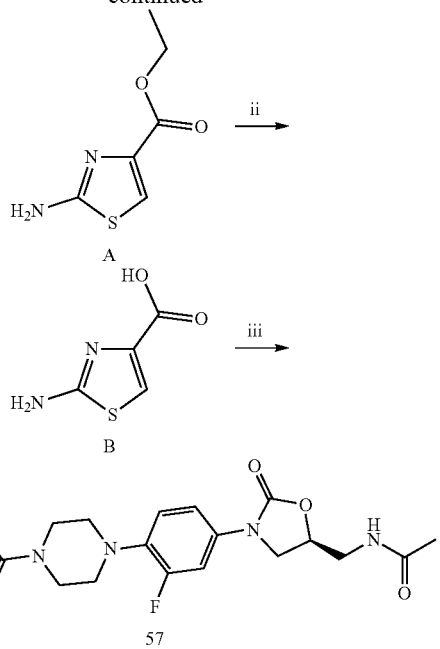

57

Reagents and condition: i) Thiourea, Ethanol, overnight, reflux; ii) 10%, NaOH, overnight, R.T.; iii) (S)-N-((3-(3-fluoro-4-(piperazin-1-yl)phenyl)-2-oxooxazolidin-5-yl)methyl)acetamide hydrochloride (LA, Linezolid Analogue), Hydroxybenzotriazole, 1-Ethyl-3-(3-dimethylaminopropyl)-carbodiimide hydrochloride (EDC·HCl), N,N-diisopropylethylamine, DMF, 18 h, R.T.

Ethyl 2-aminothiazole-4-carboxylate (A)

A stirred solution of ethyl bromopyruvate (0.97 g, 0.62 ml, 8.54 mmol) in ethanol was reacted with thiourea (0.5 g, 6.57 mmol) and the reaction mixture was refluxed overnight. After completion the final solution was concentrated under reduced pressure and the resultant residue was extracted with ethyl acetate, washed with brine, and dried over sodium sulphate. The crude mass was purified by flash column chromatography over silica gel with 4% methanol-DCM eluent to obtain compound A as pale yellow solid (0.88 g, 85%). $^1$H NMR (DMSO-d₆): δ 7.45 (s, 1H, ArH), 7.21 (brs, 2H, NH), 4.19 (q, 2H, $J_{AB}$=7.0 Hz, CH₂), 1.25 (t, 3H, $J_{AB}$=7.5 Hz, CH₃).

2-Aminothiazole-4-carboxylic acid (B)

A suspension of compound A (500 mg, 2.9 mmol) in 10% aqueous sodium hydroxide solution (10 ml) was stirred at room temperature for overnight. After completion the reaction was cooled and pH of the medium was adjusted to 1 by 1N HCl. The obtained precipitated mass was filtered off, washed with cold water, and finally dried to obtain compound B as an off white solid (400 mg, 96%). $^1$H NMR (DMSO): δ 7.41 (s, 1H, ArH), 7.34 (brs, 2H, NH₂).

(S)—N-((3-(4-(4-(2-aminothiazole-4-carbonyl)piperazin-1-yl)-3-fluorophenyl)-2-oxooxazolidin-5-yl)methyl)acetamide (57)

To a stirred solution of 1-ethyl-3-(3-dimethylaminopropyl)-carbodiimide hydrochloride (EDC.HCl, 134 mg, 0.7 mmol) in DMF at 0° C., compound B (95 mg, 0.65 mmol) was added, followed by hydroxybenzotriazole (HOBt, 95 mg, 0.7 mmol). The reaction mixture was stirred at 0° C. for 30 min and LA (200 mg, 0.54 mmol) and N,N-diisopropylethylamine (DIPEA 0.7 ml, 6 mmol) were added and the resultant solution was allowed to stir at room temperature for overnight. After completion of the reaction DMF was evaporated and crude mass was purified by silica column chromatography using 4% methanol-DCM eluent to obtain the final compound 57 as an off white solid (29.9 mg, 12%). $^1$H NMR (DMSO-$d_6$): δ 8.27 (t, 1H, $J_{AB}$=6.0 Hz, NH), 7.53-7.49 (m, 2H, ArH), 7.19 (dd, 1H, $J_{AB}$=7.5, $J_m$=2.0 Hz, ArH), 7.09 (t, 1H, $J_{AB}$=9.0 Hz, ArH), 4.74-4.69 (m, 1H, CHOCO), 4.09 (t, 1H, $J_{AB}$=7.2 Hz, $CH_2NHCO$), 3.99-3.88 (m, 1H, $CH_2NHCO$), 3.73-3.70 (m, 2H, $CH_2NCO$), 3.12 (q, 4H, $J_{AB}$=7.5 Hz $CH_2N$—Ar), 3.03-2.92 (m, 4H, $CH_2$—N), 1.84 (s, 3H, $CH_3$). ESI-MS (m/z): 462.9 (M+H). Specific rotation, $[α]_λ^T$=−2.22° at 30.6° C. and 589 nm at 9 mg/mL 1:1 chlorofom:methanol mixture, (0.9%).

Example 19: Synthesis of Compound 58

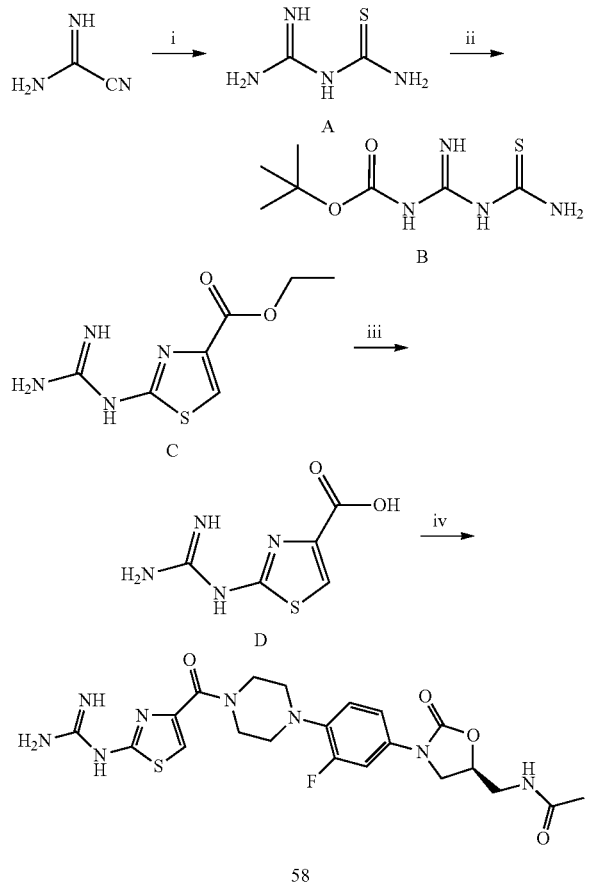

Reagents and condition: i) Concentrated HCl, Sodium thiosulfate pentahydrate, Ammonium hydroxide (aqueous $NH_3$), 1 h, 10-20° C.; ii) Di-tert-butyl dicarbonate, DMF, 4-Dimethylaminopyridine, 20 h, R.T; iii) Ethyl bromopyruvate, acetone, 20 h, 0° C. R.T.; iv) 10%, NaOH, overnight, R.T.; v) (S)-N-((3-(3-fluoro-4-(piperazin-1-yl)phenyl)-2-oxooxazolidin-5-yl)methyl)acetamide hydrochloride (LA, Linezolid Analogue), Hydroxybenzotriazole, 1-ethyl-3-(3-dimethylaminopropyl)-carbodiimide hydrochloride (EDC•HCl), N,N-diisopropylethylamine, DMF, 18 h, R.T.

1-[Amino(imino)methyl]thiourea (Guanylthiourea) (A)

To a solution of dicyandiamide (1 g, 1.9 mmol) in water (250 ml) conc. HCl (2.38 ml) was added dropwise over a period of 10 minutes by maintaining the reaction temperature below 20° C. With continued stirring, a solution of sodium thiosulfate pentahydrate (2.98 g, 1.9 mmol) in water (125 ml) was added dropwise over 30 minutes, by then the nearly insoluble gutimine hydrogen sulfate was precipitated out. After that pH of the mixture was adjusted to 8-10 by addition of ammonium hydroxide (2.86 ml, 25%) at 0° C. The obtained precipitate was collected, washed with cold water and dried to obtain 2.25 g (80%) of compound A as colorless crystals. $^1$H NMR (DMSO-$d_6$): δ 7.15 (brs, 3H, NH), 6.99 (brs, 3H, NH).

tert-Butyl {[(aminocarbonothioyl)amino](imino) methyl}carbamate (B)

A solution of di-tert-butyl dicarbonate (1.7 g, 7.8 mmol) in DMF—(10 ml) was added dropwise over 1 h to a mixture of compound A (1 g, 7.8 mmol) and 4-dimethylaminopyridine (85 mg, 0.7 mmol) in DMF (10 ml). After complete addition the mixture was stirred for 20 h at 35° C. The mixture was concentrated in vacuo and the residue was manually shaken with water (10 ml). The precipitate starts coming within 1 min and manual shaking was continued for another 6 min, and the mixture was kept at 4° C. for 1 h. The precipitate was collected by filtration, washed with cold water (15 ml) and dried in vacuo to afford compound B as white solid (1.36 g, 80% yield). $^1$H NMR (DMSO-$d_6$): 7.96 (brs, 1H, NH), 7.31 (brs, 1H, NH), 1.42 (s, 9H, $CH_3$).

2-Guanidino-thiazole-4-carboxylic acid ethyl ester (C)

A solution of 90% ethyl bromopyruvate (0.67 g, 0.43 ml, 3.5 mmol) in acetone (2 ml) was added dropwise over 1 h to an ice cooled stirred suspension of B (1 g, 4.6 mmol) in acetone (5.2 ml). After complete addition the reaction mixture was stirred at room temperature for an additional 16 h and the solvent was then reduced under pressure and the crude so obtained was purified by silica column chromatography using 4% methanol-DCM as eluent to afford C as pale yellow solid (0.53 g, 71%). $^1$H NMR (DMSO-$d_6$): 12.06 (brs, 1H, NH), 8.18 (s, 1H, ArH), 4.29 (q, 2H, $J_{AB}$=7.0 Hz, $CH_2$), 1.29 (t, 3H, $J_{AB}$=7.0 Hz, $CH_3$). ESI-MS (m/z): 214.94 (M+H).

2-Guanidino-thiazole-4-carboxylic acid (D)

A suspension of C (500 mg, 2.3 mmol) in 10% aqueous sodium hydroxide solution (10 ml) was stirred at room temperature for overnight. After completion the reaction was cooled in an ice bath and pH of the medium was adjusted to 1 by adding 1N HCl. Precipitated mass was filtered and dried to obtain D as a yellow solid (0.41 g, 96% yield).

(S)—N-((3-(3-fluoro-4-(4-(2-guanidinothiazole-4-carbonyl)piperazin-1-yl)phenyl)-2-oxooxazolidin-5-yl)methyl)acetamide (58)

To a stirred solution of 1-ethyl-3-(3-dimethylaminopropyl)-carbodiimide hydrochloride (EDC.HCl, 66.9 mg, 0.35 mmol) in DMF at 0° C., compound B (59.8 mg, 0.32 mmol) was added, followed by hydroxybenzotriazole (HOBt, 47.2 mg, 0.35 mmol). The reaction mixture was stirred at 0° C. for 30 min and LA (100 mg, 0.27 mmol) and N,N-diisopropylethylamine (DIPEA 0.2 ml, 1.1 mmol) were added and the resultant solution was allowed to stir at room temperature for overnight. After completion of the reaction DMF was evaporated and crude mass was purified by silica column chromatography using 4% methanol-DCM eluent to obtain the final compound 58 as an amber colour solid. $^1$H NMR (DMSO-$d_6$): δ δ 8.27 (t, 1H, $J_{AB}$=6.0 Hz, NH), 7.53-7.49 (m, 2H, ArH), 7.19 (dd, 1H, $J_{AB}$=7.5, $J_m$=2.0 Hz, ArH), 7.09 (t, 1H, $J_{AB}$=9.0 Hz, ArH), 4.74-4.69 (m, 1H, CHOCO), 4.09 (t, 1H, $J_{AB}$=7.2 Hz, CH$_2$NHCO), 3.99-3.88 (m, 1H, CH$_2$NHCO), 3.73-3.70 (m, 2H, CH$_2$NCO), 3.12 (q, 4H, $J_{AB}$=7.5 Hz CH$_2$N—Ar), 3.03-2.92 (m, 4H, CH$_2$—N), 1.84 (s, 3H, CH$_3$). ESI-MS (m/z): 462.9 (M+H). Specific rotation, $[α]_λ^T$=−27.68° at 32.2° C. and 589 nm at 9 mg/mL 1:1 chloroform:methanol mixture (0.9%).

Example 20: Synthesis of Compound 65

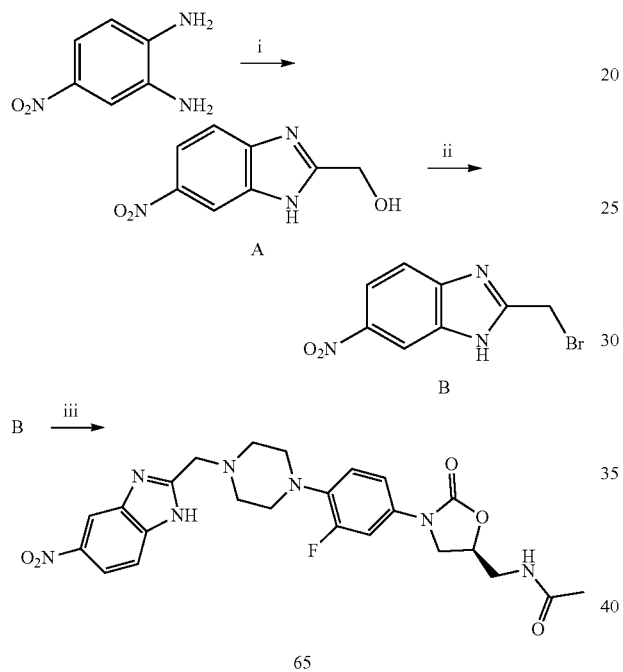

Reagents and condition: i) Glycolic acid, 6N HCl, overnight, reflux; ii) Thionyl bromide, DMF, benzene, 18 h, reflux; iii) (S)-N-((3-(3-fluoro-4-(piperazin-1-yl)phenyl)-2-oxooxazolidin-5-yl)methyl)acetamide hydrochloride (LA, Linezolid Analogue), Et$_3$N, DMF, RT, 18 h.

6-Nitro-1H-benzoimidazol-2-yl)-methanol (A)

A solution of 1,2-diamino-4-nitrobenzene (5.00 g, 32.60 mol) and glycolic acid (3.72 g, 49 mol) in 6 N hydrogen chloride (50 ml) was refluxed overnight. The reaction mixture was cooled and neutralized with 10% sodium hydroxide solution. The precipitate was filtered and dried to obtain A as a pale brown solid (5 g, 80%). $^1$H NMR (DMSO-$d_6$): δ 13.04 (bs, 1H, NH), 8.37 (s 1H, ArH), 8.07 (dd, 1H, dd, $J_{AB}$=10 Hz, J, =2.5 Hz, ArH), 7.65 (d, 1H, J=5 Hz, ArH), 5.94 (bs, 1H, NH), 4.76 (s, 2H, CH$_2$).

2-(Bromomethyl)-6-nitro-1H-benzo[d]imidazole (B)

To a stirred solution of A (300 mg, 1.55 mmol) in benzene, thionyl bromide (0.16 ml, 2 mmol) and DMF (0.20 ml) were added at 0° C. and reaction mixture was refluxed for 18 h. After completion of the reaction, solvent was evaporated and crude was dissolved in DCM and washed with water. Organic layer was passed through sodium sulphate and evaporated under reduced pressure to obtain crude mass which was further purified by column chromatography over silica gel with 2% methanol-DCM eluent to obtain compound B as an off white solid (330 mg, 84%). $^1$H NMR (DMSO-$d_6$): δ 8.48 (d, 1H, $J_{AB}$=2.0 Hz, ArH), 8.14 (dd, 1H, $J_{AB}$=10 Hz, $J_m$=2.5 Hz, ArH), 7.74 (d, 1H, $J_{AB}$=9 Hz, ArH), 4.86 (s, 2H, CH$_2$).

(S)—N-((3-(3-Fluoro-4-(4-((6-nitro-1H-benzo[d]imidazol-2-yl)methyl)piperazin-1-yl)phenyl)-2-oxooxazolidin-5-yl)methyl)acetamide (65)

To a stirred solution of LA (100 mg, 0.26 mmol) in DMF (10 ml), triethylamine (0.1 ml, 0.92 mmol) and compound B (100 mg, 0.4 mmol) were added and the reaction mixture was stirred at room temperature for 18 h. After completion of the reaction, excess ethyl acetate was added into the reaction mixture and solids were filtered out. The organic layer was concentrated and crude obtained was further purified by flash column chromatography over silica gel using 6% methanol-DCM eluent to yield the final compound 65 as amber solid (135 mg, 13%) $^1$H NMR (DMSO-$d_6$): δ 8.48 (s, 1H, ArH), 8.14 (dd, 1H, $J_{AB}$=7.6 Hz, $J_m$=1.2 Hz, ArH), 7.64-7.55 (m, 1H, ArH), 7.35 (dd, 1H, $J_{AB}$=11.2 Hz, $J_m$=2 Hz, ArH), 7.02 (dd, 1H, $J_{AB}$=7 Hz, $J_m$=1.6 Hz, ArH), 6.90 (t, 1H, $J_{AB}$=7.2 Hz, ArH), 4.71-4.68 (m, 1H, CHOCO), 3.99 (t, 1H, $J_{AB}$=7.2 Hz, CH$_2$NHCO), 3.92 (s, 2H, CH$_2$NCO), 3.73-3.67 (m, 1H, CH$_2$NHCO), 3.55 (s, 2H, ArCH$_2$), 3.23-3.22 (m, 4H, CH$_2$N—Ar), 2.82-2.77 (m, 4H, CH$_2$NH), 1.94 (s, 3H, CH$_3$). ESI-MS (m/z): 511.96 (M+).

Example 21: Synthesis of Compound 66

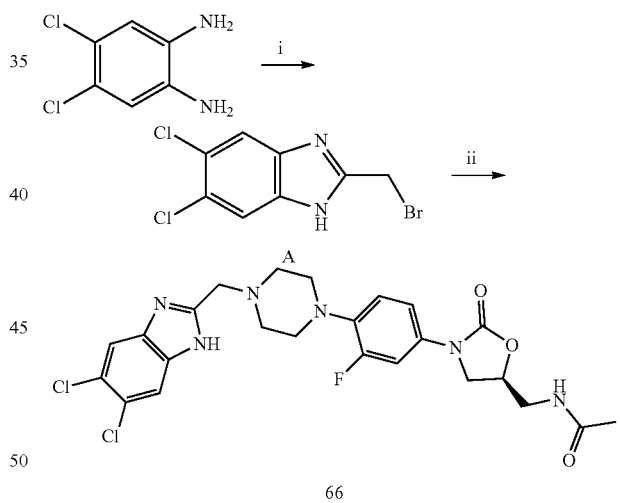

Reagents and condition: i) Bromoacetic acid, 6N HCl, overnight, reflux; ii) (S)-N-((3-(3-fluoro-4-(piperazin-1-yl)phenyl)-2-oxooxazolidin-5-yl)methyl)acetamide hydrochloride (LA, Linezolid Analogue), Et$_3$N, DMF, RT, 18 h, R.T.

2-(Bromomethyl)-5,6-dichloro-1H-benzo[d]imidazole (A)

To a stirred solution of 4,5-dichlorobenzene-1,2-diamine (1 g, 5.65 mmol) in 6 N HCl, bromoacetic acid (2.51 g, 18.08 mmol) was added and reaction mixture was refluxed for overnight. After completion, the reaction mixture was cool to room temperature and neutralized with 10% sodium hydroxide solution. The resultant precipitate was filtered and dried to obtain compound A as a beige solid (1.57 g, 64%). $^1$H NMR (DMSO-$d_6$): δ 7.61 (s 1H, ArH), 4.69 (s, 2H, CH$_2$).

(S)—N-((3-(4-(4-((5,6-Dichloro-1H-benzo[d]imidazol-2-yl)methyl)piperazin-1-yl)-3-fluorophenyl)-2-oxooxazolidin-5-yl)methyl)acetamide (66)

To a stirred solution of LA (100 mg, 0.26 mmol) in DMF (10 ml), triethylamine (0.2 ml, 1.56 mmol) and compound A (160 mg, 0.65 mmol) were added and the reaction mixture was stirred at room temperature for 18 h. After successful completion of the reaction, excess ethyl acetate was added into the reaction mixture and solids were filtered out. The filtrate was evaporated to dryness and the crude mass was further purified by silica column chromatography using 6% methanol-DCM as eluent to obtain the final compound 66 as pale yellow solid (78 mg, 10%). $^1$H NMR (DMSO): δ 8.24 (t, 1H, $J_{AB}$=5.6, NH), 7.86 (s, 1H, ArH), 7.78 (s, 1H, ArH), 7.45 (dd, 1H, $J_{AB}$=14.8 Hz, $J_m$=2.4 Hz ArH), 7.16 (dd, 1H, $J_{AB}$=9 Hz, $J_m$=2.4 Hz ArH), 7.06 (t, 1H, $J_{AB}$=9.2 Hz, ArH), 4.73-4.66 (m, 1H, CHOCO), 4.07 (t, 2H, $J_{AB}$=8.8 Hz, CH$_2$NHCO), 3.70 (s, 2H, ArCH$_2$), 3.69-3.67 (m, 2H, CH$_2$NCO), 3.17-3.16 (m, 4H, CH$_2$N—Ar), 2.72-2.62 (m, 4H, CH$_2$NH), 1.79 (s, 3H, CH$_3$). ESI-MS (m/z): 536.13 (M+H).

Example 22: Synthesis of Compound 68

Tris-boc-2-amino-4-nitrobenzimidazole (A)

4-Nitro-1,2-phenylenediamine (2.76 g, 17.66 mmol) was suspended in methanol (200 ml) and 5 M cyanogen bromide (4 ml) in acetonitrile was added dropwise over a period of 20 min followed by addition of 50 ml water into the reaction mixture. The final resulting reaction mixture was stirred at room temperature for overnight and 30 ml water was added into it. The reaction mixture was concentrated to about 80 ml and made basic with saturated sodium bicarbonate solution. The yellow precipitate formed was filtered, washed with cold water and dried to obtain 2-amino-4-nitrobenzimidazole as a yellow solid (2.94 g, 93%). $^1$H NMR (DMSO-d$_6$): δ 11.90 (brs, 1H, NH), 7.87 (d, 1H, $J_{AB}$=2.5 Hz, ArH), 7.81 (1H, dd, $J_{AB}$=11 Hz, J, =2.5 Hz, ArH), 7.12 (1H, d, $J_{AB}$=9 Hz, ArH), 6.87 (s, 2H, NH$_2$). Di-tert-butyl dicarbonate (12 ml, 50 mmol) was added to a suspension of synthesized 2-amino-4-nitrobenzimidazole (3.6 g, 20 mmol) in THF (200 ml). The mixture was stirred at room temperature for 5 hours. Then another portion of di-tert-butyl dicarbonate (12 ml, 50 mmol) was added to the reaction mixture, followed by addition of 4-dimethylaminopyridine (250 mg, 2.05 mmol). After stirring at room temperature for overnight, solvent was evaporated and the residue was purified by

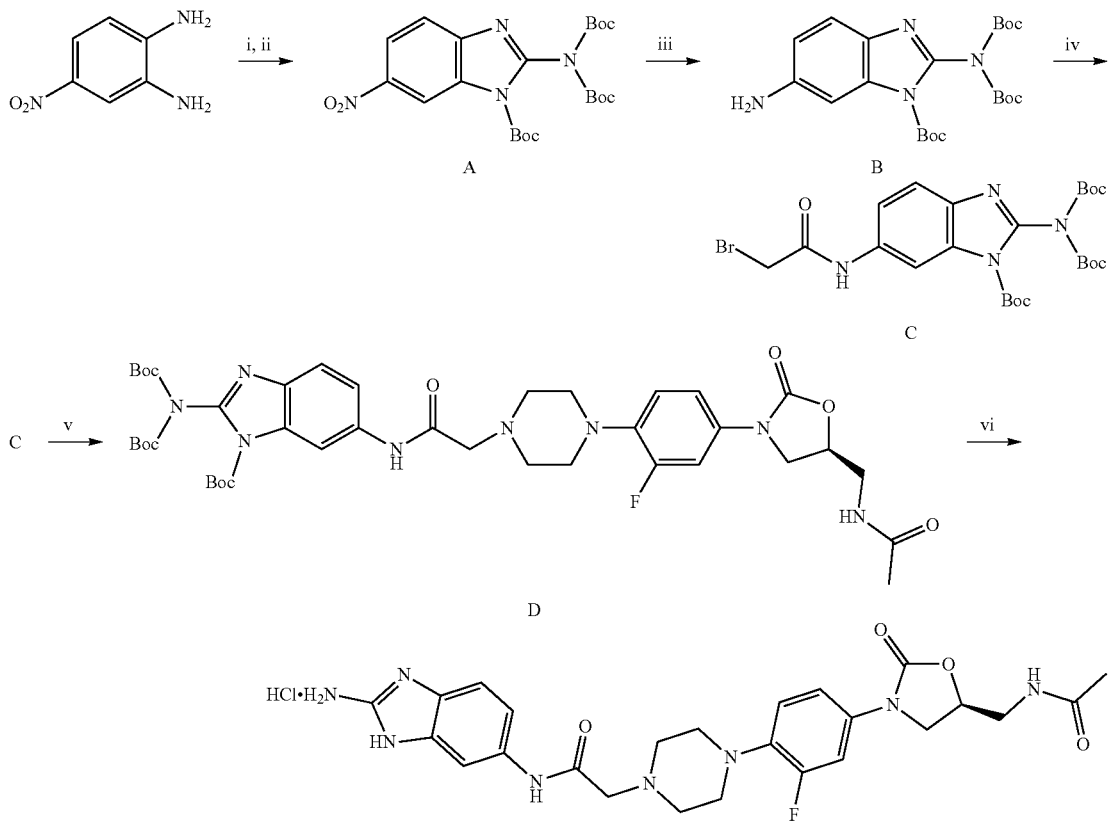

68

Reagents and condition: i) Cyanogen bromide, methanol; ii) Di-tert-butyl dicarbonate, 4-Dimethylaminopyridine, THF; iii) Zinc, ammonium chloride, EtOH—H$_2$O; iv) Bromoacetyl bromide, Et$_3$N, DCM, v) (S)-N-((3-(3-fluoro-4-(piperazin-1-yl)phenyl)-2-oxooxazolidin-5-yl)methyl)acetamide hydrochloride (LA, Linezolid Analogue), Et$_3$N, DMF, RT, 18 h. vi) 6N HCl, THF, overnight, R.T.

chromatography over silica gel (eluent: DCM) to obtain tri-boc protected compound A as an off-white solid which was a mixture of two isomers (6.0 g, 63%). $^1$H NMR (CDCl$_3$): isomer I: δ 8.96 (d, 1H, $J_{AB}$=2.5 Hz, ArH), 8.29 (dd, 1H, $J_{AB}$=11 Hz, $J_m$=2.5 Hz, ArH), 7.85 (d, 1H, $J_{AB}$=9.0 Hz, ArH), 1.70 (s, 9H, CH$_3$), 1.42 (s, 18H, CH$_3$); Isomer II: δ 8.64 (d, 1H, $J_{AB}$=2.0 Hz, ArH), 8.33 (dd, 1H, $J_{AB}$=9.2 Hz, $J_m$=2.0 Hz, ArH), 8.15 (d, 1H, $J_{AB}$=9.0 Hz, ArH), 1.68 (s, 9H, CH$_3$), 1.42 (s, 18H, CH$_3$).

Tris-boc-2,4-diaminobenzimidazole (B)

To a suspension of A (300 mg, 0.62 mmol) in ethanol-water (3:1, 5 mL), zinc powder (500 mg, 7.50 mmol) and ammonium chloride (400 mg, 7.50 mmol) were added at 0° C. and reaction mixture was stirred at room temperature for two hours. On completion of the reaction, aqueous ammonia solution was added and inorganic materials were filtered out and filtrate was extracted with DCM and dried over sodium sulphate. On evaporation of the solvent compound B was obtained as white solid (200 mg, 71%)$^1$H NMR (CDCl$_3$): isomer I: δ 7.74 (d, 1H, $J_{AB}$=8.5 Hz, ArH), 7.00 (d, 1H, $J_{AB}$=2 Hz, ArH), 6.73 (dd, 1H, $J_{AB}$=10 Hz, $J_m$=2.0 Hz, ArH), 1.64 (s, 9H, CH$_3$), 1.39 (s, 18H, CH$_3$); Isomer II: δ 7.48 (d, 1H, $J_{AB}$=8.5 Hz, ArH), 7.33 (d, 1H, $J_{AB}$=2 Hz, ArH), 6.71 (dd, 1H, $J_{AB}$=10 Hz, $J_m$=2.0 Hz, ArH), 1.64 (s, 9H, CH$_3$), 1.39 (s, 18H, CH$_3$).

Tris-N-boc-N-(2-amino-1H-benzo[d]imidazol-6-yl)-2-bromoacetamide (C)

To a stirred solution of B (1 g, 2.23 mmol) and triethylamine (0.5 ml, 3.60 mmol) in DCM, bromoacetyl bromide (0.25 ml, 3 mmol) was added at 0° C. and reaction mixture was stirred at room temperature for four hours. After completion of the reaction, the final mixture was washed with water and organic layer was dried over sodium sulphate. Crude C was obtained after evaporation which was used for the next step without further purification (1 g, 85%).

Tris-N-boc-(S)-2-(4-(4-(5-(acetamidomethyl)-2-oxooxazolidin-3-yl)-2-fluorophenyl)piperazin-1-yl)-N-(2-amino-1H-benzo[d]imidazol-6-yl)acetamide (D)

To a stirred solution of LA (200 mg, 0.4 mmol) and triethylamine (0.25 ml, 1.8 mmol) in DMF (5 ml), compound C (379 mg, 0.6 mmol) was added and reaction mixture was stirred for overnight at room temperature. After completion of the reaction, solvents were evaporated and crude was dissolved in ethyl acetate and washed with water. After evaporation of the organic solvents, crude mass was purified by flash column chromatography over silica gel using 4% methanol-DCM as eluent to yield D as off white solid (82 mg, 25%).

(S)-2-(4-(4-(5-(acetamidomethyl)-2-oxooxazolidin-3-yl)-2-fluorophenyl)piperazin-1-yl)-N-(2-amino-1H-benzo[d]imidazol-6-yl)acetamide (68)

To a solution of compound D (82 mg, 99.5 mmol) in THF (5 ml), 6 N HCl was added at 0° C. and the reaction mixture was stirred overnight at room temperature. After successful completion of the reaction, solvent was evaporated to dryness. The crude obtained was dissolved in minimum methanol and dichloromethane mixture and precipitated out by addition of excess of diethyl ether. The process was repeated for 2-3 times to finally obtain pure compound 84 as an off white solid (15 mg, 30%). $^1$H NMR (DMSO-d$_6$): δ 8.56 (s, 1H, NH), 8.29 (t, 1H, $J_{AB}$=4.8 Hz, NH), 7.84 (s, 1H, ArH), 7.53 (dd, 1H, $J_{AB}$=12.4 Hz, $J_m$=2.0 Hz, ArH), 7.36-7.31 (m, 2H, ArH), 7.23 (dd, 1H, $J_{AB}$=6 Hz, $J_m$=2.4 Hz, ArH), 7.17 (t, 1H, $J_m$=7.6 Hz, ArH), 4.74-4.70 (m, 1H, CHOCO), 4.10 (t, 1H, $J_{AB}$=7.2 Hz, CH$_2$NHCO), 3.76-3.70 (m, 2H, CH$_2$NCO), 3.43-3.38 (m, 2H, CH$_2$N—Ar), 3.13-3.08 (m, 4H, CH$_2$NH), 1.84 (s, 3H, CH$_3$). ESI-MS (m/z): 525.16 (M+H).

Example 23: Synthesis of Compound 75

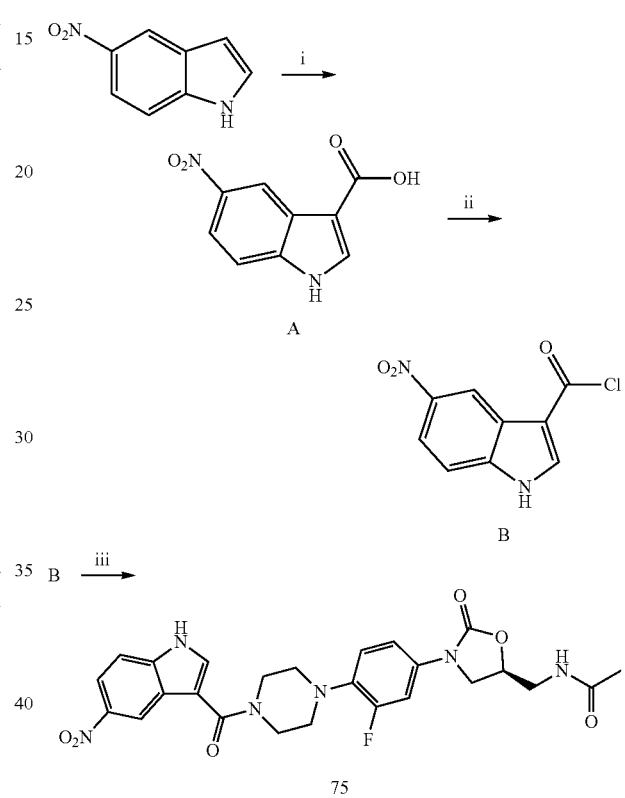

Reagents and condition: i) a) Oxalyl chloride, diethyl ether, 24 h, 0° C.; b) KOH, 2 hr reflux, c) 10% hydrogen peroxide, 4 hr reflux; ii) Thionyl chloride, toluene, 5 h, reflux: iii) (S)-N-((3-(3-fluoro-4-(piperazin-1-yl)phenyl)-2-oxooxazolidin-5-yl)methyl)acetamide hydrochloride (LA, Linezolid Analogue), DMF, Et$_3$N, R.T, overnight.

5-Nitro-1H-indole-3-carboxylic acid (A)

5-Nitroindole (1 g, 6.2 mmol) was suspended in diethyl ether and oxalyl chloride (4.3 ml, 49.4 mmol) was added under nitrogen atmosphere at 0° C. The resulting reaction mixture was stirred at 0° C. for 24 h and the resulting precipitate was filtered washed with cold diethyl ether and dried. After drying mass was further dissolved in the solution of potassium hydroxide (1.63 g, 29 mmol) in water (40 ml) and refluxed for 2 hours. The reaction mixture was ice cooled, acidified with 12 N HCl to pH 1. The obtained precipitated was filtered, washed with 1N HCl and dried. This precipitate was further dissolved in 10% hydrogen peroxide solution (75 ml), refluxed for 4 h and cooled to room temperature. The obtained precipitated was filtered, washed with cold water and dried to obtain A as a greenish yellow solid (750 mg, 61%). $^1$H NMR (DMSO-d$_6$): δ

12.49-12.46 (2H, NH & OH), 8.91 (d, 1H, $J_{AB}$=2.0 Hz, ArH), 8.29 (d, 1H, $J_{AB}$=2.0 Hz, ArH), 8.10 (dd, 1H, $J_{AB}$=9.0 Hz, $J_m$=2.5 Hz, ArH), 7.68 (d, 1H, $J_{AB}$=9.0 Hz, ArH); ESI-MS (m/z): 206.93 (M+H).

5-Nitro-1H-indole-3-carbonyl Chloride (B)

5-Nitro-1H-indole-3-carboxylic acid (700 mg, 3.4 mmol) was suspended in toluene (20 ml), followed by addition of thionyl chloride (8.4 ml, 115 mmol). The reaction mixture was allowed to reflux for 5 hours. After completion of reaction, excess of thionyl chloride and toluene were evaporated under reduced pressure and dried (690 mg, 91%).

(S)—N-((3-(3-fluoro-4-(4-(5-nitro-1H-indole-3-carbonyl)piperazin-1-yl)phenyl)-2-oxooxazolidin-5-yl)methyl)acetamide (75)

To a stirred solution of LA (100 mg, 0.27 mmol) and triethylamine (0.15 ml, 1.07 mmol) in DMF (5 ml), a solution of compound A (60 mg, 0.27 mmol) in DMF (5 ml) was added dropwise at 0° C. and reaction mixture was stirred overnight at room temperature. After completion of the reaction, solvent was evaporated and crude was purified by flash column chromatography over silica gel (eluent: 4% methanol-DCM) to yield 75 as off white solid (120 mg, 81.6%). $^1$H NMR (DMSO-$d_6$): δ 12.42 (brs, 1H, NH), 8.70 (d, 1H, $J_{AB}$=2.5 Hz, ArH), 8.29 (t, 1H, $J_{AB}$=6.0 Hz, NH), 8.08 (dd, 1H, $J_{AB}$=10.75 Hz, J, =2.0 Hz, ArH), 8.05 (d, 1H, $J_{AB}$=2.5 Hz, ArH), 7.66 (d, 1H, $J_{AB}$=9.0 Hz, ArH), 7.52 (dd, 1H, $J_{AB}$=14.75 Hz, $J_m$=2.5 Hz, ArH), 7.20 (dd, 1H, $J_{AB}$=8.75 Hz, J, =2.5 Hz, ArH), 7.11 (t, 1H, $J_{AB}$=9.5, ArH), 4.74-4.69 (m, 1H, CHOCO), 4.10 (t, $J_{AB}$=9.0 Hz, 1H, CH$_2$NHCO), 3.74-3.71 (m, 1H, CH$_2$NCO), 3.63-3.57 (m, 2H, CH$_2$N—Ar), 3.43-3.39 (m, 4H, CH$_2$N), 3.16-3.11 (m, 4H, CH$_2$N), 1.84 (s, 3H, CH$_3$). ESI-MS (m/z): 524.91 (M+H).

Example 24: Synthesis of Compound 76

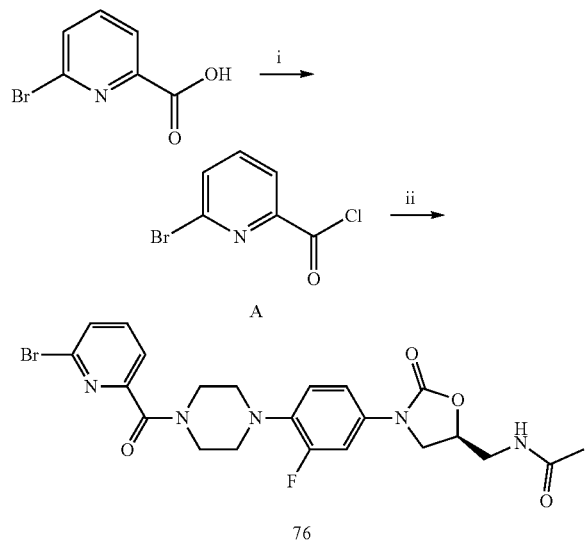

Reagents and condition: i) Oxalyl chloride, DCM, 3 h, R.T.; ii) (S)-N-((3-(3-fluoro-4-piperazin-1-yl)phenyl)-2-oxooxazolidin-5-yl)methyl)acetamide hydrochloride (LA, Linezolid Analogue), Et$_3$N, DMF, 18 h, R.T.

6-Bromopicolinoyl Chloride (A)

To a suspension of 6-bromo-pyridin-2-carboxylic acid (500 mg, 2.5 mmol) in DCM (50 ml) oxalyl chloride (0.25 ml, 7.50 mmol) was added dropwise followed by the addition of catalytic amount of DMF at 0° C. After that reaction mixture was allowed to stir at room temperature for three hours. After completion of the reaction, mixture was concentrated under vacuum to obtain A as a yellow solid with a quantitative yield (545 mg).

(S)—N-((3-(4-(4-(6-Bromopicolinoyl)piperazin-1-yl)-3-fluorophenyl)-2-oxooxazolidin-5-yl)methyl)acetamide (76)

To a stirred solution of LA (50 mg, 0.13 mmol) and triethylamine (0.06 ml, 0.47 mmol) in DMF (5 ml), a solution of compound A (38.5 mg, 0.47 mmol) in DMF (5 ml) was added dropwise at 0° C. and reaction mixture was stirred overnight at room temperature. After completion of the reaction, solvent was evaporated and crude was purified by flash column chromatography over silica gel (eluent: 4% methanol-DCM) to yield 76 as amber solid (18 mg, 26.5%). $^1$H NMR (CDCl$_3$): δ 8.27 (t, 1H, $J_{AB}$=4.8 Hz, NH), 7.92 (t, 1H, $J_{AB}$=6 Hz, ArH), 7.78 (d, 1H, $J_{AB}$=6.4 Hz, ArH), 7.68-7.64 (m, 1H, $J_{AB}$=11.6 Hz, $J_m$=5.6 Hz, ArH), 7.51 (dd, 1H $J_{AB}$=12 Hz, J, =2 Hz, ArH), 7.19 (dd, 1H, $J_{AB}$=8 Hz, J, =2 Hz, ArH), 7.11 (t, 1H, $J_{AB}$=7.6 Hz, ArH), 4.74-4.69 (m, 1H, CHOCO), 4.09 (t, 1H, $J_{AB}$=7.2 Hz, CH$_2$NHCO), 3.82-3.80 (m, 2H, CH$_2$NCO), 3.72-3.69 (m, 1H, CH$_2$NHCO), 3.55-3.53 (t, 2H, $J_{AB}$=4 Hz, CH$_2$N—Ar), 3.42-3.40 (t, 2H, $J_{AB}$=4 Hz, CH$_2$N—Ar), 3.08-3.06 (m, 2H, CH$_2$NH), 3.0-2.96 (m, 2H, CH$_2$NH), 1.83 (s, 3H, CH$_3$). ESI-MS (m/z): 521.89 (M+H).

Example 25: Synthesis of Compound 77

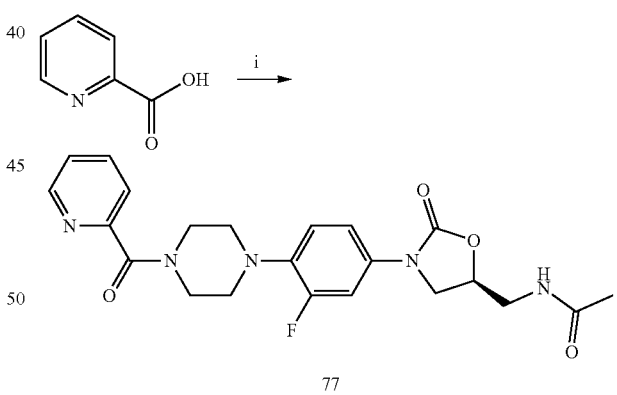

Reagents and condition: i) (S)-N-((3-(3-fluoro-4-(piperazin-1-yl)phenyl)-2-oxooxazolidin-5-yl)methyl)acetamide hydrochloride (LA, Linezolid Analogue), Hydroxybenzotriazole, N,N'-dicyclohexylcarbodiimide, N,N-diisopropylethylamine, DMF, 18 h, R.T.

(S)—N-((3-(3-fluoro-4-(4-picolinoylpiperazin-1-yl)phenyl)-2-oxooxazolidin-5-yl)methyl)acetamide (77)

To a stirred solution of N,N'-dicyclohexylcarbodiimide (DCC, 82.6 mg, 0.4 mmol) in dry DMF at 0° C., 2-picolinic acid (32.8 mg, 0.26 mmol) was added followed by addition of hydroxybenzotriazole (HOBt, 54 mg, 0.4 mmol). After 30 min LA (100 mg, 0.26 mmol) and triethylamine (0.2 ml, 0.9 mmol) was added and reaction mixture was allowed to stir overnight at room temperature. After completion of the reaction, DMF was evaporated and crude mass was further purified by silica column chromatography using 6% methanol-DCM as eluent to yield 77 as amber solid (28.6 mg, 25%). $^1$H NMR (DMSO-$d_6$): δ8.61 (d, 1H, $J_{AB}$=3.6.0 Hz, ArH), 8.27 (t, 1H, $J_{AB}$=4.0 Hz, NH), 7.96 (dd, 1H, $J_{AB}$=14.8, $J_m$=6 Hz, ArH), 7.70 (d, 1H, $J_{AB}$=6.4 Hz, ArH), 7.61 (d, 1H, $J_{AB}$=2.4 Hz, ArH), 7.57-7.54 (m, 1H, ArH), 7.51-7.48 (d, 1H, $J_{AB}$=6 Hz, ArH), 7.10 (t, 1H, $J_{AB}$=7.2 Hz, ArH), 4.72-4.70 (m, 1H, CHOCO), 4.08 (t, 1H, $J_{AB}$=7.2 Hz, CH$_2$NHCO), 3.81 (m, 2H, CH$_2$NCO), 3.73-3.66 (m, 1H, CH$_2$NHCO), 3.42-3.37 (m, 4H, CH$_2$N—Ar), 3.06-2.959 (m, 4H, CH$_2$NH), 1.83 (s, 3H, CH$_3$). ESI-MS (m/z): 463.97 (M+Na).

Example 26: Synthesis of Compound 78

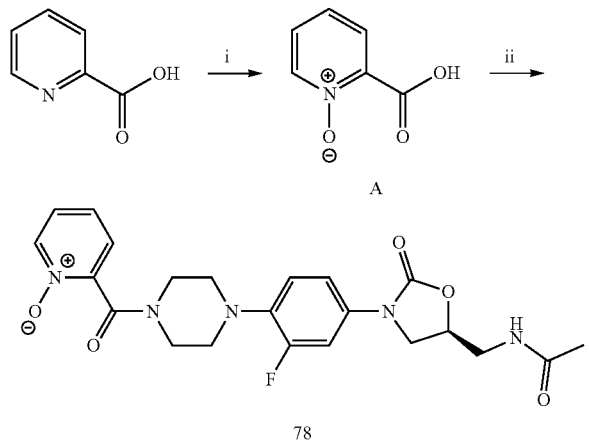

Reagents and condition: i) Hydrogen peroxide (30%) TFA, reflux; ii) (S)-N-((3-(3-fluoro-4-(piperazin-1-yl)phenyl)-2-oxooxazolidin-5-yl)methyl)acetamide hydrochloride (LA, Linezolid Analogue), N,N,N',N'-tetramethyl-O-(1H-benzotriazol-1-yl)uronium hexafluorophosphate (HBTU), N,N-diisopropylethylamine, DMF, 18 h, R.T.

2-Carboxypyridine 1-oxide (A)

2-Picolinic acid (1.23 g, 10 mmol) was suspended in trifluoroacetic acid (25 ml) and 30% hydrogen peroxide (30% w/w, 16 ml) was added into it and reaction mixture was refluxed for 16 h. On completion of the reaction, all volatiles were evaporated under reduced pressure and crude mass was washed for 2-3 times with cold water. Upon drying under vacuum compound A was obtained as a white solid (1 g, 72%).

(S)-2-(4-(4-(5-(acetamidomethyl)-2-oxooxazolidin-3-yl)-2-fluorophenyl)piperazine-1-carbonyl)-pyridine 1-oxide (78)

To a stirred solution of N,N,N',N'-tetramethyl-O-(1H-benzotriazol-1-yl)uronium hexafluorophosphate (HBTU, 263 mg, 0.69 mmol) in DMF at 0° C., compound A (113 mg, 0.8 mmol) was added and the reaction mixture was allowed to stir for 10 min followed by addition of LA (200 mg, 0.53 mmol) and N,N-diisopropylethylamine (DIPEA, 0.37 ml, 2.1 mmol) and reaction mixture was allowed to stir for overnight at room temperature. After completion of the reaction DMF was evaporated and crude mass was further purified by column chromatography over silica gel using 8% methanol-DCM as eluent to obtain final compound 78 as an amber solid (30 mg, 12%). $^1$H NMR (CDCl$_3$): δ 8.22-8.21 (m, 1H, $J_{AB}$=2 Hz, ArH), 7.47-7.42 (m, 2H, ArH), 7.35-7.33 (m, 2H, ArH), 7.04 (d, 1H, $J_{AB}$=6.8 Hz, ArH), 6.91 (t, 1H, $J_{AB}$=7.2 Hz, ArH), 6.39 (t, 1H, $J_{AB}$=5.2 Hz, NH), 4.80-4.72 (m, 1H, CHOCO), 4.19-4.12 (m, 1H, CH$_2$NHCO), 4.01 (t, 1H, $J_{AB}$=7.2 Hz, CH$_2$NHCO), 3.82-3.72 (m, 2H, CH$_2$NCO), 3.71-3.55 (m, 4H, CH$_2$N—Ar), 3.16-3.08 (m, 4H, CH$_2$NH), 2.01 (s, 3H, CH$_3$). ESI-MS (m/z): 457.90 (M+H).

Example 27: Synthesis of Compound 80

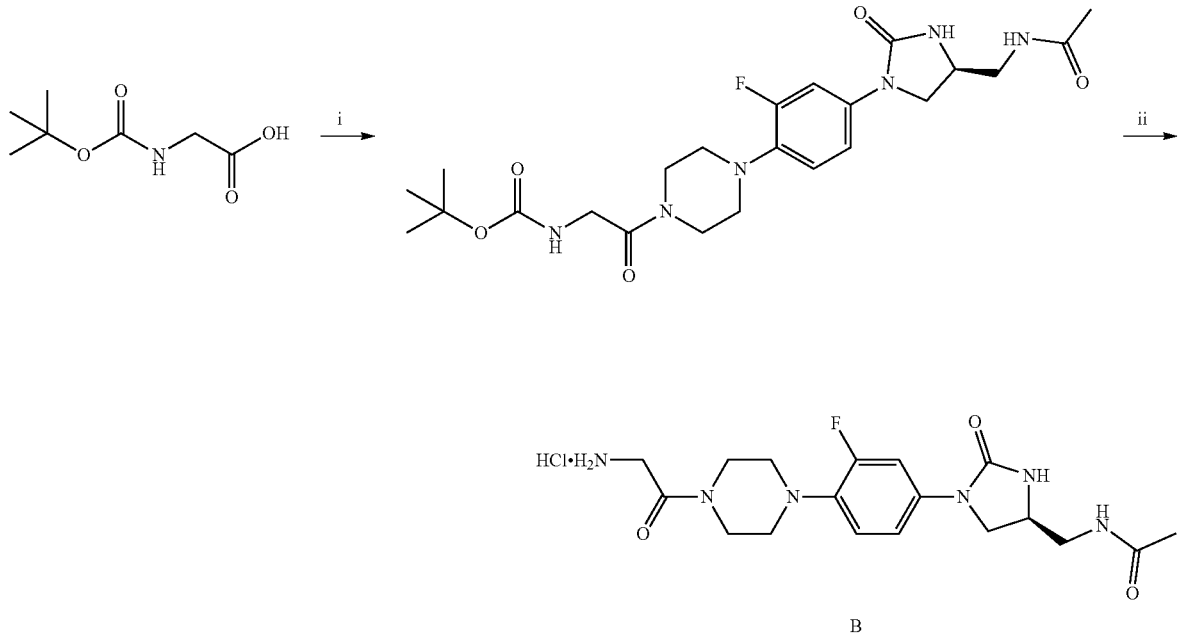

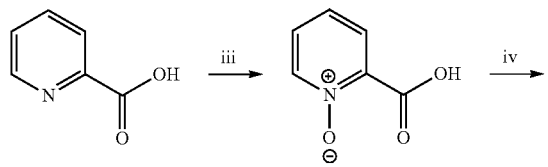
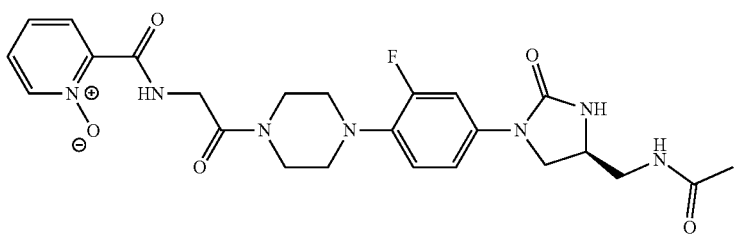

Reagents and condition: i) (tert-Butoxycarbonyl)glycine, (S)-N-((3-(3-fluoro-4-(piperazin-1-yl)phenyl)-2-oxooxazolidin-5-yl)methyl)acetamide hydrochloride (LA, Linezolid Analogue), N-hydroxysuccinimide, 1-Ethyl-3-(3-dimethylaminopropyl)carbodiimide hydrochloride, N,N-diisopropylethylamine, DMF, 18 h, R.T.; ii) 6N HCl, overnight, R.T.; iii) Hydrogen peroxide (30%) TFA, 16 h reflux; iv) B, Hydroxybenzotriazole, 1-Ethyl-3-(3-dimethylaminopropyl)-carbodiimide hydrochloride (EDC•HCl), N,N-diisopropylethylamine, DMF, 18 h, R.T.

tert-Butyl (S)-(2-(4-(4-(4-(acetamidomethyl)-2-oxoimidazolidin-1-yl)-2-fluorophenyl)piperazin-1-yl)-2-oxoethyl)carbamate (A)

To a stirred solution of 1-Ethyl-3-(3-dimethylaminopropyl)-carbodiimide hydrochloride (EDC.HCl 179 mg, 0.93 mmol) in DMF (5 ml), BOC-glycine (109 g, 0.62 mmol) and N-hydroxysuccinimide (HOSu, 107 mg, 093 mmol) were added at 0° C. and the mixture was allowed to stir for 4 h, followed by addition of LA (200 mg, 0.54 mmol) and diisopropylethylamine (0.32 ml, 1.8 mmol) at 0° C. The reaction mixture was further allowed to stir for overnight at room temperature. At end, the reaction mixture was t concentrated under reduced pressure and the crude product was purified by flash column chromatography over silica gel using 3% methanol-DCM as eluent to afford compound A as pale yellow solid (160 mg, yield: 60%).

(S)-(2-(4-(4-(4-(Acetamidomethyl)-2-oxoimidazolidin-1-yl)-2-fluorophenyl)piperazin-1-yl)-2-oxoethyl)carbamic acid (B)

A suspension of compound A (150 mg, 0.3 mmol) in 6N HCl (10 mL) was stirred for overnight, after which solvent was evaporated and crude mass was dissolved in methanol-DCM followed by addition of diethyl ether to obtain the precipitate. This process was repeated for 2-3 times to finally obtain pure compound B as yellow solid (120 mg, 92%). $^1$H NMR (DMSO-d$_6$): δ 8.34 (t, 1H, J$_{AB}$=6 Hz, NH), 8.30-8.22 (m, 3H, NH), 7.52 (dd, 1H, J$_{AB}$=15 Hz, J, =2.5 Hz, ArH), 7.21 (dd, 1H, J$_{AB}$=5.25 Hz, J$_m$=2 Hz, ArH), 7.10 (t, 1H, J$_{AB}$=9.5 Hz, ArH), 4.74-4.69 (m, 1H, CHOCO), 4.11-4.07 (m, 1H, CH$_2$NHCO), 3.91 (q, 2H, J$_{AB}$=5.5 Hz, CH$_2$—N), 3.75-3.72 (m, 1H, CH$_2$NHCO), 3.67 (t, 2H, J$_{AB}$=5 Hz, CH$_2$NCO), 3.58-3.52 (m, 2H, CH$_2$N—Ar), 3.40 (t, 1H, J$_{AB}$=5.5 Hz, CH$_2$N—Ar), 3.03-3.01 (m, 2H, CH$_2$—N), 2.99-2.97 (m, 2H, CH$_2$—N), 1.84 (s, 3H, CH$_3$). ESI-MS (m/z): 394.01 (M+H).

2-Carboxypyridine 1-oxide (C)

2-Picolinic acid (1.23 g, 10 mmol) was suspended in trifluoroacetic acid (25 ml) and 30% hydrogen peroxide (30% w/w, 16 ml) was added into it and reaction mixture was refluxed for 16 h. On completion of the reaction, all volatiles were evaporated under reduced pressure and crude mass was washed for 2-3 times with cold water. Upon drying under vacuum compound C was obtained as a white solid (1 g, 72%).

(S)-2-((2-(4-(4-(4-(Acetamidomethyl)-2-oxoimidazolidin-1-yl)-2-fluorophenyl)piperazin-1-yl)-2-oxoethyl)carbamoyl)pyridine 1-oxide (80)

To a stirred solution of 1-ethyl-3-(3-dimethylaminopropyl)carbodiimide (EDC.HCl, 65.8 mg, 0.3 mmol) in DMF (5 ml), compound C (38.8 mg, 0.27 mmol) was added, followed by the addition of hydroxybenzotriazole (44.6 mg, 0.3 mmol). The reaction mixture was allowed to stir for 1 hour. Later compound B (100 mg, 0.25 mmol) was added along with N, N-diethylisopropyl amine (0.2 ml, 1.0 mmol) and the reaction mixture was allowed to stir at room temperature for overnight. After completion of reaction, solvent was evaporated; crude reaction mixture was washed with water, and purified by flash chromatography over silica gel with 4% methanol-DCM as eluent to afford 80 as off white solid (20 mg, 14.9%). $^1$H NMR (DMSO-d$_6$): δ 11.57 (t, 1H, J$_{AB}$=4.5 Hz, NH), 7.72 (d, 1H, J$_{AB}$=8.5 Hz, ArH), 7.67-7.64 (m, 1H, ArH), 7.62-7.59 (m, 1H, ArH), 7.55-7.53 (m, 1H, ArH), 7.52-7.51 (m, 1H, ArH), 7.41 (t, 1H, J$_{AB}$=7.5 Hz, ArH), 7.21-7.18 (m, 1H, J$_{AB}$=4.5 Hz, ArH), 7.10 (t, 1H, J$_{AB}$=9 Hz, ArH), 4.73-4.70 (m, 1H, CHOCO), 4.37 (d, 1H, J$_{AB}$=8.5 z, CH$_2$), 4.10 (t, 1H, J$_{AB}$=9 Hz, CH$_2$NHCO), 3.74-3.71 (m, 1H, CH$_2$NHCO), 3.65-3.68 (m, 1H, CH$_2$NCO), 3.41 (t, 2H, J$_{AB}$=5.5 Hz, CH$_2$N—Ar), 3.01-3.05 (m, 2H, CH$_2$N), 2.95-3.0 (m, 1H, CH$_2$N), 2.55 (s, 3H, CH$_3$). ESI-MS (m/z): 514.20 (M+H), 36.94 (M+Na), 552.9 (M+K)

Example 28: Synthesis of Compound 84

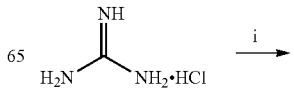

119

-continued

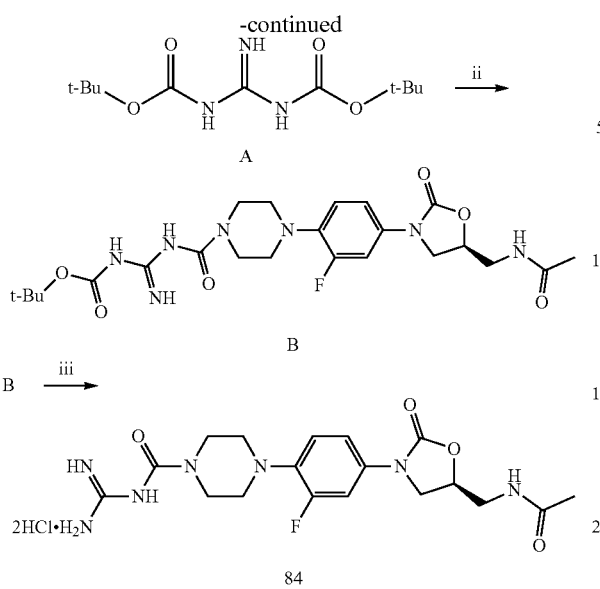

Reagents and condition: i) N,N-di-tert-butyl dicarbonate, sodium hydroxide, H₂O, 16 h, R.T.; ii) (S)-N-((3-(3-fluoro-4-(piperazin-1-yl)phenyl)-2-oxooxazolidin-5-yl)methyl)acetamide hydrochloride (LA, Linezolid Analogue), DMF, 18 h, 80° C.; iii) 6N HCl, THF, overnight, R.T.

Di-(tert-butoxycarbonyl)-guanidine (A)

Guanidine hydrochloride (1.23 g, 12.80 mmol) and sodium hydroxide (2.10 g, 52.5 mmol) were dissolved in water (15 ml), and 1,4-dioxane (25 ml). The mixture was cooled to 0° C. and N,N-di-tert-butyl dicarbonate (6.3 g, 28.90 mmol) was added and reaction mixture was allowed to stir at room temperature for 16 h. The reaction mixture was concentrated under vacuum to one-third of its initial volume and extracted with ethyl acetate. The organic phase was then washed with 10% citric acid, water and brine, dried over anhydrous sodium sulfate, filtered and concentrated under reduced pressure to obtain A which was used for the next step without further purification.

(S)-4-(4-(5-(acetamidomethyl)-2-oxooxazolidin-3-yl)-2-fluorophenyl)-N-(tert-butoxycarbonyl)-carbamimidoylpiperazine-1-carboxamide (B)

To a stirred solution LA (150 mg, 0.4 mmol) in DMF (5 ml) added triethylamine (0.2 ml, 1.4 mmol), followed by the addition of compound A (135 mg, 0.52 mmol) and the final solution was heated at 80° C. for overnight. After completion of the reaction solvent was evaporated and crude was purified by flash column chromatography over silica gel using 4% methanol-DCM eluent to obtain the compound B as a white solid (76 mg, 45%). $^1$H NMR (CDCl$_3$): δ 8.05 (brs, 1H, NH), 7.46 (dd, 1H, $J_{AB}$=11.2 Hz, $J_m$=2 Hz ArH), 7.20 (dd, 1H, $J_{AB}$=7.2 Hz, $J_m$=1.6 Hz, ArH), 6.94 (t, 1H, $J_{AB}$=7.2 Hz, ArH), 6.09 (t, NH, $J_{AB}$=4.8 Hz, ArH), 4.80-4.78 (m, 1H, CHOCO), 4.04 (t, 1H, $J_{AB}$=7.2 Hz, CH$_2$NHCO), 3.98-3.87 (m, 2H, CH$_2$NCO), 3.78-3.75 (m, 2H, CH$_2$NHCO, CH$_2$N—Ar), 3.73-3.70 (m, 2H, CH$_2$N—Ar), 3.65-3.62 (m, 1H, CH$_2$N—Ar), 3.08-2.97 (m, 4H, CH$_2$NH$_2$), 2.04 (s, 3H, CH$_3$), 1.35 (s, 9H, CH$_3$) ESI-MS (m/z): 422.2 (M+H).

120

(S)-4-(4-(5-(Acetamidomethyl)-2-oxooxazolidin-3-yl)-2-fluorophenyl)-N-carbamimidoylpiperazine-1-carboxamide (84)

To a solution of B (75.7 mg, 0.14 mmol) in THF (10 ml), 6 N HCl (10 ml) was added at 0° C. and the reaction mixture was stirred overnight at room temperature. After successful completion of the reaction, solvent was evaporated to dryness. The crude obtained was dissolved in minimum methanol and dichloromethane mixture and precipitated out by addition of excess of diethyl ether. The process was repeated for 2-3 times to finally obtain pure compound 84 as an off white solid (30 mg, 49%). ESI-MS (m/z): 422.02 (M+H). Specific rotation, $[α]_λ^T$=−2.22° at 30.6° C. and 589 nm at 9 mg/mL 1:1 chloroform:methanol mixture (0.9%).

Example 29: Synthesis of Compound 107

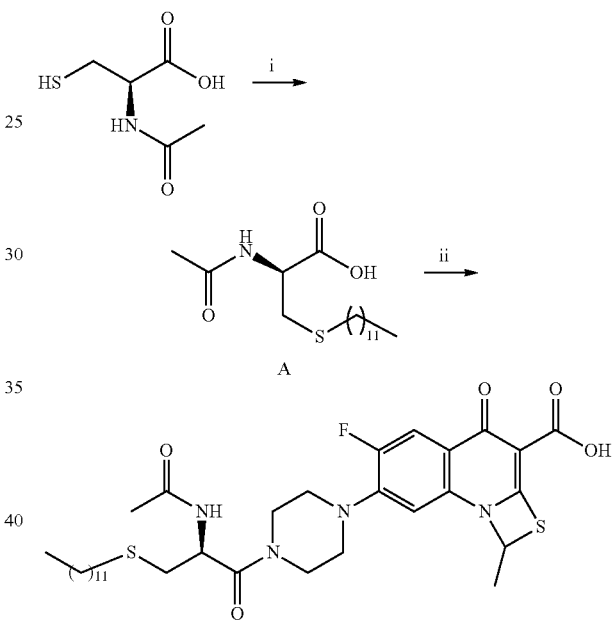

Reagents and condition: i) Sodium, ethanol, 5 h reflux; ii) 1-ethyl-3-(3-dimethylaminopropyl)-carbodiimide hydrochloride, N-hydroxysuccinimide, 6-Fluoro-1-methyl-7-(4-((5-nitro-1H-benzo[d]-imidazol-2-yl)methyl)piperazin-1-yl)-4-oxo-1H,4H-[1,3]thiazeto[3,2-a]-quinoline-3-carboxylic acid, N,N-diisopropylethylamine, DMF, overnight, R.T.

N-Acetyl-S-dodecyl-L-cysteine (A)

Freshly cut sodium metal (180 mg, 7.8 mmol) was dissolved in anhydrous ethanol (15 ml) under nitrogen atmosphere. To this solution N-acetyl-L-cysteine (500 mg, 3.1 mmol) was added followed by 1-bromododecane (0.89 ml, 3.72 mmol) and the reaction mixture heated at reflux for 4 hours. Upon cooling, the reaction was quenched with a small amount of water, the solvent was removed under reduced pressure and the residue was redissolved in ethyl acetate. The solution was washed with 1 M HCl, brine, dried over anhydrous sodium sulphate and finally the solvent removed under reduced pressure to obtain give compound as a white solid (810 mg, 80%). $^1$H NMR (CDCl$_3$): δ 4.78 (q, 1H, $J_{AB}$=6 Hz, CH), 3.50-3.45 (m, 1H, CH$_2$S), 3.41 (t, 1H, $J_{AB}$=6 Hz, CH$_2$S), 3.03 (t, 2H, $J_{AB}$=4.5 Hz, CH$_2$S). 2.55-

2.52. (m, 2H, CH$_2$), 2.1 (s, 3H, COCH$_3$), 1.58-1.52 (m, 2H, CH$_2$), 0.87 (t, 2H, J$_{AB}$=6.5 Hz, CH$_3$). ESI-MS (m/z): 331.99 (M+H).

7-(4-(N-acetyl-S-dodecyl-L-cysteinyl)piperazin-1-yl)-6-fluoro-1-methyl-4-oxo-1H,4H-[1,3]thiazeto-[3,2-a]quinoline-3-carboxylic acid (107)

To a stirred solution of 1-ethyl-3-(3-dimethylaminopropyl)-carbodiimide hydrochloride (EDC.HCl, 576 mg, 3 mmol) in DMF at 0° C., compound A (662 mg, 2.0 mmol) was added, followed by addition of N-hydroxysuccinimide (HOSu, 345 mg, 3 mmol). After 30 min 6-fluoro-1-methyl-7-(4-((5-nitro-1H-benzo[d]imidazol-2-yl)methyl)piperazin-1-yl)-4-oxo-1H,4H-[1,3]thiazeto[3,2-a]-quinoline-3-carboxylic acid (690 mg, 2.0 mmol) and N,N-diisopropylethylamine (DIPEA, 0.53 ml, 3 mmol) were added and reaction mixture was allowed to stir at room temperature for overnight. After completion of the reaction DMF was evaporated and crude mass was digested with water, the obtained precipitate was filtered and dried, which was further purified by flash column chromatography over silica gel using 3% methanol-DCM as eluent to obtain compound 107 as an off white solid (200 mg, 15%). $^1$H NMR (CDCl$_3$): δ 14.14 (brs, 1H, COOH), 7.88 (d, 1H, J$_{AB}$=13.0 Hz, ArH), 6.58 (d, 1H, J$_{AB}$=7.5 Hz, ArH), 6.42 (brs, 1H, NH), 6.19-6.04 (m, 1H, SCHN), 5.14 (q, 1H, J$_{AB}$=7 Hz, CH), 4.02-3.89 (m, 2H, CH$_2$S), 3.91-3.82 (m, 1H, CH$_2$S), 3.80-3.73 (m, 1H, CH$_2$S), 3.46-3.21 (m, 4H, CH$_2$), 2.92-2.78 (m, 2H, CH$_2$), 2.54 (t, 1H, J$_{AB}$=7.5 Hz, CH$_2$), 2.21-2.14 (m, 2H, CH$_2$S), 2.21-2.14 (m, 3H, SCH$_3$), 2.02 (s, 3H, COCH$_3$), 1.58-1.53 (m, 2H, CH$_2$), 1.38-1.33 (m, 2H, CH$_2$), 1.26-1.21 (m, 16H, CH$_2$), 0.86 (t, 2H, J$_{AB}$=7 Hz, CH$_3$). ESI-MS (m/z): 663.05 (M+H).

Example 30: Synthesis of Compound 108

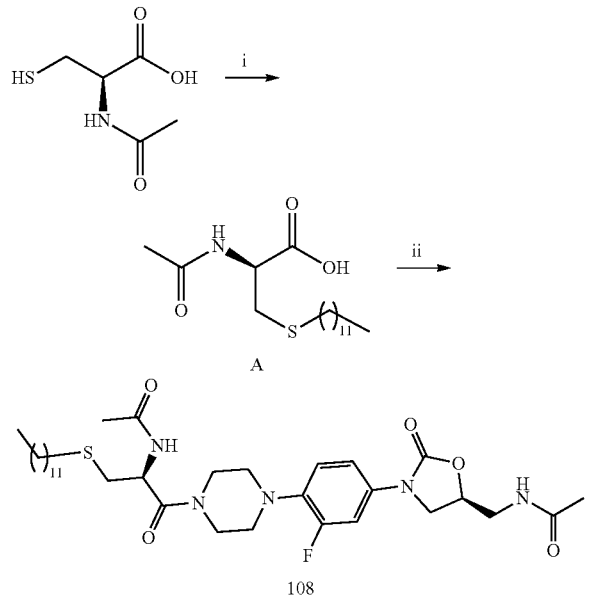

Reagents and condition: i) Sodium, ethanol, 5 h reflux; ii) 1-Ethyl-3-(3-dimethylaminopropyl)-carbodiimide hydrochloride, N-hydroxysuccinimide, (S)-N-((3-(3-fluoro-4-(piperazin-1-yl)phenyl)-2-oxooxazolidin-5-yl)methyl)acetamide hydrochloride (LA, Linezolid Analogue), N,N-diisopropylethylamine, DMF, overnight, R.T.

N-Acetyl-S-dodecyl-L-cysteine (A)

Freshly cut sodium metal (180 mg, 7.8 mmol) was dissolved in anhydrous ethanol (15 ml) under nitrogen atmosphere. To this solution N-acetyl-L-cysteine (500 mg, 3.1 mmol) was added followed by 1-bromododecane (0.89 ml, 3.72 mmol) and the reaction mixture heated at reflux for 4 h. Upon cooling, the reaction was quenched with a small amount of water, the solvent was removed under reduced pressure and the residue redissolved in ethyl acetate. The solution was washed with 1 M HCl, brine, dried over anhydrous sodium sulphate and the solvent removed under reduced pressure to obtain compound as a white solid (810 mg, 80%). $^1$H NMR (CDCl$_3$): δ 4.78 (q, 1H, J$_{AB}$=6 Hz, CH), 3.50-3.45 (m, 1H, CH$_2$S), 3.41 (t, 1H, J$_{AB}$=6 Hz, CH$_2$S), 3.03 (t, 2H, J$_{AB}$=4.5 Hz, CH$_2$S). 2.55-2.52. (m, 2H, CH$_2$), 2.1 (s, 3H, COCH$_3$), 1.58-1.52 (m, 2H, CH$_2$), 0.87 (t, 2H, J$_{AB}$=6.5 Hz, CH$_3$). ESI-MS (m/z): 331.99 (M+H).

(S)—N-[2-(4-{4-[5-(Acetylamino-methyl)-2-oxo-oxazolidin-3-yl]-2-fluoro-phenyl}-piperazin-1-yl)-1-dodecylstannanylmethyl-2-oxo-ethyl]-acetamide (108)

To a stirred solution of 1-ethyl-3-(3-dimethylaminopropyl)-carbodiimide hydrochloride (EDC.HCl, 115 mg, 0.6 mmol) in DMF at 0° C., compound (165 mg, 0.48 mmol) was added, followed by addition of N-hydroxysuccinimide (HOSu, 69.6 mg, 0.6 mmol). After 30 min compound LA (150 mg, 0.4 mmol) and N,N-diisopropylethylamine (DIPEA, 0.28 ml, 1.6 mmol) were added and reaction mixture was allowed to stir at room temperature for overnight. After completion of the reaction DMF was evaporated and crude mass was digested with water, obtained precipitate was filtered and dried to obtain crude, which was further purified by flash column chromatography over silica gel using 3% methanol-DCM as eluent to obtain compound 108 as an off white solid (28 mg, 11%). $^1$H NMR (DMSO-d$_6$): δ 7.49 (d, 1H, J$_{AB}$=13 Hz, ArH), 7.10 (d, 1H, J$_{AB}$=8 Hz, ArH), 6.95 (t, 1H, J$_{AB}$=9 Hz, ArH), 6.59 (d, 1H, J$_{AB}$=8 Hz, NH), 6.12 (brs, 1H, NH), 5.18 (q, 1H, J$_{AB}$=7 Hz, CH), 4.85-4.76 (m, 1H, CHOCO), 4.05 (t, 1H, J$_{AB}$=8 Hz, CH$_2$NHCO), 3.95-3.87 (m, 1H, CH$_2$NHCO), 3.85-3.81 (m, 2H, CH$_2$NCO), 3.77-3.80 (m, 1H, CH$_2$S), 3.74-3.68 (m, 1H, CH$_2$S), 3.68-3.60 (m, 1H, CH$_2$S), 3.21-3.13 (m, 1H, CH$_2$S), 3.13-3.04 (m, 3H, CH$_2$NHCO), 2.95-2.90 (m, 1H, CH$_2$), 2.85-2.78 (m, 1H, CH$_2$), 2.75 (s, 1H, CH$_2$), 2.56 (t, 2H, J$_{AB}$=7.5 Hz, CH$_2$N—Ar), 2.20 (s, 3H, CH$_3$), 2.05 (s, 3H, CH$_3$), 1.28 (s, 17H, CH$_2$), 0.91 (t, 3H, J$_{AB}$=10 Hz, CH$_3$). ESI-MS (m/z): 650.04 (M+H).

Example 31: Synthesis of Compound 110

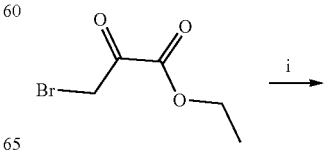

-continued

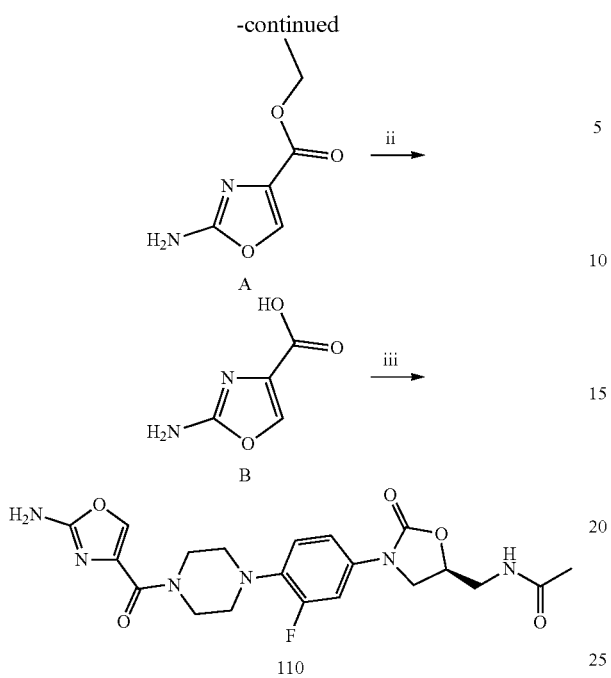

Reagents and condition: i) Urea, ethanol, overnight, reflux; ii) 10%, NaOH, overnight, R.T.; iii) N-[3-(3-fluoro-4-(piperazin-1-yl-phenyl)-2-oxo-oxazolidin-5-ylmethyl]-acetamide hydrochloride salt (LA, Linezolid Analogue), Hydroxybenzotriazole, 1-Ethyl-3-(3-dimethylaminopropyl)-carbodiimide hydrochloride (EDC•HCl), N,N-diisopropylethylamine, DMF, 18 h, R.T.

Ethyl 2-amino-1,3-oxazole-4-carboxylate (A)

A stirred solution of ethyl bromopyruvate (2.44 g, 1.32 ml, 2.54 mmol) in ethanol was treated with urea (1 g, 6.5 mmol) and for refluxed overnight. After completion the resultant reaction mixture was concentrated under vacuum resultant residue and extracted with ethyl acetate, washed with water, brine and finally dried over sodium sulphate. After concentration of the organic layer under reduced pressure, the crude mass was purified by flash column chromatography over silica gel with 4% methanol-DCM eluent to obtain A as pale yellow solid (0.34 g, 85%). $^1$H NMR (DMSO): δ 8.07 (s, 1H, ArH), 6.92 (brs, 2H, NH), 4.19 (q, 2H, $J_{AB}$=7.0 Hz, CH$_2$), 1.24 (t, 3H, $J_{AB}$=7.0 Hz, CH$_3$).

2-Amino-oxazole-4-carboxylic acid (B)

A suspension of A (354 mg, 2.2 mmol) in 10% aqueous sodium hydroxide solution (10 ml) was stirred at room temperature for overnight. After that reaction was cooled in an ice bath and pH of the medium was adjusted to 1 by adding 1N HCl. Precipitated mass was filtered, washed with cold water for 2-3 times and finally dried to obtain compound B as an off white solid (270 mg, 96%). $^1$H NMR (DMSO): δ 8.71 (brs, 2H, NH), 7.14 (s, 1H, ArH)

(S)—N-(3-{4-[4-(2-amino-oxazole-4-carbonyl)-piperazin-1-yl]-3-fluoro-phenyl}-2-oxo-oxazolidin-5-ylmethyl)-acetamide (110)

To a stirred solution of 1-ethyl-3-(3-dimethylaminopropyl)-carbodiimide hydrochloride (EDC.HCl, 104 mg, 0.5 mmol) in DMF at 0° C., compound B (56.7 mg, 0.4 mmol) was added, followed by hydroxybenzotriazole (HOBt, 70.7 mg, 0.5 mmol). The reaction mixture was stirred at 0° C. for 30 min and LA (150 mg, 0.4 mmol) and N,N-diisopropylethylamine (DIPEA, 0.28 ml, 1.6 mmol) were added and the resultant solution was allowed to stir at room temperature for overnight. After completion of the reaction DMF was evaporated and crude mass was purified by silica column chromatography using 4% methanol-DCM eluent to obtain the final compound 110 as an off white solid (30 mg, 16.8%). $^1$H NMR (DMSO-d$_6$): δ 8.28 (t, 1H, $J_{AB}$=5.5 Hz, NH), 7.52 (dd, 1H, $J_{AB}$=14.8, $J_m$=2 Hz, ArH), 7.19 (dd, 1H, $J_{AB}$=8.5 Hz, $J_m$=1.5 Hz, ArH), 7.09 (t, 1H, $J_{AB}$=9.5 Hz, ArH), 6.96 (brs, 1H, NH), 4.74-4.69 (m, 1H, CHOCO), 4.09 (t, 1H, $J_{AB}$=9.0 Hz CH$_2$NHCO), 3.77-3.72 (m, 4H, CH$_2$NHCO, CH$_2$NCO), 3.02-2.98 (m, 4H, CH$_2$N—Ar), 2.93-2.89 (m, 4H, CH$_2$—N), 1.84 (s, 3H, CH$_3$). ESI-MS (m/z): 446.98 (M+), 468.95 (M+Na), 484.92 (M+K).

Example 32: Synthesis of Compound 111

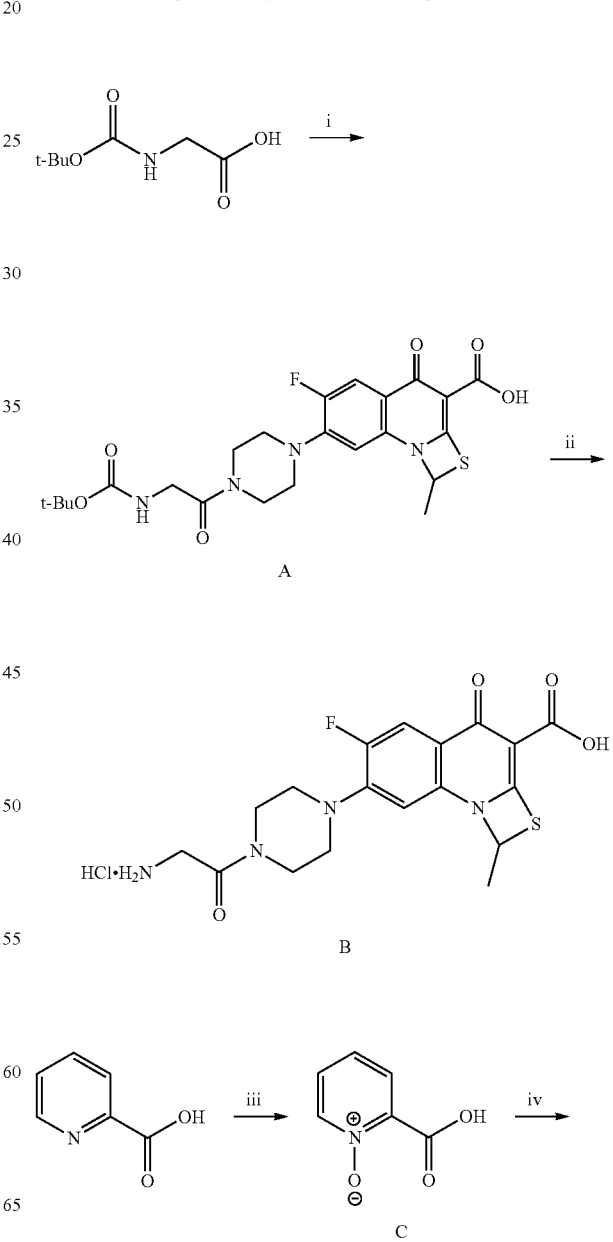

-continued

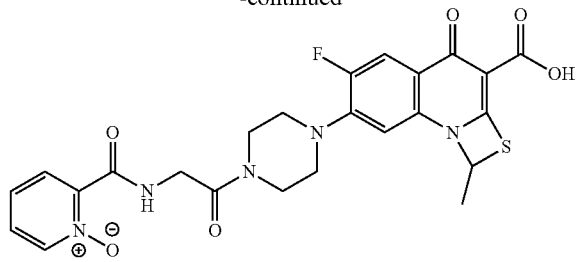

111

Reagents and condition: i) (tert-Butoxycarbonyl)glycine, 6-Fluoro-1-methyl-4-oxo-7-(piperazin-1-yl)-1H,4H-[1,3]thiazeto[3,2-a]quinoline-3-carboxylic acid, Hydroxybenzotriazole, 1-Ethyl-3-(3-dimethylaminopropyl)carbodiimide hydrochloride, N,N-Diisopropylethylamine, DMF, 18 h, R.T.; ii) 6N HCl, overnight R.T.; iii) Hydrogen peroxide (30%) TFA, 16 h reflux; iv). B, Hydroxybenzotriazole, 1-Ethyl-3-(3-dimethylaminopropyl)-carbodiimide hydrochloride, N,N-Diisopropylethylamine, DMF, 18 h, R.T.

7-(4-((tert-Butoxycarbonyl)glycyl)piperazin-1-yl)-6-fluoro-1-methyl-4-oxo-1H,4H-[1,3]thiazeto[3,2-a]quinoline-3-carboxylic acid (A)

To a stirred solution of DCC (0.9 g, 4.3 mmol) in DMF (20 ml), BOC-glycine (0.5 g, 2.85 mmol) and hydroxybenzotriazole (HOBt, 0.5 g, 4.3 mmol) were added at 0° C. and the mixture was allowed to stir for 4 h, followed by addition of 6-fluoro-1-methyl-7-(4-((5-nitro-1H-benzo[d]imidazol-2-yl)methyl)piperazin-1-yl)-4-oxo-1H,4H-[1,3]thiazeto[3,2-a]quinoline-3-carboxylic acid (0.9 g, 2.85 mmol) and triethylamine (0.4 g, 0.6 ml, 4.3 mmol) at 0° C. The reaction mixture was further allowed to stir overnight at room temperature. The reaction mixture was then concentrated under reduced pressure to obtain crude product which was purified by flash column chromatography over silica gel using 3% methanol-DCM as eluent to afford compound A as pale yellow solid (0.75 g, yield: 65%).

6-Fluoro-7-(4-glycylpiperazin-1-yl)-1-methyl-4-oxo-1H,4H-[1,3]thiazeto[3,2-a]quinoline-3-carboxylic acid (B)

A suspension of compound A (950 mg, 1.88 mmol) in 6N HCl (20 mL) was stirred for overnight, after which solvent was evaporated and crude mass was dissolved in methanol-DCM followed by addition of diethyl ether, the process was repeated for 2-3 times and finally obtain almost pure compound B as yellow solid (500 mg, 66%).

2-Carboxypyridine 1-oxide (C)

2-Picolinic acid (1.23 g, 10 mmol) was suspended in trifluoroacetic acid (25 ml) and 30% hydrogen peroxide (16 ml) was added into it. The final reaction mixture was refluxed for 16 h. At end, all the volatiles were evaporated under reduced pressure and crude mass was washed 2-3 times with cold water. Upon drying under vacuum compound C was obtained as a white solid (1 g, 72%).

2-((2-(4-(3-carboxy-6-fluoro-1-methyl-4-oxo-1H,4H-[1,3]thiazeto[3,2-a]quinolin-7-yl)piperazin-1-yl)-2-oxoethyl)carbamoyl)pyridine 1-oxide (111)

To a stirred solution of 1-ethyl-3-(3-dimethylaminopropyl)carbodiimide (EDC.HCl, 286 mg, 1.8 mmol) in DMF (5 ml), compound C (205 mg, 1.5 mmol) was added, followed by the addition of hydroxybenzotriazole (282 mg, 1.8 mmol). The reaction mixture was allowed to stir for 1 hour. Later compound B (500 mg, 1.23 mmol) was added along with N, N-diethyl isopropyl amine (0.3 ml, 1.6 mmol) and the reaction mixture was allowed to stir at room temperature for overnight. After completion of reaction, solvent was evaporated; crude reaction mixture was washed with water, and purified by flash chromatography over silica gel with 4% methanol-DCM as eluent to afford 111 as white solid (70 mg, 11%). $^1$H NMR (DMSO-d$_6$): δ 14.64 (s, 1H, COOH), 11.59 (s, 1H, NH), 8.48 (d, 1H, $J_{AB}$=6.0 Hz, ArH), 8.27 (d, 1H, $J_{AB}$=8.0 Hz, ArH), 7.68-7.60 (m, 3H, ArH), 7.49 (t, 1H, $J_{AB}$=7.5 Hz, ArH), 7.38 (t, $^1$H, $J_{AB}$=7.5 Hz, ArH) 7.04-6.92 (m, 1H, ArH), 6.51-6.32 (m, 1H, SCHN), 4.39 (d, 2H, $J_{AB}$=3.5 Hz, CH$_2$), 3.71-3.67 (m, 4H, CH$_2$N), 2.17-2.11 (m, 3H, CH$_3$). ESI-MS (m/z): 549.90 (M+Na).

Example 33: Synthesis of Compound 112

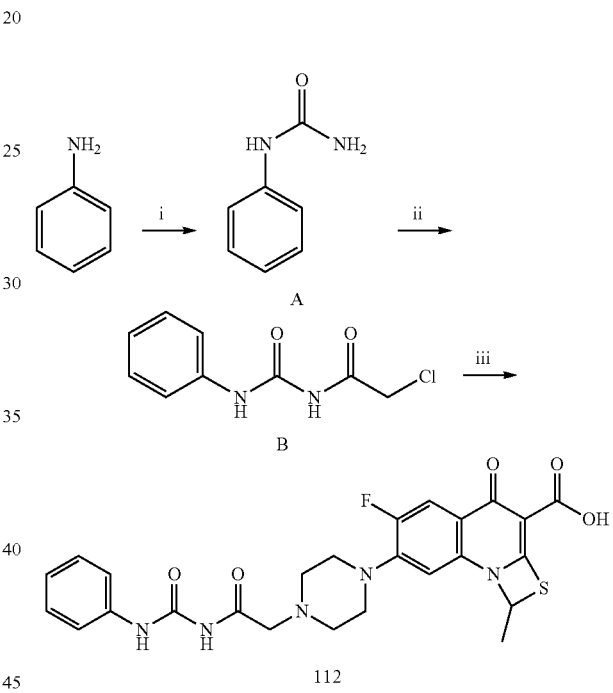

Reagents and condition: i) Urea, HCl, acetic acid; ii) Chloroacetyl chloride, Et$_3$N, CH$_3$CN, 16 h, reflux; iii) 6-Fluoro-1-methyl-4-oxo-7-(piperazin-1-yl)-1H,4H-[1,3]thiazeto[3,2-a]quinoline-3-carboxylic acid, Et$_3$N, DMF, overnight, R.T.

1-Phenylurea (A)

To a mixture of aniline (5.4 ml, 5.92 mmol) and urea (12 g, 0.2 mol) in water (20 ml) conc. HCl (0.4 ml) and glacial acetic acid (0.4 ml) was added and reaction mixture was refluxed for overnight. After that reaction mixture was cooled in an ice bath, the obtained precipitate was collected. The crude solid was crystallized from boiling water to obtain pure compound A as white solid (1 g, 10%). $^1$H NMR (DMSO-d$_6$): δ 8.50 (brs, 1H, NH), 7.38 (d, 2H, $J_{AB}$=8 Hz, ArH), 7.20 (t, 2H, $J_{AB}$=8 Hz, ArH), 6.88 (t, $J_{AB}$=7.5 Hz, ArH), 5.83 (brs, 2H, NH$_2$).

2-Chloro-N-(phenylcarbamoyl)acetamide (B)

To a stirred solution of A (408 mg, 3.0 mmol) and triethyl amine (0.63 ml, 4.5 mmol) in acetonitrile (20 ml), chloroacetyl chloride (0.36 ml, 4.5 mmol) was added and the solution was refluxed for four hours. After that solvent was evaporated under reduced pressure and water was added and extracted with ethyl acetate. After evaporation of the solvent crude B was obtained which was used for next step without further purification (450 mg, 70%)?

6-Fluoro-1-methyl-4-oxo-7-(4-(2-oxo-2-(3-phenylureido)ethyl)piperazin-1-yl)-1H,4H-[1,3]thiazeto-[3,2-a]quinoline-3-carboxylic acid (112)

To a stirred solution of 6-fluoro-1-methyl-4-oxo-7-(piperazin-1-yl)-1H,4H-[1,3]thiazeto[3,2-a]quinoline-3-carboxylic acid (400 mg, 1.15 mmol) and triethyl amine (630 µL, 4.5 mmol) in DMF (10 ml), compound B (320 mg, 1.5 mmol) was added and reaction mixture was stirred at room temperature for 16 h. After completion of the reaction solvent was evaporated and crude material was purified by flash column chromatography over silica gel using 3% methanol-DCM as eluent to obtain the compound 112 as an off white solid (90 mg, 15%). $^1$H NMR (DMSO-$d_6$): δ 14.63 (brs, 1H, COOH), 10.40 (brs, 1H, NHAr), 10.33 (brs, 1H, NH), 7.80 (d, 1H, $J_{AB}$=13.5 Hz, ArH), 7.52 (d, 1H, $J_{AB}$=8.0 Hz, ArH), 7.34 (t, 1H, $J_{AB}$=8 Hz, ArH), 7.09 (t, 1H, $J_{AB}$=7.5 Hz, ArH), 6.97 (d, 1H, $J_{AB}$=6 Hz, ArH), 6.45-6.33 (m, 1H, SCHN), 2.78-2.72 (m, 4H, CH$_2$N), 2.12 (d, 3H, $J_{AB}$=5.5 Hz, CH$_3$). ESI-MS (m/z): 489.18 (M+H).

Example 34: Synthesis of Compound 113

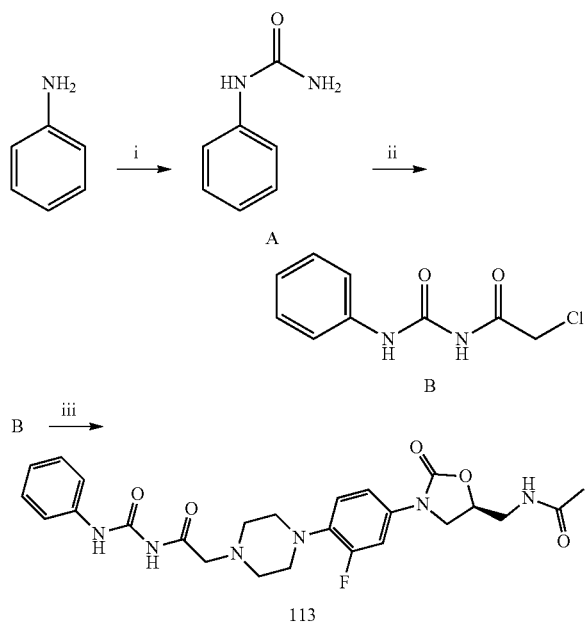

Reagents and condition: i) Urea, HCl, acetic acid; ii) Chloroacetyl chloride, Et$_3$N, CH$_3$CN, 16 h, reflux; iii) (S)-N-((3-(3-fluoro-4-(piperazin-1-yl)phenyl)-2-oxooxazolidin-5-yl)methyl)acetamide hydrochloride salt (LA, Linezolid Analogue), Et$_3$N, DMF, overnight, R.T.

1-Phenylurea (A)

To a mixture of aniline (5.4 ml, 5.92 mmol) and urea (12 g, 0.2 mol) in water (20 ml) conc. HCl (0.4 ml) and glacial acetic acid (0.4 ml) was added and reaction mixture was refluxed for overnight. The reaction mixture was then cooled in an ice bath and precipitated solid was collected. The crude solid was crystallized from boiling water to obtain pure compound A as white solid (1 g, 10%). %). $^1$H NMR (DMSO-$d_6$): δ 8.50 (brs, 1H, NH), 7.38 (d, 2H, $J_{AB}$=8 Hz, ArH), 7.20 (t, 2H, $J_{AB}$=8 Hz, ArH), 6.88 (t, $J_{AB}$=7.5 Hz, ArH), 5.83 (brs, 2H, NH$_2$).

2-Chloro-N-(phenylcarbamoyl)acetamide (B)

To a stirred solution of A (408 mg, 3.0 mmol) and triethyl amine (0.63 ml, 4.5 mmol) in acetonitrile (20 ml) chloroacetyl chloride (0.36 ml, 4.5 mmol) was added and the solution was refluxed for four hours. After that solvent was evaporated under reduced pressure and water was added and extracted with ethyl acetate. After evaporation of the solvent, crude B was obtained which was used for next step without further purification (450 mg, 70%).

(S)-2-(4-(4-(5-(Acetamidomethyl)-2-oxooxazolidin-3-yl)-2-fluorophenyl)piperazin-1-yl)-N-(phenylcarbamoyl)acetamide (113)

To a stirred solution of LA (70 mg, 0.19 mmol) and triethyl amine (105 µL, 0.75 mmol) in DMF (2 ml) compound B (60 mg, 0.28 mmol) was added and reaction mixture was stirred at room temperature for 16 h. After completion of the reaction solvent was evaporated and crude was purified by flash column chromatography over silica gel using 3% methanol-DCM as eluent to obtain the compound 113 as an off white solid (15 mg, 15%). $^1$H NMR (DMSO-$d_6$): δ 7.52 (d, 1H, $J_{AB}$=6.4 Hz, ArH) 7.46 (dd, 1H, $J_{AB}$=14.0 Hz, $J_m$=2.5 Hz ArH), 7.36-7.32 (m, 1H, ArH), 7.15-7.01 (m, 1H, ArH), 7.07 (dd, 1H, $J_{AB}$=8.75 Hz, $J_m$=2.0 Hz, ArH), 6.94 (t, 1H, $J_{AB}$=9 Hz, ArH), 6.59 (brs, 1H, NH), 6.09 (t, 1H, $J_{AB}$=6.0 Hz, NH), 4.78-4.76 (m, 1H, CHOCO), 4.73 (brs, 1H, NH), 4.02 (t, 1H, $J_{AB}$=9 Hz, CH$_2$NHCO), 3.76-3.71 (m, 1H, CH$_2$NHCO), 3.70-3.68 (m, 1H, CH$_2$NCO), 3.62-3.57 (m, 1H, CH$_2$NCO), 3.24 (s, 2H, CH$_2$—N), 3.17-3.11 (m, 4H, CH$_2$N—Ar), 2.8-2.78 (m, 4H, CH$_2$—N), 2.02 (s, 3H, CH$_3$). ESI-MS (m/z): 513.00 (M+H).

Example 35: In Vitro Biology Results

Exemplary compounds of the invention were tested in vitro against various susceptible and resistant Gram-positive bacterial strains.

Determination of Minimum Inhibitory Concentration (MIC)

Reagents:

Brain heart infusion broth, bacterial cultures, 96 well-plate, autoclave, incubator, Alamar blue.

Protocol:

MIC of DART molecules were determined by micro broth dilution as per CLSI guidelines. Bacterial strains were cultured in Brain Heart Infusion Agar (BHIA) at 37° C. for 24 h. For MIC determination, BHI broth (100 µl) was added to each of the wells of a 96 well plate. 100 µl of broth containing drug was added to the first well (1A to 1H) and thereafter serial (double) dilutions were carried out for up to 10 wells (column 1 to column 10 of the 96 well plate). Bacterial inoculum was prepared by adjusting the bacterial culture turbidity to 0.5 McFarland standard (approximately 1.5×10$^8$ cells/ml) and further diluted (100 times with sterile BHI broth). Diluted bacterial suspension (100 µl) was added to each well except sterility control wells (column 12 of 96 well plate). The plates were incubated at 37° C. for 24 h. The MIC of the test compound was measured after addition of Alamar blue dye.

Minimum inhibitory concentration (MIC) in µg/ml for various synthesized molecules against various susceptible and resistant Gram-positive and Gram negative bacterial strains is shown in Tables 1 and 2, respectively.

TABLE 1

Minimum inhibitory concentration (MIC) in μg/ml for various synthesized molecules against various Gram-positive Bacteria

| Compound No. | S. aureus MTCC 6908 | S. aureus ATCC 43300 | S. aureus CCARM 3505 | S. epidermidis ATCC 35984 | S. epidermidis S12-1 | E. faecium NCIM 5421 | E. faecium CCARM 5207 | E. fecalis CCARM 5168 |
|---|---|---|---|---|---|---|---|---|
| 1 | 1.5 | 1 | 32 | 0.13 | >64 | >16 | ND* | ND |
| 2 | 0.53 | 0.13 | 16 | 0.03 | 8 | 0.25 | ND | ND |
| 6 | 0.1 | <0.13 | 4 | <0.03 | 4 | 0.25 | ND | ND |
| 10 | 0.04 | <0.02 | 1 | <0.03 | 2.25 | 0.125 | >16 | 1 |
| 11 | 0.125 | 0.03 | 1 | <0.03 | 0.13 | 0.625 | 8 | 4 |
| 16 | 0.25 | <0.01 | 0.5 | <0.03 | 0.13 | 0.12 | ND | ND |
| 18 | 1 | 1 | >4 | 0.25 | >16 | 0.5 | ND | ND |
| 19 | >64 | 32 | >16 | 16 | >16 | >16 | >16 | >16 |
| 20 | 8 | 0.5 | >16 | 0.13 | >16 | 1 | ND | ND |
| 21 | 0.25 | 0.13 | >16 | <0.03 | >16 | 0.25 | ND | ND |
| 31 | 0.5 | 0.25 | 16 | 0.13 | 8 | 0.06 | ND | ND |
| 32 | 0.5 | 0.06 | 8 | 0.13 | 4 | ND | ND | ND |
| 33 | 0.25 | 0.25 | >16 | 0.13 | 8 | 0.125 | 8 | 0.5 |
| 34 | 4 | 0.13 | 8 | 0.13 | 8 | 1 | ND | ND |
| 43 | 8 | 8 | >16 | >16 | >16 | >16 | ND | ND |
| 44 | 8 | 4 | >16 | 4 | >16 | >16 | ND | ND |
| 48 | 2 | 1 | >16 | 0.5 | >16 | >16 | ND | ND |
| 55 | 0.25 | 0.5 | 0.25 | 0.06 | 0.5 | 0.06 | ND | ND |
| 57 | 8 | 16 | >16 | >16 | >16 | >16 | ND | ND |
| 58 | >16 | >16 | >16 | >16 | >16 | >16 | ND | ND |
| 65 | 16 | >16 | >16 | 16 | >16 | >16 | ND | ND |
| 66 | 8 | 8/16 | >16 | 8 | >16 | >16 | ND | ND |
| 68 | 16 | >64 | >16 | >16 | >16 | >16 | ND | ND |
| 75 | 4 | 16 | >16 | >16 | >16 | >16 | ND | ND |
| 76 | 4 | 8 | 8 | 2 | 4 | >16 | ND | ND |
| 77 | 4 | 8 | 8 | 4 | 4 | 0.5 | ND | ND |
| 78 | 8 | 16 | >16 | 8 | 8 | >16 | ND | ND |
| 80 | 16 | 16 | >16 | >16 | >16 | >16 | ND | ND |
| 84 | >16 | >16 | >16 | 16 | 8 | >16 | ND | ND |
| 108 | >16 | >16 | >16 | >16 | >16 | >16 | ND | ND |
| 110 | >16 | >16 | >16 | >16 | >16 | >16 | ND | ND |
| 111 | >16 | 16 | >16 | >16 | >16 | >16 | ND | ND |
| 112 | 0.25 | 0.13 | >16 | 0.13 | 8 | >16 | ND | ND |

*Not Determined

TABLE 2

Minimum inhibitory concentration (MIC) in μg/ml for various synthesized molecules against various Gram-negative Bacteria

| Compound No. | E. coli MTCC 1687 | E. coli BAA 196 | K. pneumonia ATCC 13883 | P. aeruginosa ATCC 27853 | P. aeruginosa CCARM 2161 | P. aeruginosa CCARM 2204 | A. baumannii ATCC 1906 | A. baumannii CCARM 12001 | A. baumannii CCARM 12020 | E. aerogenes M2-1 | E. aerogenes NCIM 5139 |
|---|---|---|---|---|---|---|---|---|---|---|---|
| 1 | 16 | 16 | ND* | >16 | >16 | >16 | >16 | >16 | >16 | >16 | >16 |
| 2 | 1 | 8 | 4 | 8 | ND | ND | 8 | ND | ND | 8 | 4 |
| 6 | 1 | 16 | 0.25 | 8 | ND | ND | 8 | ND | ND | 4 | 4 |
| 10 | 0.13 | 4 | 0.25 | 1 | >16 | 4 | 1 | >16 | 8 | 0.25 | 0.125 |
| 11 | 0.25 | 1 | 0.5 | 1 | >16 | >16 | 1 | >16 | >16 | 0.25 | 0.125 |
| 16 | 4 | >16 | 0.25 | 2 | ND | ND | .05 | 16 | >16 | 4 | 2 |
| 18 | >4 | >4 | 0.12 | >16 | >16 | >16 | 1 | ND | ND | >16 | 0.25 |
| 20 | 1 | >16 | 0.25 | 4 | ND | ND | 8 | ND | ND | 4 | 0.5 |
| 21 | 8 | >16 | 0.5 | 16 | >16 | >16 | 16 | >16 | >16 | 16 | 16 |
| 31 | 2 | 4 | 0.12 | 8 | ND | ND | 2 | ND | ND | 8 | 1 |
| 32 | 4 | 8 | 0.5 | 16 | >16 | >16 | 2 | >16 | >16 | 16 | 16 |
| 33 | <0.03 | 2 | 0.06 | 0.5 | 16 | 8 | 0.06 | 16 | 4 | 0.06 | 0.0312 |
| 34 | >16 | >16 | ND | ND | ND | ND | ND | ND | ND | ND | ND |
| 43 | 0.25 | >16 | ND | ND | ND | ND | ND | ND | ND | ND | ND |
| 44 | 0.5 | >16 | 0.12 | 4 | ND | >16 | 16 | >16 | >16 | 1 | 1 |
| 55 | >16 | >16 | >16 | >16 | >16 | >16 | >16 | >16 | >16 | ND | ND |
| 112 | 1 | ND | ND | ND | ND | ND | ND | ND | ND | ND | ND |

*Not Determined

MIC Interpretations

The above MIC results highlight some interesting structure activity relationship (SAR) between the different classes of antibiotics with varying functional groups to finally obtain effective antibacterial agents. All fluoroquinolones functionalized with five-membered heterocyclic motifs with varying Y and Z substituents are found to be equally active against susceptible and resistant S. aureus species. For example, fluoroquinolones with similar $R_4$ and B group behave differently while changing the Y and Z substituents of 5 membered heterocyclic ring as depicted in the Formula I. All these new fluoroquinolones 1, 2, 6, 10 and 11 are equally active in both susceptible *S. aureus* and MRSA as well as against *E. faecium*. Different Y and Z substituents with similar B changes the specificity of a particular molecule against a particular pathogen. For example, compound 2 and 6 are found to be specific towards Gram positive pathogens in comparison to Gram negative pathogen except compound 6 is active against susceptible *E. coli* and *Enterobacter aerogens*. In most of the Gram negative pathogens compound 2 shows activity in the range of 4-8 μg/ml. Surprisingly, the compounds with Y=S, Z=N (compound 6) and Y=C and Z=O, (compound 10) are active even against quinolone resistant *S. aureus* and quinolone and erythromycin resistant *S. epidermidis* strains. Among compounds 6 and 10, compound 10 is found to be more active against quinolone resistant *S. aureus* and *S. epidermidis* strains. Compound 10 and compound 11 have different B groups, yet they have similar activity against both susceptible and resistant Gram positive pathogens.

Most of the quinolone compounds 6, 10, 11, 16, 18, 20, 21, 31, 32, 33 are all active against *Klebsiella pneumonia* (susceptible) but some of them fell to work against other Gram negative pathogens like *P. aeruginosa, A. baumanni, E. coli*, and *Enterobacter* aerogens.

Compound 10 and 11 are found to be broad spectrum antibiotics and work against entire Gram positive (susceptible and resistant) as well as Gram negative (susceptible) pathogens. The change in B group in compound 10 and 11 made one of them to be active against a particular resistant Gram negative pathogen in comparison to the other. For example, compound 10 is active against resistant *P. aeruginosa, A. baumanni* in comparison to compound 11 with similar functional structure with slight change in B group as mentioned in Formula I. However, compound 11 has better activity against resistant *E. coli* (BAA 196) than compound 10. This indicates that the nature of B group plays an important role in determining the specificity of fluoroquinolone antibacterial activity.

Compound 11 and compound 16 are different fluoroquinolones and functionalized with similar five-membered heterocyclic motifs with similar B group. Both compounds are active against both susceptible and resistant Gram positive strains but interestingly compound 11 maintains broad spectrum activity through inhibition of both susceptible and resistant *E. coli* and other Gram negative pathogens. On the other hand, compound 16 failed to show activity against Gram negative pathogens specially against *E. coli* and *Enterobacter aerogens* while the respective parent fluoroquinolone is known to be active against most of the Gram negative species. However, compound 16 is found to be active against susceptible *P. aeruginosa, A. baumanni* species.

The differences in bioactivity among compounds 18, 20 and 21 indicate that bioactivity of these fluoroquinolones depends on the nature of substituents at R5 and R6 in the benzene scaffold that is fused with 5 membered heterocyclic ring. For example, dichloro substituted compound 21 has good bioactivity against MRSA and susceptible *S. aureus* unlike other molecules, 18 and 20. Compound 19 and 20 are both amino substituted benzimidazole derivatives with the amino substitution at distinct sites. Compound 20 is amino substituted on the benzene scaffold and has better bioactivity against *S. aureus* in comparison to compound 19 which bears the amino substitution on the five-membered heterocyclic ring. Further compound 20 shows better bio-activity against MRSA compared to susceptible *S. aureus* strains. All these molecules 18-21 are found to be inactive against Gram negative pathogens and failed to show any activity against quinolone resistant *S. aureus*.

All pyridine substituted quinolone derivatives, as shown in FORMULA I, including compounds 31-33 showed good bio-activity against susceptible *S. aureus, S. epidermnidis* and MRSA strains. Except compound 33 all others are found to be inactive against most of the Gram negative pathogens. Compound 34 is same as compound 31 except compound 34 has N-hydroxyl group that makes it specifically active against MRSA without having activity against susceptible *S. aureus* strain.

Compound 33 is found to be very active molecule and found to be broad spectrum antibiotics against both susceptible and resistant Gram positive and Gram negative pathogens. It is very potent against susceptible *P. aeruginosa, A. baumnanni, E. coli*, and *Enterobacter aerogens* and depending on different resistant strains of *P. aeruginosa, A. baumanni*, the bio-activity of compound 33 varies from 4-16 μg/ml. But it is very active (MIC≤1 μg/ml) against resistant *E. coli* (MDR) and *E. aerogens*.

Interestingly most of the pyridine analogs, compounds 31, 32 and 33 are found to be equally active against both susceptible and resistant *E. coli*.

Position of the N-hydroxy pyridine moiety from the quinolone scaffold does influence a lot towards the activity of the final molecule. For example, compound 111 was found to be completely inactive in comparison to compound 34. Thus functional moiety with appropriate position with respect to the main structural scaffold determine the binding of the molecule against a particular target thus the activity against different pathogens.

Fluoroquinolones with substituted mono/di-guanidine scaffolds, for example, compound 43 and 44 under Formula I fail to act against any Gram positive pathogens and resistant *E. coli* strain but retain their activity against susceptible *E. coli* species. In general, guanidine scaffold is known to have interaction with *E. coli* membrane (J. App. Microbiol. 2010, 108, 898). The above results suggest that guanidine functional group present in compounds 43 and 44 might sterically hinder the interaction between the fluoroquinolones and DNA-gyrase while retaining the interaction with *E. coli* membrane.

All these above results highlight the difficulty in predicting the activity of fluoroquinolones based on the derivatization with known functional moiety. The overall activity of a molecule solely depends on the hydrophobicity, net charge and overall spatial orientation of different functional moieties present in the molecule and their respective interaction with bacterial membrane, bacterial efflux system and binding interaction with target protein present of the target bacteria.

The compounds 55, 65, 66, 68, 76, 77 and 78 are representatives of some of the oxazolidinone derivatives with different functional moieties as depicted in the FORMULA II. Among all the compounds, interestingly nitroheterocyclic containing oxazolidinone derivative where Y=S and Z=N, so called compound 55 showed 8-fold better activity in comparison to commercial linezolid against MRSA. It showed better activity against both MRSA, quinolone resistant *S. epidermidis* and other susceptible and resistant Gram positive pathogen but failed to show potency against Gram negative pathogens. Compound 55 has found to be active against *Enterococcus faecium*. On the other hand, benzimidazole, pyridine as well as bi-guanidine substituted oxazolidine analogs failed to show activity against both Gram positive Gram negative pathogens.

The above results demonstrate that oxazolidinones with various known functional moieties, which retain their activity with fluoroquinolones, fail to maintain similar activity while present with oxazolidine scaffold. So judicious and logical placement of different functional moieties, choice of suitable functional moieties along with their appropriate orientation with respect to oxazolidinone moiety would determine the overall activity of the final molecule.

Example 36: In Vitro Assay for Implant Associated Infections

Sequential ZIB Assay for PMMA Beads
Materials:
Brain heart infusion agar, S. epidermidis S5-2, petri plates, autoclave, incubator, UV spectrophotometer.
Method:
S. epidermidis S5-2 cells were grown in Brain Heart Infusion Agar (BHIA) at 37° C. for 24 h. 100 µl of 0.5 McFarland equal bacterial suspension was spread on BHA plates. Drug loaded beads were placed above these plates. Plates were incubated at 37° C. for 24 h. Next day, zone of inhibition (ZOI) the beads were measured following which the beads were placed on fresh BHA plates with bacterial suspension spread and this experiment was continued up to seven days. The drug release pattern was determined by compiling and analyzing the ZOI data of beads on each ZOI cycle up to seven days.

Results on in vitro drug release assay from bone cement are shown in Table 3.

TABLE 3

Sequential ZOI(cm) of SmartSet ®HV impregnated DARTs against S. epidermidis (S5-2)

| Matrix | Compound | Day-1 | Day-2 | Day-3 | Day-4 | Day-5 | Day-6 | Day-7 |
|---|---|---|---|---|---|---|---|---|
| Smartset HV | No compound | 0 | 0 | 0 | 0 | 0 | 0 | 0 |
| Smartset HV | Compound 2 | 2.2 | 2.1 | 1.6 | 0.8 | 1.6 | 1.8 | 1.4 |
| Smartset HV | Compound 10 | 2.2 | 2 | 1.8 | 1.7 | 1.7 | 1.6 | 1.8 |
| Smartset HV | Vancomycin | 1.4 | 1.2 | 0.7 | 0.7 | 0 | 0 | 0 |

Results & Interpretations

Bone infections associated with implants require compounds that can be loaded in bone cement, PMMA. These compounds should necessarily have good release properties from the cement for their action in bone, the release should be sustained as the treatment is for a prolonged time and should be extremely potent against the microbes generally associated with bone infections like S. aiureus, opportunistic pathogens like S. epidermidis, P. acnes etc. Compounds 2 and 10 having good potency against the above microbes were loaded on SmartSet HV (a FDA approved PMMA), at appropriate ratio and compared with the antibiotic, vancomycin loaded cement predominantly used in bone infections. In vitro zone of inhibition (ZOI) assay was performed using Staphylococcus epidermidis strain S5-2. A sustained release was obtained with Compounds 2 and 10 as observed from the ZOI in FIG. 1. The progressive release was found to be higher for these two compounds than vancomycin. Thus these compounds are potentially lead molecules for action against bone implant associated infections.

The invention provides novel compounds of formulas as depicted in the FORMULAE I-VII as described herein. The complete synthetic process of some of the compounds representative of the FORMULAE I-VII and their respective intermediates are described herein as examples. Some of the intermediates described herein are the useful intermediates for the synthesis of other class of compounds as well.

The present invention further provides the use of a particular class of effective molecule(s) as described herein to prepare a medicament for the treatment of bacterial infection comprising either Gram positive or Gram negative or both pathogen. The bacterial infection can be caused by at either Enterococcus spp. or S. aureus strains. The bacterial infection can also be caused by drug resistant pathogens like MRSA. In certain specific embodiments, the bacterial infection is caused by MRSA as well as vancomycin resistant strain, VRSA.

In certain specific embodiments the invention provides the use of certain novel compounds like 2, 6, 10 and 11 related to the FORMULA I or respective appropriate pharmaceutically acceptable salt thereof for the treatment of bacterial infection caused by MRSA and other opportunistic pathogens like Staphylococcus epidermidis and quinolone resistant S. aureus and S. epidermidis. The invention further provides different form of formulation comprising novel compounds in various therapeutic dosage forms to optimally deliver the active at the site of action and overall improve therapeutic efficacy of a particular medicament. The invention includes different forms of topical and oral formulations. Topical formulations include cream, gel, emulgel, ointment, spray, foams, lotions and powder for the treatment of acute bacterial skin and skin structure infections (ABSSI), complicated skin structure infections, boils, furuncles, styes, cellulitis, impetigo and other superfacial skin infections as well as other complicated infections including the infections involving deeper skin soft tissues like surgical site infections or infected ulcers, burns and major abscesses.

The present invention describes the development of different topical cream and gel formulation with appropriate novel molecules that offer effective skin retention with good PK profile resulting improvement of dose regime and fast onset of action resulting patient compliance. The novel compounds selected in this formulation provide good hydrophobicity and log P values and additionally form stable topical formulations with pharmaceutically accepted diluent, excipient and carriers (Table 4 and Table 5).

The composition of topical cream and gel consists of penetration enhancer like diethyleneglycol monoethyl ether, caprylic/capric triglyceride, dimethyl isosorbide, emollients like cetostearyl alcohol, cetyl alcohol, stearyl alcohol, oleyl alcohol, light liquid paraffin, petrolatum; and emulsifier like Steareth 2, Steareth 21, Tween 80, Span 40, Span60, cetostearyl ether 12, cetostearyl ether 20, cresmer 1000, humectants like propylene glycol, glycerol, polyethylene glycol 400, gelling agents like hydroxyethyl cellulose (HEC), hydroxypropyl cellulose (HPC), hydroxypropylmethyl cellulose (HPMC), different acrylic acid based polymers, pH modifier like citric acid, triethanolamine, dilute HCl. Formulations include preservatives like benzyl alcohol, sodium benzoate, methyl paraben, propyl paraben, phenoxyethanol etc.

Method of Preparation of Topical Gel Comprising Compound 2 (Table 4)

Briefly the method involves homogenous mixing of accurately weighed quantity of diethylene glycol monoethylether, polyethylene glycol 400 and propylene glycol to obtain homogenous transparent solution. A specific quantity of active (Compound 2) was added in portions to the above mixture with stirring to form phase A. Separately, hydroxyethyl cellulose was solubilized in water with stirring for 30-40 minutes to form transparent gel base (phase B).

Phase A was slowly added into phase B with stirring to form homogenous gel mixture. Phase C ingredient (benzyl alcohol) was added in portion wise to obtain the final mixture and stirring is continued for another 10 minutes to obtain homogenous topical gel. Finally, pH of the gel was adjusted to 5.0-5.5 with 20% citric acid solution.

Method of Preparation of Topical Cream Comprising Compound 2 (Table 2)

In brief the method comprises of homogenous mixing of different phase A ingredients like cyclopentosiloxane, cetostearyl alcohol, dimethyl isosorbide, steareth 2 and steareth 21 while heating at 60° C. to forms a transparent solution. Accurately weighed amount of active compound 2 was added in portion wise into transparent solution of phase A by maintaining temperature at 60° C. Phase B was prepared by adding carbopol 980 into water (while stirring) and pH was adjusted to 5 to form uniform gel base. Humectants like propylene glycol and polyethylene glycol 400 were added into carbopol gel base and the mixture was heated at 60° C. to obtain phase B. Phase A was added into phase B at 60° C. with stirring and the mixture was allowed to cool to 40° C. Then, phase C ingredients (benzyl alcohol) was added into the above mixture, stirred and allow to cool to room temperature to prepare the cream formulation.

The present invention focuses on delivery of some of the effective novel antibiotics in the form of beads, injectable hydrogel, hydrogel, polymeric films, foams, in-situ gel, hydrocolloids for the treatment of inflammatory bone infections so called osteomyelitis, implant associated infections, surgical site infection, diabetic foot infections, diabetic ulcer, mild to moderate wound infections etc. The present invention provides the use of the novel compounds in the form of novel local/topical formulation described herein for the treatment of bacterial infections caused mainly by MRSA and other opportunistic pathogens like *Staphylococcus epidermidis* and quinolone resistant *S. aureus* and *S. epidermidis* or mixture of Gram positive and Gram negative pathogens.

The present invention includes bone cement formulation with novel hydrophobic or amphipathic or hydrophilic antibiotics and bio-degradable or non-biodegradable polymer to obtain beads with particular dimension as mentioned in Table 3. The above formulation will be capable of releasing the drug through the matrix in controlled manner for an extended period of time for the treatment and prevention of osteomyelitis mainly caused by MRSA and other opportunistic pathogens and even by VRSA.

The present invention provides improved delivery of some of the novel antibiotics at the site of infection to achieve sustained release of optimal concentration of antibiotic over a prolonged period of time as evidenced from in vitro sequential zone of inhibition studies and sequential drug release studies along with good anti-inflammatory effect. This kind of local treatment minimizes the nephrotoxicity, ototoxicity and gastrointestinal side effect generally caused by long exposure (4 to 6 week) of high drug concentration in serum for some of the known antibiotics prescribed for oral and parenteral treatment of osteomyelitis. The present invention further provides an effective formulation with new antibiotics that could inhibit or prevent biofilm formation with substantial antibacterial and anti-inflammatory effect.

TABLE 4

Composition of topical gel with Compound 2

| Phase | Ingredients | Amount used |
|---|---|---|
| A | Active (compound 2) | 1% |
|   | Diethylene glycol monoethyl ether (Penetration enhancer) | 10% |
|   | PEG 400 (Humectant) | 5% |
|   | Propylene glycol (Humectant) | 5% |
| B | Hydroxyethyl cellulose (gelling agent) | 1.7% |
|   | Water | q.s |
| C | Benzyl alcohol (preservative) | 1 |
|   | 20% Citric acid (pH modifier) | q.s |

TABLE 5

Composition of topical cream formulation with Compound 2

| Phase | Ingredients | Amount used |
|---|---|---|
| A | Active (compound 2) | 1% |
|   | Cyclopentasiloxane (silicone) | 3% |
|   | Cetostearyl alcohol (Emollient) | 2.5% |
|   | Dimethyl isosorbide (Emollient/Penetration enhancer) | 5% |
|   | Steareth 2 (Emulsifier) | 2% |
|   | Steareth 21 (Emulsifier) | 2% |
| B | Carbopol 980 (Gelling agent) | 0.5% |
|   | Water | q.s |
|   | 10% TEA (pH modifier) | q.s |
|   | Propylene glycol (Humectant) | 5% |
|   | Polyethylene glycol 400 (Humectant) | 5% |
| C | Preservative (Benzyl alcohol) | 1% |

TABLE 6

Bone cement composition comprises of following ingredients:

| Ingredients | F1 | F2 | F3 | F4 | F5 | F6 | F7 | F8 | F9 | F10 | F11 |
|---|---|---|---|---|---|---|---|---|---|---|---|
| Stimulan Rapid Cure ® | 40 g | 40 g | — | — | — | — | — | — | — | — | — |
| Simplex-P ® | — | — | 40 g | 40 g | 40 g | 40 g | 40 g | — | — | — | — |
| Smart set HV ® | — | — | — | — | — | — | — | 40 g | 40 g | 40 g | 40 g |
| Compound 2 | 1 g | — | 4 g | — | 1 g | — | 1 g | 1 g | — | 1 g | — |
| Compound 10 | — | 1 g | — | 4 g | — | 1 g | — | — | 1 g | — | 1 g |

TABLE 6-continued

Bone cement composition comprises of following ingredients:

| Ingredients | F1 | F2 | F3 | F4 | F5 | F6 | F7 | F8 | F9 | F10 | F11 |
|---|---|---|---|---|---|---|---|---|---|---|---|
| Monomer | — | — | 20 ml | 20 ml | 20 ml | 20 ml | 20 ml | 20 ml | 20 ml | 20 ml | 20 ml |
| Mixing solution/Monomer | 12.48 ml | 12.48 ml | — | — | — | — | — | — | — | — | — |
| Polyvinylpyrrolidone K90 | — | — | — | — | — | — | — | — | — | — | — |
| DMDM Hydantoin | — | — | — | — | — | — | — | — | — | 0.16 g | 0.16 g |

TABLE 7

In situ hydrogel composition with Compound 2, 6, 10 and 55

| Ingredients | F1 | F2 | F3 | F4 | F5 | F6 | F7 | F8 |
|---|---|---|---|---|---|---|---|---|
| Compound 2/compound 10/compound 55/compound 6 | 1% | 1% | 1% | 1% | 1% | 1% | 1% | 1% |
| Chitosan | 1.5% | 0.6% | — | — | — | — | — | 1.5% |
| Sodium alginate (Manucol LKX ®) | — | — | — | — | — | 0.5% | — | — |
| Poloxamer 407 | — | 15% | 20% | 5% | 5% | — | — | — |
| Carbopol 980 | — | — | — | 0.1% | 0.1% | 0.5% | — | — |
| PLGA | — | — | — | — | — | — | 16% | — |
| Glycerin | — | — | — | — | 3% | — | — | — |
| Diethyleneglycol monoethyl ether | — | — | 5% | — | — | — | — | — |
| β-glycerophosphate | 5% | 1% | — | — | — | — | — | 5% |
| Triethyl citrate | — | — | — | — | — | — | 82.93% | — |
| 0.1N HCl | q.s | q.s | — | — | — | — | — | q.s |
| Purified water | q.s | q.s | q.s | q.s | q.s | q.s | q.s | q.s |
| Methyl paraben | — | — | 0.1% | 0.1% | 0.1% | — | — | — |
| Propyl paraben | — | — | 0.01% | 0.01% | 0.01% | — | — | — |
| Sodium benzoate | 0.07% | 0.07% | — | — | — | 0.07% | 0.07% | 0.07% |

TABLE 8

Hydrogel composition containing with Compounds 2, 6 and 10

| Ingredients | F1 | F2 | F3 | F4 | F5 | F6 | F7 |
|---|---|---|---|---|---|---|---|
| Compound 10/compound 2/compound 6 | 1% | 1% | 1% | 1% | 1% | 1% | 1% |
| Hydroxyethyl cellulose | 1.5% | — | — | — | 1.5% | 1.7% | 1.7% |
| Poloxamer 407 | 1% | 1% | — | — | — | — | — |
| Carbopol 980 | — | 0.3% | 0.2% | 0.4% | — | — | — |
| Ascorbyl palmitate | 0.4% | 0.6% | 0.2% | 0.6% | 0.2% | 0.6% | 1% |
| Trancutol-P | 5% | 6% | 5% | 6% | 5% | 6% | 8% |
| Tween 80 | — | — | — | 2% | 1.2% | 2% | 2% |
| Collagen | 0.1% | 0.1% | 0.1% | 0.1% | 0.1% | 0.1% | 0.1% |
| Water | q.s | q.s | q.s | q.s | q.s | q.s | q.s |
| 10% Triethanolamine | — | q.s | q.s | q.s | — | — | — |

TABLE 9

Hydrogel composition containing sodium alginate with Compound 2, compound 10 and compound 55

| Ingredients | F1 | F2 | F3 | F4 | F5 | F6 | F7 |
|---|---|---|---|---|---|---|---|
| Compound 2/compound 10/compound 55 | 1% | 1% | 1% | 1% | 1% | 1% | 1% |
| Sodium alginate (Manucol LKX ®) | 2% | 2% | 2% | 3% | 2% | 2% | 2% |
| Hydroxypropylmethyl cellulose | 2% | — | 2% | — | — | — | — |
| Hydroxypropyl cellulose | — | — | — | — | — | — | — |
| Hydroxyethyl cellulose | — | — | — | — | 1.5% | 2% | 2% |
| Poloxamer 407 | — | — | 0.7% | 0.5% | — | — | — |
| Carbopol 980 | — | 0.7% | — | 0.5% | — | — | — |
| Collagen | 0.1% | 0.1% | 0.1% | 0.1% | 0.1% | 0.1% | 0.1% |
| Glycerol | — | — | — | — | 1% | — | — |
| Propylene glycol | — | — | — | — | — | 1% | — |
| Polyvinyl alcohol | — | — | — | — | — | — | 2% |

TABLE 9-continued

Hydrogel composition containing sodium alginate with Compound 2, compound 10 and compound 55

| Ingredients | F1 | F2 | F3 | F4 | F5 | F6 | F7 |
|---|---|---|---|---|---|---|---|
| Water | q.s | q.s | q.s | q.s | q.s | q.s | q.s |
| 10% Triethanolamine | — | q.s | — | q.s | — | — | — |
| Methyl paraben | — | 0.1% | 0.1% | 0.1% | — | — | — |
| Propyl paraben | — | — | 0.01% | 0.01% | — | — | — |
| Sodium benzoate | 0.07% | 0.07% | — | — | 0.07% | 0.07% | 0.07% |

TABLE 10

Hydrogel film composition with Compound 2 and Compound 10

| Ingredients | F1 | F2 | F3 | F4 | F5 | F6 | F7 |
|---|---|---|---|---|---|---|---|
| Compound 2/compound 10 | 1% | 1% | 1% | 1% | 1% | 1% | 1% |
| Sodium alginate | 3% | 1.5% | 3% | 3% | 2% | — | — |
| Gelatin | — | — | 2% | — | — | — | — |
| Dextran | — | — | — | — | — | 0.75% | — |
| Chitosan | — | — | — | 0.2% | — | — | — |
| Sodium CMC | — | — | — | — | 0.5% | — | — |
| Hyaluronic acid | — | — | — | — | — | — | 1% |
| Polyvinyl alcohol | — | 10% | — | — | — | 5% | 5% |
| Propylene glycol | — | — | — | — | — | — | — |
| Calcium chloride | 3% | — | — | 1% | 1% | — | — |
| Ascorbic acid | — | — | — | — | — | — | 0.3% |

TABLE 11

Compound 33 loaded liposomal hydrogel composition

| Ingredients | F1 | F2 | F3 | F4 | F5 | F6 | F7 |
|---|---|---|---|---|---|---|---|
| Compound | 1% | 1% | 1% | 1% | 1% | 1% | 1% |
| Soya lecithin | 5% | 5% | — | — | — | — | — |
| Phosphatidyl-choline | — | — | 3% | 4% | — | — | — |
| Phosphatidyl-choline dimyristoyl | — | — | — | — | — | — | 3% |
| Dicetyl phosphate | — | — | — | — | 4% | 5% | — |
| Cholesterol | 2% | 2% | 1% | 1.5% | 2% | 2% | 3% |
| Ascorbyl palmitate | 0.5% | 0.5% | 0.5% | 0.5% | 0.5% | 0.5% | 0.5% |
| Hydroxyethyl cellulose | 1.7% | 1.7% | 1.7% | 1.7% | 1.7% | 1.7% | 1.7% |
| Purified water | q.s | q.s | q.s | q.s | q.s | q.s | q.s |
| Poloxamer 407 | 0.5% | — | — | — | 0.5% | — | 0.5% |

Example 37: Emergence of Resistance Assay Against S. epidemidis and S. aureus

Reagents:
Brain heart infusion broth, S. aureus MTCC 6908 & S. epidermidis S5-2, 96 well plate, autoclave, incubator, multiwell plate reader, UV spectrophotometer.

Method:
The in vitro emergence of resistance assay was performed for the compounds as per methods reported in literatures. The resistance assay for the test compounds was done in the same manner as documented in the MIC assay using micro broth dilution method as per CLSI guidelines. For the second cycle, bacterial culture was collected from the well showing growth, containing the next lowest concentration to the MIC of test compound, and used as inoculum for the next cycle containing the same or higher range of concentrations depending on the MIC in each cycle. The same procedure was repeated in subsequent cycles for 20-30 days. The concentration of the test compound was increased over the study as when MIC was found to increase. The serial passaging was repeated for 20-30 consecutive cycles. The assay was done in duplicates in each cycle.

An increase in MIC≥8 fold compared to the MIC of the test compound in cycle 1 was considered as a significant development of resistance.

Example 38: Biofilm Disruption Assay with Exemplary Compounds of the Invention and Compound Loaded Beads Materials:
Brain heart infusion broth, S. epidermidis ATCC 35984, 96 well plate, autoclave, incubator, MTT, multi-well plate reader.

Method:
S. epidermidis ATCC 35984 was grown in Brain Heart Infusion Agar (BHIA) at 37° C. for 24 h. The loop full of bacterial culture was suspended in sterile water and matched the turbidity against 0.5 McFarland Standard (approximately $1.5 \times 10^8$), 100 μl of culture suspension was added into each well of the 96 well plate and plates were incubated at 37° C. for 48 h for biofilm formation. The biofilm formed in each well was washed twice with sterile water to remove the planktonic cells. Then biofilm was treated with 100 yl of BHI broth suspended with various concentrations of DART molecules, followed by incubation of the plates at 37° C. for 24 h. Subsequently the biofilm in the wells were stained with MTT reagent and the plates were incubated at 37° C. for 2 h. The precipitate formed in the wells was dissolved in 100 μl of dimethyl sulfoxide (DMSO) and the absorbance was measured at 600 nm in multi well plate reader to determine the minimum biofilm inhibitory concentration (MBIC). The MBIC was calculated by subtracting the absorbance value of each drug treated sample from that of 48 h growth control.

Results of the biofilm disruption assay are shown in Tables 12 and 13.

TABLE 12

| S. No. | Compounds | Concentration of compounds (mg/ml) for 50% biofilm disruption |
|---|---|---|
| 1 | Compound 2 | 0.5-1.0 |
| 2 | Compound 16 | 0.06 |
| 3 | Compound 141 | 0.03-0.06 |
| 4 | Compound 55 | 2.0 |
| 5 | Vancomycin | 0.02-0.03 |

TABLE 13

| S. No. | PMMA beads of 3 mm diameter | Biofilm disruption |
| --- | --- | --- |
| 1 | Smartset HV | No inhibition |
| 2 | PalacosR + G | 10-28 |
| 3 | Smartset HV with Compound 141 (0.4%) | 18 |
| 4 | Smartset HV with Compound 10 | 26 |
| 5 | Smartset HV with Compound 10 and Compound 141 (0.4%) | 42 |
| 5 | Smartset HV with Compound 2 | No inhibition |
| 6 | Smartset HV with Compound 2 and Compound 141 (0.4%) | 13 |
| 8 | Vancomycin | 40 |

Compounds 141 and 16 showed efficient biofilm disruption ability. 50% of biofilm disruption was achieved at around 0.06 mg/ml. Compound 2 at a concentration of 0.5-1.0 mg/ml resulted in 50% biofilm disruption ability. Compound 55 had no effect on biofilm up to 2 mg/ml. The beads containing combination of compound 10 was able to disrupt biofilms with similar efficacy as marketed gentamycin. Addition of compound 141 (0.4%) to Compound 10 containing beads further increased the biofilm disruption potency of the formulated bead.

Example 39: In Vivo Preclinical Results

Anti-Inflammatory Action Using In Vivo Rat Paw Edema Model.

Host inflammation is one of the crucial clinical feature of most of the indications associated with bacterial infections. The inventors used an exemplary compound of the invention (Compound 2) to test the anti-inflammatory effects in vivo using rat paw edema model. Inflammation was induced using one of the opportunistic pathogens *Propionibacterium acnes* prevalent in implant associated infections. Sprague Dawley rats were used for the study and infection was induced by *P. acnes* CCARM 9010. An inoculum of $1 \times 10^9$ CFU/ml of the heat killed bacteria was injected to the plantar side of the right hind paw (~$2 \times 10^7$ CFU/paw) except in sham control where saline was injected. Treatments were initiated 8 h post injection by applying the test formulation of Compound 2 (30 mg) twice daily to the plantar surface of the right hind paw and gently rubbing 50 times with the index finger. Comparators Acnedap (dapsone 5% gel) and adapalene gel (Adaferin®) were applied twice daily and once daily based on clinical prescription dosage. Paw sizes were measured in millimeters using Vernier calipers at the start of the infection, 8 h post infection, and 24 h post initiation of treatment (32 h post induction of inflammation). The change in paw size, due to inflammation, was evaluated as the difference between the paw size measured at each time point and the basal paw size measured immediately before edema induction. The inhibition of inflammation at 32 h post induction was calculated using the following equation:

$$\text{Percentage of inhibition (\%)} = 100 \times (1 - X/Y)$$

where, X=mean increase in paw size of treated rats (mm) and Y=mean increase in paw size of control rats (mm).

The increase in paw size was observed at 8 h which indicated inflammation of paw after *P. acnes* induction and differences in paw sizes between treated and untreated animals were clear at 24 h after treatment. At 24 h post treatment, Compound 2 gave rise to 43% inhibition of inflammation as compared to untreated which was equivalent to the inhibition mediated by dapsone, a known anti-inflammatory agent (Table 14). These in vivo results suggest that Compound 2 is effective in combating *P. acnes*-induced inflammation.

TABLE 14

Inhibition of inflammation

| Drugs | Inhibition of inflammation (%) at 24 h post treatment |
| --- | --- |
| Vehicle Control (No Drug) | 0 |
| Adapalene | 31.55 |
| Dapsone | 43.82 |
| Compound 2 | 43.20 |

Example 40: Docking Studies

Over the years β-lactams were the drug of choice for the infections caused by *S. aureus*. However, the broad use of these antibiotics was antiquated with emergence of resistance to the old β-lactam antibiotics however some of the new generation β-lactams like ceftaroline ceftabiprole are known to work against MRSA. Currently vancomycin, daptomycin, and linezolid were available drugs that work against MRSA as well as ceftaroline resistant MRSA pathogens. But widespread antibiotic resistance to all these antibiotics worldwide has required the development of new strategies to combat bacterial infections especially caused by resistant MRSA.

Resistance to β-lactams against *S. aureus* was acquired because of the presence of mecA gene, that codes for a protein PBP2a in MRSA (Acebron et al, Curr. Med. Chem. 2015, 22, 1678; Lim et al., *Nat. Struct. Biol.* 2002, 9, 870-876). PBP2a is involved in cross linking the adjacent glycan strands resulting the formation of bacterial cell wall composed of peptidoglycan polymer for both Gram positive and Gram negative pathogens (Llarrull et al Antimicrob. Agents Chemotherap. 2009, 53, 4051) Ceftaroline, a recently FDA approved β-lactam antibiotic has been found to work against MRSA. Ceftaroline binds to the allosteric site of PBP2a that triggers a conformational change resulting in opening up of the active site followed by irreversible binding to the serine residue present at active site of PBP2a (Fishovitz et al J. Am. Chem. Soc. 2015, 137, 6500, Lavanya et al., J. Cell. Biochem. 2016 (117) 542-548). Thus ceftaroline binds to both allosteric and active site of PBP2a and found to be active against MRSA.

Recently ceftaroline resistant PBP2a was isolated from the clinical strain. The two mutations include asparagine (N) to lysine (K) at 146 and glutamic acid (E) to lysine (K) at 150 residues are responsible for ceftaroline resistant MRSA strains (Lavanya et al., *Journal of Cellular Biochemistry* 2016 (117) 542-548). There is an urgent need to develop new strategy for designing new antibiotics that should act on ceftaroline resistant PBP2a (Bouley et al J. Am. Chem. Soc. 2015, 137, 1738; Turk at al Plos one 2011, 6, e19418).

The present study provides a fragment based and structure based design approach to generate new class of antibiotics which are designed to inhibit ceftaroline resistant PBP2a by binding to the allosteric site. Here the optimized lead molecule can act as an antibiotic by binding to the allosteric site followed by forming covalent adduct with serine residue of the active site of a PBP2a or might act as a potentiator to enhance the activity of other β-lactam antibiotics by opening the active site through salt bridges or synergistically effect the activity of known β-lactam antibiotics.

Figures 2A, 2B:
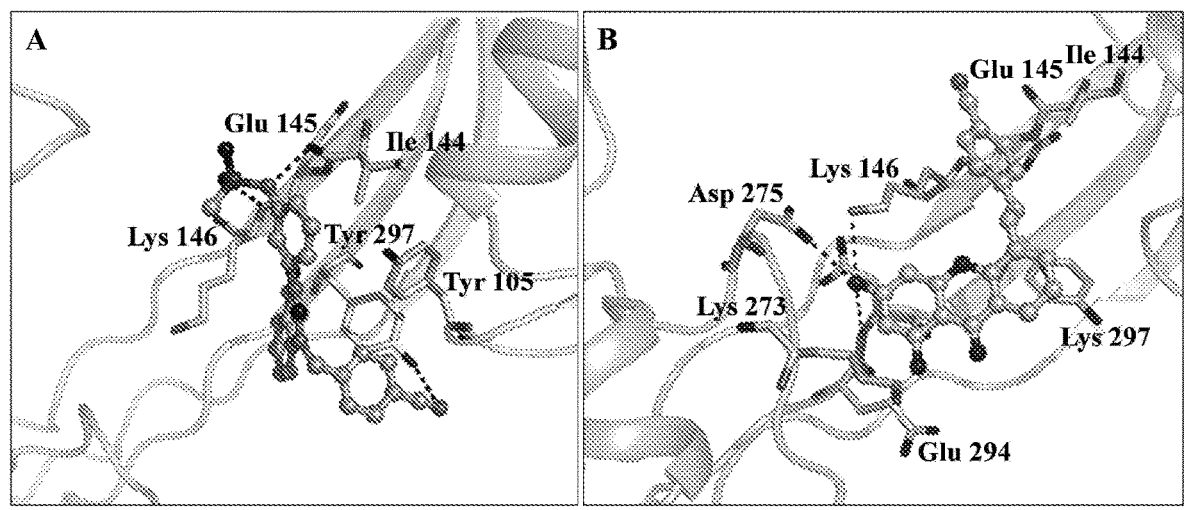
FIGS. 2A and 2B show docking of exemplary Compound 99 (FIG. 2A) and Compound 104 (FIG. 2B) in the allosteric binding site of mutated PBP2a (PDB ID: 4CPK) of ceftaroline resistant MRSA. The compounds are represented in ball and stick model. The amino acid residues of the protein are represented as sticks. The H-bonds of the compound with amino acid residues residues are represented as dotted lines.

In the present study, we design a new class of scaffolds like quinazoline-dione and xanthene-9-one as depicted in Formula III and IV are found to bind PBP2a (PDB: 3ZFZ and 4CPK) allosteric site as well as active site with good binding energy as evidenced by docking analysis (FIGS. 2A and 2B).

Docking studies were conducted to design and understand the interactions of some of the molecules as mentioned in FORMULAE VI and VII with PBP2a as well as with mutated PBP2a. Studies were carried out using Autodock 4.2.6. on known X-ray crystal structure of PBP2a from ceftaroline resistant MRSA (PDB ID: 4CPK)

The complex structure of ceftaroline with PBP2a (PDB ID: 3ZFZ) of a wild-type strain is known. It was reported that ceftaroline binds to the allosteric site of PBP2a having interactions with residues Glu145 and Asn146 (Otero et al. Proc. Natl. Acad. Sci. 2013, 110, 16808). In ceftaroline resistant MRSA, Asn146 of PBP2a is mutated to Lys146 which interferes binding of ceftaroline to PBP2a resulting in generation of ceftaroline resistant strains.

The two compounds synthesized, Compounds 99 and 104 were able to bind and interact strongly at the allosteric site of the protein. Some of the key interacting residues involved in H-bonding are Ile144, Lys146, Asp275, Glu294 and Tyr297. It was also observed that these compounds are involved in hydrophobic interactions with the residues of the allosteric site. The strong binding energies and the interactions with mutated PBP2a clearly indicate their ability to inhibit the protein, and eventually their action against ceftaroline resistant strains of MRSA.

Example 41: Method of Preparation of Compound 2 Loaded into Commercially Available Non-Biodegradable PMMA Cement (Smart Set HV®)

Typically, 40 gm of smart set HV® powder was mixed properly with 1 gm of compound 10 under sterile conditions to get the uniform mixture. Then, 20 ml sealed monomeric solution was added into the mixture of PMMA polymer and active and mixing is continued for 30 seconds to form the homogenous mixture at room temperature. The above mixture was allowed to set for 2 minutes to obtain the required viscosity and doughy homogenous mix that no longer adheres to the rubber gloves. The doughy, soft mixture was spread into a 4.8 mm bead mold. The filled mold was allowed to set for 7 to 8 minutes for hardening of cement at room temperature, 25° C. The hardened cement beads were pulled out of the mold and stored under sterile condition at room temperature. The drug content of each bead was measured by HPLC that matches with the calculated drug content. Antibiotic loaded cement beads are further studied for in-vitro drug release assay, in-vitro sequential ZIB assay and in-vitro biofilm inhibition study But rampant antibiotic resistance to all these antibiotics in worldwide has challenged to develop new strategies to combat bacterial infections especially caused by resistant MRSA.

Example 42: Method of Preparation of Compound 2 Loaded into Commercially Available Biodegradable CaSO$_4$ Cement (Stimulan Rapid Cure®)

Typically, 40 gm of stimulan rapid Cure® powder was mixed properly with 1 gm of compound 2 under sterile conditions to get the uniform mixture. Then, 12.48 ml of mixing solution was added into drug-polymer mixture and mixed for 30 seconds to form the uniform soft doughy mixture. The soft mixture was spread into a 4.8 mm bead mold. The filled mold was allowed to set for 3-5 minutes for hardening of cement at room temperature, 25° C. The hardened bone cement beads were pulled out of the mold and stored under sterile condition at room temperature. The drug content of each bead was measured by HPLC that matches with the calculated drug content. Antibiotic loaded cement beads are further studied for in-vitro drug release assay, in-vitro sequential ZIB assay and in-vitro biofilm inhibition study.

Example 43: Drug Release Assay of Compound 2 and 10 Impregnated Smart Set HV®

The drug release study with compound 2 and compound 10 were conducted in sample vial containing 1.5 ml of dissolution media i.e., PBS buffer (pH 6.8):acetonitrile (9:1). The sample was kept in incubator rotator at 32° C. at 40 rpm. The release medium was withdrawn at specified interval of time (2 hr, 4 hr, 6 hr, day 1, day 2, day 3, day 4, day 5, day 6, day 7 and replaced by fresh 1.5 ml dissolution medium each time. All the samples were kept at −20° C. till the analysis is done. The measurement of drug release was done by HPLC.

Figure 3:
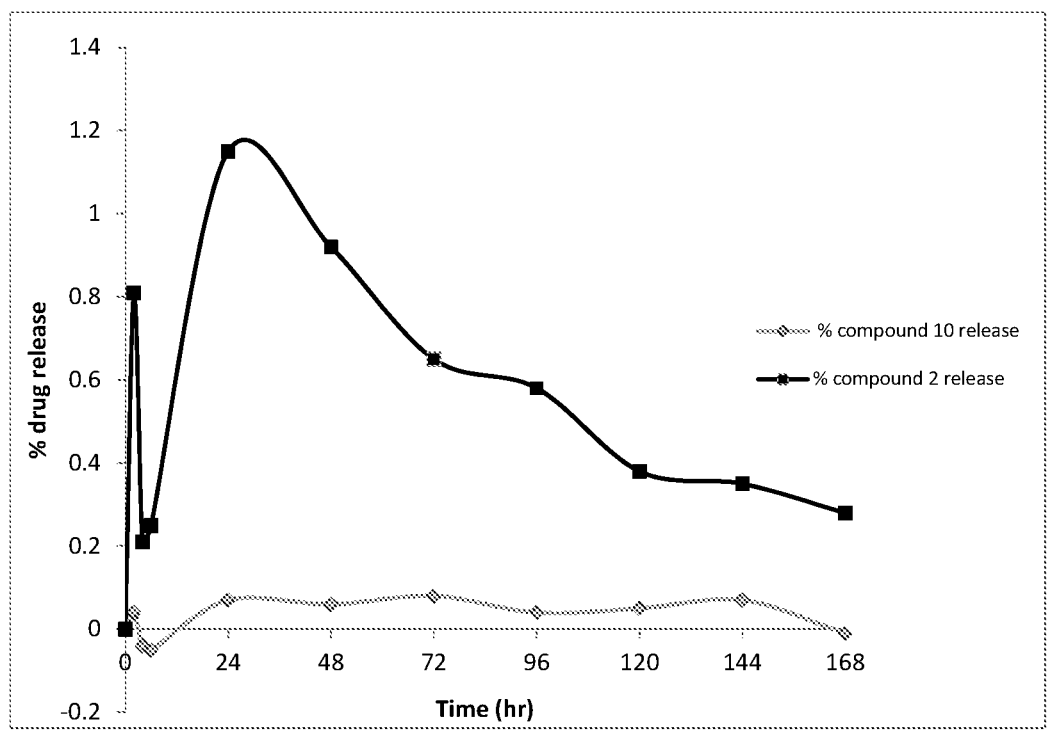
FIG. 3 is a line graph showing drug release for Compound 2 and Compound 10 from drug impregnated Smart set HV®. Drug release is plotted as % drug release vs time (hours)

Results of the drug release are shown in FIG. 3. As seen from FIG. 3, commercially loaded smart set HV® loaded with Compound 2 and Compound 10 showed sustained release of active over a period of 7 days. Compound 2 loaded bone cement showed higher release of active than Compound 10 loaded bone cement at given time.

Example 44: Method of Preparation of Compound 55 Loaded In Situ Gel with Chitosan-β-glycerophosphate Mixture (Table 7; F8)

Typically, 1.5 gm of chitosan was dissolved in 75 gm of 0.1 N HCl. The mixture was stirred thoroughly until chitosan was completely dissolved. The chitosan solution was cooled to 4° C. 5 gm of β-glycerophosphate was weighed and dissolved in 17.5 gm of water. Drug solution was prepared by dispersing 1 gm of compound 55 in β-glycerophosphate solution, cooled at 4° C. Compound 55-β-glycerophosphate solution was added drop-wise to chitosan mixture (precooled) while stirring under aseptic conditions. 0.07 gm of sodium benzoate is added into the formulation and stirred until formed a uniform solution. Formulation was stored at 4° C. for further use. The final 100 ml formulation contain 1.5% chitosan corresponds to 0.082M, and 5% of β-glycerophosphate corresponds to 0.163M which helps to transform the system from sol state (4-10° C.) at neutral pH to gel state at body temperature 37° C.

Example 45: Method of Preparation of Compound 2 Loaded In Situ Gel with Thermosensitive Polymer, PLGA (Table 7; F7)

Briefly, 15 gm of PLGA was transferred to 82.3 gm of triethyl citrate and the mixture was kept on stirring at 900 rpm for 1 hour at 70° C. The resulting solution was cooled to 4° C. Accurately weighed 1 gm of compound 2 was added into PLGA solution and mixed properly. The formulation was cooled to 4° C. in the form of sol state which transforms into gel form at 34° C. Formulation was stored at 4° C. for further use.

Example 46: Method of Preparation of Compound 6 Loaded In Situ Gel Using Thermosensitive Polymer, Poloxamer 407 (Table 7; F3)

Typically, 73.9 gm of purified water was weighed and cooled to 4° C. 20 gm of poloxamer 407 was weighed and dissolved in pre-cooled water while stirring. Accurately, 1 gm of the compound 6 was weighed and dispersed in 5 gm of diethyleneglycolmonoethylether. Drug-diethyleneglycol-monoethylether mixture was added slowly to pre-cooled poloxamer 407 solution while stirring. Then, 0.1 gm of methyl paraben and 0.01 gm of propyl paraben were added, and stirred until formed a uniform solution by maintaining temperature at 4° C. The formulation was allowed to stir to get a uniform dispersion that remains in sol state at 4-10° C. but gels at body temperature, 37° C. The formulation was stored at 4° C. for further use.

Example 47: Method of Preparation of Compound 6 Loaded Hydrogel Using Ascorbyl Palmitate (Table 8; F1)

Typically, 0.4 gm of ascorbyl palmitate was weighed and dissolved in 5 gm of diethyleneglycolmonoethylether. 1 gm of compound 6 was added into ascorbyl palmitate solution and mixed properly. Separately, hydroxyethyl cellulose gel base was prepared by dissolving 1.5 gm of hydroxyethyl cellulose in 76 gm water while stirring. To hydroxyethyl cellulose gel base, collagen (0.1 gm in 5 gm of water) and poloxamer 407 (1 gm in 10 gm of water) were added with continuous stirring. Drug-ascorbyl palmitate mixture was added into gel base mixture while stirring. The formulation mixture was allowed to stir until formed a uniform gel. The formulation was stored at 4° C. for further use.

Example 48: Method of Preparation of Compound 33 Loaded Liposomal Hydrogel Using Ascorbyl Palmitate (Table 11; F1)

The multi-lamellar liposome loaded compound 33 and ascorbyl pamitate was prepared by thin film hydration technique. Briefly, 0.2 gm of compound 33, 1 gm lecithin, 0.4 gm cholesterol and 0.1 gm ascorbyl palmitate were added to 20 ml of choloroform:methanol (2:1) mixture. The thin lipid film was formed by evaporating the organic solvent under vacuum (45° C., 50 rpm). The thin film obtained was dried in vacuum for 6 h and rehydrated with 5 ml of water containing 0.5% poloxamer 407 to form stable liposomal dispersion. The liposomal gel was prepared by adding liposomal dispersion in pre-swollen 1.7% of hydroxyethyl cellulose gel (0.34 gm in 12.96 gm of water) and mixed properly to form a uniform gel.

Example 49: Method of Preparation of Compound 55 Loaded Sodium Alginate Hydrogel (Table 9; F5)

Typically, 2 gm of sodium alginate (Manucol LKX®) solution was weighed accurately and dissolved in 30 gm of water while stirring. Accurately 1 gm of compound 55 (dispersed in transcutol or DMI or any other solubilizer) was added into sodium alginate solution and mixed properly. Separately, hydroxyethyl cellulose gel base was prepared by adding 1.5 gm of hydroxyethyl cellulose in 60.3 gm of water while stirring, and allowed to stir until dissolved. Collagen solution (0.1 gm in 5 gm of water) was added slowly into hydroxyethyl cellulose gel base by maintaining stirring at room temperature. Compound 55-sodium alginate mixture was added into gel base containing collagen and hydroxyethyl cellulose under stirring condition. The complete mixture was allowed to stir until formed a uniform gel. Preservative, 0.07 gm of sodium benzoate was added to the above formulation mixture while stirring. The mixture was stirred until formed a uniform hydrogel. The formulation prepared was stored at 4° C. for further use.

Example 50: Method of Preparation of Compound 2 Loaded Hydrogel Film (Table 10; F1)

Typically, 1 g of sodium alginate (Manucol LKX®) was weighed and dissolved in 50 ml of water while stirring. Compound 2 was added into sodium alginate solution while stirring. 3% calcium chloride solution was poured into petri plates and excess was discarded after it forms thin layer on the plate surface. Compound 2-sodium alginate (Manucol LKX®) solution (50 ml) was poured into petri plate and allowed to dry at 45° C. for 6-8 hours. Cross linker calcium chloride would help to solidify the alginate solution and forms hydrogel film. After proper drying the film was taken out from the plate and stored for further use. Film of desired thickness can be controlled by preparing different concentration of alginate solution.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

We claim:
1. A compound of Formula (I):

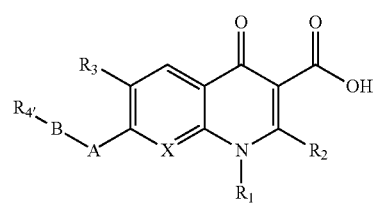

FORMULA I wherein:
X is N or CRs;
$R_1$ is a cyclopropyl, or $R_1$ forms a link to $R_2$ to form a ring when X=CH;
$R_2$ is H, SH or alkyl;

R₃ is H or halo;

R₈ is H, $C_1$-$C_6$alkyl, $C_1$-$C_6$alkoxy or halo;

A is absent or a linker, wherein the linker is a bond or the linker is selected from the group consisting of:

unsubstituted piperazinyl; 3-methylamino piperidine; pyrrolidinyl [3,4-b]piperidine; piperidin-4-ol; 1-H-benzoimidazol-2-yl; (1-H-benzoimidazol-2-yl)-amino; 2-Amino-1-H-benzoimidazolyl;

5,6-mono and di-substituted 1-H-benzoimidazol-2-yl optionally substituted with alkyl $C_1$-$C_{11}$alkyl, halo, nitro, carboxyl, amino, thiol, mono or di or polyguanidino group: —NH[C($M_1$)NHC($M_1$)]$_n$-D (wherein $M_1$ is NH, O, S or CH; n is 1-10; D is $NH_2$, COOH or $CONH_2$), amino acid analogues, spermine, norspermidine, spermidine analogues, guanidino amino acid, spermine linked through an amide linkage, norspermidine linked through an amide linkage, spermidine analogues linked through an amide linkage, or any combinations thereof; or 6-carboxyl-2-pyridyl ring; 5-Bromo-2-pyridyl ring or 5 or 6 mono or di-substituted 2-pyridyl ring wherein the 3, 4, 5 or 6 position of each can be independently substituted with a hydrogen atom, —$CH_3$, $CH_3(CH_2)_m$— wherein m=1-10, halo, nitro, amino, carboxyl, methyl amino, thiol, —$R_7(CH_2)_0$NHCO—, —$R_7(CH_2)_0$CONH—, —$R_7(CH_2)_0$—OCO—, —$R_7(CH_2)_0$—COO—, or mono or di or polyguanidino group —NH[C($M_2$)NHC($M_2$)]$_t$-D, an amino acid analogue, spermine, norspermidine, spermidine analogues, guanidino amino acid, spermine, norspermidine, or spermidine analogues through amide linkage, wherein $R_7$=NH or S and o=0-10, $M_2$=NH, oxygen atom, sulfur atom, or CH, D=$NH_2$, COOH, $CONH_2$, and t=1-10; wherein 'A' is functionalized with (CO—$R_L$—CY')$_q$—Z' or (CS—$R_4$—CY')$_q$—Z', wherein q is 1-10; $R_L$ is NH; Y' is NH, O, S or CH; and Z' is $NH_2$, COOH, $CONH_2$, OH, SH or alkyl group;

B is absent or a linker wherein the linker is a bond, or the linker is selected from the group consisting of a straight or branched alkyl chain, functionalized alkyl chain, alkyl chain with ester or amide linkages, —C(O)$CH_2$—, —C(O)$CH_2$NH—, —NHC(O)$CH_2$—, —C(O)—, —C(O)NH($CH_2$)$_r$C(O)— (r is 1, 2, 3, 4 or 5), —CH=N—, —NH—, —$OCH_2CH_2$—, (OH)NHC(O)$CH_2$, [(HO)NHC(O)]CH[{$CH_3$(OH)}CH], [(HO)NHC(O)]CH[$CH_2$(OH)CH], —$CH_2CH_2NHCH_2CH_2$—, or —$CH_2$(CO)NH(CO)NH—Ar wherein 'Ar' represents aryl or phenyl substituted or not substituted, —CO-cysteine, —CO—(S-dodecane cysteine), —CO—S—(N-acetyl cysteine), and —CO—S—(N-acetyl dodecane cysteine); and $R_4$ is a 5-membered aryl or heteroaryl, optionally substituted with 1 or 2 substituents; or $R_4$ is a 6-membered aryl or heteroaryl, optionally substituted with 1, 2 or 3 substituents; or $R_4$ is a fused ring 9-10-membered aryl or heteroaryl, optionally substituted with 1, 2 or 3 substituents; or $R_4$ is a fused ring 9-10-membered aryl or heteroaryl, optionally substituted with 1, 2 or 3 substituents, or $R_4$ is

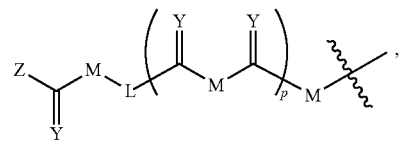

where p is 0-10; M is CH, NH, or S; Y is NH, CH, O or S; L is a linker, wherein the linker is selected from the group consisting of amino, phenyl amino, substituted phenyl amino, straight or branched alkyl chain, —($CH_2$)$_v$—, ($CH_2$)$_v$—NH—($CH_2$)$_n$, —CO($CH_2$)$_v$—$R_5$, CO—C(NHCO$CH_3$)—$CH_2$SH—NH—, —O—, —S—, alkylene, —CO—, and —CONH, wherein $R_5$=OH, $NH_2$, N-alkyl amine, alkyl, thiol or any halogen atoms and v=0-10; and Z is $NH_2$, NHOH, OH, SH, alkyl, —COOH, or $CONH_2$.

2. A compound selected from the group consisting of:

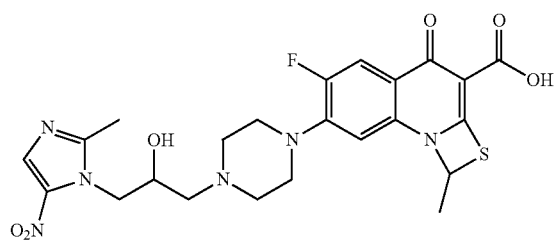

1

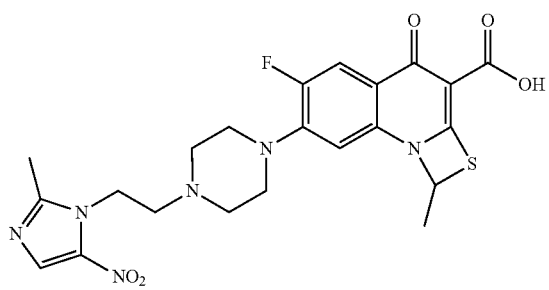

2

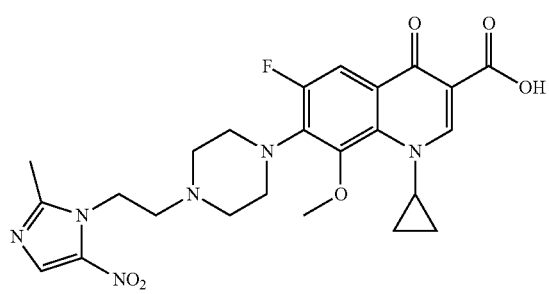

3

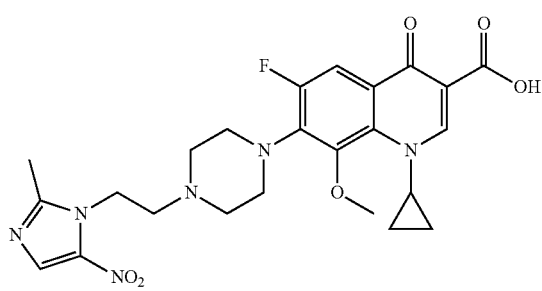

4

-continued
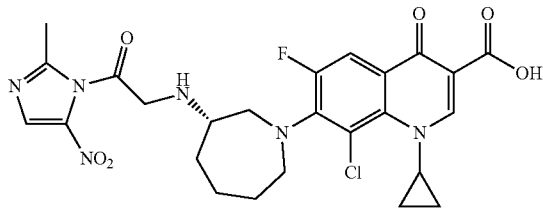
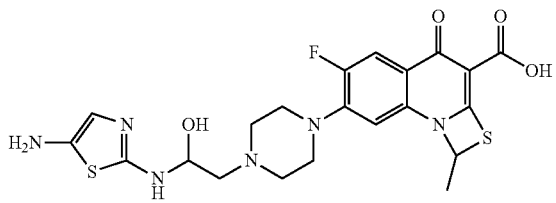
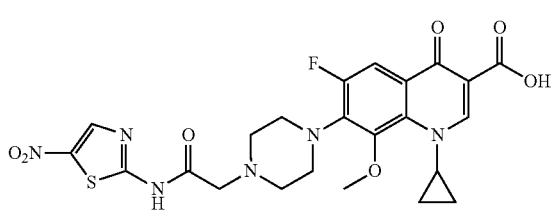
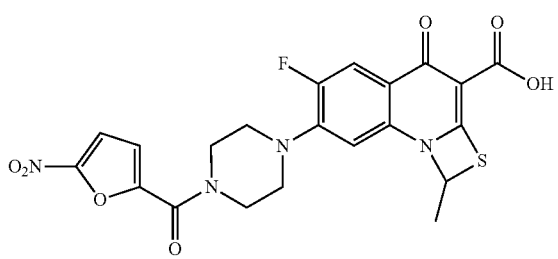
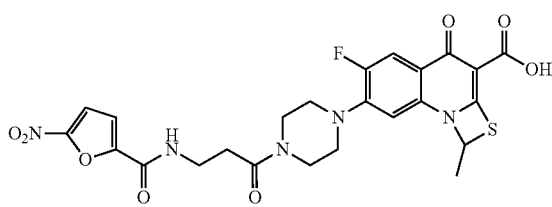
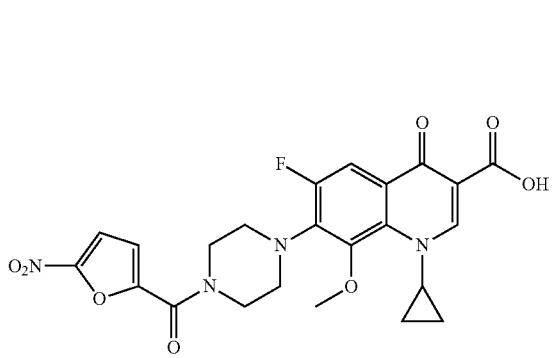
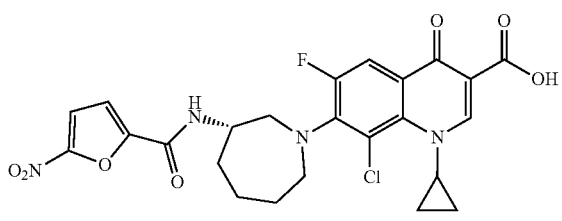

-continued
17
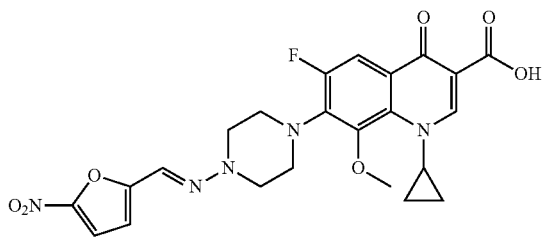
18
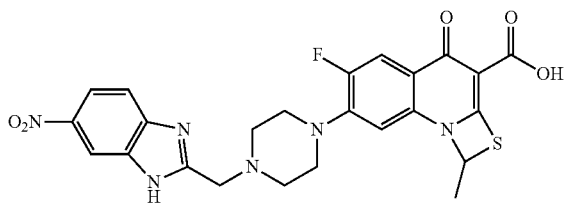
19
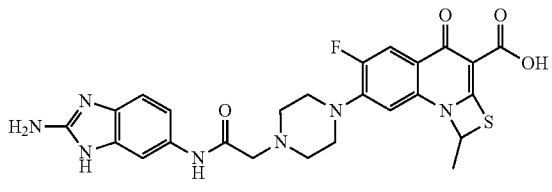
20
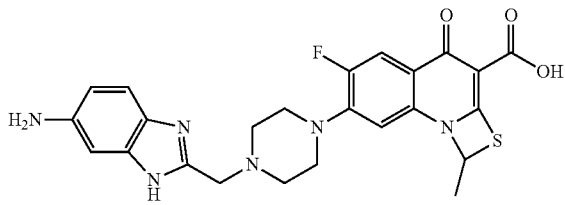
21
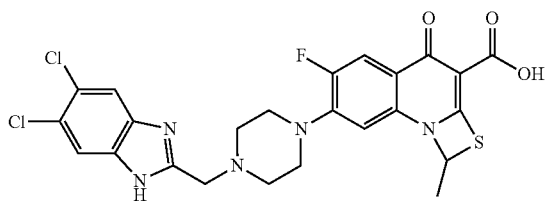
22
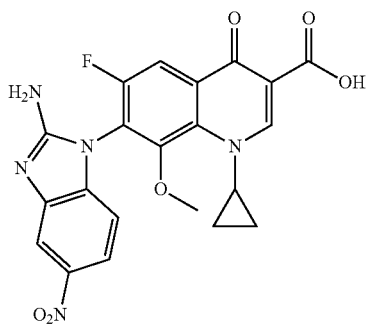
23
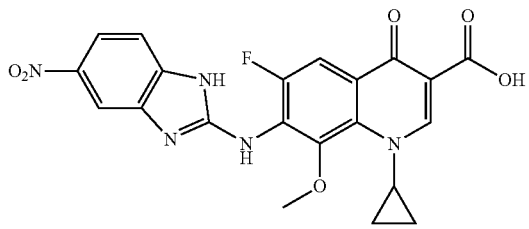
24
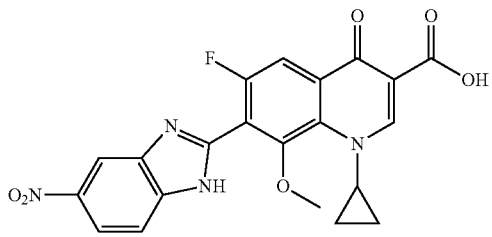
25
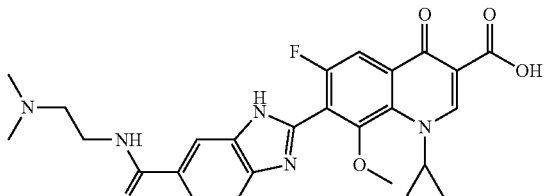
26
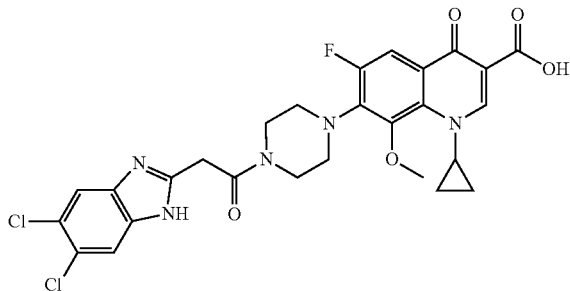

-continued
27
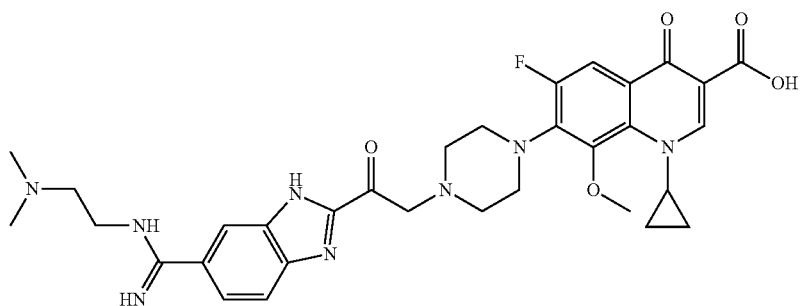
28
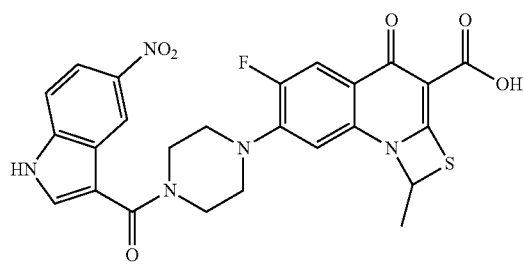
29
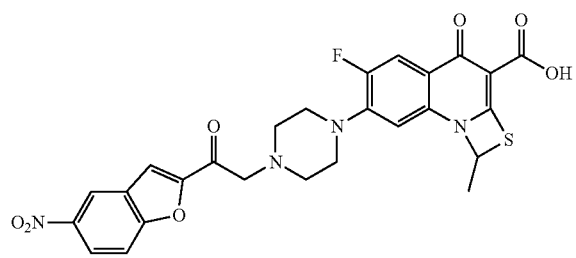
30
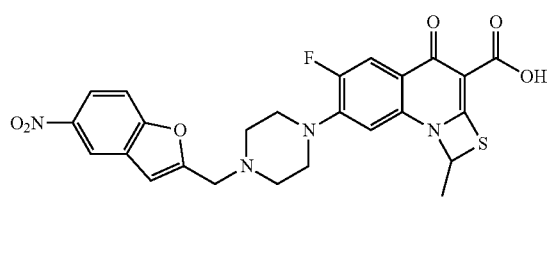
31
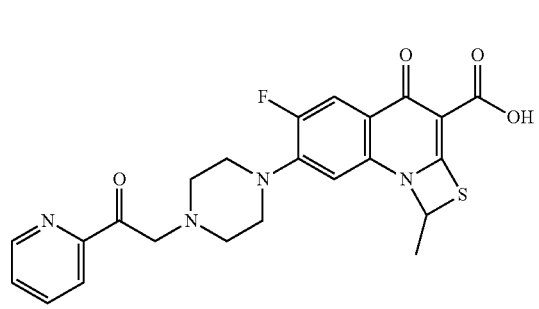
32
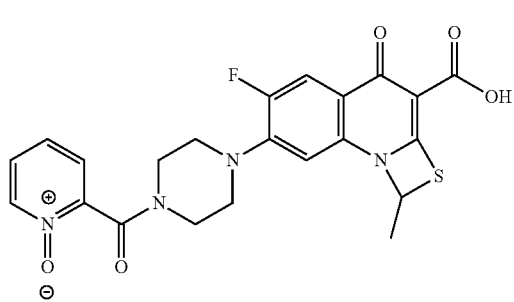
33
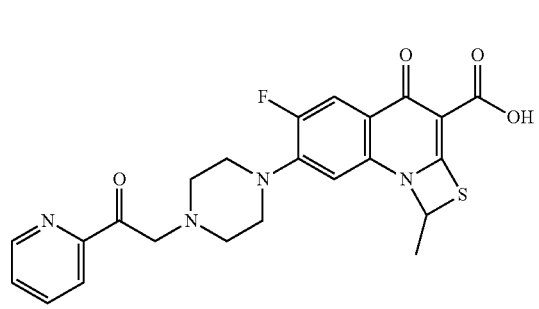
34
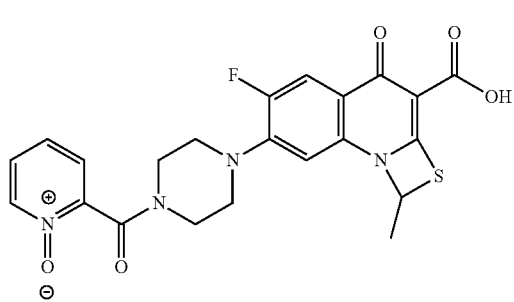
35
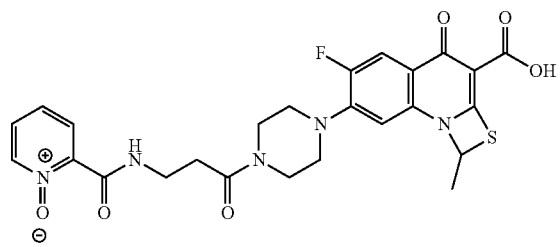

-continued
36
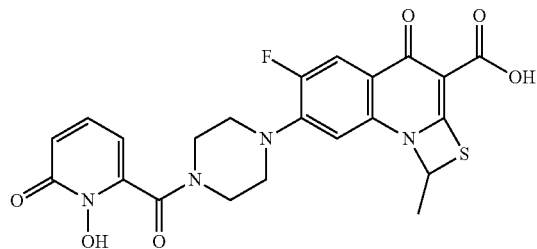
37
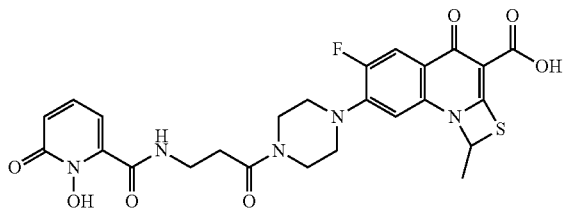
38
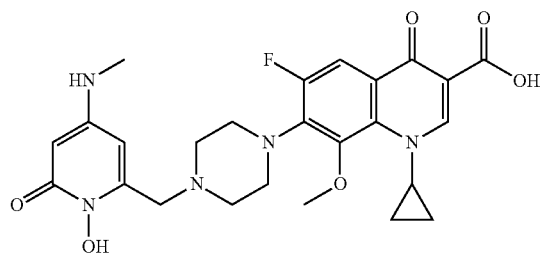
39
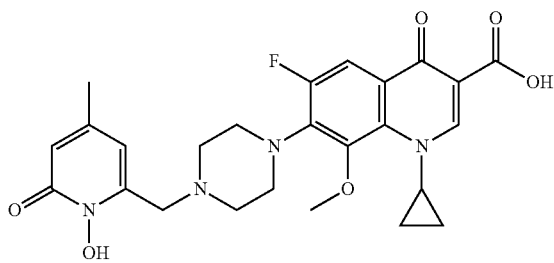
40
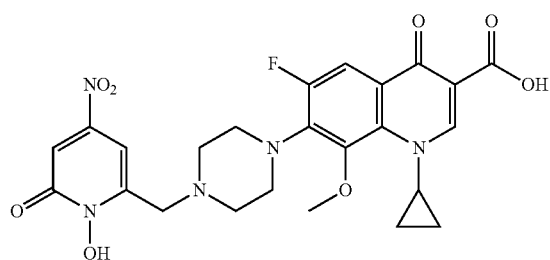
41
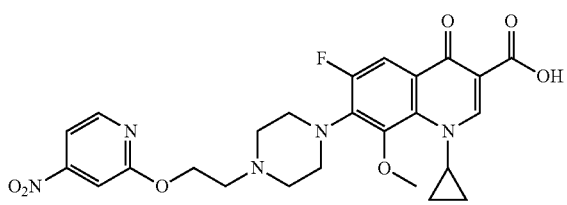
42
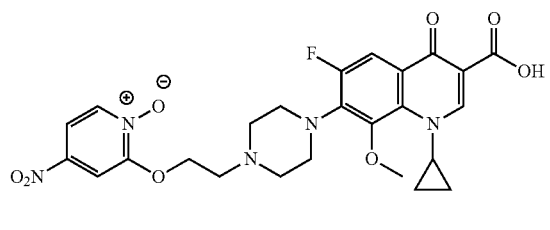
43
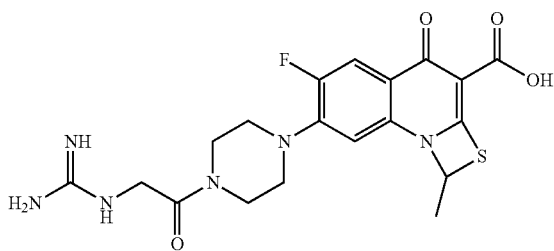
44
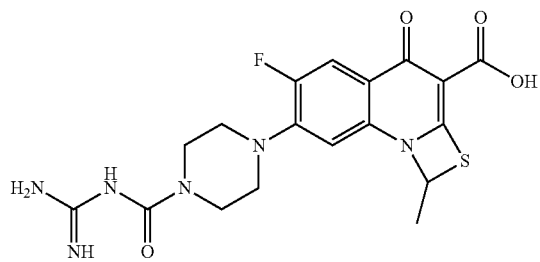
45
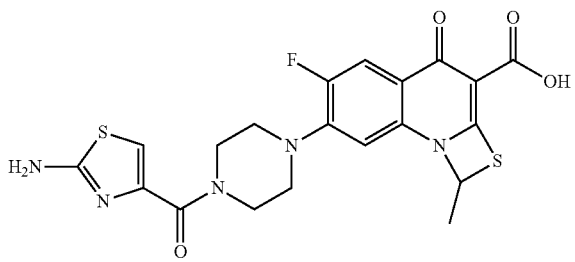

-continued
46
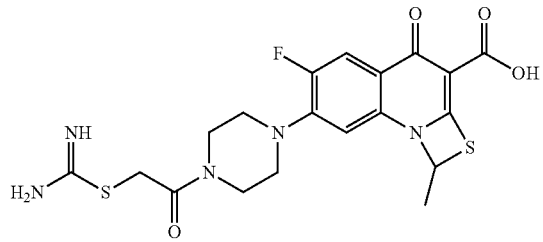
47
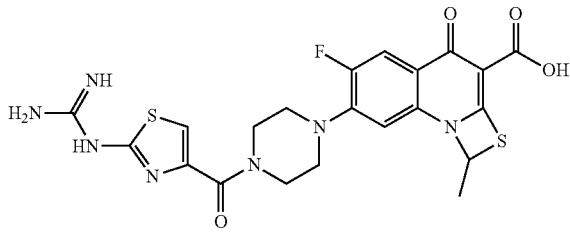
48
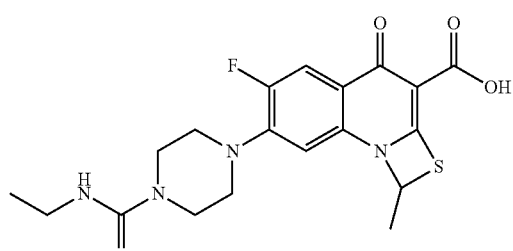
49
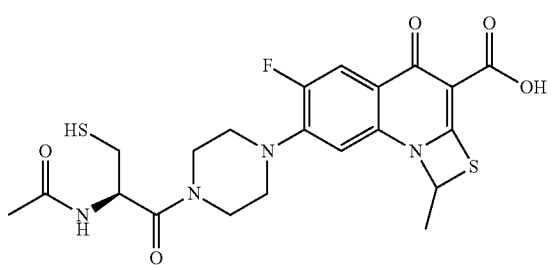
50
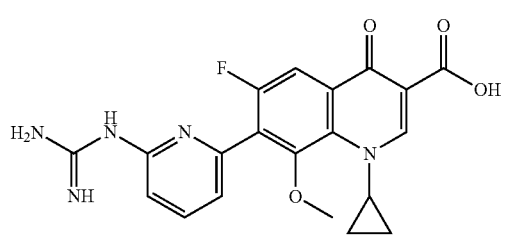
51
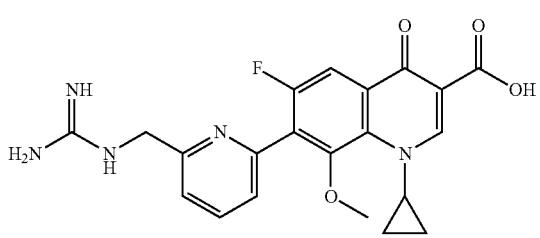
52
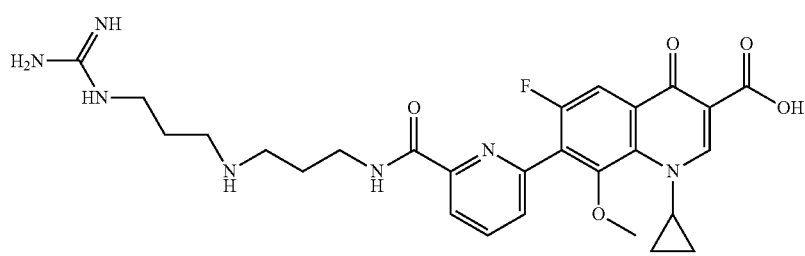
53
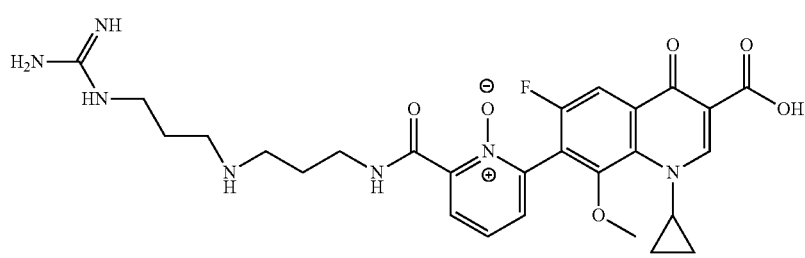
54
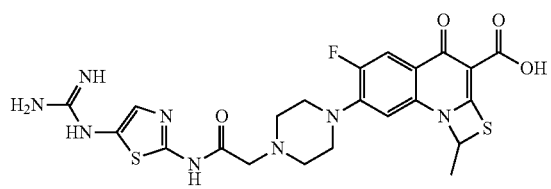
107
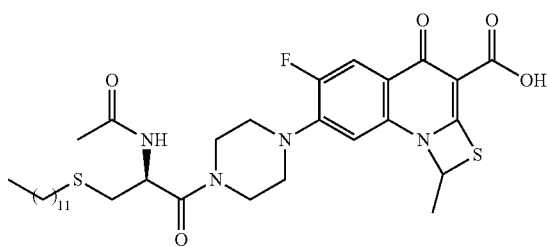

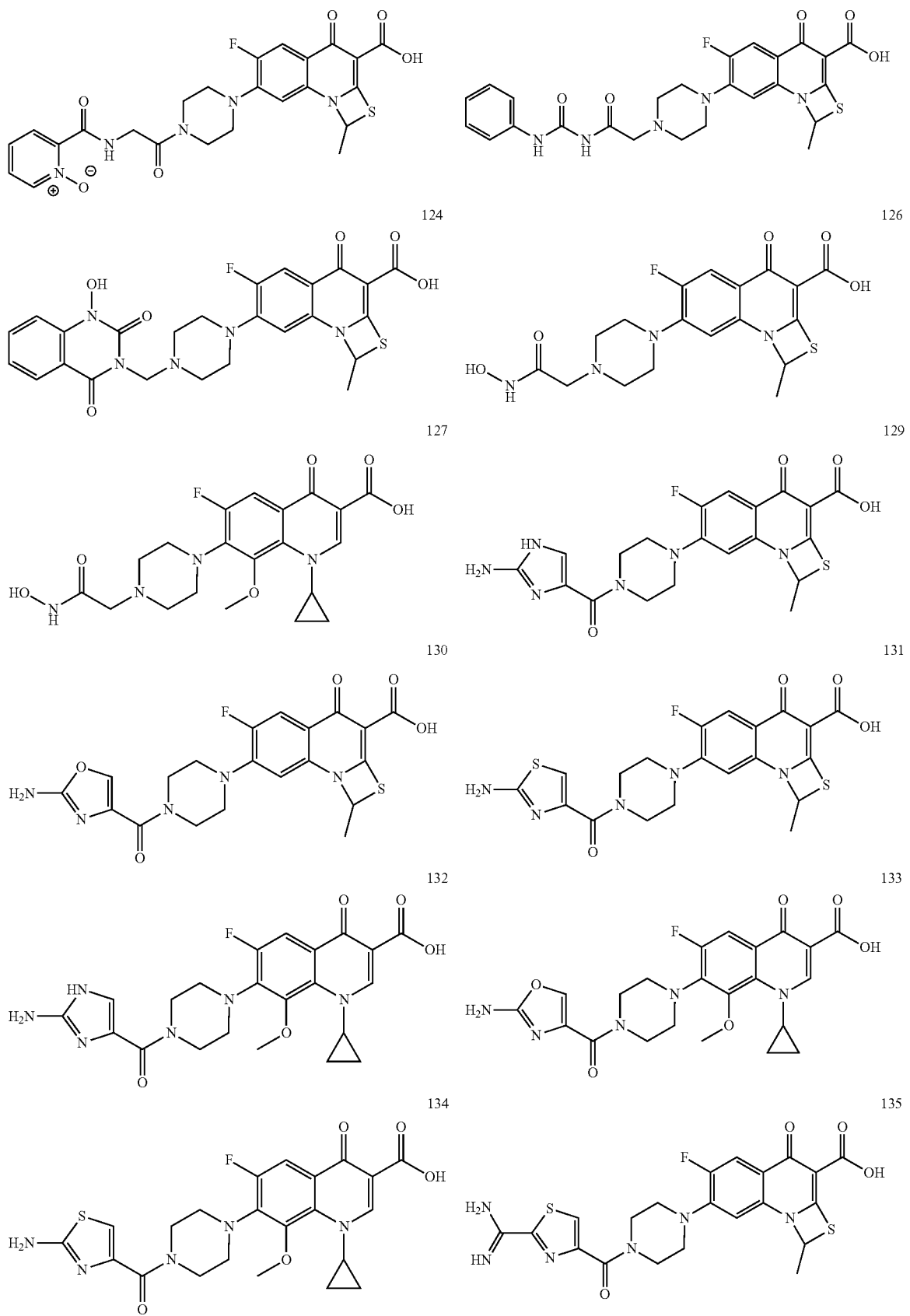

-continued

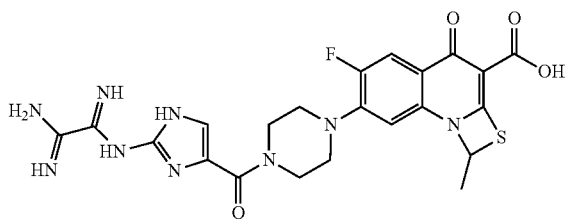
136

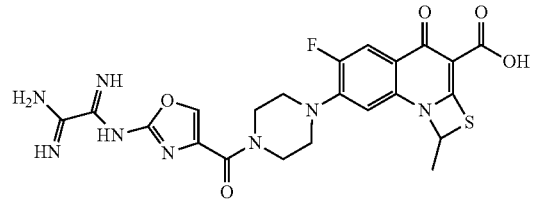
137

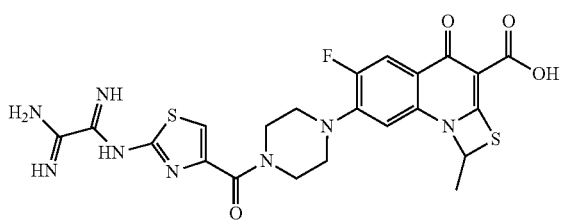
138

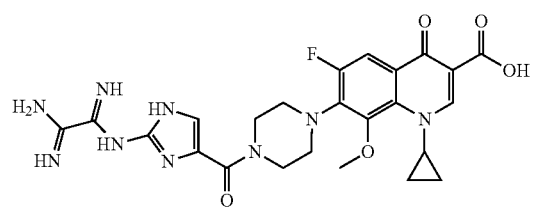
139 and

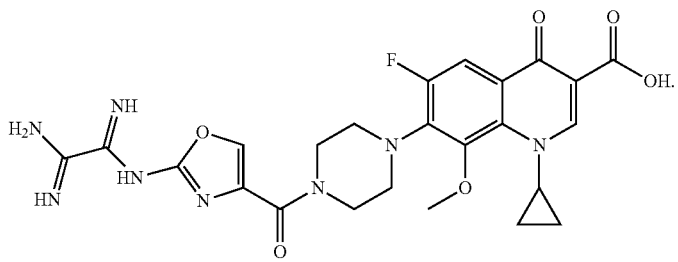
140

3. A pharmaceutical composition comprising the compound of claim 1 and a pharmaceutically acceptable carrier or excipient.

4. A composition for topical application comprising the compound of claim 1.

5. A composition for oral administration comprising the compound of claim 1.

6. A composition for administration by injection comprising the compound of claim 1.

7. A composition comprising a polymer matrix and the compound of claim 1.

8. A method for treating an infection, the method comprising administering a therapeutically effective amount of the compound of claim 1 to a subject in need thereof.

9. The method of claim 8, wherein said infection is caused by a resistant pathogen.

10. The method of claim 8, wherein said infection is caused by a methicillin resistant or vancomycin-resistant pathogen.

11. The method of claim 8, wherein said infection is caused by a quinolone resistant pathogen.

12. A method for wound treatment, the method comprising applying the compound of claim 1 to a wound.

13. A method for reducing infection caused by an implant, the method comprising applying the compound of claim 1 to the implant.

14. A method for reducing infection caused by an implant, the method comprising administering the compound of claim 1 to a subject in need thereof.

15. A method for the treatment of pneumonia, the method comprising administering the compound of claim 1 to a subject in need thereof.

16. A method for the treatment of urinary tract infection, the method comprising administering the compound of claim 1 to a subject in need thereof.

17. A method for the treatment of impetigo, the method comprising administering the compound of claim 1 to a subject in need thereof.

18. A method for the treatment of acne, the method comprising administering the compound of claim 1 to a subject in need thereof.

19. A method of inhibiting or reducing biofilm formation, the method comprising applying the compound of claim 1 to a surface or biofilm.

20. A compound which is:

VCD-064

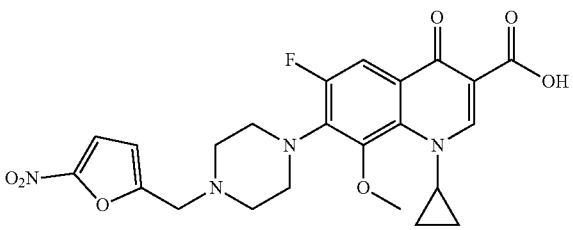

163
-continued
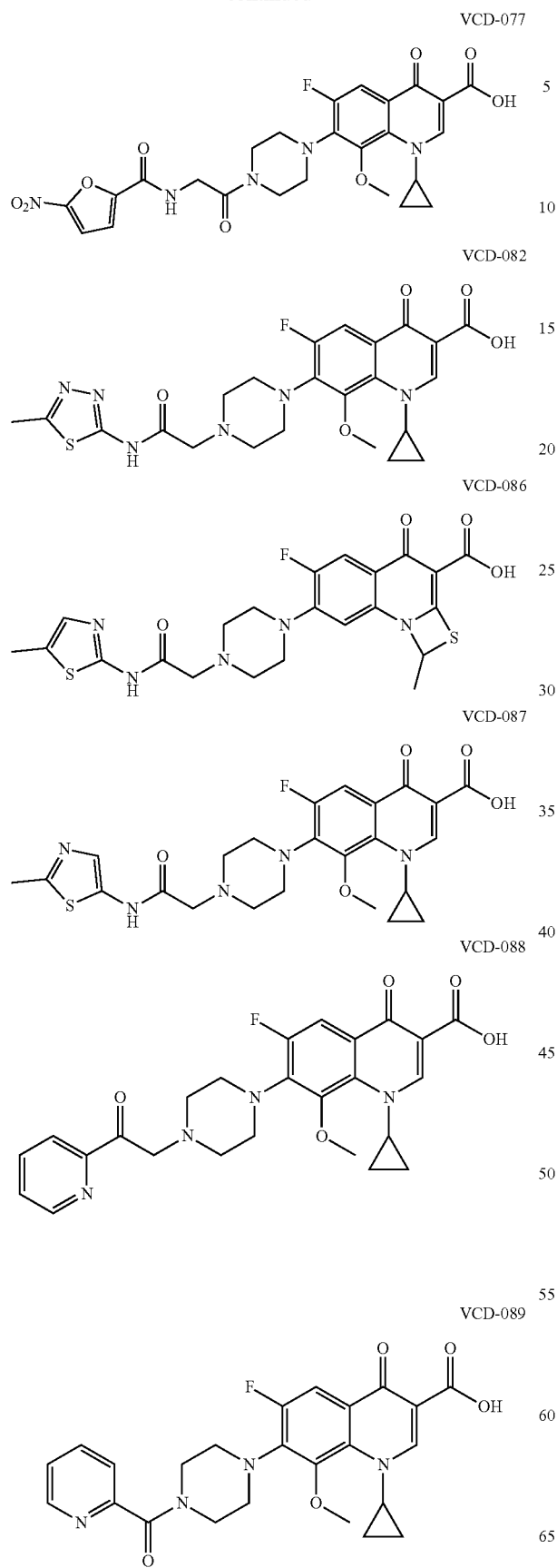
164
-continued
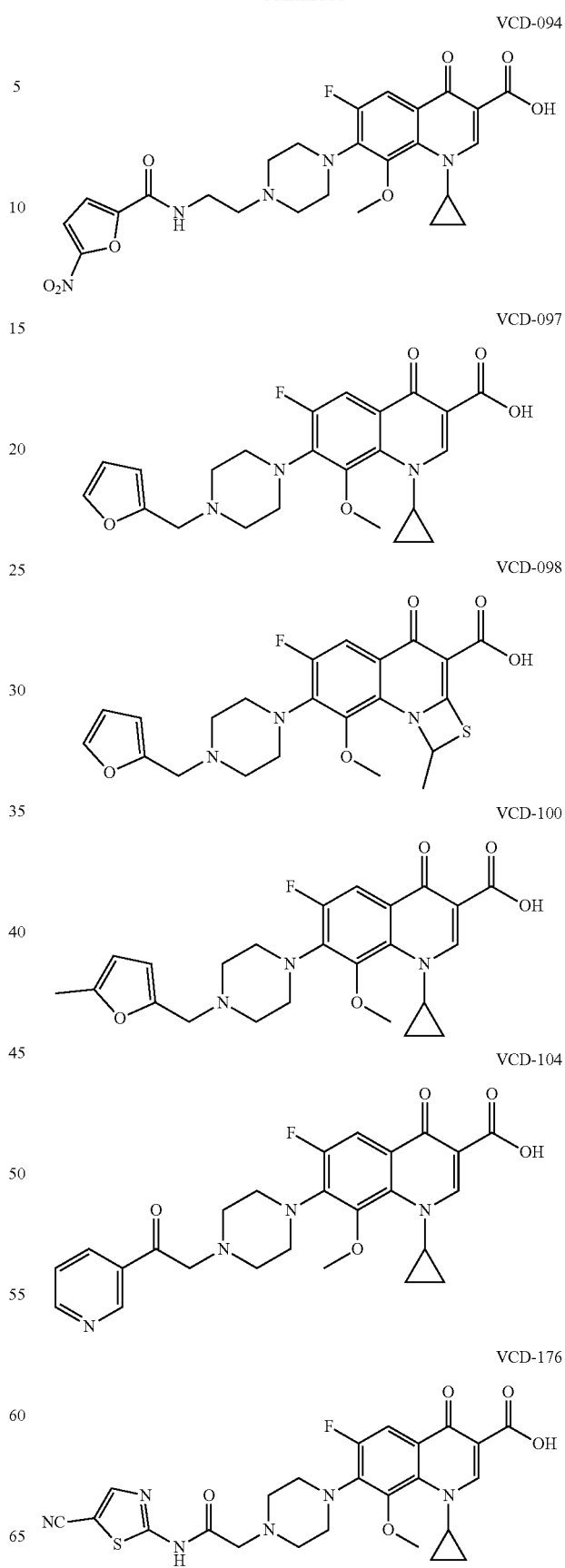

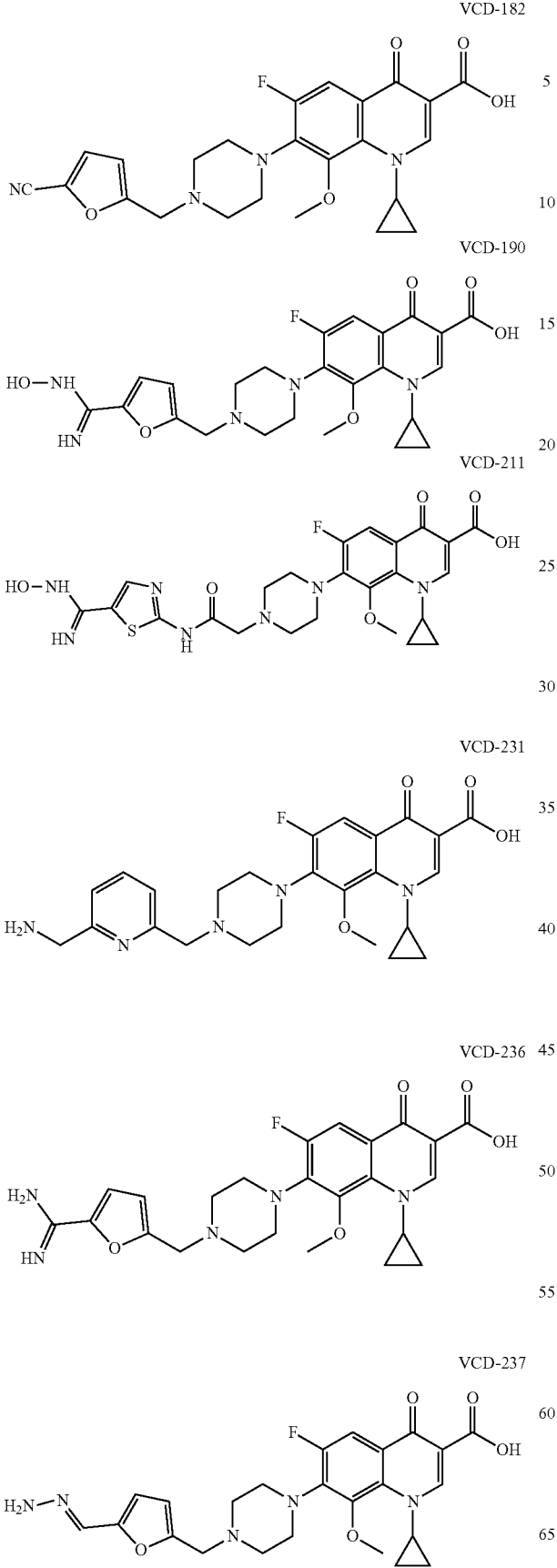
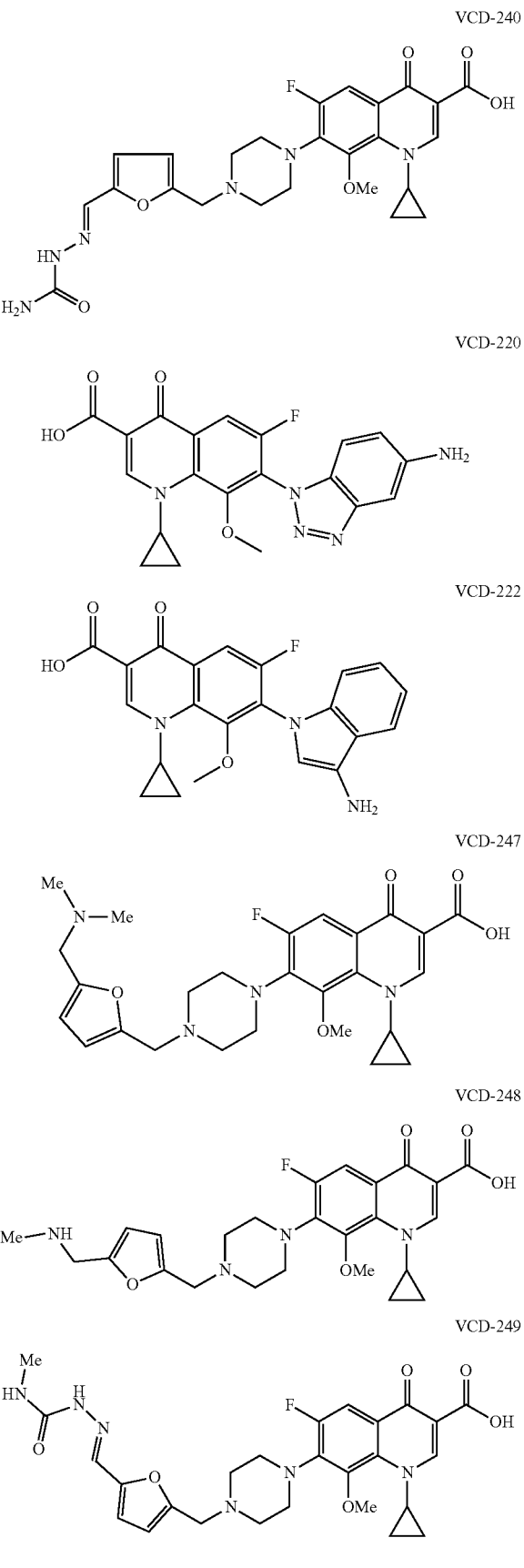

-continued
VCD-253
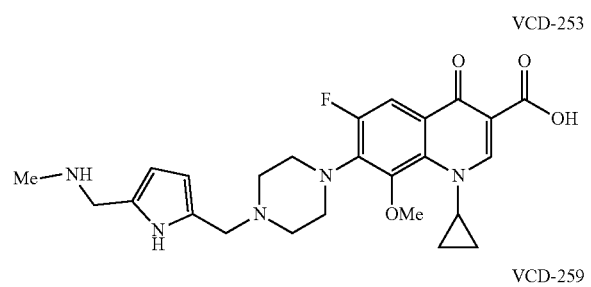
VCD-259
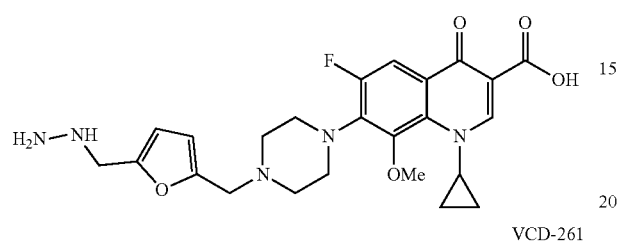
VCD-261
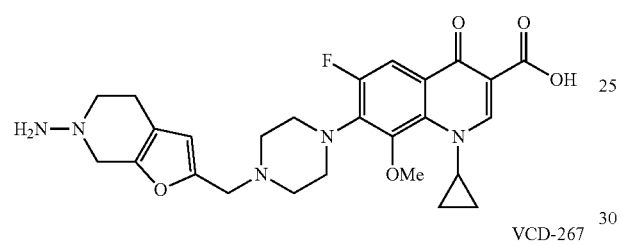
VCD-267
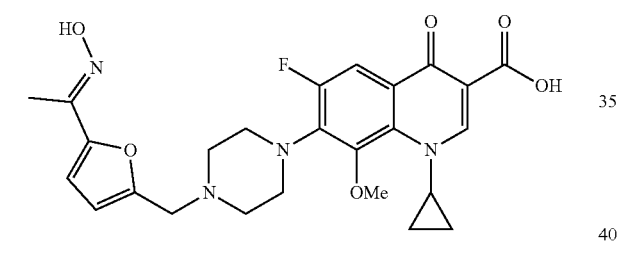
VCD-268
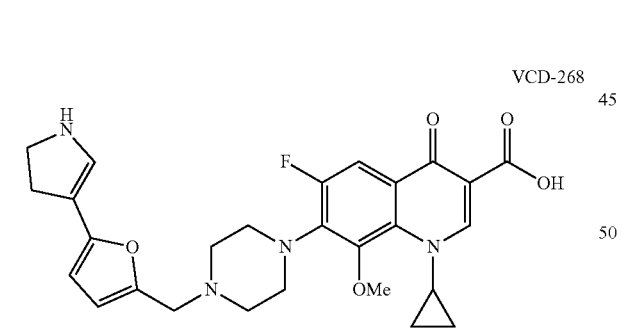
VCD-269
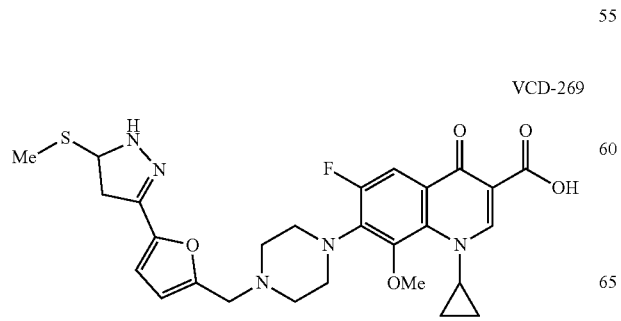
-continued
VCD-270
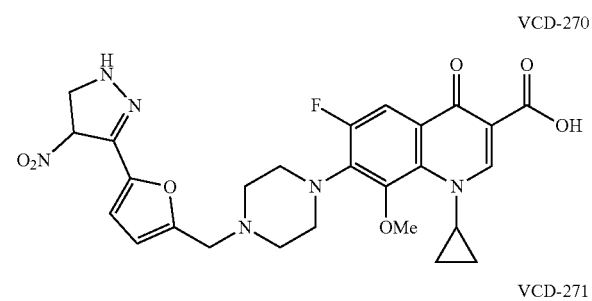
VCD-271
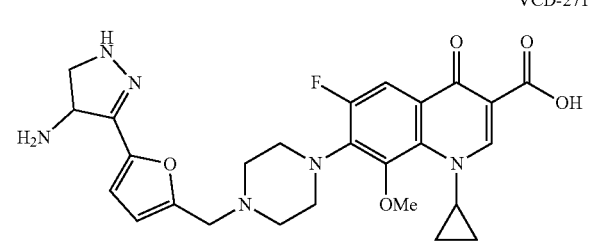
VCD-272
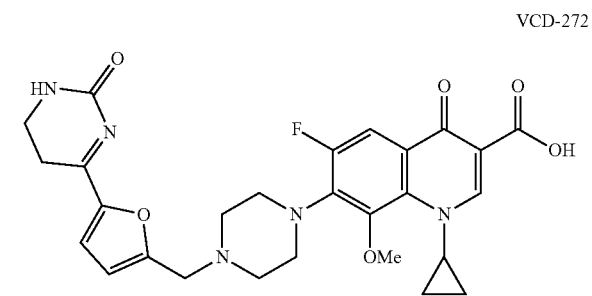
VCD-273
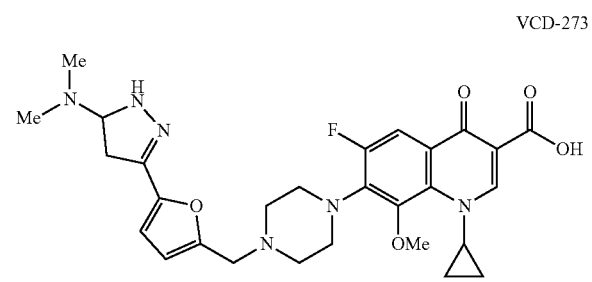
VCD-274
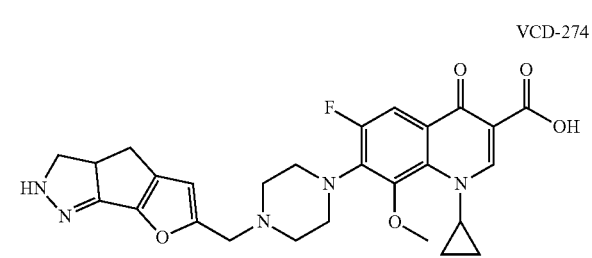
VCD-283
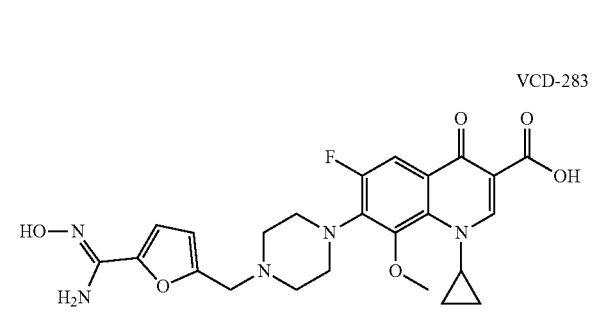

-continued
VCD-235
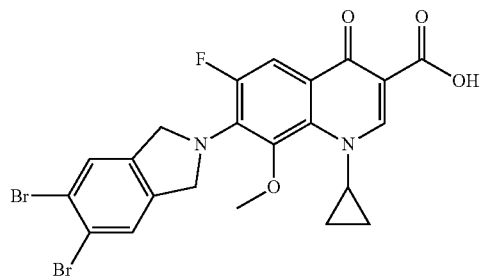
VCD-284
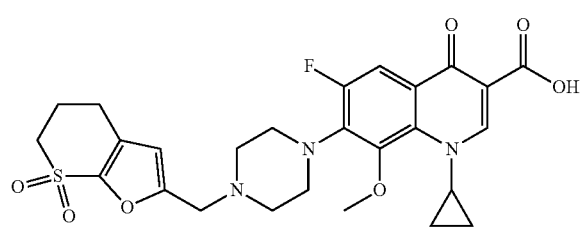
-continued
VCD-285
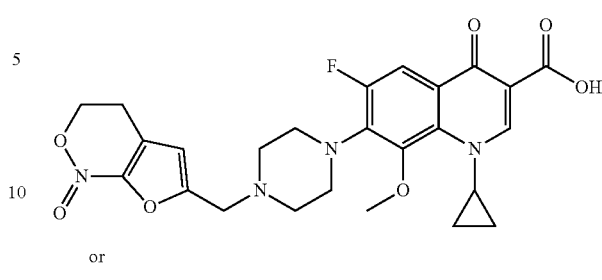
or
VCD-286
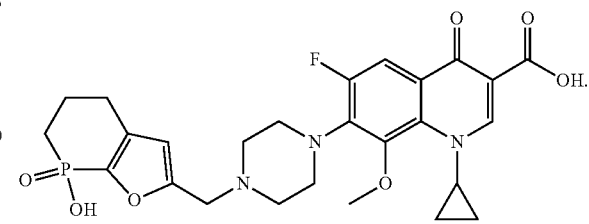
* * * * *